(12) United States Patent
Colburn et al.

(10) Patent No.: US 8,558,011 B2
(45) Date of Patent: Oct. 15, 2013

(54) COLD MENTHOL RECEPTOR-1 ANTAGONISTS

(75) Inventors: Raymond W Colburn, Chalfont, PA (US); Scott L Dax, Landenberg, PA (US); Christopher Flores, Lansdale, PA (US); Jay M Matthews, Lansdale, PA (US)

(73) Assignee: Janssen Pharmaceutica, NV, Beerse (BE)

( * ) Notice: Subject to any disclaimer, the term of this patent is extended or adjusted under 35 U.S.C. 154(b) by 197 days.

(21) Appl. No.: 12/872,866

(22) Filed: Aug. 31, 2010

(65) Prior Publication Data

US 2012/0053347 A1 Mar. 1, 2012

(51) Int. Cl.
*C07D 333/72* (2006.01)
(52) U.S. Cl.
USPC ............................................................ 549/6
(58) Field of Classification Search
USPC ............................................................ 549/6
See application file for complete search history.

(56) References Cited

U.S. PATENT DOCUMENTS

2005/0176769 A1  8/2005  Hawkins et al.

FOREIGN PATENT DOCUMENTS

| DE | 10215321 A1 | 10/2003 |
|----|----|----|
| WO | WO 00/12092 A | 3/2000 |
| WO | WO 02/101045 A2 | 12/2002 |
| WO | WO 2005/094569 A1 | 10/2005 |
| WO | WO 2006/029142 A2 | 3/2006 |
| WO | WO 2006/040103 A1 | 4/2006 |
| WO | WO 2006/040136 A1 | 4/2006 |
| WO | WO 2007/017092 A1 | 2/2007 |
| WO | WO 2007/017093 A1 | 2/2007 |
| WO | WO 2007/017094 A1 | 2/2007 |
| WO | 2007/134107 | * 11/2007 |

OTHER PUBLICATIONS

Abe, J. et al.: "$Ca^{2+}$-dependent PKC activation mediates menthol-induced desensitization of transient receptor potential M8"; Neuroscience Letters (2006) 397: 140-144.
Arbuzov, B.A.: "Reactions of trialkyl phosphates and dialkyl phosphonates with .alpha., Ibeta.-unsaturated carbonyl compounds"; Abstract, Chemical Abstracts Service, Columbus, Ohio, US (XP002456631) 1973.
Behrendt, H.J. et al.: "Characterization of the mouse cold-menthol receptor TRPM8 and vanilloid receptor type-1 VR1 using a fluorometric imaging plate reader (FLIPR) assay"; Br. J. of Pharmacology (2004) 141: 737-745.
Bennett, G.J. et al.: "A peripheral mononeuropathy in rat that produces disorders of pain sensation like those seen in man"; Pain (1988) 33(1): 87-107.

Bhatnagar, S. et al.: "Tramadol for Postoperative Shivering: A Double-Blind Comparison with Pethidine"; Anaesth Intensive Care (2001) 29(2): 149-154.
Bolser, D.C. et al.: "Pharmacological studies of allergic cough in the guinea pig"; European J. of Pharmacology (1995) 277: 159-164.
Braga, P.C.: "Destrorphan and Dextromethorphan: Comparative Antitussive Effects on Guinea Pigs"; Drugs Exper. Clin. Res. (1994) 20(5): 199-203.
Braw, Y. et al.: "Anxiety-like behaviors in pre-pubertal rats of the Flinders Sensitive Line (FSL) and Wistar-Kyoto (WKY) animal models of depression"; Behavioural Brain Research (2006) 167: 261-269.
Butler, S.H. et al.: "A limited arthritic model for chronic pain studies in the rat"; Pain (1992) 48: 73-81.
Collier, H.O.J. et al.: "The Abdominal Constriction Response and Its Suppression by Analgesic Drugs in the Mouse"; Br. J. Pharmacol. Chemother. (1968) 32(2): 295-310.
Cryan, J.F. et al.: "The Ascent of Mouse: Advances in Modelling Human Depression and Anxiety"; Nature Reviews Drug Discovery (Sep. 2005) 4(9): 775-790.
Defrin, R. et al.: "Characterization of chronic pain and somatosensory function in spinal cord injury subjects"; Pain (2001) 89: 253-263.
Defrin, R. et al.: "Sensory determinants of thermal pain"; Brain (2002) 125(Pt 3): 501-510.
Desmeules, J.A. et al.: "Neurophysiologic Evidence for a Central Sensitization in Patients With Fibromyalgia"; Arthritis & Rheumatism (May 2003) 48(5): 1420-1429.
El Mouedden, M. et al.: "Evaluation of pain-related behavior, bone destruction and effectiveness of fentanyl, sufentanil, and morphine in a murine model of cancer pain", Pharmacology Biochem. and Behavior (2005) 82: 109-119.
Erichsen, H.K. et al.: "Comparative actions of the opioid analgesics morphine, methadone and codeine in rat models of peripheral and central neuropathic pain"; Pain (2005) 116: 347-358.
Finnerup, N.B., MD et al.: "Intravenous Lidocaine Relieves Spinal Cord Injury Pain"; Anesthesiology (2005) 102(5): 1023-1030.
Fox, A. et al.: "Critical evaluation of the streptozotocin model of painful diabetic neuropathy in the rat"; Pain (1999) 31: 307-316.
Ghilardi, J.R. et al.: "Selective Blockade of the Capsaicin Receptor TRPV1 Attenuates Bone Cancer Pain"; The J. of Neuroscience (Mar. 23, 2005) 25(12): 3126-3131.
Grahn, D.A. et al.: "Appropriate thermal manipulations eliminate tremors in rats recovering from halothane anesthesia"; J. Applied Physiology (1996) 81: 2547-2554.
Greenspan, J.D. et al.: "Allodynia in patients with post-stroke central pain (CPSP) studied by statistical quantitative sensory testing within individuals"; Pain (2004) 109: 357-366.
Hall, E. et al.: "Time-course of infection and responses in a coughing rat model of pertussis"; J Med. Microbiol. (1999) 48: 95-98.

(Continued)

*Primary Examiner* — Taofiq A Solola
(74) *Attorney, Agent, or Firm* — Thomas J. Dodd

(57) ABSTRACT

The invention is directed to TRPM8 antagonists of Formula (I). More specifically, the present invention relates to certain novel compounds, methods for preparing compounds, compositions, intermediates and derivatives thereof and methods for treating TRPM8-mediated disorders. Pharmaceutical and veterinary compositions and methods of treating pain and various other disease states or conditions using compounds of the invention are also described.

4 Claims, No Drawings

(56) References Cited

OTHER PUBLICATIONS

Hallas, B., PhD et al.: "Establishment of behavioral parameters for the evaluation of osteopathic treatment principles in a rat model of arthritis; J. Am. Osteopath Assoc. (1997) 97(4): 207-214.
Hirayama, Y. et al.: "Effect of FK3657, a non-peptide bradykinin $B_2$ receptor antagonist, on allergic airway disease models"; European J. of Pharmacology (2003) 467: 197-203.
Hunter, J.C. et al.: "The effect of novel anti-epileptic drugs in rat experimental models of acute and chronic pain"; European J. of Pharmacology (1997) 324: 153-160.
Iyengar, S. et al.: "Efficacy of Duloxetine, a Potent and Balanced Serotonin-Norepinephrine Reuptake Inhibitor in Persistent Pain Models in Rats"; The J. of Pharmacol. and Exper. Thera. (2004) 311(2): 576-584.
Jørum, E. et al.: "Cold allodynia and hyperalgesia in neuropathic pain: the effect of N-methyl-D-aspartate (NMDA) receptor antagonist ketamine—a double-blind, cross-over comparison with alfentanil and placebo"; Pain (2003) 101: 229-235.
Kobayashi, K. et al.: "Distinct Expression of TRPM8, TRPA1, and TRPV1 mRNAs in Rat Primary Afferent Neurons with Aδ/C-Fibers and Colocalization with Trk Receptors"; The J. of Comparative Neurology (2005) 493: 596-606.
Koltzenburg, M. et al.: "Differential sensitivity of three experimental pain models in detecting the analgesic effects of transdermal fentanyl and buprenorphine"; Pain (2006) 126: 165-174.
Kozak, W. et al.: "Non-Prostaglandin Eicosanoids in Fever and Anapyrexia"; Frontiers in Bioscience (Sep. 1, 2004) 9: 3339-3355.
Kydonieus, A. et al.: "Elimination of Transdermal Drug-Induced Hypersensitivity by Topical Delivery of Ion Channel Modulating Agents"; Proceedings of the International Symposium on Controlled Release of Bioactive Materials (1997) $24^{th}$: 23-24.
Luger, N.M. et al.: "Efficacy of systemic morphine suggests a fundamental difference in the mechanisms that generate bone cancer vs. inflammatory pain"; Pain (2002) 99: 397-406.
Magyar, T. et al.: "Evaluation of vaccines for atrophic rhinitis—a comparison of three challenge models"; Vaccine (2002) 20: 1797-1802.
McKemy, D.D. et al.: "Identification of a cold receptor reveals a general role for TRP channels in thermosensation"; Nature (Mar. 7, 2002) 416: 52-58.
McMurray, G. et al.: "Animal models in urological disease and sexual dysfunction"; British J. of Pharmacology (2006) 147: S62-S79.
Morin, C., PhD et al.: "Disruption of Thermal Perception in a Multiple Sclerosis Patient With Central Pain"; The Clin. J. of Pain. (2002) 18(3): 191-195.
Motta, A.F. et al.: "The antinociceptive effect of iontophoretic direct application of diclofenac to arthritic knee-joints of rats"; Life Sciences (2003) 73: 1995-2004.
Mukerji, G. et al.: "Cool and menthol receptor TRPM8 in human urinary bladder disorders and clinical correlations"; BMC Urology (2006) 6:6.
Nagakura, Y. et al.: "Allodynia and Hyperalgesia in Adjuvant-Induced Arthritic Rats: Time Course of Progression and Efficacy of Analgesics"; The J. of Pharmacology and Exper. Therapeutics (2003) 306(2): 490-497.
Nikki, P. et al.: "Halothane-Induced Heat Loss and Shivering in Rats"; Acta Anaesthesiol. Scandinav. (1968) 12(3): 125-134.
Nozaki-Taguchi, N. et al.: "Vincristine-induced allodynia in the rat"; Pain (2001) 93: 69-76.
Pomonis, J.D. et al.: "N-(4-Tertiarybutylphenyl)-4-(3-cholorphyridin-2-yl)tetrahydropyrazine-1(2H)-carbox-amide (BCTC), a Novel, Orally Effective Vanilloid Receptor 1 Antagonist with Analgesic Properties: II. In Vivo Characterization in Rat Models of Inflammatory and Neuropathic Pain"; J. of Pharmacol. and Exper. Thera. (JPET) (2003) 306(1): 387-393.
Premkumar, L.S. et al.: "Downregulation of Transient Receptor Potential Melastatin 8 by Protein Kinase C-Mediated Dephosphorylation"; The J. of Neuroscience (Dec. 7, 2005) 25-(49): 11322-11329.

Ribeiro, R.A. et al.: "Involvement of resident macrophages and mast cells in the writhing nociceptive response induced by zymosan and acetic acid in mice."; Euro J. of Pharmacology (2000) 387: 111-118.
Roza, C. et al.: "Cold sensitivity in axotomized fibers of experimental neuromas in mice"; Pain (2006) 120: 24-35.
Rupniak, Nadia M.J. et al.: "Effects of the bradykinin $B_1$ receptor antagonist des-Arg$^9$[Leu$^8$]bradykinin and genetic disruption of the $B_2$ receptor on nociception in rats and mice"; Pain (1997) 71: 89-97.
Sabino, Mary Ann C. et al.: "Simultaneous Reduction in Cancer Pain, Bone Destruction, and Tumor Growth by Selective Inhibition of Cyclooxygenase-$2^1$", Cancer Research (Dec. 15, 2002) 62(24):7343-7349.
Saint-Mezard, P. et al.: "Allergic contact dermatitis"; Eur. J. Dermatol. (2004) 14(5): 284-295.
Sluka, K.A. et al.: "Behavioral and immunohistochemical changes in an experimental arthritis model in rats"; Pain (1993) 55(3): 367-377.
Soulard, C. et al.: "Pharmacological Evaluation of JO 1870: Relation to the Potential Treatment of Urinary Bladder Incontinence"; The J. of Pharmacology and Exper. Thera. (1992) 260(3): 1152-1158.
Stein, R.J. et al.: "Cool (TRPM8) and Hot (TRPV1) Receptors in the Bladder and Male Genital Tract"; The J. of urology (Sep. 2004) 172: 1175-1178.
Suzuki, R. et al.: "The effectiveness of spinal and systemic morphine on rat dorsal horn neuronal responses in the spinal nerve ligation model of neuropathic pain"; Pain (1999) 80: 215-228.
Svendsen, K.B. et al.: "Sensory function and quality of life in patients with multiple sclerosis and pain"; Pain (2005) 114: 473-481.
Tanaka, M. et al.: "Mechanisms of Capsaicin- and Citric-Acid-Induced Cough Reflexes in Guinea Pigs"; J. Pharmacol. Sci. (2005) 99(1): 77-82.
Thomsen, J.S. et al.: "The effect of topically applied salicylic compounds on serotonin-induced scratching behaviour in hairless rats"; Experimental Dermatology (2002) 11(4): 370-375.
Tiniakov, R.L. et al.: "Canine model of nasal congestion and allergic rhinitis"; J. Appl Physiol (2003) 94(5): 1821-1828.
Tomazetti, J. et al.: "Baker yeast-induced fever in young rats: Characterization and validation of an animal model for antipyretics screening"; J. of Neuroscience Methods (2005) 147: 29-35.
Trevisani, M. et al.: "Antitussive activity of iodo-resiniferatoxin in guinea pigs"; Thorax (2004) 59(9): 769-772.
Tsai, Y-C et al.: "A Comparison of Tramadol, Amitriptyline, and Meperidine for Postepidural Anesthetic Shivering in Parturients"; Anesthesia Analg. (2001) 93: 1288-1292.
Tsukimi, Y. et al.: "Cold Response of the Bladder in Guinea Pig: Invovement of Transietn Receptor Potential Channel, TRPM8"; J. Urology (2005)10: 406-410.
Van Miert, Adelbert S.J.P.A.M. et al.: "The Antipyretic Effect of Flurbiprofen"; Eur. J. of Pharmacol. (1977) 44(3): 197-204.
Wei, E.T. et al.: "AG-3-5: a chemical producing sensations of cold"; J. Pharm Pharmacol. (1983) 35: 110-112.
Weisshaar, E. et al.: "Effect of topical capsaicin on the cutaneous reactions and itching to histamine in atopic eczema compared to healthy skin"; Arch Dermatol. Res. (1998) 290(6): 306-311.
Weisshaar, e. et al.: "Systemic Drugs With Antipruritic Potency"; Skin Therapy Letters (2000) 5(5): 1-6.
Wille, J.J. et al.: "cis-Urocanic Acid Induces Mast Cell Degranulation and Release of Preformed TNF-a: A Possible Mechanism Linking UVB and cis-Urocanic Acid to Immunosuppression of Contact Hypersensitivity"; Skin Pharmacol. Appl Skin Physiol. (1999) 12(1-2): 18-27.
Woods, M. et al.: "Efficacy of the β3-Adrenergic Receptor Agonist CL-316243 on Experimental Bladder Hyperreflexia and Detrusor Instability in the Rat"; J. of Urology (Sep. 2001) 166: 1142-1147.
Xing, H. et al.: "Chemical and Cold Sensitivity of Two Distinct Populations of TRPM8-Expressing Somatosensory Neurons"; J. Neurophysiol. (2006) 95(2): 1221-1230.
Younes, S. et al.: "Synthesis and pharmacological study of new calcium antagonists, analogues of cinnarizine and flunarizine"; Eur. J. Med. Chem. (1993) 28: 943-948.
Partial International Search Report dated Feb. 1, 2008 for PCT Appln No. PCT/US2007/068566.
PCT Search Report, PCT/US2007/068566, date of mailing Jan. 23, 2009.

\* cited by examiner

COLD MENTHOL RECEPTOR-1 ANTAGONISTS

CROSS REFERENCE TO RELATED APPLICATIONS

This Application claims priority to U.S. Ser. No. 12/114,325, filed May 2, 2007, which claims priority to U.S. Provisional Patent Application No. 60/799,275, filed May 10, 2006, and U.S. Provisional Patent Application No. 60/915,527, filed May 2, 2007, which are hereby incorporated by reference in their entirety.

STATEMENT REGARDING FEDERALLY SPONSORED RESEARCH OR DEVELOPMENT

The research and development of the invention described below was not federally sponsored.

BACKGROUND OF THE INVENTION

Transient receptor potential (TRP) channels are non-selective cation channels that are activated by a variety of stimuli. Numerous members of the ion channel family have been identified to date, including the cold-menthol receptor-1, also called TRPM8 (McKemy D D et al. Nature 2002; 416(6876): 52-8). Collectively, the TRP channels and related TRP-like receptors connote sensory responsivity to the entire continuum of thermal exposure, selectively responding to threshold temperatures ranging from noxious hot through noxious cold as well as to certain chemicals that mimic these sensations. Specifically, TRPM8 is known to be stimulated by cool to cold temperatures as well as by menthol and icilin, which may be responsible for the therapeutic cooling sensation that these agents evoke. TRPM8 is located on primary nociceptive neurons (A-delta and C-fibers) and is modulated by inflammation-mediated second messenger signals (Abe J et al. Neurosci Lett 2006, 397(1-2):140-4; Premkumar L S et al. J Neurosci 2005; 25(49): 11322-9). The localization of TRPM8 on both Aδ and C-fibers may provide a basis for abnormal cold sensitivity in pathologic conditions wherein these neurons are altered, resulting in pain, often of a burning nature (Kobayashi K et al. J Comp Neurol 2005; 493(4): 596-606; Roza C et al. Pain 2006; 120(1-2): 24-35; Xing H et al. J Neurophysiol 2006; 95(2): 1221-30). Cold intolerance and paradoxical burning sensations induced by chemical or thermal cooling closely parallel symptoms seen in a wide range of clinical disorders and thus provide a strong rationale for the development of TRPM8 modulators as novel antihyperalgesic or antiallodynic agents. TRPM8 is also known to be expressed in the brain, lung, bladder, gastrointestinal tract, blood vessels, prostate and immune cells, thereby providing the possibility for therapeutic modulation in a wide range of maladies.

In International Patent Application WO 2006/040136 A1, Lampe, T. et al of Bayer Healthcare AG disclose substituted 4-benzyloxy-phenylmethylamide derivatives as cold menthol receptor-1 (CMR-1) antagonists for the treatment of urological disorders.

In International Patent Application WO 2006/040103 A1, Alonso-Alija, C. et al of Bayer Healthcare AG disclose methods and pharmaceutical compositions for treatment and/or prophylaxis of respiratory diseases or disorders.

In International Patent Application WO 2007/017092 A1, Lampe, Thomas et al of Bayer Healthcare AG disclose substituted 4-benzyloxy-benzoic acid amide derivatives as cold menthol receptor-1 (CMR-1) antagonists for the treatment of urological diseases or disorders, chronic pain, neuropathic pain, postoperative pain, rheumatoid arthritic pain, neuralgia, neuropathies, algesia, nerve injury, ischaemia, neurodegeneration, stroke, and inflammatory disorders such as asthma and chronic obstructive pulmonary (or airways) disease (COPD).

In International Patent Application WO 2007/017093 A1, Lampe, Thomas et al of Bayer Healthcare AG disclose substituted 2-benzyloxy-benzoic acid amide derivatives as cold menthol receptor-1 (CMR-1) antagonists for the treatment of urological diseases or disorders, chronic pain, neuropathic pain, postoperative pain, rheumatoid arthritic pain, neuralgia, neuropathies, algesia, nerve injury, ischaemia, neurodegeneration, stroke, and inflammatory disorders such as asthma and chronic obstructive pulmonary (or airways) disease (COPD).

In International Patent Application WO 2007/017094 A1, Lampe, Thomas et al of Bayer Healthcare AG disclose substituted benzyloxy-phenylmethylcarbamate derivatives as cold menthol receptor-1 (CMR-1) antagonists for the treatment of urological diseases or disorders, chronic pain, neuropathic pain, postoperative pain, rheumatoid arthritic pain, neuralgia, neuropathies, algesia, nerve injury, ischaemia, neurodegeneration, stroke, and inflammatory disorders such as asthma and chronic obstructive pulmonary (or airways) disease (COPD).

It is an object of the present invention to provide compounds that are TRPM8 antagonists useful for treating TRPM8-mediated disorders. It is another object of the invention to provide a process for preparing compounds, compositions, intermediates and derivatives thereof. It is a further object of the invention to provide methods for treating chronic or acute pain, or the diseases that lead to such pain, and pulmonary or vascular dysfunction. More particularly, the compounds of the present invention are useful for the treatment of diseases or conditions including, but not limited to, those that cause inflammatory or neuropathic pain, cold intolerance or cold allodynia, peripheral vascular pain, itch or urinary incontinence, chronic obstructive pulmonary disease, pulmonary hypertension and anxiety or stress-related disorders.

SUMMARY OF THE INVENTION

The present invention is directed to compounds of Formula (I)

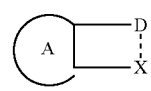

Formula (I)

wherein:
A is benzo or pyrido;
wherein benzo is optionally substituted with a substituent selected from the group consisting of $C_{1-2}$alkyl, $C_{1-2}$alkoxy, hydroxy, fluoro, chloro, bromo, $C_{1-2}$alkoxycarbonyl, aminocarbonyl, ($C_{1-2}$alkyl)aminocarbonyl, di($C_{1-2}$alkyl)aminocarbonyl, and trifluoromethyl; and benzo is optionally further substituted with a substituent selected from the group consisting of methyl, methoxy, hydroxy, fluoro, and chloro;
and wherein pyrido is optionally substituted with a substituent selected from the group consisting of fluoro, chloro, bromo, and methyl; and pyrido is optionally further substituted with fluoro;

D is d-1 or d-2

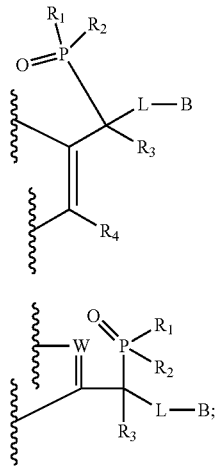

X is O, S, S(=O), S(O$_2$), or N—R$_6$; wherein R$_6$ is phenyl, C$_{1-4}$alkyl, allyl, C$_{1-4}$alkylsulfonyl, C$_{1-4}$alkylcarbonyl, or pyridinyl;

W is C(R$_4$) or N;

R$_4$ is hydrogen; C$_{1-8}$alkyl; C$_{1-8}$alkoxy; C$_{1-6}$alkoxycarbonyl; chloro; bromo; cyano; trifluoromethyl; phenyl; a heteroaryl selected from the group consisting of furyl, thienyl, pyrrolyl, oxazolyl, thiazolyl, pyrazolyl, pyridinyl, and pyrimidinyl; or a C$_{3-6}$cycloalkyl;

wherein phenyl is optionally substituted with an aminocarbonyl, trifluoromethyl, or trifluoromethoxy substituent; or phenyl is optionally substituted with one to two substituents independently selected from the group consisting of C$_{1-2}$alkyl, C$_{1-2}$alkoxy, fluoro, chloro, hydroxy, and cyano;

and wherein heteroaryl is optionally substituted with bromo or one to two substituents independently selected from the group consisting of methyl, fluoro, and chloro;

R$_1$ and R$_2$ are independently selected from the group consisting of C$_{1-8}$alkyl; C$_{1-8}$alkoxy; —O(CH$_2$)$_p$O(CH$_2$)$_q$CH$_3$; —O(CH$_2$)$_p$O(CH$_2$)$_q$OCH$_3$; —O(CH$_2$)$_r$C(O)OCH$_3$; —O(CH$_2$)$_p$OC(O)CH$_3$; —(CH$_2$)$_p$O(CH$_2$)$_q$CH$_3$; phenyl(C$_{1-3}$)alkyl; phenyl(C$_{1-3}$)alkoxy; and C$_{3-8}$cycloalkyloxy;

wherein p is an integer from 2 to 6; and wherein q is an integer from 0 to 4, such that the sum of p and q is less than or equal to six; wherein r is an integer from 1 to 4;

and, wherein the phenyl portion of phenyl(C$_{1-3}$)alkyl and phenyl(C$_{1-3}$)alkoxy is optionally substituted with one to two substituents independently selected from the group consisting of C$_{1-2}$alkyl, C$_{1-2}$alkoxy, trifluoromethyl, hydroxy, cyano, and halogen;

and further, wherein C$_{1-8}$alkyl and C$_{1-8}$alkoxy of R$_1$ and R$_2$ are optionally substituted with hydroxy, difluoromethyl, trifluoromethyl, C$_{3-6}$cycloalkyl, carboxy, C$_{1-2}$alkoxycarbonyl, di(C$_{1-3}$alkyl)amino, aminocarbonyl, (C$_{1-3}$alkyl)aminocarbonyl, or di(C$_{1-3}$alkyl)aminocarbonyl; provided that when R$_1$ is 2-(N,N-dimethylamino)-ethoxy, R$_2$ is other than 2-(N,N-dimethylamino)-ethoxy;

R$_3$ is hydrogen, methyl, fluoro, chloro, bromo, or hydroxy; or R$_3$ is absent when L is alkene =CH—;

L is absent, —(CH$_2$)$_n$—, —OC$_{1-2}$alkyl-, or =CH—; wherein n is 1 or 2;

B is hydrogen, phenyl, naphthyl, or a heteroaryl selected from the group consisting of benzothiophenyl, benzo(1,3)dioxalyl, oxazolyl, thienyl, furanyl, and benzofuranyl;

wherein the phenyl of B is optionally substituted with hydroxy, C$_{1-3}$alkoxy, trifluoromethyl, nitro, amino, phenyl or a heteroaryl selected from the group consisting of pyridinyl, thienyl, furanyl, pyrrolyl, oxazolyl, and thiazolyl; and wherein phenyl of B is optionally further substituted with a substituent selected from the group consisting of methyl, fluoro, chloro, trifluoromethyl, methoxy, and hydroxy;

and wherein the naphthyl of B is optionally substituted with 1 or 2 substituents selected from the group consisting of hydrogen, methyl, fluoro, chloro, bromo, C$_{1-3}$alkoxy, hydroxy, and dimethylamino;

or, the phenyl or heteroaryl substituent of B is optionally substituted with a substituent independently selected from the group consisting of C$_{1-3}$alkyl, C$_{1-3}$alkoxy, C$_{1-3}$alkylthio, fluoro, chloro, bromo, cyano, hydroxy, trifluoromethyl, trifluoromethylthio, trifluoromethoxy, difluoromethoxy, trifluoromethanesulfonyl, C$_{1-2}$alkoxycarbonyl, aminocarbonyl, (C$_{1-2}$alkyl)aminocarbonyl, and di(C$_{1-2}$alkyl)aminocarbonyl;

and the phenyl or heteroaryl substituent of B is optionally further substituted with one to two fluoro or chloro substituents;

provided that when B is hydrogen and L is absent or —(CH$_2$)$_n$—, then at least one of R$_1$ and R$_2$ is selected from the group consisting of phenyl(C$_{1-6}$)alkyl and phenyl(C$_{1-6}$)alkoxy;

and enantiomers, diastereomers, racemates, and pharmaceutically acceptable salts thereof;

provided that a compound of Formula (I) is other than
a compound wherein A is 5-fluoro-benzo, D is d-2, W is C(R$_4$), R$_4$ is methyl, X is S, R$_1$ and R$_2$ are each isopropyloxy, R$_3$ is hydrogen, L is CH$_2$, and B is 3,4-difluorophenyl;
a compound wherein A is 6-trifluoromethyl-benzo, D is d-2, W is C(R$_4$), R$_4$ is methyl, X is S, R$_1$ and R$_2$ are each ethoxy, R$_3$ is hydrogen, L is CH$_2$, and B is 3,4-difluorophenyl;

and further provided that when D is d-2, R$_3$ is hydrogen, and L is —(CH$_2$)$_n$—, then B is optionally substituted with a substituent other than aminocarbonyl, (C$_{1-2}$alkyl)aminocarbonyl, or di(C$_{1-2}$alkyl)aminocarbonyl.

Illustrative of the invention is a pharmaceutical composition comprising a pharmaceutically acceptable carrier and a compound of Formula (I). Also illustrative of the invention is a process for making a pharmaceutical composition comprising mixing a compound of Formula (I) and a pharmaceutically acceptable carrier.

The present invention is further directed to methods for treating or ameliorating a TRPM8-mediated disorder. In particular, the method of the present invention is directed to treating or ameliorating a TRPM8 receptor-mediated disorder including, but not limited to, inflammatory pain, cold-intolerance or cold allodynia, peripheral vascular pain, itch or urinary incontinence, chronic obstructive pulmonary disease, pulmonary hypertension and anxiety or stress-related disorders.

The present invention is also directed to methods for producing the instant compounds and pharmaceutical compositions and medicaments thereof.

DETAILED DESCRIPTION OF THE INVENTION

As used herein, with reference to substituents, the term "independently" means that when more than one of such substituent is possible, such substituents may be the same or different from each other.

As used herein, unless otherwise noted, "alkyl" whether used alone or as part of a substituent group refers to straight and branched carbon chains having 1 to 8 carbon atoms or any number within this range. Therefore, designated numbers of carbon atoms (e.g. $C_{1-8}$) shall refer independently to the number of carbon atoms in an alkyl moiety or to the alkyl portion of a larger alkyl-containing substituent. In substituent groups with multiple alkyl groups such as $(C_{1-6}alkyl)_2amino-$ the $C_{1-6}alkyl$ groups of the dialkylamino may be the same or different.

As used herein, unless otherwise noted, the term "alkoxy" refers to an —Oalkyl substituent group, wherein alkyl is as defined supra. To the extent substituted, an alkyl and alkoxy chain may be substituted on a carbon atom.

As used herein, the terms "alkenyl" and "alkynyl" refer to straight and branched carbon chains having 2 or more carbon atoms, wherein an alkenyl chain has at least one double bond in the chain and an alkynyl chain has at least one triple bond in the chain.

The term "cycloalkyl" refers to saturated or partially unsaturated, monocyclic or polycyclic hydrocarbon rings of from 3 to 14 carbon atom members. Examples of such rings include, and are not limited to cyclopropyl, cyclobutyl, cyclopentyl, cyclohexyl, cycloheptyl and adamantyl. Similarly, "cycloalkenyl" refers to a cycloalkyl that contains at least one double bond in the ring. Additionally, a "benzo-fused cycloalkyl" is a cycloalkyl ring that is fused to a benzene ring. A "heteroaryl-fused cycloalkyl" is a cycloalkyl ring that is fused to a 5 or 6 membered heteroaryl ring (containing one of O, S or N and, optionally, one additional nitrogen).

The term "heterocyclyl" refers to a nonaromatic cyclic ring of 5 to 7 members in which 1 to 2 members are nitrogen, or a nonaromatic cyclic ring of 5 to 7 members in which zero, one or two members are nitrogen and up to two members are oxygen or sulfur; wherein, optionally, the ring contains zero to one unsaturated bonds, and, optionally, when the ring is of 6 or 7 members, it contains up to two unsaturated bonds. The term "benzo-fused heterocyclyl" includes a 5 to 7 membered monocyclic heterocyclic ring fused to a benzene ring. The term "heteroaryl-fused heterocyclyl" refers to 5 to 7 membered monocyclic heterocyclic ring fused to a 5 or 6 membered heteroaryl ring (containing one of O, S or N and, optionally, one additional nitrogen). The term "cycloalkyl-fused heterocyclyl" refers to a 5 to 7 membered monocyclic heterocyclic ring fused to a 5 to 7 membered cycloalkyl or cycloalkenyl ring. Furthermore, the term "heterocyclyl-fused heterocycyl" refers to a 5 to 7 membered monocyclic heterocyclic ring fused to a 5 to 7 membered heterocyclyl ring (of the same definition as above but absent the option of a further fused ring). For instant compounds of the invention, the carbon atom ring members that form the heterocyclyl ring are fully saturated. Other compounds of the invention may have a partially saturated heterocyclyl ring. The term "heterocyclyl" also includes a 5 to 7 membered monocyclic heterocycle bridged to form bicyclic rings. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Preferred aryl groups for the practice of this invention are phenyl and naphthalenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent.

Optionally, the heteroaryl ring is fused to a benzene ring to form a "benzo fused heteroaryl"; similarly, the heteroaryl ring is optionally fused to a 5 or 6 membered heteroaryl ring (containing one of O, S or N and, optionally, one additional nitrogen) to form a "heteroaryl-fused heteroaryl"; similarly, the heteroaryl ring is optionally fused to a 5 to 7 membered cycloalkyl ring or a 5 to 7 membered heterocyclo ring (as defined supra but absent the option of a further fused ring) to form a "cycloalkyl-fused heteroaryl". Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; examples of heteroaryl groups with the optionally fused benzene rings include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl or quinazolinyl.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

The term "halogen" refers to fluorine, chlorine, bromine and iodine. Substituents that are substituted with multiple halogens are substituted in a manner that provides compounds that are stable.

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_{1-6}$) refer independently to the number of carbon atoms in an alkyl moiety, an aryl moity, or in the alkyl portion of a larger substituent in which alkyl appears as its prefix root. For alkyl and alkoxy substituents, the designated number of carbon atoms includes all of the independent members included within a given range specified. For example $CO_{1-6}$ alkyl would include methyl, ethyl, propyl, butyl, pentyl and hexyl individually as well as subcombinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

As used herein, when L is "=CH—" in the compounds of Formula (I), L represents an alkene between B and the carbon atom which is bound to a phosphorus atom, taken to form d-1a or d-2a as illustrated below:

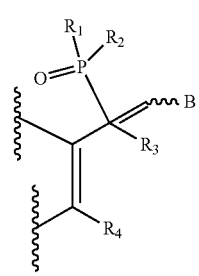

d-1a

-continued

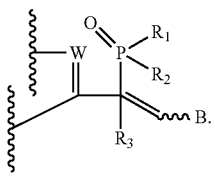
d-2a

In general, under standard nomenclature rules used throughout this disclosure, the terminal portion of the designated side chain is described first followed by the adjacent functionality toward the point of attachment. Thus, for example, a "phenyl$C_1$-$C_6$ alkylamido$C_1$-$C_6$alkyl" substituent refers to a group of the formula:

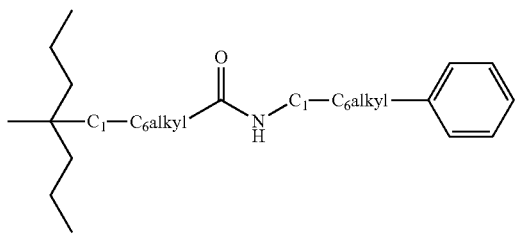

Unless otherwise noted, substituents of ring A of the present invention are named according to the numbering system shown below, in which "X" is labeled position 1.

For example, when A is benzo, then the following numbering system applies:

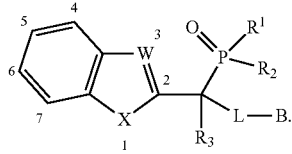

Unless otherwise noted, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "subject" as used herein, refers to an animal, preferably a mammal, most preferably a human, who has been the object of treatment, observation or experiment.

As used herein, the term "enantiomeric excess" refers to when one enantiomer is present in greater quantity than the other enantiomer. Such mixtures of two enantiomers, unlike a racemic mixture, will show a net optical rotation. The specific rotation of the mixture may be determined with knowledge of the specific rotation of the pure enantiomer, and subsequently the enantiomeric excess (ee) can be determined using equation (1)

$$ee = ([\alpha]_{obs}/[\alpha]_{max}) \times 100\% \quad (1).$$

One skilled in the art may determine specific amounts of each enantiomer using HPLC on a chiral stationary phase. When the amounts of each enantiomer are known, the enantiomeric excess may be determined using equation (2):

$$ee = ((R-S)/R+S)) \times 100\% \quad (2)$$

wherein R and S are the respective fractions of enantiomers in a mixture such that R+S=1.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation or partial alleviation of the symptoms of the disease or disorder being treated.

As used herein, the term "composition" is intended to encompass a product comprising the specified ingredients in the therapeutically effective amounts, as well as any product which results, directly or indirectly, from combinations of the specified ingredients in the specified amounts.

For the purposes of the present invention, the term "antagonist" is used to refer to a compound capable of producing, depending on the circumstance, a functional antagonism of the TRPM8 ion channel, including but not limited to competitive antagonists, non-competitive antagonists, desensitizing agonists, and partial agonists.

For the purposes of the present invention, the term inflammatory/hypersensitivity is used to refer to a condition that is characterized by one or more hallmarks of inflammation, including but not limited to edema, erythema, hyperthermia and pain, and/or by an exaggerated physiologic or pathophysiologic response to one or more than one type of stimulation, including but not limited to thermal, mechanical and/or chemical stimulation.

An embodiment of the invention is a method of treating or preventing migraine, post herpetic neuralgia, post traumatic neuralgia, post chemotherapy neuralgia, complex regional pain syndrome I and II (CRPS I/II), fibromyalgia, inflammatory bowel disease, pruritis, asthma, chronic obstructive pulmonary disease, toothache, bone pain or pyresis in a mammal, which method comprises administering to a mammal in need of such treatment or prevention a therapeutically effective amount of a TRPM8 antagonist.

Another embodiment of the invention is a method of treating or preventing hypertension, peripheral vascular disease, Raynaud's disease, reperfusion injury or frostbite in a mammal, which method comprises administering to a mammal in need of such treatment or prevention a therapeutically effective amount of a TRPM8 antagonist.

A further embodiment of the invention is a method of accelerating post-anesthetic recovery or post hypothermia recovery in a mammal, which method comprises administering to a mammal in need of such treatment a therapeutically effective amount of a TRPM8 antagonist.

An embodiment of the present invention is directed to compounds of Formula (I)

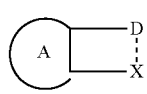

Formula (I)

wherein:
A is benzo or pyrido;
  wherein benzo is optionally substituted with a substituent selected from the group consisting of hydrogen, $C_{1-2}$alkyl, $C_{1-2}$alkoxy, hydroxy, fluoro, chloro, bromo, $C_{1-2}$alkoxycarbonyl, aminocarbonyl, ($C_{1-2}$alkyl)aminocarbonyl, di($C_{1-2}$alkyl)aminocarbonyl, and trifluoromethyl; and benzo is optionally further substituted with a substituent selected from the group consisting of hydrogen, methyl, methoxy, hydroxy, fluoro, chloro;

and wherein pyrido is optionally substituted with a substituent selected from the group consisting of fluoro, chloro, bromo, and methyl; and pyrido is optionally further substituted with fluoro;

D is d-1 or d-2

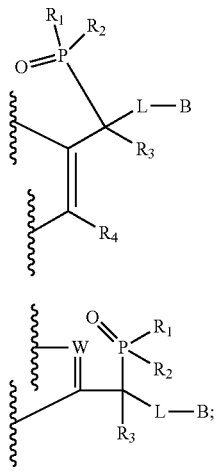

X is O, S, S(=O), S($O_2$), or N—$R_6$; wherein $R_6$ is phenyl, $C_{1-4}$alkyl, allyl, $C_{1-4}$-alkylsulfonyl, $C_{1-4}$alkylcarbonyl, or pyridinyl;

W is C($R_4$) or N;

$R_4$ is hydrogen; $C_{1-6}$alkyl; $C_{1-6}$alkoxy; $C_{1-6}$alkoxycarbonyl; chloro; bromo; cyano; trifluoromethyl; phenyl; a heteroaryl selected from the group consisting of furyl, thienyl, pyrrolyl, oxazolyl, thiazolyl, pyrazolyl, pyridinyl, and pyrimidinyl; or a $C_{3-6}$cycloalkyl;

wherein phenyl is optionally substituted with a trifluoromethyl or trifluoromethoxy substituent, or phenyl is optionally substituted with one to two substituents independently selected from the group consisting of hydrogen, $C_{1-2}$alkyl, $C_{1-2}$alkoxy, fluoro, chloro, hydroxy, and cyano;

and wherein heteroaryl is optionally substituted with bromo or one to two substituents independently selected from the group consisting of methyl, fluoro, and chloro;

$R_1$ and $R_2$ are independently selected from the group consisting of $C_{1-8}$alkyl; $C_{1-8}$alkoxy; —O($CH_2$)$_p$O($CH_2$)$_q$$CH_3$; —($CH_2$)$_p$—O—($CH_2$)$_q$$CH_3$; phenyl($C_{1-3}$)alkyl; phenyl ($C_{1-3}$)alkoxy; and $C_{3-8}$cycloalkyloxy;

wherein p is an integer from 2 to 6; and wherein q is an integer from 0 to 4, such that the sum of p and q is less than or equal to six;

and, wherein the phenyl portion of phenyl($C_{1-3}$)alkyl and phenyl($C_{1-3}$)alkoxy is optionally substituted with one to two substituents independently selected from the group consisting of $C_{1-2}$alkyl, $C_{1-2}$alkoxy, trifluoromethyl, hydroxy, cyano, and halogen;

and further, wherein $C_{1-8}$alkyl and $C_{1-8}$alkoxy of $R_1$ and $R_2$ are optionally substituted with hydroxy, difluoromethyl, trifluoromethyl, $C_{3-6}$cycloalkyl, carboxy, $C_{1-2}$alkoxycarbonyl, di($C_{1-3}$alkyl)amino, aminocarbonyl, ($C_{1-3}$alkyl)aminocarbonyl, or di($C_{1-3}$alkyl)aminocarbonyl; provided that when $R_1$ is 2-(N,N-dimethylamino)-ethoxy, $R_2$ is other than 2-(N,N-dimethylamino)-ethoxy;

$R_3$ is hydrogen, methyl, fluoro, chloro, bromo, or hydroxy;

L is absent, —($CH_2$)$_n$—, or —O$C_{1-2}$alkyl-; wherein n is 1 or 2;

B is hydrogen, phenyl, naphthyl, or a heteroaryl selected from the group consisting of benzothiophenyl, benzo(1,3)dioxalyl, oxazolyl, thienyl, furanyl, and benzofuranyl; wherein the phenyl of B is optionally substituted with phenyl or a heteroaryl selected from the group consisting of pyridinyl, thienyl, furanyl, oxazolyl, and thiazolyl; and wherein phenyl is optionally further substituted with a substituent selected from the group consisting of methyl, fluoro, chloro, trifluoromethyl, methoxy, and hydroxy; and wherein the naphthyl of B is optionally substituted with 1 or 2 substituents selected from the group consisting of hydrogen, methyl, fluoro, chloro, bromo, methoxy, hydroxyl, and dimethylamino;

or, a B substituent other than hydrogen is optionally substituted with a substituent independently selected from the group consisting of $C_{1-3}$alkyl, $C_{1-3}$alkoxy, fluoro, chloro, bromo, cyano, hydroxy, trifluoromethyl, trifluoromethylthio, trifluoromethoxy, methanesulfonyl, trifluoromethanesulfonyl, $C_{1-2}$alkoxycarbonyl, aminocarbonyl, ($C_{1-2}$alkyl)aminocarbonyl, and di($C_{1-2}$alkyl)aminocarbonyl; and B is optionally further substituted with one to two fluoro or chloro substituents;

provided that when B is hydrogen and L is absent or —($CH_2$)$_n$—, then at least one of $R_1$ and $R_2$ is selected from the group consisting of phenyl($C_{1-6}$)alkyl and phenyl ($C_{1-6}$)alkoxy;

and enantiomers, diastereomers, racemates, and pharmaceutically acceptable salts thereof;

provided that a compound of Formula (I) is other than a compound wherein A is 5-fluoro-benzo, D is d-2, W is C($R_4$), $R_4$ is methyl, X is S, $R_1$ and $R_2$ are each isopropyloxy, $R_3$ is hydrogen, L is $CH_2$, and B is 3,4-difluorophenyl; or a compound wherein A is 6-trifluoromethyl-benzo, D is d-2, W is C($R_4$), $R_4$ is methyl, X is S, $R_1$ and $R_2$ are each ethoxy, $R_3$ is hydrogen, L is $CH_2$, and B is 3,4-difluorophenyl;

and further provided that when D is d-2, $R_3$ is hydrogen, and L is —($CH_2$)$_n$—, then B is optionally substituted with a substituent other than aminocarbonyl, ($C_{1-2}$alkyl)aminocarbonyl, or di($C_{1-2}$alkyl)aminocarbonyl.

Embodiments of the present invention include a compound of Formula (I) wherein:

a) A is benzo optionally substituted with trifluoromethyl, $C_{1-2}$alkyl, or $C_{1-2}$alkoxy, and optionally further substituted with a substituent selected from the group consisting of methyl, methoxy, fluoro, and chloro;

b) A is benzo optionally substituted with trifluoromethyl, $C_{1-2}$alkyl, $C_{1-2}$alkoxy, fluoro, or chloro;

c) A is benzo optionally substituted with $C_{1-2}$alkyl, fluoro, or chloro;

d) D is d-2

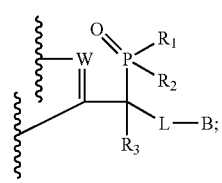

e) X is O, S, S($O_2$), or N—$R_6$; wherein $R_6$ is phenyl;

f) X is O, S, or S($O_2$);

g) X is O or S;
h) W is C(R₄);
i) R₄ is hydrogen, $C_{1-6}$alkyl, chloro, bromo, trifluoromethyl, phenyl, pyridinyl optionally substituted with fluoro, or $C_{3-6}$cycloalkyl;
j) R₄ is hydrogen, methyl, isopropyl, 2,2-dimethyl-propyl, chloro, bromo, trifluoromethyl, phenyl, pyridinyl optionally substituted with fluoro, or $C_{3-6}$cycloalkyl;
k) R₄ is hydrogen, methyl, isopropyl, chloro, bromo, trifluoromethyl, pyridinyl optionally substituted with fluoro, cyclopropyl, cyclobutyl, or cyclopentyl;
l) R₄ is methyl, isopropyl, chloro, bromo, trifluoromethyl, pyridinyl optionally substituted with fluoro, cyclopropyl, cyclobutyl, or cyclopentyl;
m) R₁ and R₂ are independently selected from the group consisting of $C_{1-4}$alkyl optionally substituted with di($C_{1-3}$alkyl)amino, $C_{1-4}$alkoxy optionally substituted with di($C_{1-3}$alkyl)amino, —O(CH₂)$_p$O(CH₂)$_q$CH₃, phenyl($C_{1-3}$)alkyl, phenyl($C_{1-3}$)alkoxy, and $C_{3-6}$cycloalkyloxy; wherein p is an integer from 2 to 4 and q is 0;
wherein the phenyl portion of phenyl($C_{1-3}$)alkyl and phenyl($C_{1-3}$)alkoxy is optionally substituted with one to two substituents independently selected from the group consisting of methyl, methoxy, fluoro, chloro, and bromo; provided that when R₁ is 2-(N,N-dimethylamino)-ethoxy, R₂ is other than 2-(N,N-dimethylamino)-ethoxy;
further provided that only one of R₁ and R₂ is phenyl ($C_{1-3}$)alkyl or phenyl($C_{1-3}$)alkoxy;
n) R₁ and R₂ are independently selected from the group consisting of $C_{1-4}$alkyl, phenyl($C_{1-3}$)alkyl, and $C_{1-4}$alkoxy; wherein the phenyl portion of phenyl($C_{1-3}$) alkyl is optionally substituted with methoxy;
o) R₁ and R₂ are independently selected from the group consisting of methyl, isobutyl, ethoxy, and isopropyloxy;
p) R₃ is hydrogen, methyl, fluoro, or bromo;
q) R₃ is hydrogen or methyl;
r) R₃ is hydrogen;
s) L is absent, —(CH₂)$_n$—, or —OCH₂—; and n is 1 or 2;
t) L is —(CH₂)$_n$— or —OCH₂—; and n is 1;
u) L is —(CH₂)$_n$—; and n is 1;
v) B is phenyl, naphthyl, or a heteroaryl selected from the group consisting of benzothiophenyl and benzo(1,3)dioxalyl;
wherein the phenyl of B is optionally substituted with phenyl or pyridinyl; and the phenyl of B is optionally further substituted with a substituent independently selected from the group consisting of methyl, fluoro, and chloro;
or, B is optionally substituted with a substituent selected from the group consisting of $C_{1-3}$alkyl, $C_{1-3}$alkoxy, fluoro, chloro, bromo, cyano, hydroxy, trifluoromethyl, trifluoromethoxy, $C_{1-2}$alkoxycarbonyl, aminocarbonyl, ($C_{1-2}$alkyl)aminocarbonyl, and di($C_{1-2}$alkyl)aminocarbonyl; and B is optionally further substituted with a chloro or fluoro substituent;
provided that when R₃ is hydrogen, and L is —(CH₂)$_n$— wherein n is 1 or 2, B is optionally substituted with a substituent other than aminocarbonyl, ($C_{1-3}$alkyl)aminocarbonyl, or di($C_{1-3}$alkyl)aminocarbonyl;
w) B is phenyl, naphthyl, or benzo(1,3)dioxalyl; wherein the phenyl of B is optionally substituted with phenyl or pyridinyl;
or, B is optionally substituted with a substituent selected from the group consisting of $C_{1-3}$alkyl, fluoro, chloro, bromo, trifluoromethyl, and trifluoromethoxy; and B is optionally further substituted with a chloro or fluoro substituent;
x) B is phenyl optionally substituted with phenyl or pyridinyl; or, B is phenyl optionally substituted with a substituent independently selected from the group consisting of $C_{1-3}$alkyl, fluoro, chloro, bromo, trifluoromethyl, and trifluoromethoxy; and B is optionally further substituted with a chloro or fluoro substituent;
y) B is phenyl substituted with a substituent selected from the group consisting of $C_{1-3}$alkyl, fluoro, chloro, bromo, trifluoromethyl, and trifluoromethoxy; and B is optionally further substituted with a chloro or fluoro substituent; and
z) B is phenyl substituted with a substituent selected from the group consisting of fluoro, chloro, and trifluoromethyl; and B is optionally further substituted with a chloro or fluoro substituent;
and any combination of embodiments a) through z) above, provided that it is understood that combinations in which different embodiments of the same substituent would be combined are excluded.

Another embodiment of the present invention includes a compound of Formula (I)

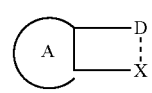

Formula (I)

wherein:
A is benzo or pyrido;
wherein benzo is optionally substituted with a substituent selected from the group consisting of $C_{1-2}$alkyl, $C_{1-2}$alkoxy, hydroxy, fluoro, chloro, bromo, $C_{1-2}$alkoxycarbonyl, aminocarbonyl, ($C_{1-2}$alkyl)aminocarbonyl, di($C_{1-2}$alkyl)aminocarbonyl, and trifluoromethyl; and benzo is optionally further substituted with a substituent selected from the group consisting of methyl, methoxy, hydroxy, fluoro, and chloro;
and wherein pyrido is optionally substituted with a substituent selected from the group consisting of fluoro, chloro, bromo, and methyl; and pyrido is optionally further substituted with fluoro;
D is d-1 or d-2

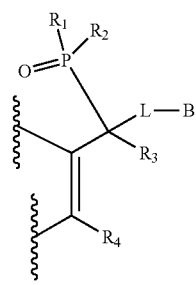

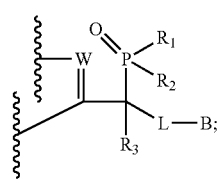

X is O, S, S(=O), S(O₂), or N—R₆; wherein R₆ is phenyl, $C_{1-4}$alkyl, allyl, $C_{1-4}$alkylsulfonyl, $C_{1-4}$alkylcarbonyl, or pyridinyl; provided that X is other than N—R₆ when W is N;

W is C(R$_4$) or N;

R$_4$ is hydrogen; C$_{1-6}$alkyl; C$_{1-6}$alkoxy; C$_{1-6}$alkoxycarbonyl; chloro; bromo; cyano; trifluoromethyl; phenyl; a heteroaryl selected from the group consisting of furyl, thienyl, pyrrolyl, oxazolyl, thiazolyl, pyrazolyl, pyridinyl, and pyrimidinyl; or a C$_{3-6}$cycloalkyl;

wherein phenyl is optionally substituted with an aminocarbonyl, trifluoromethyl, or trifluoromethoxy substituent; or phenyl is optionally substituted with one to two substituents independently selected from the group consisting of C$_{1-2}$alkyl, C$_{1-2}$alkoxy, fluoro, chloro, hydroxy, and cyano;

and wherein heteroaryl is optionally substituted with bromo or one to two substituents independently selected from the group consisting of methyl, fluoro, and chloro;

R$_1$ and R$_2$ are independently selected from the group consisting of C$_{1-8}$alkyl; C$_{1-8}$alkoxy; —O(CH$_2$)$_p$O(CH$_2$)$_q$CH$_3$; —O(CH$_2$)$_p$O(CH$_2$)$_q$OCH$_3$; —O(CH$_2$)$_r$C(O)OCH$_3$; —O(CH$_2$)$_p$OC(O)CH$_3$; —(CH$_2$)$_p$O(CH$_2$)$_q$OCH$_3$; phenyl(C$_{1-3}$)alkyl; phenyl(C$_{1-3}$)alkoxy; and C$_{3-8}$cycloalkyloxy;

wherein p is an integer from 2 to 6; and wherein q is an integer from 0 to 4, such that the sum of p and q is less than or equal to six; wherein r is an integer from 1 to 4;

and, wherein the phenyl portion of phenyl(C$_{1-3}$)alkyl and phenyl(C$_{1-3}$)alkoxy is optionally substituted with one to two substituents independently selected from the group consisting of C$_{1-2}$alkyl, C$_{1-2}$alkoxy, trifluoromethyl, hydroxy, cyano, and halogen;

and further, wherein C$_{1-8}$alkyl and C$_{1-8}$alkoxy of R$_1$ and R$_2$ are optionally substituted with hydroxy, difluoromethyl, trifluoromethyl, C$_{3-6}$cycloalkyl, carboxy, C$_{1-2}$alkoxycarbonyl, di(C$_{1-3}$alkyl)amino, aminocarbonyl, (C$_{1-3}$alkyl)aminocarbonyl, or di(C$_{1-3}$alkyl)aminocarbonyl; provided that when R$_1$ is 2-(N,N-dimethylamino)-ethoxy, R$_2$ is other than 2-(N,N-dimethylamino)-ethoxy;

R$_3$ is hydrogen, methyl, fluoro, chloro, bromo, or hydroxy; or R$_3$ is absent when L is alkene =CH—;

L is absent, —(CH$_2$)$_p$—, —OC$_{1-2}$alkyl-, or =CH—; wherein n is 1 or 2;

B is hydrogen, phenyl, naphthyl, or a heteroaryl selected from the group consisting of benzothiophenyl, benzo(1,3)dioxalyl, oxazolyl, thienyl, furanyl, and benzofuranyl;

wherein the phenyl of B is optionally substituted with hydroxy, C$_{1-3}$alkoxy, trifluoromethyl, nitro, amino, phenyl or a heteroaryl selected from the group consisting of pyridinyl, thienyl, furanyl, pyrrolyl, oxazolyl, and thiazolyl; and wherein phenyl of B is optionally further substituted with a substituent selected from the group consisting of methyl, fluoro, chloro, trifluoromethyl, methoxy, and hydroxy;

and wherein the naphthyl of B is optionally substituted with 1 or 2 substituents selected from the group consisting of hydrogen, methyl, fluoro, chloro, bromo, C$_{1-3}$alkoxy, hydroxy, and dimethylamino;

or, the phenyl or heteroaryl substituent of B is optionally substituted with a substituent independently selected from the group consisting of C$_{1-3}$alkyl, C$_{1-3}$alkoxy, C$_{1-3}$alkylthio, fluoro, chloro, bromo, cyano, hydroxy, trifluoromethyl, trifluoromethylthio, trifluoromethoxy, difluoromethoxy, trifluoromethanesulfonyl, C$_{1-2}$alkoxycarbonyl, aminocarbonyl, (C$_{1-2}$alkyl)aminocarbonyl, and di(C$_{1-2}$alkyl)aminocarbonyl;

and the phenyl or heteroaryl substituent of B is optionally further substituted with one to two fluoro or chloro substituents;

provided that when B is hydrogen and L is absent or —(CH$_2$)$_n$—, then at least one of R$_1$ and R$_2$ is selected from the group consisting of phenyl(C$_{1-6}$)alkyl and phenyl(C$_{1-6}$)alkoxy;

and enantiomers, diastereomers, racemates, and pharmaceutically acceptable salts thereof;

provided that a compound of Formula (I) is other than a compound wherein A is 5-fluoro-benzo, D is d-2, W is C(R$_4$), R$_4$ is methyl, X is S, R$_1$ and R$_2$ are each isopropyloxy, R$_3$ is hydrogen, L is CH$_2$, and B is 3,4-difluorophenyl;

a compound wherein A is 6-trifluoromethyl-benzo, D is d-2, W is C(R$_4$), R$_4$ is methyl, X is S, R$_1$ and R$_2$ are each ethoxy, R$_3$ is hydrogen, L is CH$_2$, and B is 3,4-difluorophenyl;

and further provided that when D is d-2, R$_3$ is hydrogen, and L is —(CH$_2$)$_n$—, then B is optionally substituted with a substituent other than aminocarbonyl, (C$_{1-2}$alkyl)aminocarbonyl, or di(C$_{1-2}$alkyl)aminocarbonyl.

Further embodiments of the present invention include a compound of Formula (I) wherein:

a) A is unsubstituted pyrido or benzo optionally substituted with trifluoromethyl, C$_{1-2}$alkyl, fluoro, chloro, bromo, or C$_{1-2}$alkoxy, and optionally further substituted with a substituent selected from the group consisting of methyl, methoxy, fluoro, and chloro;

b) A is benzo optionally substituted with trifluoromethyl, C$_{1-2}$alkyl, C$_{1-2}$alkoxy, fluoro, chloro, or bromo;

c) A is benzo optionally substituted with C$_{1-2}$alkyl, fluoro, or chloro;

d) D is d-2 e) X is O, S, S(O$_2$), or N—R$_6$; wherein R$_6$ is phenyl; provided that X is other than N—R$_6$ when W is N;

f) X is O, S, or S(O$_2$);

g) X is O or S;

h) W is C(R$_4$);

i) R$_4$ is hydrogen; C$_{1-6}$alkyl; chloro; bromo; trifluoromethyl; phenyl optionally substituted with hydroxy, aminocarbonyl, or fluoro; pyridinyl optionally substituted with fluoro; thienyl; or C$_{3-6}$cycloalkyl;

j) R$_4$ is hydrogen; methyl; isopropyl; 2,2-dimethyl-propyl; chloro; bromo; trifluoromethyl; phenyl optionally substituted with hydroxy, aminocarbonyl, or fluoro; pyridinyl optionally substituted with fluoro; thienyl; or C$_{3-6}$cycloalkyl;

k) R$_4$ is hydrogen; methyl; isopropyl; chloro; bromo; trifluoromethyl; phenyl optionally substituted with hydroxy or fluoro; pyridinyl optionally substituted with fluoro; thienyl; cyclopropyl; cyclobutyl; or cyclopentyl;

l) R$_4$ is methyl; isopropyl; chloro; bromo; trifluoromethyl; pyridinyl optionally substituted with fluoro; thienyl; cyclopropyl; cyclobutyl; or cyclopentyl;

m) R$_1$ and R$_2$ are independently selected from the group consisting of C$_{1-4}$alkyl optionally substituted with di(C$_{1-3}$alkyl)amino; C$_{1-5}$alkoxy optionally substituted with di(C$_{1-3}$alkyl)amino; —O(CH$_2$)$_p$O(CH$_2$)$_q$CH$_3$; —O(CH$_2$)$_r$C(O)OCH$_3$; —O(CH$_2$)$_p$OC(O)CH$_3$; phenyl(C$_{1-3}$)alkyl; phenyl(C$_{1-3}$)alkoxy; and C$_{3-6}$cycloalkyloxy; wherein p is an integer from 2 to 4, q is 0, and r is 1; wherein the phenyl portion of phenyl(C$_{1-3}$)alkyl and phenyl(C$_{1-3}$)alkoxy is optionally substituted with one to two substituents independently selected from the group consisting of methyl, methoxy, fluoro, chloro, and bromo; provided that when $R_1$ is 2-(N,N-dimethylamino)-ethoxy, $R_2$ is other than 2-(N,N-dimethylamino)-ethoxy; further provided that only one of $R_1$ and $R_2$ is phenyl($C_{1-3}$)alkyl or phenyl($C_{1-3}$)alkoxy;

n) $R_1$ and $R_2$ are independently selected from the group consisting of $C_{1-4}$alkyl, phenyl($C_{1-3}$)alkyl, —OCH$_2$C(O)OCH$_3$, —O(CH$_2$)$_2$OC(O)CH$_3$, and $C_{1-4}$alkoxy; wherein the phenyl portion of phenyl($C_{1-3}$)alkyl is optionally substituted with methoxy;

o) $R_1$ and $R_2$ are independently selected from the group consisting of methyl, isobutyl, ethoxy, and isopropyloxy;

p) $R_3$ is hydrogen, methyl, fluoro, or bromo; or $R_3$ is absent when L is =CH—;

q) $R_3$ is hydrogen or methyl; or $R_3$ is absent when L is =CH—;

r) $R_3$ is hydrogen;

s) L is absent, —(CH$_2$)$_n$—, —OCH$_2$—, or =CH—; and n is 1 or 2;

t) L is —(CH$_2$)$_n$—, —OCH$_2$—, or =CH—; and n is 1;

u) L is —(CH$_2$)$_n$—; and n is 1;

v) B is phenyl, naphthyl, or a heteroaryl selected from the group consisting of benzothiophenyl and benzo(1,3)dioxalyl;
wherein the phenyl of B is optionally substituted with phenyl or pyridinyl; and the phenyl of B is optionally further substituted with a substituent independently selected from the group consisting of methyl, fluoro, or chloro;
or, the phenyl or heteroaryl of B is optionally substituted with a substituent selected from the group consisting of $C_{1-3}$alkyl, $C_{1-3}$alkoxy, fluoro, chloro, bromo, cyano, hydroxy, trifluoromethyl, trifluoromethoxy, $C_{1-2}$alkoxycarbonyl, aminocarbonyl, ($C_{1-2}$alkyl)aminocarbonyl, and di($C_{1-2}$alkyl)aminocarbonyl; and B is optionally further substituted with a chloro or fluoro substituent;
provided that when $R_3$ is hydrogen, and L is —(CH$_2$)$_n$— wherein n is 1 or 2, B is optionally substituted with a substituent other than aminocarbonyl, ($C_{1-3}$alkyl)aminocarbonyl, or di($C_{1-3}$alkyl)aminocarbonyl;

w) B is phenyl, naphthyl, or benzo(1,3)dioxalyl; wherein the phenyl of B is optionally substituted with phenyl or pyridinyl;
or, B other than naphthyl is optionally substituted with a substituent selected from the group consisting of $C_{1-3}$alkyl, fluoro, chloro, bromo, trifluoromethyl, and trifluoromethoxy; and B is optionally further substituted with a chloro or fluoro substituent;

x) B is phenyl optionally substituted with phenyl or pyridinyl;
or, B is phenyl optionally substituted with a substituent independently selected from the group consisting of $C_{1-3}$alkyl, fluoro, chloro, bromo, trifluoromethyl, and trifluoromethoxy; and B is optionally further substituted with a chloro or fluoro substituent;

y) B is phenyl substituted with a substituent selected from the group consisting of $C_{1-3}$alkyl, fluoro, chloro, bromo, trifluoromethyl, and trifluoromethoxy; and B is optionally further substituted with a chloro or fluoro substituent; and z) B is phenyl substituted with a substituent selected from the group consisting of fluoro, chloro, and trifluoromethyl; and B is optionally further substituted with a chloro or fluoro substituent;

and any combination of embodiments a) through z) above, provided that it is understood that combinations in which different embodiments of the same substituent would be combined are excluded.

A further embodiment of the present invention is directed to a compound of Formula (I) wherein:

A is unsubstituted pyrido or benzo optionally substituted with trifluoromethyl, $C_{1-2}$alkyl, fluoro, chloro, bromo, or $C_{1-2}$alkoxy, and optionally further substituted with a substituent selected from the group consisting of methyl, methoxy, fluoro, and chloro;

D is d-1 or d-2

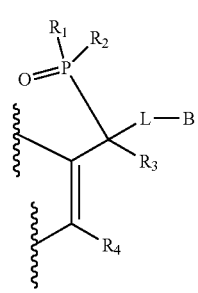

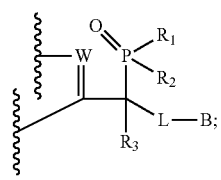

X is O, S, S(O$_2$), or N—R$_6$; wherein R$_6$ is phenyl; provided that X is other than N—R$_6$ when W is N;

W is C(R$_4$) or N;

$R_4$ is hydrogen; $C_{1-6}$alkyl; chloro; bromo; trifluoromethyl; phenyl optionally substituted with hydroxy, aminocarbonyl, or fluoro; pyridinyl optionally substituted with fluoro; thienyl; or $C_{3-6}$cycloalkyl;

$R_1$ and $R_2$ are independently selected from the group consisting of $C_{1-4}$alkyl optionally substituted with di($C_{1-3}$alkyl)amino; $C_{1-5}$alkoxy optionally substituted with di($C_{1-3}$alkyl)amino; —O(CH$_2$)$_p$O(CH$_2$)$_q$CH$_3$; —O(CH$_2$)$_r$C(O)OCH$_3$, —O(CH$_2$)$_p$OC(O)CH$_3$, phenyl($C_{1-3}$)alkyl; phenyl($C_{1-3}$)alkoxy; and $C_{3-6}$cycloalkyloxy;

wherein p is an integer from 2 to 4, q is 0, and r is 1;

wherein the phenyl portion of phenyl($C_{1-3}$)alkyl and phenyl($C_{1-3}$)alkoxy is optionally substituted with one to two substituents independently selected from the group consisting of methyl, methoxy, fluoro, chloro, and bromo;

provided that when $R_1$ is 2-(N,N-dimethylamino)-ethoxy, $R_2$ is other than 2-(N,N-dimethylamino)-ethoxy;

further provided that only one of $R_1$ and $R_2$ is phenyl($C_{1-3}$)alkyl or phenyl($C_{1-3}$)alkoxy;

$R_3$ is hydrogen, methyl, fluoro, or bromo; or $R_3$ is absent when L is =CH—;

L is absent, —(CH$_2$)$_n$—, —OCH$_2$—, or =CH—; and n is 1 or 2;

B is phenyl, naphthyl, or a heteroaryl selected from the group consisting of benzothiophenyl and benzo(1,3)dioxalyl;

wherein the phenyl of B is optionally substituted with phenyl or pyridinyl; and the phenyl of B is optionally further substituted with a substituent independently selected from the group consisting of methyl, fluoro, or chloro;

or, the phenyl or heteroaryl of B is optionally substituted with a substituent selected from the group consisting of $C_{1-3}$alkyl, $C_{1-3}$alkoxy, fluoro, chloro, bromo, cyano, hydroxy, trifluoromethyl, trifluoromethoxy, $C_{1-2}$alkoxycarbonyl, aminocarbonyl, $(C_{1-2}$alkyl)aminocarbonyl, and di($C_{1-2}$alkyl)aminocarbonyl; and B is optionally further substituted with a chloro or fluoro substituent;

provided that when $R_3$ is hydrogen, and L is —$(CH_2)_n$— wherein n is 1 or 2, B is optionally substituted with a substituent other than aminocarbonyl, $(C_{1-3}$alkyl)aminocarbonyl, or di($C_{1-3}$alkyl)aminocarbonyl;

provided that a compound of Formula (I) is other than a compound wherein A is 5-fluoro-benzo, D is d-2, W is $C(R_4)$, $R_4$ is methyl, X is S, $R_1$ and $R_2$ are each isopropyloxy, $R_3$ is hydrogen, L is $CH_2$, and B is 3,4-difluorophenyl; or a compound wherein A is 6-trifluoromethyl-benzo, D is d-2, W is $C(R_4)$, $R_4$ is methyl, X is S, $R_1$ and $R_2$ are each ethoxy, $R_3$ is hydrogen, L is $CH_2$, and B is 3,4-difluorophenyl;

and further provided that when D is d-2, $R_3$ is hydrogen, and L is —$(CH_2)_n$—, then B is optionally substituted with a substituent other than aminocarbonyl, $(C_{1-3}$alkyl)aminocarbonyl, or di($C_{1-3}$alkyl)aminocarbonyl.

A further embodiment of the present invention is directed to a compound of Formula (I) wherein:

A is unsubstituted pyrido or benzo optionally substituted with trifluoromethyl, $C_{1-2}$alkyl, fluoro, chloro, bromo, or $C_{1-2}$alkoxy, and optionally further substituted with a substituent selected from the group consisting of methyl, methoxy, fluoro, and chloro;

D is d-1 or d-2

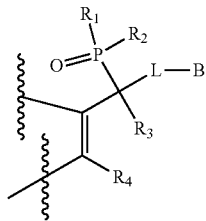

d-1

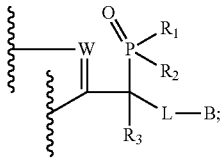

d-2

X is O, S, $S(O_2)$, or N—$R_6$; wherein $R_6$ is phenyl; provided that X is other than N—$R_6$ when W is N;

W is $C(R_4)$ or N;

$R_4$ is hydrogen; $C_{1-6}$alkyl; chloro; bromo; trifluoromethyl; phenyl optionally substituted with hydroxy, aminocarbonyl, or fluoro; pyridinyl optionally substituted with fluoro; thienyl; or $C_{3-6}$cycloalkyl;

$R_1$ and $R_2$ are independently selected from the group consisting of $C_{1-4}$alkyl optionally substituted with di($C_{1-3}$alkyl)amino; $C_{1-5}$alkoxy optionally substituted with di($C_{1-3}$alkyl)amino; —$O(CH_2)_pO(CH_2)_qCH_3$; —$O(CH_2)_rC(O)OCH_3$; —$O(CH_2)_pOC(O)CH_3$; phenyl($C_{1-3}$)alkyl; phenyl($C_{1-3}$)alkoxy; and $C_{3-6}$cycloalkyloxy; wherein p is an integer from 2 to 4, q is 0, and r is 1;

wherein the phenyl portion of phenyl($C_{1-3}$)alkyl and phenyl($C_{1-3}$)alkoxy is optionally substituted with one to two substituents independently selected from the group consisting of methyl, methoxy, fluoro, chloro, and bromo;

provided that when $R_1$ is 2-(N,N-dimethylamino)-ethoxy, $R_2$ is other than 2-(N,N-dimethylamino)-ethoxy;

further provided that only one of $R_1$ and $R_2$ is phenyl($C_{1-3}$)alkyl or phenyl($C_{1-3}$)alkoxy;

$R_3$ is hydrogen, methyl, fluoro, or bromo;

L is absent, —$(CH_2)_p$—, or —$OCH_2$—; and n is 1 or 2;

B is phenyl, naphthyl, or a heteroaryl selected from the group consisting of benzothiophenyl and benzo(1,3)dioxalyl;

wherein the phenyl of B is optionally substituted with phenyl or pyridinyl; and the phenyl of B is optionally further substituted with a substituent independently selected from the group consisting of methyl, fluoro, or chloro;

or, the phenyl or heteroaryl of B is optionally substituted with a substituent selected from the group consisting of $C_{1-3}$alkyl, $C_{1-3}$alkoxy, fluoro, chloro, bromo, cyano, hydroxy, trifluoromethyl, trifluoromethoxy, $C_{1-2}$alkoxycarbonyl, aminocarbonyl, $(C_{1-2}$alkyl)aminocarbonyl, and di($C_{1-2}$alkyl)aminocarbonyl; and B is optionally further substituted with a chloro or fluoro substituent;

provided that when $R_3$ is hydrogen, and L is —$(CH_2)_n$— wherein n is 1 or 2, B is optionally substituted with a substituent other than aminocarbonyl, $(C_{1-3}$alkyl)aminocarbonyl, or di($C_{1-3}$alkyl)aminocarbonyl; provided that a compound of Formula (I) is other than a compound wherein A is 5-fluoro-benzo, D is d-2, W is $C(R_4)$, $R_4$ is methyl, X is S, $R_1$ and $R_2$ are each isopropyloxy, $R_3$ is hydrogen, L is $CH_2$, and B is 3,4-difluorophenyl; or a compound wherein A is 6-trifluoromethyl-benzo, D is d-2, W is $C(R_4)$, $R_4$ is methyl, X is S, $R_1$ and $R_2$ are each ethoxy, $R_3$ is hydrogen, L is $CH_2$, and B is 3,4-difluorophenyl;

and further provided that when D is d-2, $R_3$ is hydrogen, and L is —$(CH_2)_n$—, then B is optionally substituted with a substituent other than aminocarbonyl, $(C_{1-3}$alkyl)aminocarbonyl, or di($C_{1-3}$alkyl)aminocarbonyl.

A further embodiment of the present invention is directed to a compound of Formula (I) wherein:

A is benzo optionally substituted with trifluoromethyl, $C_{1-2}$alkyl, $C_{1-2}$alkoxy, fluoro, chloro, or bromo;

D is d-1 or d-2

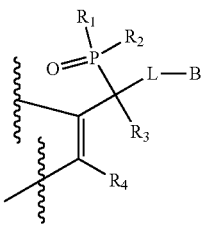

d-1

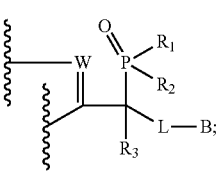

d-2

X is O, S, or $S(O_2)$;

W is $C(R_4)$;

$R_4$ is hydrogen; methyl; isopropyl; 2,2-dimethyl-propyl; chloro; bromo; trifluoromethyl; phenyl optionally substituted with hydroxy, aminocarbonyl, or fluoro; pyridinyl optionally substituted with fluoro; thienyl; or $C_{3-6}$cycloalkyl;

$R_1$ and $R_2$ are independently selected from the group consisting of $C_{1-4}$alkyl, phenyl($C_{1-3}$)alkyl, —OCH$_2$C(O)OCH$_3$, —O(CH$_2$)$_2$OC(O)CH$_3$, and $C_{1-4}$alkoxy; wherein the phenyl portion of phenyl($C_{1-3}$)alkyl is optionally substituted with methoxy;

$R_3$ is hydrogen or methyl; or $R_3$ is absent when L is =CH—;

L is —(CH$_2$)$_n$—, —OCH$_2$—, or =CH—; and n is 1;

B is phenyl, naphthyl, or benzo(1,3)dioxalyl; wherein the phenyl of B is optionally substituted with phenyl or pyridinyl;

or, B other than naphthyl is optionally substituted with a substituent selected from the group consisting of $C_{1-3}$alkyl, fluoro, chloro, bromo, trifluoromethyl, and trifluoromethoxy; and B is optionally further substituted with a chloro or fluoro substituent;

and enantiomers, diastereomers, racemates, and pharmaceutically acceptable salts thereof;

provided that a compound of Formula (I) is other than a compound wherein A is 5-fluoro-benzo, D is d-2, W is C(R$_4$), R$_4$ is methyl, X is S, R$_1$ and R$_2$ are each isopropyloxy, R$_3$ is hydrogen, L is CH$_2$, and B is 3,4-difluorophenyl; or a compound wherein A is 6-trifluoromethyl-benzo, D is d-2, W is C(R$_4$), R$_4$ is methyl, X is S, R$_1$ and R$_2$ are each ethoxy, R$_3$ is hydrogen, L is CH$_2$, and B is 3,4-difluorophenyl;

and further provided that when D is d-2, R$_3$ is hydrogen, and L is —(CH$_2$)$_n$—, then B is optionally substituted with a substituent other than aminocarbonyl, (C$_{1-3}$alkyl)aminocarbonyl, or di(C$_{1-3}$alkyl)aminocarbonyl.

Further embodiments of the present invention are directed to a compound of Formula (I) wherein:

A is benzo optionally substituted with $C_{1-2}$alkyl, fluoro, or chloro;

D is d-2

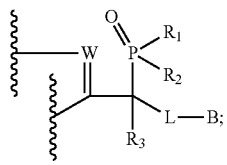

d-2

X is O or S;
W is C(R$_4$);
R$_4$ is hydrogen; methyl; isopropyl; chloro; bromo; trifluoromethyl; phenyl optionally substituted with hydroxy or fluoro; pyridinyl optionally substituted with fluoro; thienyl; cyclopropyl; cyclobutyl; or cyclopentyl;
R$_1$ and R$_2$ are independently selected from the group consisting of methyl, isobutyl, ethoxy, and isopropyloxy;
R$_3$ is hydrogen;
L is —(CH$_2$)$_n$—; and n is 1;
B is phenyl optionally substituted with phenyl or pyridinyl;
or, B is phenyl optionally substituted with a substituent independently selected from the group consisting of $C_{1-3}$alkyl, fluoro, chloro, bromo, trifluoromethyl, and trifluoromethoxy; and B is optionally further substituted with a chloro or fluoro substituent;
and enantiomers, diastereomers, racemates, and pharmaceutically acceptable salts thereof;

provided that a compound of Formula (I) is other than a compound wherein A is 5-fluoro-benzo, D is d-2, W is C(R$_4$), R$_4$ is methyl, X is S, R$_1$ and R$_2$ are each isopropyloxy, R$_3$ is hydrogen, L is CH$_2$, and B is 3,4-difluorophenyl.

Further embodiments of the present invention are directed to a compound of Formula (I) wherein:

A is benzo optionally substituted with $C_{1-2}$alkyl, fluoro, or chloro;

D is d-2

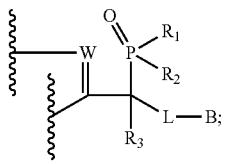

d-2

X is O or S;
W is C(R$_4$);
R$_4$ is methyl; isopropyl; chloro; bromo; trifluoromethyl; phenyl optionally substituted with hydroxy or fluoro; pyridinyl optionally substituted with fluoro; thienyl; cyclopropyl; cyclobutyl; or cyclopentyl;
R$_1$ and R$_2$ are independently selected from the group consisting of methyl, isobutyl, ethoxy, and isopropyloxy;
R$_3$ is hydrogen;
L is —(CH$_2$)$_n$—; and n is 1;
B is phenyl substituted with a substituent selected from the group consisting of $C_{1-3}$alkyl, fluoro, chloro, bromo, trifluoromethyl, and trifluoromethoxy; and B is optionally further substituted with a chloro or fluoro substituent;
and enantiomers, diastereomers, racemates, and pharmaceutically acceptable salts thereof;

provided that a compound of Formula (I) is other than a compound wherein A is 5-fluoro-benzo, D is d-2, W is C(R$_4$), R$_4$ is methyl, X is S, R$_1$ and R$_2$ are each isopropyloxy, R$_3$ is hydrogen, L is CH$_2$, and B is 3,4-difluorophenyl.

Further embodiments of the present invention are directed to a compound of Formula (I) wherein:

A is benzo optionally substituted with $C_{1-2}$alkyl, fluoro, or chloro;

D is d-2

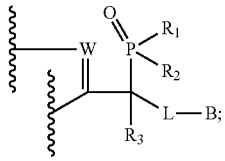

d-2

X is O or S;
W is C(R$_4$);
R$_4$ is methyl; isopropyl; chloro; bromo; trifluoromethyl; pyridinyl; cyclopropyl; cyclobutyl; or cyclopentyl; wherein pyridinyl is optionally substituted with fluoro;
R$_1$ and R$_2$ are independently selected from the group consisting of methyl, isobutyl, ethoxy, and isopropyloxy;
R$_3$ is hydrogen;
L is —(CH$_2$)$_n$—; and n is 1;
B is phenyl substituted with a substituent selected from the group consisting of fluoro, chloro, and trifluoromethyl; and B is optionally further substituted with a chloro or fluoro substituent;

and enantiomers, diastereomers, racemates, and pharmaceutically acceptable salts thereof;
provided that a compound of Formula (I) is other than
a compound wherein A is 5-fluoro-benzo, D is d-2, W is $C(R_4)$, $R_4$ is methyl, X is S, $R_1$ and $R_2$ are each isopropyloxy, $R_3$ is hydrogen, L is $CH_2$, and B is 3,4-difluorophenyl.

A further embodiment of the present invention is directed to a compound Formula (Ia)

Formula (Ia)

selected from the group consisting of
a compound of Formula (Ia) wherein A is benzo, W is $C(R_4)$, $R_4$ is methyl, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is $C(R_4)$, $R_4$ is i-propyl, X is S, $R_1$ is ethoxy, $R_2$ is ethoxy, $R_3$ is H, L is $CH_2$, and B is 3,4-difluoro-phenyl;
a compound of Formula (Ia) wherein A is 4-fluoro-benzo, W is $C(R_4)$, $R_4$ is methyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 3-chloro-phenyl;
a compound of Formula (Ia) wherein A is benzo, W is $C(R_4)$, $R_4$ is cyclopentyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is isobutyl, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 3-fluoro-phenyl;
a compound of Formula (Ia) wherein A is 7-fluoro-benzo, W is $C(R_4)$, $R_4$ is methyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is $C(R_4)$, $R_4$ is methyl, X is O, $R_1$ is ethoxy, $R_2$ is ethoxy, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 2,3-difluoro-phenyl;
a compound of Formula (Ia) wherein A is benzo, W is $C(R_4)$, $R_4$ is methyl, X is O, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is $C(R_4)$, $R_4$ is chloro, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is isobutyl, $R_2$ is isobutyl, $R_3$ is H, L is $OCH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 3,4-difluoro-phenyl;
a compound of Formula (Ia) wherein A is 6-fluoro-benzo, W is $C(R_4)$, $R_4$ is methyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 3,5-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 3-methyl-phenyl;
a compound of Formula (Ia) wherein A is benzo, W is $C(R_4)$, $R_4$ is i-propyl, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is $C(R_4)$, $R_4$ is cyclopropyl, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 3,4-dichloro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 2-fluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 2-fluoro-3-chloro-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 3,4-dichloro-phenyl;
a compound of Formula (Ia) wherein A is benzo, W is N, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 2-methyl-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 2-chloro-4-fluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 2-chloro-3,5-difluoro-phenyl;
a compound of Formula (Ia) wherein A is benzo, W is $C(R_4)$, $R_4$ is cyclopropyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is methyl, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 3-trifluoromethyl-4-fluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 3-methoxy-phenyl;
a compound of Formula (Ia) wherein A is benzo, W is $C(R_4)$, $R_4$ is methyl, X is S, $R_1$ is isobutyl, $R_2$ is isobutyl, $R_3$ is H, L is $CH_2$, and B is 3,4-difluoro-phenyl;
a compound of Formula (Ia) wherein A is (2,3-b)pyridin-2-yl, W is $C(R_4)$, $R_4$ is methyl, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 2,3-dichloro-phenyl;
a compound of Formula (Ia) wherein A is benzo, W is $C(R_4)$, $R_4$ is methyl, X is S, $R_1$ is ethoxy, $R_2$ is isobutyl, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 2-fluoro-3-trifluoromethyl-phenyl;
a compound of Formula (Ia) wherein A is benzo, W is $C(R_4)$, $R_4$ is cyclopentyl, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 3-trifluoromethyl-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-bromo-phenyl;
a compound of Formula (Ia) wherein A is benzo, W is C(R$_4$), R$_4$ is cyclobutyl, X is S, R$_1$ is ethoxy, R$_2$ is ethoxy, R$_3$ is H, L is CH$_2$, and B is 3,4-difluoro-phenyl;
a compound of Formula (Ia) wherein A is benzo, W is C(R$_4$), R$_4$ is methyl, X is S, R$_1$ is n-propyl, R$_2$ is n-propyl, R$_3$ is H, L is OCH$_2$, and B is 3,4-difluoro-phenyl;
a compound of Formula (Ia) wherein A is benzo, W is C(R$_4$), R$_4$ is trifluoromethyl, X is S, R$_1$ is isopropyloxy, R$_2$ is isopropyloxy, R$_3$ is H, L is CH$_2$, and B is 3,4-difluoro-phenyl;
a compound of Formula (Ia) wherein A is benzo, W is C(R$_4$), R$_4$ is methyl, X is S, R$_1$ is n-propyl, R$_2$ is n-propyl, R$_3$ is H, L is CH$_2$, and B is 3,4-difluoro-phenyl;
a compound of Formula (Ia) wherein A is 5-fluoro-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is naphthalen-2-yl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,5-dichloro-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-chloro-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-trifluoromethyl-4-chloro-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 4-fluoro-phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 4-fluoro-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-trifluoromethyl-phenyl;
a compound of Formula (Ia) wherein A is benzo, W is C(R$_4$), R$_4$ is methyl, X is S, R$_1$ is 2,2-dimethyl-propyl, R$_2$ is 2,2-dimethyl-propyl, R$_3$ is H, L is CH$_2$, and B is 3,4-difluoro-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,6-dichloro-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 4-trifluoromethoxy-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-fluoro-5-trifluoromethyl-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-trifluoromethoxy-phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 3-fluoro-4-trifluoromethyl-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-trifluoromethyl-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-3-methyl-6-chloro-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-trifluoromethoxy-phenyl;
a compound of Formula (Ia) wherein A is 5-methyl-benzo, W is C(R$_4$), R$_4$ is methyl, X is S, R$_1$ is isopropyloxy, R$_2$ is isopropyloxy, R$_3$ is H, L is CH$_2$, and B is 3,4-difluoro-phenyl;
a compound of Formula (Ia) wherein A is benzo, W is C(R$_4$), R$_4$ is H, X is S, R$_1$ is isopropyloxy, R$_2$ is isopropyloxy, R$_3$ is H, L is CH$_2$, and B is 3,4-difluoro-phenyl;
a compound of Formula (Ia) wherein A is benzo, W is C(R$_4$), R$_4$ is phenyl, X is S, R$_1$ is ethoxy, R$_2$ is ethoxy, R$_3$ is H, L is CH$_2$, and B is 3,4-dichloro-phenyl;
a compound of Formula (Ia) wherein A is 4-chloro-benzo, W is C(R$_4$), R$_4$ is methyl, X is S, R$_1$ is ethoxy, R$_2$ is ethoxy, R$_3$ is H, L is CH$_2$, and B is 3,4-dichloro-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-bromo-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-5-trifluoromethyl-phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 4-trifluoromethyl-phenyl;
a compound of Formula (Ia) wherein A is benzo, W is C(R$_4$), R$_4$ is H, X is S, R$_1$ is isopropyloxy, R$_2$ is isopropyloxy, R$_3$ is H, L is CH$_2$, and B is 3-trifluoromethyl-phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 4-bromo-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 5-chloro-benzo[1,3]dioxol-6-yl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-(pyridin-4-yl)-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-3-chloro-5-trifluoromethyl-phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 3,4-difluoro-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,4-dichloro-5-fluoro-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-biphenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 3,4-dichloro-phenyl;
a compound of Formula (Ia) wherein A is benzo, W is C(R$_4$), R$_4$ is methyl, X is S, R$_1$ is ethoxy, R$_2$ is ethoxy, R$_3$ is CH$_3$, L is CH$_2$, and B is 3,4-difluoro-phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 2-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-chloro-3-trifluoromethyl-phenyl;

a compound of Formula (Ia) wherein A is 6-methoxy-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is naphthalen-2-yl;

a compound of Formula (Ia) wherein A is 4-trifluoromethyl-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 2-chloro-phenyl;

a compound of Formula (Ia) wherein A is benzo, W is C(R$_4$), R$_4$ is H, X is O, R$_1$ is ethoxy, R$_2$ is ethoxy, R$_3$ is H, L is CH$_2$, and B is 4-fluoro-phenyl;

a compound of Formula (Ia) wherein A is benzo, W is C(R$_4$), R$_4$ is methyl, X is SO$_2$, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 2-methyl-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is benzothiophen-2-yl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 4-trifluoromethyl-phenyl;

a compound of Formula (Ia) wherein A is 5-chloro-benzo, W is C(R$_4$), R$_4$ is methyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is bromo, L is CH$_2$, and B is 3,4-difluoro-phenyl;

a compound of Formula (Ia) wherein A is benzo, W is C(R$_4$), R$_4$ is H, X is S, R$_1$ is ethoxy, R$_2$ is 2,6-dichloro-phenyl-methoxy, R$_3$ is H, L is absent, and B is H;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 2,6-dichloro-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 3,5-trifluoromethyl-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 2-chloro-4-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-chloro-5-trifluoromethyl-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 2,3-dichloro-phenyl;

a compound of Formula (Ia) wherein A is benzo, W is C(R$_4$), R$_4$ is methyl, X is S, R$_1$ is cyclohexyloxy, R$_2$ is cyclohexyloxy, R$_3$ is H, L is CH$_2$, and B is 3,4-difluoro-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 2-trifluoromethyl-phenyl;

a compound of Formula (Ia) wherein A is benzo, W is C(R$_4$), R$_4$ is methyl, X is S, R$_1$ is ethoxy, R$_2$ is 2-(N,N-dimethylamino)-ethoxy, R$_3$ is H, L is CH$_2$, and B is 3,4-difluoro-phenyl;

a compound of Formula (Ia) wherein A is benzo, W is C(R$_4$), R$_4$ is H, X is S, R$_1$ is ethoxy, R$_2$ is 2-methyl-phenyl-methoxy, R$_3$ is H, L is absent, and B is H;

a compound of Formula (Ia) wherein A is benzo, W is C(R$_4$), R$_4$ is H, X is S, R$_1$ is ethoxy, R$_2$ is 2-chloro-phenylmethoxy, R$_3$ is H, L is absent, and B is H;

a compound of Formula (Ia) wherein A is benzo, W is C(R$_4$), R$_4$ is methyl, X is S, R$_1$ is ethoxy, R$_2$ is methyl, R$_3$ is H, L is CH$_2$, and B is 3,4-difluoro-phenyl;

a compound of Formula (Ia) wherein A is benzo, W is C(R$_4$), R$_4$ is H, X is S, R$_1$ is ethoxy, R$_2$ is 4-fluoro-phenylmethoxy, R$_3$ is H, L is absent, and B is H;

a compound of Formula (Ia) wherein A is benzo, W is C(R$_4$), R$_4$ is H, X is S, R$_1$ is ethoxy, R$_2$ is 2-fluoro-phenylmethoxy, R$_3$ is H, L is absent, and B is H;

a compound of Formula (Ia) wherein A is benzo, W is C(R$_4$), R$_4$ is H, X is S, R$_1$ is ethoxy, R$_2$ is 2-bromo-phenylmethoxy, R$_3$ is H, L is absent, and B is H;

a compound of Formula (Ia) wherein A is benzo, W is C(R$_4$), R$_4$ is H, X is S, R$_1$ is ethoxy, R$_2$ is phenylmethoxy, R$_3$ is H, L is absent, and B is H;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 5-chloro-benzo[1,3]dioxol-6-yl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,5-di-trifluoromethyl-phenyl;

a compound of Formula (Ia) wherein A is benzo, W is C(R$_4$), X is S, R$_4$ is N,N-dimethylamino-methyl, R$_1$ is ethoxy, R$_2$ is ethoxy, R$_3$ is H, L is CH$_2$, and B is 2-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-biphenyl;

a compound of Formula (Ia) wherein A is 7-trifluoromethyl-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is 6-chloro-benzo, W is C(R$_4$), R$_4$ is cyclopentyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S(O), R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is cyclohexyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is H, X is O, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is H, X is S, R$_1$ is isopropyloxy, R$_2$ is isopropyloxy, R$_3$ is H, L is CH$_2$, and B is 3,5-difluoro-phenyl;

a compound of Formula (Ia) wherein A is benzo, W is C(R$_4$), R$_4$ is H, X is S, R$_1$ is isopropyloxy, R$_2$ is isopropyloxy, R$_3$ is H, L is CH$_2$, and B is 2,3-difluoro-phenyl;

a compound of Formula (Ia) wherein A is benzo, W is C(R$_4$), R$_4$ is bromo, X is O, R$_1$ is isobutyl, R$_2$ is isobutyl, R$_3$ is H, L is CH$_2$, and B is 3,4-difluoro-phenyl;

a compound of Formula (Ia) wherein A is benzo, W is C(R$_4$), R$_4$ is bromo, X is O, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is H, X is S, R$_1$ is isopropyloxy, R$_2$ is isopropyloxy, R$_3$ is H, L is CH$_2$, and B is 3-trifluoromethyl-4-fluoro-phenyl;

a compound of Formula (Ia) wherein A is benzo, W is C(R$_4$), R$_4$ is H, X is S, R$_1$ is isopropyloxy, R$_2$ is isopropyloxy, R$_3$ is H, L is CH$_2$, and B is 2-fluoro-3-chloro-5-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is 2-fluoro-pyridin-3-yl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is 2,2-dimethyl-propyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is 2-fluoro-pyridin-5-yl, X is S, $R_1$ is ethoxy, $R_2$ is ethoxy, $R_3$ is H, L is $CH_2$, and B is 3,4-difluoro-phenyl;

a compound of Formula (Ia) wherein A is (2,3-b)pyridin-2-yl, W is C($R_4$), $R_4$ is H, X is S, $R_1$ is ethoxy, $R_2$ is ethoxy, $R_3$ is H, L is $CH_2$, and B is 3,4-difluoro-phenyl;

a compound of Formula (Ia) wherein A is (2,3-b)pyridin-2-yl, W is C($R_4$), $R_4$ is bromo, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is H, X is S, $R_1$ is isopropyloxy, $R_2$ is isopropyloxy, $R_3$ is H, L is $CH_2$, and B is 3-fluoro-phenyl;

a compound of Formula (Ia) wherein A is benzo, W is C($R_4$), $R_4$ is H, X is S, $R_1$ is isopropyloxy, $R_2$ is isopropyloxy, $R_3$ is H, L is $CH_2$, and B is 3-chloro-phenyl;

diastereomer A, a compound of Formula (Ia) wherein A is benzo, W is C($R_4$), $R_4$ is methyl, X is S, $R_1$ is ethoxy, $R_2$ is 3-(4-methoxy-phenyl)-propyl, $R_3$ is H, L is $CH_2$, and B is 3,4-difluoro-phenyl;

diastereomer B, a compound of Formula (Ia) wherein A is benzo, W is C($R_4$), $R_4$ is methyl, X is S, $R_1$ is ethoxy, $R_2$ is 3-(4-methoxy-phenyl)-propyl, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-3-trimethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-chloro-3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-5-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-3-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-4-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trifluoromethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-5-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-chloro-5-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-4-trifluoromethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-4-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-chloro-3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trifluoromethyl-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethylthio-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-methoxy-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-methoxy-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-4-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2,3,5,6-tetrafluoro-4-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2,3,5,6-tetrafluoro-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-3-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-4-chloro-5-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-4-chloro-5-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-4-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-3-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-fluoro-5-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-phenyl;

a compound of Formula (Ia) wherein A is benzo, W is ($R_4$), $R_4$ is chloro, X is S, $R_1$ is isopropyloxy, $R_2$ is isopropyloxy, $R_3$ is H, L is $CH_2$, and B is 3,5-di-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-5-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-fluoro-4-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-4-methoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-chloro-3-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-chloro-5-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-bromo-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2,6-dichloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-4-trifluoromethoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-3-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-5-fluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-fluoro-4-chloro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-4-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-4-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3,5-difluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2,3-difluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-3-chloro-5-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-fluoro-phenyl;

a compound of Formula (Ia) wherein A is 4-bromo-benzo, W is C($R_4$), $R_4$ is bromo, X is S, $R_1$ is isopropyloxy, $R_2$ is isopropyloxy, $R_3$ is H, L is $CH_2$, and B is 2-fluoro-phenyl;

a compound of Formula (Ia) wherein A is 6-bromo-benzyl, W is C($R_4$), $R_4$ is bromo, X is S, $R_1$ is isopropyloxy, $R_2$ is isopropyloxy, $R_3$ is H, L is $CH_2$, and B is 2-fluoro-phenyl;

a compound of Formula (Ia) wherein A is 6-bromo-benzyl, W is C($R_4$), $R_4$ is bromo, X is S, $R_1$ is isopropyloxy, $R_2$ is isopropyloxy, $R_3$ is H, L is $CH_2$, and B is 4-fluoro-phenyl;

a compound of Formula (Ia) wherein A is benzo, W is C($R_4$), $R_4$ is bromo, X is S, $R_1$ is methoxy, $R_2$ is methoxy, $R_3$ is H, L is $CH_2$, and B is 3,4-difluoro-phenyl;

a compound of Formula (Ia) wherein A is 4-fluoro-benzo, W is C($R_4$), $R_4$ is methyl, X is O, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is s-butyl, $R_2$ is s-butyl, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is s-butyl, $R_2$ is s-butyl, $R_3$ is H, L is $OCH_2$, and B is 3,4-difluoro-phenyl;

a compound of Formula (Ia) wherein A is 4-fluoro-benzo, W is C($R_4$), $R_4$ is bromo, X is O, $R_1$ is isopropyloxy, $R_2$ is isopropyloxy, $R_3$ is H, L is $CH_2$, and B is 3,4-difluoro-phenyl;

a compound of Formula (Ia) wherein A is 4-fluoro-benzo, W is C($R_4$), $R_4$ is bromo, X is O, $R_1$ is ethoxy, $R_2$ is ethoxy, $R_3$ is H, L is $CH_2$, and B is 3,4-difluoro-phenyl;

a compound of Formula (Ia) wherein A is (2,3-b)pyridin-2-yl, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is thien-3-yl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is n-butyloxy, $R_2$ is n-butyloxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is 2-(2-methoxy-ethoxy)-ethoxy, $R_2$ is 2-(2-methoxy-ethoxy)-ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is 3-methyl-butoxy, $R_2$ is 3-methyl-butoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is methoxycarbonyl-methoxy, $R_2$ is methoxycarbonyl-methoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is 2-acetoxy-ethoxy, $R_2$ is 2-acetoxy-ethoxy, $R_3$ is H, L is $CH_2$, and B is 3,4-difluoro-phenyl;

a compound of Formula (Ia) wherein A is benzo, W is C($R_4$), $R_4$ is phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is 2-hydroxy-phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is 2-fluoro-phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is 3-fluoro-phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is 3-aminocarbonyl-phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is 3-methoxycarbonyl-phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is 4-fluoro-phenyl, X is S, $R_1$ is ethoxy, $R_2$ is ethoxy, $R_3$ is H, L is $CH_2$, and B is 3,4-difluoro-phenyl;

a compound of Formula (Ia) wherein A is 4-fluoro-benzo, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

a compound of Formula (Ia) wherein A is 4-fluoro-benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is 4-fluoro-benzo, W is C($R_4$), $R_4$ is bromo, X is S, $R_1$ is ethoxy, $R_2$ is ethoxy, $R_3$ is H, L is $CH_2$, and B is 3-trifluoromethyl-4-fluoro-phenyl;

a compound of Formula (Ia) wherein A is 4-fluoro-benzo, W is C($R_4$), $R_4$ is bromo, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-hydroxy-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-4-hydroxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-4-hydroxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2,3,5,6-tetrafluoro-4-hydroxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2,3,5,6-tetrafluoro-4-hydroxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-3-hydroxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-4-chloro-5-hydroxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-4-chloro-5-hydroxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trifluoromethyl-4-hydroxy-phenyl;

enantiomer A, a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

enantiomer B, a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

enantiomer A, a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethoxy-phenyl;

enantiomer B, a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-phenyl;

enantiomer A, a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-phenyl;

enantiomer B, a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

enantiomer A, a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

enantiomer B, a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-trifluoromethyl-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trimethylthio-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-methylthio-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-chloro-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-trifluoromethyl-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-trifluoromethylthio-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-methylthio-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-methylsulfonyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-chloro-4-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-trifluoromethyl-4-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethylthio-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-methylthio-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-chloro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-4-chloro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-chloro-5-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3,5-di-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-trifluoromethylsulfonyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-trifluoromethylsulfonyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-trifluoromethylsulfonyl-phenyl;

a compound of Formula (Ia) wherein A is benzo, W is C(R$_4$), R$_4$ is H, X is O, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is O, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-chloro-2-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-chloro-3-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-chloro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-trifluoromethoxy-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-chloro-4-trifluoromethoxy-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-chloro-2-fluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-fluoro-4-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-chloro-5-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-bromo-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-chloro-5-fluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-trifluoromethoxy-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-fluoro-5-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-chloro-3-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-fluoro-3-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3,5-di-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-trifluoromethylthio-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-fluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-fluoro-5-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-chloro-3-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-chloro-phenyl;

a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 2-fluoro-4-trifluoromethyl-phenyl;
a compound of Formula (Ia) wherein A is benzo, W is $C(R_4)$, $R_4$ is chloro, X is S, $R_1$ is ethoxy, $R_2$ is ethoxy, $R_3$ is H, L is $CH_2$, and B is 3-chloro-phenyl;
a compound of Formula (Ia) wherein A is benzo, W is $C(R_4)$, $R_4$ is chloro, X is S, $R_1$ is ethoxy, $R_2$ is ethoxy, $R_3$ is H, L is $CH_2$, and B is 2-fluoro-4-trifluoromethyl-phenyl;
a compound of Formula (Ia) wherein A is benzo, W is $C(R_4)$, $R_4$ is chloro, X is S, $R_1$ is ethoxy, $R_2$ is ethoxy, $R_3$ is H, L is $CH_2$, and B is 4-methoxy-3-trifluoromethyl-phenyl;
a compound of Formula (Ia) wherein A is benzo, W is $C(R_4)$, $R_4$ is chloro, X is S, $R_1$ is ethoxy, $R_2$ is ethoxy, $R_3$ is H, L is $CH_2$, and B is 4-chloro-phenyl;
a compound of Formula (Ia) wherein A is benzo, W is $C(R_4)$, $R_4$ is chloro, X is S, $R_1$ is ethoxy, $R_2$ is ethoxy, $R_3$ is H, L is $CH_2$, and B is 4-fluoro-3-trifluoromethyl-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 3-bromo-phenyl;
a compound of Formula (Ia) wherein A is benzo, W is $C(R_4)$, $R_4$ is chloro, X is S, $R_1$ is ethoxy, $R_2$ is ethoxy, $R_3$ is H, L is $CH_2$, and B is 3-trifluoromethylthio-phenyl;
a compound of Formula (Ia) wherein A is benzo, W is $C(R_4)$, $R_4$ is chloro, X is S, $R_1$ is ethoxy, $R_2$ is ethoxy, $R_3$ is H, L is $CH_2$, and B is 3-chloro-4-fluoro-phenyl;
a compound of Formula (Ia) wherein A is benzo, W is $C(R_4)$, $R_4$ is chloro, X is S, $R_1$ is ethoxy, $R_2$ is ethoxy, $R_3$ is H, L is $CH_2$, and B is 4-fluoro-3-trifluoromethyl-phenyl;
a compound of Formula (Ia) wherein A is benzo, W is $C(R_4)$, $R_4$ is chloro, X is S, $R_1$ is ethoxy, $R_2$ is ethoxy, $R_3$ is H, L is $CH_2$, and B is 4-methylthio-phenyl;
a compound of Formula (Ia) wherein A is benzo, W is $C(R_4)$, $R_4$ is chloro, X is S, $R_1$ is ethoxy, $R_2$ is ethoxy, $R_3$ is H, L is $CH_2$, and B is 4-trifluoromethylsulfonyl-phenyl;
a compound of Formula (Ia) wherein A is benzo, W is $C(R_4)$, $R_4$ is chloro, X is S, $R_1$ is isopropyloxy, $R_2$ is isopropyloxy, $R_3$ is H, L is $CH_2$, and B is 3-trifluoromethoxy-phenyl;
a compound of Formula (Ia) wherein A is benzo, W is $C(R_4)$, $R_4$ is chloro, X is S, $R_1$ is isopropyloxy, $R_2$ is isopropyloxy, $R_3$ is H, L is $CH_2$, and B is 4-chloro-3-fluoro-phenyl;
a compound of Formula (Ia) wherein A is benzo, W is $C(R_4)$, $R_4$ is chloro, X is S, $R_1$ is isopropyloxy, $R_2$ is isopropyloxy, $R_3$ is H, L is $CH_2$, and B is 5-chloro-2-fluoro-phenyl;
a compound of Formula (Ia) wherein A is benzo, W is $C(R_4)$, $R_4$ is chloro, X is S, $R_1$ is isopropyloxy, $R_2$ is isopropyloxy, $R_3$ is H, L is $CH_2$, and B is 4-trifluoromethylthio-phenyl;
a compound of Formula (Ia) wherein A is benzo, W is $C(R_4)$, $R_4$ is chloro, X is S, $R_1$ is ethoxy, $R_2$ is ethoxy, $R_3$ is H, L is $CH_2$, and B is 5-chloro-2-fluoro-phenyl;
a compound of Formula (Ia) wherein A is benzo, W is $C(R_4)$, $R_4$ is chloro, X is S, $R_1$ is isopropyloxy, $R_2$ is isopropyloxy, $R_3$ is H, L is $CH_2$, and B is 4-fluoro-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 5-chloro-2-fluoro-phenyl;
a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 5-chloro-2-fluoro-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 3-cyano-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 3-pyrrol-1-yl-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 4-difluoromethoxy-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 4-cyano-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 3-methoxycarbonyl-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 3-methoxy-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 3-nitro-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 3-hydroxy-phenyl;
a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 3-methoxy-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 3-amino-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 3,5-dimethoxy-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 2-methoxy-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 4-methoxy-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 3,5-dihydroxy-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 2-hydroxy-phenyl;
a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 4-hydroxy-phenyl;
a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 3-hydroxy-phenyl;
a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 4-methoxy-3-trifluoromethyl-phenyl;
a compound of Formula (Ia) wherein A is benzo, W is $C(R_4)$, $R_4$ is bromo, X is N(t-butoxycarbonyl), $R_1$ is isopropyloxy, $R_2$ is isopropyloxy, $R_3$ is H, L is $CH_2$, and B is 4-fluoro-3-trifluoromethyl-phenyl;
a compound of Formula (Ia) wherein A is benzo, W is $C(R_4)$, $R_4$ is bromo, X is N(methyl), $R_1$ is isopropyloxy, $R_2$ is isopropyloxy, $R_3$ is H, L is $CH_2$, and B is 4-fluoro-3-trifluoromethyl-phenyl;
a compound of Formula (Ia) wherein A is 3-trifluoromethyl-4-fluoro-benzo, W is $C(R_4)$, $R_4$ is bromo, X is N(n-propyl), $R_1$ is isopropyloxy, $R_2$ is isopropyloxy, $R_3$ is H, L is $CH_2$, and B is 4-fluoro-3-trifluoromethyl-phenyl;
a compound of Formula (Ia) wherein A is 3-trifluoromethyl-4-fluoro-benzo, W is $C(R_4)$, $R_4$ is bromo, X is N(methanesulfonyl), $R_1$ is isopropyloxy, $R_2$ is isopropyloxy, $R_3$ is H, L is $CH_2$, and B is 4-fluoro-3-trifluoromethyl-phenyl;

a compound of Formula (Ia) wherein A is benzo, W is C($R_4$), $R_4$ is bromo, X is N(methylcarbonyl), $R_1$ is isopropyloxy, $R_2$ is isopropyloxy, $R_3$ is H, L is $CH_2$, and B is 4-fluoro-3-trifluoromethyl-phenyl;

a compound of Formula (Ia) wherein A is benzo, W is C($R_4$), $R_4$ is bromo, X is N(n-propylsulfonyl), $R_1$ is isopropyloxy, $R_2$ is isopropyloxy, $R_3$ is H, L is $CH_2$, and B is 4-fluoro-3-trifluoromethyl-phenyl;

a compound of Formula (Ia) wherein A is benzo, W is C($R_4$), $R_4$ is H, X is S, $R_1$ is isopropyloxy, $R_2$ is isopropyloxy, $R_3$ is absent, L is =CH— taken to form an alkene with the phosphorus-bearing adjacent atom, and B is 3,4-difluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is absent, L is =CH— taken to form an alkene with the phosphorus-bearing adjacent atom, and B is 3,4-difluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-5-trifluoromethyl-phenyl;
and
a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-trifluoromethyl-phenyl.

Further embodiments of the present invention are directed to a compound of Formula (Ia)

Formula (Ia)

selected from the group consisting of a compound of Formula (Ia) wherein A is benzo, W is C($R_4$), $R_4$ is methyl, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is i-propyl, X is S, $R_1$ is ethoxy, $R_2$ is ethoxy, $R_3$ is H, L is $CH_2$, and B is 3,4-difluoro-phenyl;

a compound of Formula (Ia) wherein A is 4-fluoro-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-chloro-phenyl;

a compound of Formula (Ia) wherein A is benzo, W is C($R_4$), $R_4$ is cyclopentyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is isobutyl, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-fluoro-phenyl;

a compound of Formula (Ia) wherein A is 7-fluoro-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is O, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2,3-difluoro-phenyl;

a compound of Formula (Ia) wherein A is benzo, W is C($R_4$), $R_4$ is methyl, X is O, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is isobutyl, $R_2$ is isobutyl, $R_3$ is H, L is $OCH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

a compound of Formula (Ia) wherein A is 6-fluoro-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3,5-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-methyl-phenyl;

a compound of Formula (Ia) wherein A is benzo, W is C($R_4$), $R_4$ is i-propyl, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is cyclopropyl, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3,4-dichloro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-3-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3,4-dichloro-phenyl;

a compound of Formula (Ia) wherein A is benzo, W is N, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-methyl-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-4-fluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-3,5-difluoro-phenyl;

a compound of Formula (Ia) wherein A is benzo, W is C($R_4$), $R_4$ is cyclopropyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is methyl, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-trifluoromethyl-4-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-methoxy-phenyl;

a compound of Formula (Ia) wherein A is benzo, W is C(R$_4$), R$_4$ is methyl, X is S, R$_1$ is isobutyl, R$_2$ is isobutyl, R$_3$ is H, L is CH$_2$, and B is 3,4-difluoro-phenyl;

a compound of Formula (Ia) wherein A is (2,3-b)pyridin-2-yl, W is C(R$_4$), R$_4$ is methyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,3-dichloro-phenyl;

a compound of Formula (Ia) wherein A is benzo, W is C(R$_4$), R$_4$ is methyl, X is S, R$_1$ is ethoxy, R$_2$ is isobutyl, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-3-trifluoromethyl-phenyl;

a compound of Formula (Ia) wherein A is benzo, W is C(R$_4$), R$_4$ is cyclopentyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 3-trifluoromethyl-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-bromo-phenyl;

a compound of Formula (Ia) wherein A is benzo, W is C(R$_4$), R$_4$ is cyclobutyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is n-propyl, R$_2$ is n-propyl, R$_3$ is H, L is OCH$_2$, and B is 3,4-difluoro-phenyl;

a compound of Formula (Ia) wherein A is benzo, W is C(R$_4$), R$_4$ is trifluoromethyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is n-propyl, R$_2$ is n-propyl, R$_3$ is H, L is CH$_2$, and B is 3,4-difluoro-phenyl;

a compound of Formula (Ia) wherein A is 5-fluoro-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is naphthalen-2-yl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,5-dichloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-chloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-trifluoromethyl-4-chloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 4-fluoro-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 4-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-trifluoromethyl-phenyl;

a compound of Formula (Ia) wherein A is benzo, W is C(R$_4$), R$_4$ is methyl, X is S, R$_1$ is 2,2-dimethyl-propyl, R$_2$ is 2,2-dimethyl-propyl, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,6-dichloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 4-trifluoromethoxy-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-fluoro-5-trifluoromethyl-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-trifluoromethoxy-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 3-fluoro-4-trifluoromethyl-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-trifluoromethyl-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-3-methyl-6-chloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-trifluoromethoxy-phenyl;

a compound of Formula (Ia) wherein A is 5-methyl-benzo, W is C(R$_4$), R$_4$ is methyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is H, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is phenyl, X is S, R$_1$ is ethoxy, R$_2$ is ethoxy, R$_3$ is H, L is CH$_2$, and B is 3,4-dichloro-phenyl;

a compound of Formula (Ia) wherein A is 4-chloro-benzo, W is C(R$_4$), R$_4$ is methyl, X is S, R$_1$ is ethoxy, R$_2$ is ethoxy, R$_3$ is H, L is CH$_2$, and B is 3,4-dichloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-bromo-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-5-trifluoromethyl-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 4-trifluoromethyl-phenyl;

a compound of Formula (Ia) wherein A is benzo, W is C(R$_4$), R$_4$ is H, X is S, R$_1$ is isopropyloxy, R$_2$ is isopropyloxy, R$_3$ is H, L is CH$_2$, and B is 3-trifluoromethyl-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 4-bromo-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 5-chloro-benzo[1,3]dioxol-6-yl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-(pyridin-4-yl)-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-3-chloro-5-trifluoromethyl-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 3,4-difluoro-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,4-dichloro-5-fluoro-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-biphenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 3,4-dichloro-phenyl;
a compound of Formula (Ia) wherein A is benzo, W is C(R$_4$), R$_4$ is methyl, X is S, R$_1$ is ethoxy, R$_2$ is ethoxy, R$_3$ is CH$_3$, L is CH$_2$, and B is 3,4-difluoro-phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 2-fluoro-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-chloro-3-trifluoromethyl-phenyl;
a compound of Formula (Ia) wherein A is 6-methoxy-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is naphthalen-2-yl;
a compound of Formula (Ia) wherein A is 4-trifluoromethyl-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 2-chloro-phenyl;
a compound of Formula (Ia) wherein A is benzo, W is C(R$_4$), R$_4$ is H, X is O, R$_1$ is ethoxy, R$_2$ is ethoxy, R$_3$ is H, L is CH$_2$, and B is 4-fluoro-phenyl;
a compound of Formula (Ia) wherein A is benzo, W is C(R$_4$), R$_4$ is methyl, X is SO$_2$, R$_1$ is ethoxy, R$_2$ is ethoxy, R$_3$ is H, L is CH$_2$, and B is 3,4-difluoro-phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 2-methyl-phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is benzothiophen-2-yl;
a compound of Formula (Ia) wherein A is benzo, W is C(R$_4$), R$_4$ is methyl, X is S, R$_1$ $_{is\ ethoxy,\ R2}$ is ethoxy, R$_3$ is H, L is CH$_2$, and B is 4-trifluoromethyl-phenyl;
a compound of Formula (Ia) wherein A is 5-chloro-benzo, W is C(R$_4$), R$_4$ is methyl, X is S, R$_1$ is isopropyloxy, R$_2$ is isopropyloxy, R$_3$ is H, L is CH$_2$, and B is 3,4-difluoro-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is bromo, L is CH$_2$, and B is 3,4-difluoro-phenyl;
a compound of Formula (Ia) wherein A is benzo, W is C(R$_4$), R$_4$ is H, X is S, R$_1$ is ethoxy, R$_2$ is 2,6-dichloro-phenyl-methoxy, R$_3$ is H, L is absent, and B is H;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 2,6-dichloro-phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 3,5-trifluoromethyl-phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 2-chloro-4-fluoro-phenyl;
a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-chloro-5-trifluoromethyl-phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 2,3-dichloro-phenyl;
a compound of Formula (Ia) wherein A is benzo, W is C(R$_4$), R$_4$ is methyl, X is S, R$_1$ is cyclohexyloxy, R$_2$ is cyclohexyloxy, R$_3$ is H, L is CH$_2$, and B is 3,4-difluoro-phenyl;
a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 2-trifluoromethyl-phenyl;
a compound of Formula (Ia) wherein A is benzo, W is C(R$_4$), R$_4$ is methyl, X is S, R$_1$ is ethoxy, R$_2$ is 2-(N,N-dimethylamino)-ethoxy, R$_3$ is H, L is CH$_2$, and B is 3,4-difluoro-phenyl;
a compound of Formula (Ia) wherein A is benzo, W is C(R$_4$), R$_4$ is H, X is S, R$_1$ is ethoxy, R$_2$ is 2-methyl-phenylmethoxy, R$_3$ is H, L is absent, and B is H;
a compound of Formula (Ia) wherein A is benzo, W is C(R$_4$), R$_4$ is H, X is S, R$_1$ is ethoxy, R$_2$ is 2-chloro-phenylmethoxy, R$_3$ is H, L is absent, and B is H;
a compound of Formula (Ia) wherein A is benzo, W is C(R$_4$), R$_4$ is methyl, X is S, R$_1$ is ethoxy, R$_2$ is methyl, R$_3$ is H, L is CH$_2$, and B is 3,4-difluoro-phenyl;
a compound of Formula (Ia) wherein A is benzo, W is C(R$_4$), R$_4$ is H, X is S, R$_1$ is ethoxy, R$_2$ is 4-fluoro-phenylmethoxy, R$_3$ is H, L is absent, and B is H;
a compound of Formula (Ia) wherein A is benzo, W is C(R$_4$), R$_4$ is H, X is S, R$_1$ is ethoxy, R$_2$ is 2-fluoro-phenylmethoxy, R$_3$ is H, L is absent, and B is H;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-methoxy-4-fluoro-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-hydroxy-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-trifluoromethyl-4-fluoro-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-hydroxy-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-3-hydroxy-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 5-chloro-2-fluoro-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-methoxy-4-fluoro-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-chloro-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2,3,5,6-tetrafluoro-4-methoxy-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-chloro-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-trifluoromethylsulfonyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-5-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3,5-dimethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 5-chloro-2-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-hydroxy-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-methoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethylthio-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethylsulfonyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-bromo-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-4-trifluoromethyl-phenyl;

a compound of Formula (Ia) wherein A is 4-fluoro-benzo, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-hydroxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-3-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-4-chloro-phenyl;

a compound of Formula (Ia) wherein A is 4-fluoro-benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-chloro-3-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-chloro-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2,3-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-nitro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-pyrrol-1-yl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethylthio-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-3-trimethyl-phenyl;

a compound of Formula (Ia) wherein A is 4-fluoro-benzo, W is C($R_4$), $R_4$ is bromo, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-methylthio-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-4-chloro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-chloro-2-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-trifluoromethylthio-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 5-chloro-2-fluoro-phenyl;

a compound of Formula (Ia) wherein A is 4-fluoro-benzo, W is C(R$_4$), R$_4$ is bromo, X is O, R$_1$ is isopropyloxy, R$_2$ is isopropyloxy, R$_3$ is H, L is CH$_2$, and B is 3,4-difluoro-phenyl;

a compound of Formula (Ia) wherein A is (2,3-b)pyridin-2-yl, W is C(R$_4$), R$_4$ is bromo, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is bromo, X is O, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-trifluoromethyl-phenyl;

a compound of Formula (Ia) wherein A is benzo, W is C(R$_4$), R$_4$ is bromo, X is O, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-chloro-5-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-trifluoromethyl-phenyl;

a compound of Formula (Ia) wherein A is 4-fluoro-benzo, W is C(R$_4$), R$_4$ is bromo, X is S, R$_1$ is ethoxy, R$_2$ is ethoxy, R$_3$ is H, L is CH$_2$, and B is 3-trifluoromethyl-4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-difluoromethoxy-phenyl;

a compound of Formula (Ia) wherein A is 4-fluoro-benzo, W is C(R$_4$), R$_4$ is methyl, X is O, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-trifluoromethyl-4-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-3-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-trifluoromethyl-4-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-5-trifluoromethyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-methylthio-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-chloro-4-trifluoromethoxy-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethylthio-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-4-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3,5-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-4-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-chloro-4-trifluoromethoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2,3,5,6-tetrafluoro-4-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-chloro-3-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-3-chloro-5-trifluoromethyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-trifluoromethoxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-chloro-5-hydroxy-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethyl-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-chloro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-fluoro-4-chloro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-trifluoromethylsulfonyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-3-chloro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 5-chloro-2-fluoro-phenyl;

a compound of Formula (Ia) wherein A is benzo, W is C(R$_4$), R$_4$ is bromo, X is S, R$_1$ is n-butyloxy, R$_2$ is n-butyloxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-fluoro-3-chloro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3,5-di-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-bromo-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-chloro-3-fluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-trifluoromethyl-4-fluoro-phenyl;

a compound of Formula (Ia) wherein A is benzo, W is C($R_4$), $R_4$ is phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-4-chloro-5-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-methoxycarbonyl-phenyl;

a compound of Formula (Ia) wherein A is benzo, W is C($R_4$), $R_4$ is 2-hydroxy-phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-fluoro-3-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-methoxy-3-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-4-chloro-5-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-cyano-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-trifluoromethylsulfonyl-phenyl;

enantiomer B, a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-cyano-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-fluoro-4-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-4-trifluoromethyl-phenyl;

a compound of Formula (Ia) wherein A is benzo, W is C($R_4$), $R_4$ is bromo, X is S, $R_1$ is s-butyl, $R_2$ is s-butyl, $R_3$ is H, L is $OCH_2$, and B is 3,4-difluoro-phenyl;

a compound of Formula (Ia) wherein A is benzo, W is C($R_4$), $R_4$ is bromo, X is S, $R_1$ is 3-methyl-butoxy, $R_2$ is 3-methyl-butoxy, $R_3$ is H, L is $CH_2$, and B is 3,4-difluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-4-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-fluoro-5-trifluoromethyl-phenyl;

a compound of Formula (Ia) wherein A is 4-fluoro-benzo, W is C($R_4$), $R_4$ is bromo, X is O, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-5-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-4-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trimethylthio-phenyl;

a compound of Formula (Ia) wherein A is benzo, W is C($R_4$), $R_4$ is thien-3-yl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-bromo-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-chloro-4-trifluoromethoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-5-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is absent, L is =CH— taken to form an alkene with the phosphorus-bearing adjacent atom, and B is 3,4-difluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-chloro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-chloro-2-fluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-chloro-5-fluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-chloro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-fluoro-4-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-trifluoromethoxy-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-fluoro-3-trifluoromethyl-phenyl;

a compound of Formula (Ia) wherein A is benzo, W is C(R$_4$), R$_4$ is bromo, X is S, R$_1$ is methoxycarbonyl-methoxy, R$_2$ is methoxycarbonyl-methoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-trifluoromethoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-chloro-3-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-methylthio-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-fluoro-4-chloro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-4-chloro-5-hydroxy-phenyl;

enantiomer A, a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-trifluoromethoxy-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-chloro-3-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-trifluoromethyl-4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-chloro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-trifluoromethylthio-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-fluoro-4-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-trifluoromethyl-phenyl;

a compound of Formula (Ia) wherein A is benzo, W is C(R$_4$), R$_4$ is 2-fluoro-phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-fluoro-5-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2,3,5,6-tetrafluoro-4-hydroxy-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethyl-4-methoxy-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2,6-dichloro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-fluoro-3-trifluoromethyl-phenyl;

a compound of Formula (Ia) wherein A is benzo, W is C(R$_4$), R$_4$ is bromo, X is S, R$_1$ is methoxy, R$_2$ is methoxy, R$_3$ is H, L is CH$_2$, and B is 3,4-difluoro-phenyl;

a compound of Formula (Ia) wherein A is 3-trifluoromethyl-4-fluoro-benzo, W is C(R$_4$), R$_4$ is bromo, X is N(methanesulfonyl), R$_1$ is isopropyloxy, R$_2$ is isopropyloxy, R$_3$ is H, L is CH$_2$, and B is 4-fluoro-3-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-trifluoromethylthio-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-chloro-3-trifluoromethyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-methylthio-phenyl;

a compound of Formula (Ia) wherein A is benzo, W is C(R$_4$), R$_4$ is 3-fluoro-phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is N(methylcarbonyl), R$_1$ is isopropyloxy, R$_2$ is isopropyloxy, R$_3$ is H, L is CH$_2$, and B is 4-fluoro-3-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2,3,5,6-tetrafluoro-4-hydroxy-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-fluoro-4-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-chloro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-5-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-fluoro-5-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-chloro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-chloro-5-trifluoromethyl-phenyl;

a compound of Formula (Ia) wherein A is benzo, W is C(R$_4$), R$_4$ is H, X is S, R$_1$ is isopropyloxy, R$_2$ is isopropyloxy, R$_3$ is absent, L is =CH— taken to form an alkene with the phosphorus-bearing adjacent atom, and B is 3,4-difluoro-phenyl;

a compound of Formula (Ia) wherein A is 3-trifluoromethyl-4-fluoro-benzo, W is C(R$_4$), R$_4$ is bromo, X is N(n-propyl), R$_1$ is isopropyloxy, R$_2$ is isopropyloxy, R$_3$ is H, L is CH$_2$, and B is 4-fluoro-3-trifluoromethyl-phenyl;

a compound of Formula (Ia) wherein A is benzo, W is C(R$_4$), R$_4$ is bromo, X is N(methyl), R$_1$ is isopropyloxy, R$_2$ is isopropyloxy, R$_3$ is H, L is CH$_2$, and B is 4-fluoro-3-trifluoromethyl-phenyl;

a compound of Formula (Ia) wherein A is benzo, W is C(R$_4$), R$_4$ is bromo, X is S, R$_1$ is 2-acetoxy-ethoxy, R$_2$ is 2-acetoxy-ethoxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-trifluoromethoxy-phenyl;

a compound of Formula (Ia) wherein A is benzo, W is C(R$_4$), R$_4$ is 4-fluoro-phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-amino-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-methoxy-3-trifluoromethyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3,5-di-trifluoromethyl-phenyl;

enantiomer B, a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-fluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-chloro-3-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3,5-di-trifluoromethyl-phenyl;

enantiomer B, a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-chloro-5-trifluoromethyl-phenyl;

enantiomer B, a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-trifluoromethoxy-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-chloro-5-trifluoromethyl-phenyl;

a compound of Formula (Ia) wherein A is 4-bromo-benzo, W is C(R$_4$), R$_4$ is bromo, X is S, R$_1$ is isopropyloxy, R$_2$ is isopropyloxy, R$_3$ is H, L is CH$_2$, and B is 2-fluoro-phenyl;

a compound of Formula (Ia) wherein A is benzo, W is C(R$_4$), R$_4$ is H, X is O, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is s-butyl, R$_2$ is s-butyl, R$_3$ is H, L is CH$_2$, and B is 3,4-difluoro-phenyl;

and a compound of Formula (Ia) wherein A is benzo, W is C(R$_4$), R$_4$ is 3-aminocarbonyl-phenyl, X is S, R$_1$ is ethoxy, R$_2$ is ethoxy, R$_3$ is H, L is CH$_2$, and B is 3,4-difluoro-phenyl.

Further embodiments of the present invention are directed to a compound of Formula (Ia)

Formula (Ia)

selected from the group consisting of a compound of Formula (Ia) wherein A is benzo, W is C(R$_4$), R$_4$ is methyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is i-propyl, X is S, R$_1$ is ethoxy, R$_2$ is ethoxy, R$_3$ is H, L is CH$_2$, and B is 3,4-difluoro-phenyl;

a compound of Formula (Ia) wherein A is 4-fluoro-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-chloro-phenyl;

a compound of Formula (Ia) wherein A is benzo, W is C(R$_4$), R$_4$ is cyclopentyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is isobutyl, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-fluoro-phenyl;

a compound of Formula (Ia) wherein A is 7-fluoro-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is O, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,3-difluoro-phenyl;

a compound of Formula (Ia) wherein A is benzo, W is C(R$_4$), R$_4$ is methyl, X is O, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is isobutyl, R$_2$ is isobutyl, R$_3$ is H, L is OCH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3,4-difluoro-phenyl;

a compound of Formula (Ia) wherein A is 6-fluoro-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3,5-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-methyl-phenyl;

a compound of Formula (Ia) wherein A is benzo, W is C($R_4$), $R_4$ is i-propyl, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is C($R_4$), $R_4$ is cyclopropyl, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3,4-dichloro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-3-chloro-phenyl;
a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3,4-dichloro-phenyl;
a compound of Formula (Ia) wherein A is benzo, W is N, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-methyl-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-4-fluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-3,5-difluoro-phenyl;
a compound of Formula (Ia) wherein A is benzo, W is C($R_4$), $R_4$ is cyclopropyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is ethoxy, $R_2$ is methyl, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-trifluoromethyl-4-fluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-methoxy-phenyl;
a compound of Formula (Ia) wherein A is benzo, W is C($R_4$), $R_4$ is methyl, X is S, $R_1$ is isobutyl, $R_2$ is isobutyl, $R_3$ is H, L is $CH_2$, and B is 3,4-difluoro-phenyl;
a compound of Formula (Ia) wherein A is (2,3-b)pyridin-2-yl, W is C($R_4$), $R_4$ is methyl, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2,3-dichloro-phenyl;
a compound of Formula (Ia) wherein A is benzo, W is C($R_4$), $R_4$ is methyl, X is S, $R_1$ is ethoxy, $R_2$ is isobutyl, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-3-trifluoromethyl-phenyl;
a compound of Formula (Ia) wherein A is benzo, W is C($R_4$), $R_4$ is cyclopentyl, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 3-trifluoromethyl-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-bromo-phenyl;
a compound of Formula (Ia) wherein A is benzo, W is C($R_4$), $R_4$ is cyclobutyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is n-propyl, $R_2$ is n-propyl, $R_3$ is H, L is $OCH_2$, and B is 3,4-difluoro-phenyl;
a compound of Formula (Ia) wherein A is benzo, W is C($R_4$), $R_4$ is trifluoromethyl, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is n-propyl, $R_2$ is n-propyl, $R_3$ is H, L is $CH_2$, and B is 3,4-difluoro-phenyl;
a compound of Formula (Ia) wherein A is 5-fluoro-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is naphthalen-2-yl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2,5-dichloro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-trifluoromethyl-4-chloro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 4-fluoro-phenyl;
a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 4-fluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-trifluoromethyl-phenyl;
a compound of Formula (Ia) wherein A is benzo, W is C($R_4$), $R_4$ is methyl, X is S, $R_1$ is 2,2-dimethyl-propyl, $R_2$ is 2,2-dimethyl-propyl, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2,6-dichloro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 4-trifluoromethoxy-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-fluoro-5-trifluoromethyl-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-trifluoromethoxy-phenyl;
a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 3-fluoro-4-trifluoromethyl-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-trifluoromethyl-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-3-methyl-6-chloro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-trifluoromethoxy-phenyl;

a compound of Formula (Ia) wherein A is 5-methyl-benzo, W is $C(R_4)$, $R_4$ is methyl, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is $C(R_4)$, $R_4$ is H, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is $C(R_4)$, $R_4$ is phenyl, X is S, $R_1$ is ethoxy, $R_2$ is ethoxy, $R_3$ is H, L is $CH_2$, and B is 3,4-dichloro-phenyl;

a compound of Formula (Ia) wherein A is 4-chloro-benzo, W is $C(R_4)$, $R_4$ is methyl, X is S, $R_1$ is ethoxy, $R_2$ is ethoxy, $R_3$ is H, L is $CH_2$, and B is 3,4-dichloro-phenyl;

a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 2-bromo-phenyl;

a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 2-fluoro-5-trifluoromethyl-phenyl;

a compound of Formula (Ia) wherein A is benzo, W is $C(R_4)$, $R_4$ is H, X is S, $R_1$ is ethoxy, $R_2$ is ethoxy, $R_3$ is H, L is $CH_2$, and B is 4-trifluoromethyl-phenyl;

a compound of Formula (Ia) wherein A is benzo, W is $C(R_4)$, $R_4$ is H, X is S, $R_1$ is isopropyloxy, $R_2$ is isopropyloxy, $R_3$ is H, L is $CH_2$, and B is 3-trifluoromethyl-phenyl;

a compound of Formula (Ia) wherein A is benzo, W is $C(R_4)$, $R_4$ is H, X is S, $R_1$ is ethoxy, $R_2$ is ethoxy, $R_3$ is H, L is $CH_2$, and B is 4-bromo-phenyl;

a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 5-chloro-benzo[1,3]dioxol-6-yl;

a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 3-(pyridin-4-yl)-phenyl;

a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 2-fluoro-3-chloro-5-trifluoromethyl-phenyl;

a compound of Formula (Ia) wherein A is benzo, W is $C(R_4)$, $R_4$ is H, X is S, $R_1$ is ethoxy, $R_2$ is ethoxy, $R_3$ is H, L is $CH_2$, and B is phenyl;

a compound of Formula (Ia) wherein A is benzo, W is $C(R_4)$, $R_4$ is H, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 2,4-dichloro-5-fluoro-phenyl;

a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 3-biphenyl;

a compound of Formula (Ia) wherein A is benzo, W is $C(R_4)$, $R_4$ is H, X is S, $R_1$ is ethoxy, $R_2$ is ethoxy, $R_3$ is H, L is $CH_2$, and B is 3,4-dichloro-phenyl;

a compound of Formula (Ia) wherein A is benzo, W is $C(R_4)$, $R_4$ is methyl, X is S, $R_1$ is ethoxy, $R_2$ is ethoxy, $R_3$ is $CH_3$, L is $CH_2$, and B is 3,4-difluoro-phenyl;

a compound of Formula (Ia) wherein A is benzo, W is $C(R_4)$, $R_4$ is H, X is S, $R_1$ is ethoxy, $R_2$ is ethoxy, $R_3$ is H, L is $CH_2$, and B is 2-fluoro-phenyl;

a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 2-chloro-3-trifluoromethyl-phenyl;

a compound of Formula (Ia) wherein A is 6-methoxy-benzo, W is $C(R_4)$, $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is $C(R_4)$, $R_4$ is H, X is S, $R_1$ is ethoxy, $R_2$ is ethoxy, $R_3$ is H, L is $CH_2$, and B is naphthalen-2-yl;

a compound of Formula (Ia) wherein A is 4-trifluoromethyl-benzo, W is $C(R_4)$, $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is $C(R_4)$, $R_4$ is H, X is S, $R_1$ is ethoxy, $R_2$ is ethoxy, $R_3$ is H, L is $CH_2$, and B is 2-chloro-phenyl;

a compound of Formula (Ia) wherein A is benzo, W is $C(R_4)$, $R_4$ is H, X is O, $R_1$ is ethoxy, $R_2$ is ethoxy, $R_3$ is H, L is $CH_2$, and B is 4-fluoro-phenyl;

a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 3-methoxy-4-fluoro-phenyl;

a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 2-hydroxy-phenyl;

a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 3-hydroxy-phenyl;

a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 2-fluoro-3-hydroxy-phenyl;

a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 5-chloro-2-fluoro-phenyl;

a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 3-methoxy-4-fluoro-phenyl;

a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 3-chloro-phenyl;

a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 2,3,5,6-tetrafluoro-4-methoxy-phenyl;

a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 2-fluoro-4-methoxy-phenyl;

a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 3-chloro-4-fluoro-phenyl;

a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 4-trifluoromethylsulfonyl-phenyl;

a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 3-methoxy-phenyl;

a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 4-chloro-phenyl;

a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 3-chloro-5-fluoro-phenyl;

a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 3,5-dimethoxy-phenyl;

a compound of Formula (Ia) wherein A is benzo, W is $C(R_4)$, $R_4$ is bromo, X is S, $R_1$ is ethoxy, $R_2$ is ethoxy, $R_3$ is H, L is $CH_2$, and B is 5-chloro-2-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-hydroxy-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-methoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethylthio-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethylsulfonyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-bromo-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-4-trifluoromethyl-phenyl;

a compound of Formula (Ia) wherein A is 4-fluoro-benzo, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-hydroxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-3-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-4-chloro-phenyl;

a compound of Formula (Ia) wherein A is 4-fluoro-benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-chloro-3-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-chloro-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2,3-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-nitro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-pyrrol-1-yl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethylthio-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-3-trimethyl-phenyl;

a compound of Formula (Ia) wherein A is 4-fluoro-benzo, W is C($R_4$), $R_4$ is bromo, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-methylthio-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-4-chloro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-chloro-2-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethylthio-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 5-chloro-2-fluoro-phenyl;

a compound of Formula (Ia) wherein A is 4-fluoro-benzo, W is C($R_4$), $R_4$ is bromo, X is O, $R_1$ is isopropyloxy, $R_2$ is isopropyloxy, $R_3$ is H, L is $CH_2$, and B is 3,4-difluoro-phenyl;

a compound of Formula (Ia) wherein A is (2,3-b)pyridin-2-yl, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is bromo, X is O, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-trifluoromethyl-phenyl;
a compound of Formula (Ia) wherein A is benzo, W is C(R$_4$), R$_4$ is bromo, X is O, R$_1$ is ethoxy, R$_2$ is ethoxy, R$_3$ is H, L is CH$_2$, and B is 3,4-difluoro-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-chloro-5-fluoro-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-trifluoromethyl-phenyl;
a compound of Formula (Ia) wherein A is 4-fluoro-benzo, W is C(R$_4$), R$_4$ is bromo, X is S, R$_1$ is ethoxy, R$_2$ is ethoxy, R$_3$ is H, L is CH$_2$, and B is 3-trifluoromethyl-4-fluoro-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-difluoromethoxy-phenyl;
a compound of Formula (Ia) wherein A is 4-fluoro-benzo, W is C(R$_4$), R$_4$ is methyl, X is O, R$_1$ is isopropyloxy, R$_2$ is isopropyloxy, R$_3$ is H, L is CH$_2$, and B is 3,4-difluoro-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-trifluoromethyl-4-fluoro-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethoxy-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-3-trifluoromethyl-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-trifluoromethyl-4-methoxy-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-5-trifluoromethyl-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-methylthio-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-chloro-4-trifluoromethoxy-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethylthio-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-4-trifluoromethyl-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3,5-difluoro-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-4-methoxy-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-chloro-4-trifluoromethoxy-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2,3,5,6-tetrafluoro-4-methoxy-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-chloro-3-trifluoromethyl-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-3-chloro-5-trifluoromethyl-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-trifluoromethoxy-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-chloro-5-hydroxy-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethyl-4-fluoro-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-chloro-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-fluoro-4-chloro-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-trifluoromethylsulfonyl-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-fluoro-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-3-chloro-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 5-chloro-2-fluoro-phenyl;
a compound of Formula (Ia) wherein A is benzo, W is C(R$_4$), R$_4$ is bromo, X is S, R$_1$ is n-butyloxy, R$_2$ is n-butyloxy, R$_3$ is H, L is CH$_2$, and B is 3,4-difluoro-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-fluoro-3-chloro-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-trifluoromethyl-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethyl-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3,5-di-trifluoromethyl-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-bromo-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-chloro-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-fluoro-3-trifluoromethyl-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-trifluoromethyl-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-chloro-3-fluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-trifluoromethyl-4-fluoro-phenyl;

a compound of Formula (Ia) wherein A is benzo, W is C(R$_4$), R$_4$ is phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-4-chloro-5-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-methoxycarbonyl-phenyl;

a compound of Formula (Ia) wherein A is benzo, W is C(R$_4$), R$_4$ is 2-hydroxy-phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-fluoro-3-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-methoxy-3-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-chloro-5-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-cyano-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-trifluoromethylsulfonyl-phenyl;

enantiomer B, a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-trifluoromethyl-4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-cyano-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-fluoro-4-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-4-trifluoromethyl-phenyl;

a compound of Formula (Ia) wherein A is benzo, W is C(R$_4$), R$_4$ is bromo, X is S, R$_1$ is s-butyl, R$_2$ is s-butyl, R$_3$ is H, L is OCH$_2$, and B is 3,4-difluoro-phenyl;

a compound of Formula (Ia) wherein A is benzo, W is C(R$_4$), R$_4$ is bromo, X is S, R$_1$ is 3-methyl-butoxy, R$_2$ is 3-methyl-butoxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethyl-4-chloro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-fluoro-5-trifluoromethyl-phenyl;

a compound of Formula (Ia) wherein A is 4-fluoro-benzo, W is C(R$_4$), R$_4$ is bromo, X is O, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-5-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-fluoro-4-chloro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-trimethylthio-phenyl;

a compound of Formula (Ia) wherein A is benzo, W is C(R$_4$), R$_4$ is thien-3-yl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-bromo-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-chloro-4-trifluoromethoxy-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-fluoro-5-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is absent, L is =CH— taken to form an alkene with the phosphorus-bearing adjacent atom, and B is 3,4-difluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-chloro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-chloro-2-fluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-chloro-5-fluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-chloro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-fluoro-4-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-trifluoromethoxy-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-fluoro-3-trifluoromethyl-phenyl;

a compound of Formula (Ia) wherein A is benzo, W is C(R$_4$), R$_4$ is bromo, X is S, R$_1$ is methoxycarbonyl-methoxy, R$_2$ is methoxycarbonyl-methoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-trifluoromethoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-chloro-3-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-methylthio-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-fluoro-4-chloro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-4-chloro-5-hydroxy-phenyl;

enantiomer A, a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethoxy-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-chloro-3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-trifluoromethyl-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-chloro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-trifluoromethylthio-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-4-trifluoromethyl-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-trifluoromethyl-phenyl;

a compound of Formula (Ia) wherein A is benzo, W is C($R_4$), $R_4$ is 2-fluoro-phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 2-fluoro-5-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2,3,5,6-tetrafluoro-4-hydroxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-4-methoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2,6-dichloro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 2-fluoro-3-trifluoromethyl-phenyl;

a compound of Formula (Ia) wherein A is benzo, W is C($R_4$), $R_4$ is bromo, X is S, $R_1$ is methoxy, $R_2$ is methoxy, $R_3$ is H, L is $CH_2$, and B is 3,4-difluoro-phenyl;

a compound of Formula (Ia) wherein A is 3-trifluoromethyl-4-fluoro-benzo, W is C($R_4$), $R_4$ is bromo, X is N(methanesulfonyl), $R_1$ is isopropyloxy, $R_2$ is isopropyloxy, $R_3$ is H, L is $CH_2$, and B is 4-fluoro-3-trifluoromethyl-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-trifluoromethylthio-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-chloro-3-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-trifluoromethyl-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-methylthio-phenyl;

a compound of Formula (Ia) wherein A is benzo, W is C($R_4$), $R_4$ is 3-fluoro-phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is N(methylcarbonyl), $R_1$ is isopropyloxy, $R_2$ is isopropyloxy, $R_3$ is H, L is $CH_2$, and B is 4-fluoro-3-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2,3,5,6-tetrafluoro-4-hydroxy-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 2-fluoro-4-trifluoromethyl-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-chloro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-5-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-trifluoromethyl-phenyl;

and a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-fluoro-5-trifluoromethyl-phenyl.

A further embodiment of the present invention is directed to a compound of Formula (Ia)

Formula (Ia)

selected from the group consisting of a compound of Formula (Ia) wherein A is benzo, W is C($R_4$), $R_4$ is methyl, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is i-propyl, X is S, $R_1$ is ethoxy, $R_2$ is ethoxy, $R_3$ is H, L is $CH_2$, and B is 3,4-difluoro-phenyl;

a compound of Formula (Ia) wherein A is 4-fluoro-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-chloro-phenyl;

a compound of Formula (Ia) wherein A is benzo, W is C($R_4$), $R_4$ is cyclopentyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is isobutyl, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-fluoro-phenyl;

a compound of Formula (Ia) wherein A is 7-fluoro-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is O, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2,3-difluoro-phenyl;

a compound of Formula (Ia) wherein A is benzo, W is C(R$_4$), R$_4$ is methyl, X is O, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is isobutyl, R$_2$ is isobutyl, R$_3$ is H, L is OCH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3,4-difluoro-phenyl;

a compound of Formula (Ia) wherein A is 6-fluoro-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3,5-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-methyl-phenyl;

a compound of Formula (Ia) wherein A is benzo, W is C(R$_4$), R$_4$ is i-propyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is cyclopropyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3,4-dichloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-3-chloro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3,4-dichloro-phenyl;

a compound of Formula (Ia) wherein A is benzo, W is N, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-methyl-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-chloro-4-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-chloro-3,5-difluoro-phenyl;

a compound of Formula (Ia) wherein A is benzo, W is C(R$_4$), R$_4$ is cyclopropyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is methyl, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-trifluoromethyl-4-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-methoxy-phenyl;

a compound of Formula (Ia) wherein A is benzo, W is C(R$_4$), R$_4$ is methyl, X is S, R$_1$ is isobutyl, R$_2$ is isobutyl, R$_3$ is H, L is CH$_2$, and B is 3,4-difluoro-phenyl;

a compound of Formula (Ia) wherein A is (2,3-b)pyridin-2-yl, W is C(R$_4$), R$_4$ is methyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,3-dichloro-phenyl;

a compound of Formula (Ia) wherein A is benzo, W is C(R$_4$), R$_4$ is methyl, X is S, R$_1$ is ethoxy, R$_2$ is isobutyl, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-3-trifluoromethyl-phenyl;

a compound of Formula (Ia) wherein A is benzo, W is C(R$_4$), R$_4$ is cyclopentyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 3-trifluoromethyl-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-bromo-phenyl;

a compound of Formula (Ia) wherein A is benzo, W is C(R$_4$), R$_4$ is cyclobutyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-methoxy-4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-trifluoromethyl-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-3-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 5-chloro-2-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-methoxy-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-chloro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2,3,5,6-tetrafluoro-4-methoxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-methoxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-chloro-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-trifluoromethylsulfonyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-chloro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-chloro-5-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3,5-dimethoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 5-chloro-2-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-hydroxy-4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-chloro-4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-methoxy-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-trifluoromethylthio-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-trifluoromethylsulfonyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-bromo-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-fluoro-4-trifluoromethyl-phenyl;

a compound of Formula (Ia) wherein A is 4-fluoro-benzo, W is C(R$_4$), R$_4$ is bromo, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-hydroxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-3-methoxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-fluoro-4-chloro-phenyl;

a compound of Formula (Ia) wherein A is 4-fluoro-benzo, W is C(R$_4$), R$_4$ is bromo, X is S, R$_1$ is isopropyloxy, R$_2$ is isopropyloxy, R$_3$ is H, L is CH$_2$, and B is 3-trifluoromethyl-4-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-chloro-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-chloro-3-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-fluoro-4-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-trifluoromethyl-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-fluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-chloro-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2,3-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-nitro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-pyrrol-1-yl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-trifluoromethylthio-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-fluoro-3-trimethyl-phenyl;

a compound of Formula (Ia) wherein A is 4-fluoro-benzo, W is C(R$_4$), R$_4$ is bromo, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-methylthio-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-4-chloro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-trifluoromethoxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-chloro-2-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-trifluoromethylthio-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 5-chloro-2-fluoro-phenyl;

a compound of Formula (Ia) wherein A is 4-fluoro-benzo, W is C(R$_4$), R$_4$ is bromo, X is O, R$_1$ is isopropyloxy, R$_2$ is isopropyloxy, R$_3$ is H, L is CH$_2$, and B is 3,4-difluoro-phenyl;

a compound of Formula (Ia) wherein A is (2,3-b)pyridin-2-yl, W is C(R$_4$), R$_4$ is bromo, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is bromo, X is O, R$_{1\text{ is isopropyloxy}}$, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-trifluoromethyl-phenyl;

a compound of Formula (Ia) wherein A is benzo, W is C(R$_4$), R$_4$ is bromo, X is O, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-chloro-5-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-trifluoromethyl-phenyl;

a compound of Formula (Ia) wherein A is 4-fluoro-benzo, W is C(R$_4$), R$_4$ is bromo, X is S, R$_1$ is ethoxy, R$_2$ is ethoxy, R$_3$ is H, L is CH$_2$, and B is 3-trifluoromethyl-4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-difluoromethoxy-phenyl;

a compound of Formula (Ia) wherein A is 4-fluoro-benzo, W is C(R$_4$), R$_4$ is methyl, X is O, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-trifluoromethyl-4-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-3-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-trifluoromethyl-4-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-5-trifluoromethyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-methylthio-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-chloro-4-trifluoromethoxy-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethylthio-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-4-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3,5-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-4-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-chloro-4-trifluoromethoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2,3,5,6-tetrafluoro-4-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-chloro-3-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-3-chloro-5-trifluoromethyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-trifluoromethoxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-chloro-5-hydroxy-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethyl-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-chloro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-fluoro-4-chloro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-trifluoromethylsulfonyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-3-chloro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 5-chloro-2-fluoro-phenyl;

a compound of Formula (Ia) wherein A is benzo, W is C(R$_4$), R$_4$ is bromo, X is S, R$_1$ is n-butyloxy, R$_2$ is n-butyloxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-fluoro-3-chloro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-trifluoromethyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3,5-di-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-bromo-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-chloro-3-fluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-trifluoromethyl-4-fluoro-phenyl;

a compound of Formula (Ia) wherein A is benzo, W is C($R_4$), $R_4$ is phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-4-chloro-5-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-methoxycarbonyl-phenyl;

a compound of Formula (Ia) wherein A is benzo, W is C($R_4$), $R_4$ is 2-hydroxy-phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-fluoro-3-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-methoxy-3-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-4-chloro-5-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-cyano-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-trifluoromethylsulfonyl-phenyl;

enantiomer B, a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-cyano-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-fluoro-4-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-4-trifluoromethyl-phenyl;

a compound of Formula (Ia) wherein A is benzo, W is C($R_4$), $R_4$ is bromo, X is S, $R_1$ is s-butyl, $R_2$ is s-butyl, $R_3$ is H, L is $OCH_2$, and B is 3,4-difluoro-phenyl;

a compound of Formula (Ia) wherein A is benzo, W is C($R_4$), $R_4$ is bromo, X is S, $R_1$ is 3-methyl-butoxy, $R_2$ is 3-methyl-butoxy, $R_3$ is H, L is $CH_2$, and B is 3,4-difluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-4-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-fluoro-5-trifluoromethyl-phenyl;

a compound of Formula (Ia) wherein A is 4-fluoro-benzo, W is C($R_4$), $R_4$ is bromo, X is O, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-5-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-trifluoromethyl-phenyl; and a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-5-trifluoromethyl-phenyl.

Further embodiments of the present invention are directed to a compound of Formula (Ib)

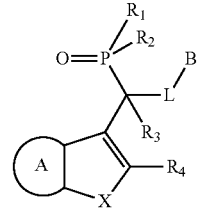

Formula (Ib)

selected from the group consisting of:

a compound of Formula (Ib) wherein A is benzo, $R_4$ is H, X is S, $R_1$ is ethoxy, $R_2$ is ethoxy, $R_3$ is H, L is $CH_2$, and B is 2-fluoro-phenyl;

a compound of Formula (Ib) wherein A is 5-fluoro-benzo, $R_4$ is H, X is S, $R_1$ is ethoxy, $R_2$ is ethoxy, $R_3$ is H, L is $CH_2$, and B is 4-fluoro-phenyl; and a compound of Formula (Ib) wherein A is 5-chloro-benzo, $R_4$ is H, X is N(phenyl), $R_1$ is ethoxy, $R_2$ is ethoxy, $R_3$ is H, L is $CH_2$, and B is 4-fluoro-phenyl.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition comprising the dextrorotatory enantiomer of a compound of formula (I) wherein said composition is substantially free from the levorotatory isomer of said compound. In the present context, substantially free means less than 25%, preferably less than 10%, more preferably less than 5%, even more preferably less than 2% and even more preferably less than 1% of the levorotatory isomer calculated as.

$$\% \text{ levorotatory} = \frac{(\text{mass levorotatory})}{(\text{mass dextrorotatory}) + (\text{mass levorotatory})} \times 100$$

Another embodiment of the present invention is a composition comprising the levorotatory enantiomer of a compound of formula (I) wherein said composition is substantially free from the dextrorotatory isomer of said compound. In the present context, substantially free from means less than 25%, preferably less than 10%, more preferably less than 5%, even more preferably less than 2% and even more preferably less than 1% of the dextrorotatory isomer calculated as $$\% \text{ dextrorotatory} = \frac{(\text{mass dextrorotatory})}{(\text{mass dextrorotatory}) + (\text{mass levorotatory})} \times 100$$

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more than one pharmaceutically acceptable carrier, excipient or diluent.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation (intratracheal or intranasal) or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly, subcutaneously, intradermally or intrathecally. In this case, the compositions will comprise a suitable carrier or diluent.

For parenteral administration, the compositions are best used in the form of a sterile aqueous solution which may contain other substances, for example, enough salts or monosaccharides to make the solution isotonic with blood.

For buccal or sublingual administration, the compositions may be administered in the form of tablets or lozenges, which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral, etc.). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations also may be coated with substances such as sugars or be entericly-coated so as to modulate the major site of absorption. For parenteral administration, the carrier will usually consist of sterile water, and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to achieve an appropriate therapeutic level. The above dosages are thus exemplary of the average case. There can be, of course, individual instances wherein higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as analgesics is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

As antagonists of the TRPM8 ion channel, the compounds of Formula (I) are useful in methods for treating or preventing a disease or condition in a mammal in which the disease or condition is affected by the modulation of TRPM8 receptors. Such methods comprise administering to a mammal in need of such treatment or prevention a therapeutically effective amount of a compound, salt or solvate of Formula (I). In particular, the compounds of Formula (I) are useful for preventing or treating chronic or acute pain, or diseases causing such pain or conditions, pulmonary or vascular dysfunction. More particularly, the compounds of Formula (I) are useful for preventing or treating inflammatory pain, inflammatory hypersensitivity conditions, neuropathic pain, anxiety and depression by administering to a subject in need thereof a therapeutically effective amount of a compound of Formula (I).

Examples of inflammatory pain include pain due to a condition or pain state selected from the group consisting of inflammatory bowel disease, visceral pain, migraine, post herpetic neuralgia, post operative pain, osteoarthritis, rheumatoid arthritis, back pain, lower back pain, joint pain, abdominal pain, chest pain, labor, musculoskeletal diseases, skin diseases, fibromyalgia, toothache, pyresis, burn, sunburn, snake bite, venomous snake bite, spider bite, insect sting, neurogenic/overactive bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual, endometriosis, sinus headache, tension headache, migraines and arachnoiditis.

One type of inflammatory pain is inflammatory hyperalgesia, which can be further distinguished as inflammatory somatic hyperalgesia or inflammatory visceral hyperalgesia.

Inflammatory somatic hyperalgesia may be characterized by the presence of an inflammatory hyperalgesic state in which a hypersensitivity to thermal, mechanical and/or chemical stimuli exists. Inflammatory visceral hyperalgesia may also be characterized by the presence of an inflammatory hyperalgesic state, however, with this state an enhanced visceral irritability exists.

Examples of inflammatory hyperalgesia include a condition or pain state selected from the group consisting of inflammation osteoarthritis, rheumatoid arthritis, back pain, joint pain, abdominal pain, musculoskeletal diseases, skin diseases, post operative pain, headaches, fibromyalgia, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, inflammatory bowel diseases, such as Crohn's Disease, and ulcerative colitis.

One embodiment of the present invention is directed to a method for treating inflammatory somatic hyperalgesia in which a hypersensitivity to thermal, mechanical and/or chemical stimuli exists, comprising the step of administering to a mammal in need of such treatment a therapeutically effective amount of a compound, salt or solvate of Formula (I).

A further embodiment of the present invention is directed to a method for treating inflammatory visceral hyperalgesia in which an enhanced visceral irritability exists, comprising the step of administering to a mammal in need of such treatment a therapeutically effective amount of a compound, salt or solvate of Formula (I).

A further embodiment of the present invention is directed to a method for treating neuropathic cold allodynia in which a hypersensitivity to a cooling stimuli exists, comprising the step of administering to a mammal in need of such treatment a therapeutically effective amount of a compound, salt or solvate of Formula (I).

Examples of an inflammatory hypersensitivity condition are urinary incontinence, benign prostatic hypertrophy, cough, asthma, rhinitis and/or nasal hypersensitivity, itch, contact dermatitis and/or dermal allergy, and chronic obstructive pulmonary disease.

Examples of a neuropathic pain include pain due to a condition or pain state selected from the group consisting of cancer, neurological disorders, spine and peripheral nerve surgery, brain tumors, traumatic brain injury (TBI), spinal cord trauma, chronic pain syndromes, chronic fatigue syndrome, neuralgias (trigeminal neuralgia, glossopharyngeal neuralgia, postherpetic neuralgia and causalgia), lupus, sarcoidosis, peripheral neuropathy, bilateral peripheral neuropathy, diabetic neuropathy, central pain, neuropathies associated with spinal cord injury, stroke, ALS, Parkinson's disease, or multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, and vidian neuralgia.

One type of neuropathic pain is neuropathic cold allodynia, which may be characterized by the presence of a neuropathy-associated allodynic state in which a hypersensitivity to cooling stimuli exists. Examples of neuropathic cold allodynia include allodynia due to a condition selected from the group consisting of neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

Examples of anxiety are selected from the group consisting of social anxiety, post traumatic stress disorder, phobias, social phobia, special phobias, panic disorder, obsessive compulsive disorder, acute stress disorder, separation anxiety disorder, and generalized anxiety disorder.

Examples of depression are selected from the group consisting of major depression, bipolar disorder, seasonal affective disorder, post natal depression, manic depression, and bipolar depression.

One embodiment of the present invention is directed to a method of treating or preventing migraine, prophylactic migraine, or hypertension in a mammal, which method comprises administering to a mammal in need of such treatment or prevention a therapeutically effective amount of a TRPM8 antagonist.

A therapeutically effective amount for use of the instant compounds or a pharmaceutical composition thereof comprises a dose range from about 0.1 mg to about 3000 mg, in particular from about 1 mg to about 1000 mg or, more particularly, from about 10 mg to about 500 mg of active ingredient in a regimen of about 1 to 4 times per day for an average (70 kg) human; although, it is apparent to one skilled in the art that the therapeutically effective amount for active compounds of the invention will vary as will the conditions being treated.

Optimal dosages of the compounds of Formula (I) to be administered for the treatment of or prevention of TRPM8-mediated disorders may be readily determined by those skilled in the art, and will vary with the particular compound used, the mode of administration, the strength of the preparation, and the advancement of the disease condition. In addition, factors associated with the particular patient being treated, including patient age, weight, diet and time of administration, will result in the need to adjust dosages.

For oral administration, a pharmaceutical composition is preferably provided in the form of tablets containing 0.01, 10.0, 50.0, 100, 150, 200, 250, and 500 milligrams of the active ingredient for the symptomatic adjustment of the dosage to the subject to be treated.

General Synthetic Methods

Representative compounds of the present invention can be synthesized in accordance with the general synthetic methods described below and are illustrated in the schemes that follow. Since the schemes are an illustration, the invention should not be construed as being limited by the chemical reactions and conditions expressed. The preparation of the various starting materials used in the schemes is well within the skill of persons versed in the art.

Abbreviations used in the instant specification, particularly the Schemes and Examples, are as follows:

| | |
|---|---|
| [α] | specific rotation |
| AcOH | glacial acetic acid |
| AIBN | 2,2'-azobisisobutyronitrile |
| Bn or Bzl | benzyl |
| BCTC | 4-(3-chloro-pyridin-2-yl)-piperizine-1-carboxylic acid (4-tert-butyl-phenyl)-amide |
| BuLi | butyllithium |
| Cpd | compound |
| DAST | (diethylamino)sulfur trifluoride |
| DCE | 1,2-dichloroethane |
| DCM | dichloromethane |
| DDQ | 2,3-dichloro-5,6-dicyano-1,4-benzoquinone |
| DMF | N,N-dimethylformamide |
| DMSO | dimethylsulfoxide |
| DIEA | diisopropylethylamine |
| dppf | 1,1'-bis(biphenylphosphine)ferrocene |
| EDTA | ethylenediaminetetraacetic acid |
| $Et_2O$ | diethyl ether |
| EtOAc | ethyl acetate |
| EtOH | ethanol |
| h | hour |
| HEK | human embryonic kidney |
| HPLC | High Performance Liquid Chromatography |
| HEPES | 4-(2-hydroxyethyl)-1-piperazine-ethanesulfonic acid |
| KOtBu | potassium t-butoxide |
| LAH | lithium aluminum hydride |
| Me | methyl |
| MeOH | methanol |
| min | minutes |
| Me | methyl |
| $MnO_2$ | manganese (IV) oxide |
| mpk | milligrams per kilogram |
| MSNT | 1-(mesitylene-2-sulfonyl)-3-nitro-1,2,4-triazole |
| NBS | N-bromosuccinimide |
| NT | not tested |
| oxone | potassium peroxymonosulfate |
| Ph | Phenyl |
| Pd/C | palladium on activated carbon |
| $PdCl_2$(dbfp) | 1,1'-bis (di-tertbutylphosphino)ferrocene palladium dichloride |
| $Pd(OAc)_2$ | palladium(II) acetate |
| $Ph_3P$ | triphenylphosphine |
| PPA | polyphosphoric acid |
| rt | room temperature |
| $TEA/Et_3N$ | triethylamine |
| THF | tetrahydrofuran |
| TMS | tetramethylsilane |
| TMS-Br | trimethylsilyl bromide |

General Synthetic Methods

Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art.

For illustrative purposes only, the intermediates of the following Schemes are those wherein D of Formula (I) is d-2. Compounds wherein D of Formula (I) is d-1 may also be prepared by the general methods described herein with the appropriate starting materials.

Scheme A illustrates the synthesis of compounds of Formula (I) wherein A, D, and W are as defined in Formula (I), and more specifically, wherein W is $C(R_4)$ and $R_4$ is hydrogen or methyl, and X is O or S. $R_a$ of Scheme A is $R_1$ or $R_2$, wherein is $R_1$ and $R_2$ are each $C_{1-8}$alkoxy, and L is $(CH_2)_n$.

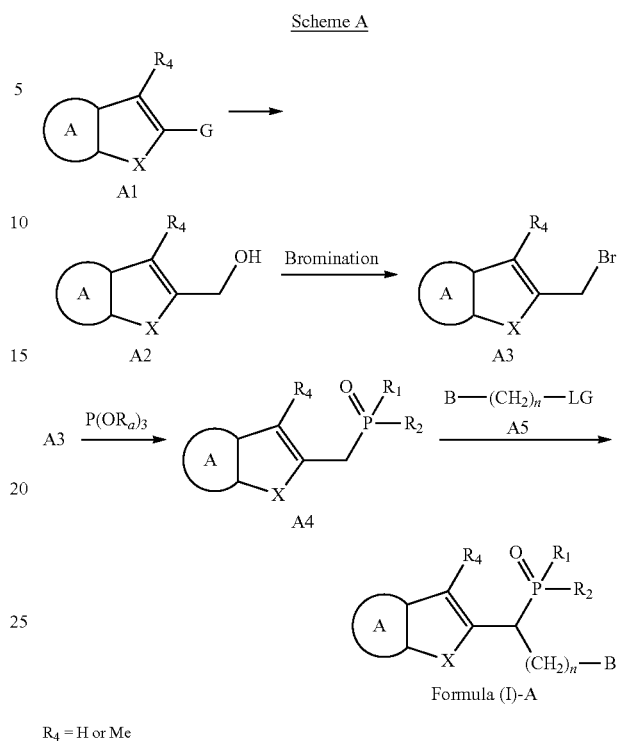

Scheme A $R_4$ = H or Me

A compound of formula A1 is either commercially available or may be prepared by known methods described in the scientific literature. Substituent G of compounds of formula A1 is a functional group that is readily converted to a methyl alcohol, such as an aldehyde, ester, anhydride, or carboxylic acid. A compound of formula A1 is converted to a compound of formula A2 using reagents and methods known to one skilled in the art. The alcohol functional group of a compound of formula A2 may be converted to its corresponding bromide of formula A3 using phosphorus tribromide, or the like. A compound of Formula A3 may be reacted with a trialkoxy phosphite to yield a compound of Formula A4. Treatment of a compound of formula A4 with an organometallic base such as n-butyllithiium or bis-lithium(trimethylsilyl)amide, followed by alkylation with a compound of formula A5 (wherein B is $C_{6-10}$aryl or a heteroaryl as defined herein) affords a compound of Formula (I)-A. Compounds of formula A5 are either commercially available or may be prepared by known methods described in the scientific literature. The LG group of formula A5 is an appropriate leaving group such as chloride, bromide, or the like.

Scheme B illustrates an alternate route for the preparation of certain intermediates of formula A1 wherein $R_4$ is hydrogen or $C_{1-6}$alkyl.

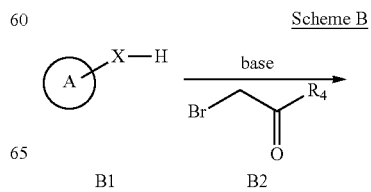

Scheme B

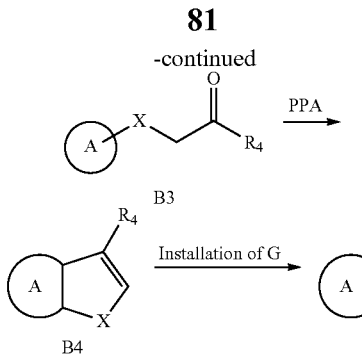

An alcohol or thiol of formula B1 (X is O or S) maybe alkylated in the presence of a base and a compound of formula B2 to yield a compound of formula B3. When X of formula B1 is oxygen, an appropriate base is sodium hydride; likewise, when X is sulfur, an appropriate base is pyridine or other tertiary amine. Treatment of a compound of formula B3 with PPA (polyphosphoric acid) provides a cyclized compound of formula B4. The installation of G may be achieved using reagents and methods known to one skilled in the art. For example, NBS or bromine in acetic acid may be used to brominate the vinylic carbon atom adjacent to X. Subsequent treatment of the vinyl bromide with n-butyllithium and DMF may generate a compound of formula A1 wherein G is an aldehyde. Alternatively, the aforementioned bromide may be carboxylated using carbon dioxide in the presence of a palladium catalyst in an aprotic solvent to afford a compound of formula A1 wherein G is a carboxyl group. Similarly, a compound of formula A1 wherein G is an ester may be prepared by the treatment via alkoxy-carbonylation of the vinyl bromide with carbon dioxide in the presence of a palladium catalyst in an alcoholic solvent.

Scheme C illustrates an alternate route for the synthesis of intermediates of formula C4 wherein W is $C(R_4)$ and $R_4$ is other than $C_{1-6}$alkoxy, $C_{1-6}$alkoxycarbonyl. In Scheme C, X is O or S and G is an ester.

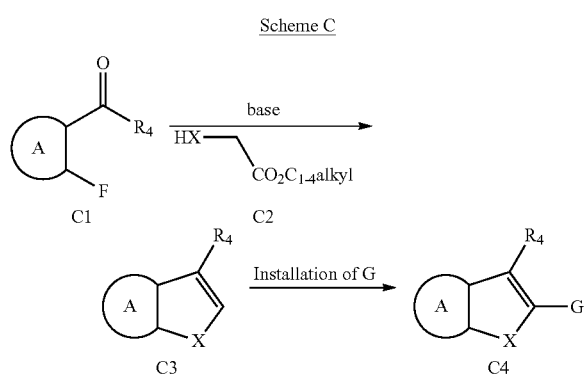

A compound of formula C1 is either commercially available or may be prepared by known methods described in the scientific literature. A compound of formula C1 may be treated with a base such as sodium hydride (or TEA when $R_4$ is trifluoromethyl), followed by the addition of an α-hydroxy or α-thiol substituted ester of formula C2 to afford a compound of formula C3. A compound of formula C3 may be further reacted using the synthetic methods described herein above to form a compound of formula C4.

Scheme D illustrates the synthesis of certain compounds of Formula (I) wherein A and D are as defined herein, and specifically wherein W is $C(R_4)$ and $R_4$ is bromo, chloro, $C_{6-10}$aryl, or a heteroaryl; X is O or S; $R_1$ and $R_2$ are each $C_{1-8}$alkoxy or $C_{1-8}$alkyl, and L is $(CH_2)_n$.

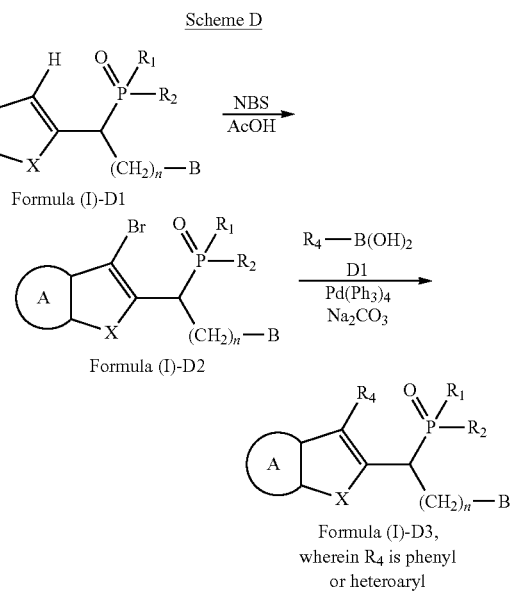

A compound of Formula (I)-D1 wherein $R_4$ is hydrogen may be treated with N-bromosuccinimide to give a compound of Formula (I)-D2 wherein $R_4$ is bromo. Similarly, a compound of Formula (I)-D1 may be converted to a compound of Formula (I)-D2 (wherein $R_4$ is chloro) by treatment with a chlorinating agent such as N-chlorosuccinimide or the like. A compound of Formula (I)-D2 may be cross-coupled with a boronic acid of formula D1 (wherein $R_4$ is phenyl or a heteroaryl as defined herein) in the presence of carbonate anion and a palladium catalyst to afford a compound of Formula (I)-D3. A compound of Formula (I)-D2 wherein $R_4$ is bromo may also be useful as an intermediate for the preparation of compounds wherein $R_4$ is $C_{1-6}$alkoxycarbonyl or cyano. A compound of Formula (I) wherein $R_4$ is $C_{1-6}$alkoxycarbonyl may be prepared by a palladium catalyzed alkoxy-carbonylation in the presence of an alcoholic solvent such as methanol, ethanol, or the like. Similarly, compound of Formula (I) wherein $R_4$ is cyano may be prepared by a palladium catalyzed reaction in the presence of zinc (II) cyanide.

Scheme E illustrates the synthesis of compounds of Formula (I) wherein X is O or S, and $R_1$ and $R_2$ are each $C_{1-8}$alkyl.

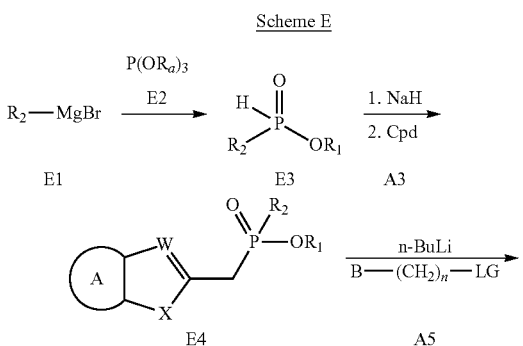

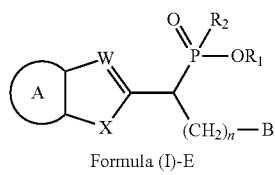

Formula (I)-E

A compound of formula E1 is either commercially available or may be prepared by known methods in the scientific literature. A trialkoxy phosphite of formula E2 may be treated with a compound of formula E1 to form a compound of formula E3. A compound of formula E3 may be deprotonated at the phosphorus atom and alkylated with a compound of formula A3 to form a compound of Formula E4. A compound of formula E4 may be treated with an organometallic base such as n-butyllithium and alkylated with a compound of formula A5 to afford a compound of Formula (I)-E.

Scheme F illustrates the synthesis of compounds of Formula (I) wherein X is O or S, and $R_1$ and $R_b$ are each $C_{1-8}$alkyl.

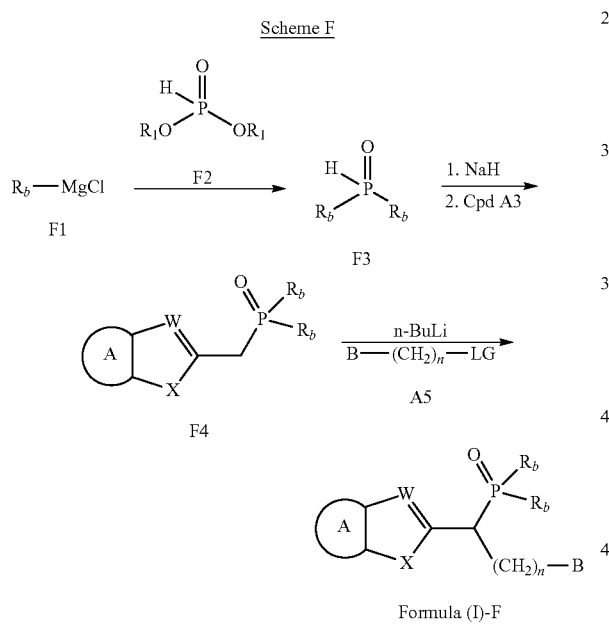

Scheme F

Formula (I)-F $R_b = C_{1-8}$alkyl

A compound of formula F1 (wherein $R_b$ is $C_{1-8}$alkyl) may be treated with a compound of formula F2 in the presence of aqueous carbonate anion to form a compound of formula F3. A compound of formula F3 may be deprotonated with a strong base and treated with a compound of formula A3 to form a compound of formula F4. A compound of formula F4 may be deprotonated and subsequently alkylated with a compound of formula A3 as described herein to yield a compound of Formula (I)-F.

Scheme G illustrates the synthesis of compounds of Formula (I) wherein X is O or S, and $R_1$ is $C_{1-8}$alkoxy and $R_2$ is $C_{1-8}$alkoxy or $C_{1-8}$alkyl. More specifically, Scheme G describes the preparation of compounds in which $R_1$ is a $C_{1-8}$alkoxy substituted with an appropriate substituent as defined in Formula (I).

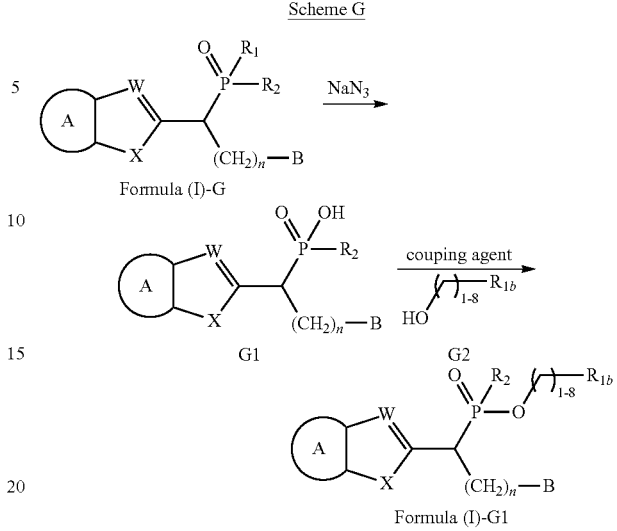

Scheme G

Formula (I)-G

G1

G2

Formula (I)-G1

$R_{1b}$ = substituent of $R_1$ alkoxy or alkyl

A compound of Formula (I)-G may be treated with sodium azide to form a compound of formula G1. The hydroxy substituent of formula G1 may be coupled with a $R_{1b}$-substituted alcohol of formula G2 in the presence of a standard coupling agent, such as MSNT, to afford a compound of Formula (I)-G1.

Scheme H illustrates the synthesis of compounds of Formula (I) wherein $R_3$ is methyl, and D is d-1 or d-2.

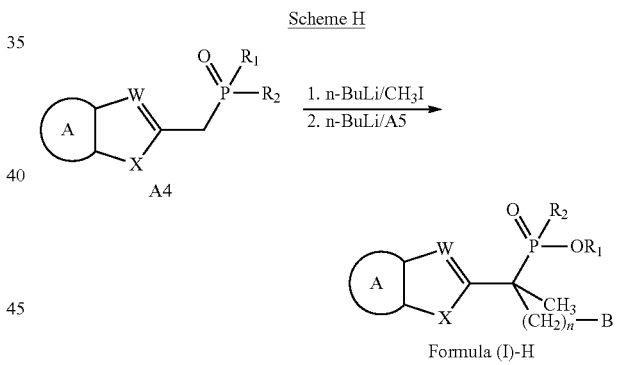

Scheme H

A4

Formula (I)-H

A compound of formula A4 may be treated with a base, such as n-butyllithium, followed by addition of a methylating agent such as methyl iodide to install a methyl group of $R_3$. Subsequent treatment with a second equivalent of n-butyllithium followed by alkylation with a compound of formula A5 affords a compound of Formula (I)-H.

Scheme I illustrates the synthesis of compounds of Formula (I) wherein X is S(=O) or S(O₂) and D is d-1 or d-2.

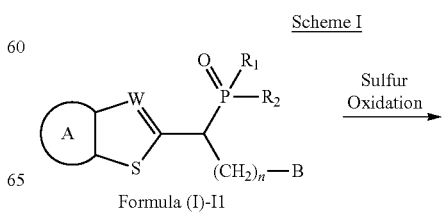

Scheme I

Sulfur Oxidation

Formula (I)-I1

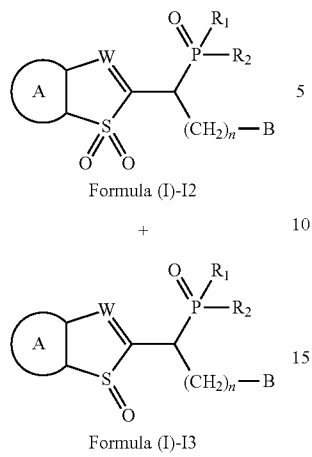

Formula (I)-I2

+

Formula (I)-I3

A compound of Formula (I)-I1 wherein X is sulfur may be treated with an oxidizing agent such as oxone, hydrogen peroxide, sodium hypochlorite, or the like, to afford a mixture of compounds of Formula (I)-I2 and Formula (I)-I3. Isolated compounds may be obtained from the mixture using separation techniques known to one of skill in the art.

Scheme J illustrates the synthesis of compounds of Formula (I) wherein L is absent, $R_3$ is hydrogen, and D is d-1 or d-2.

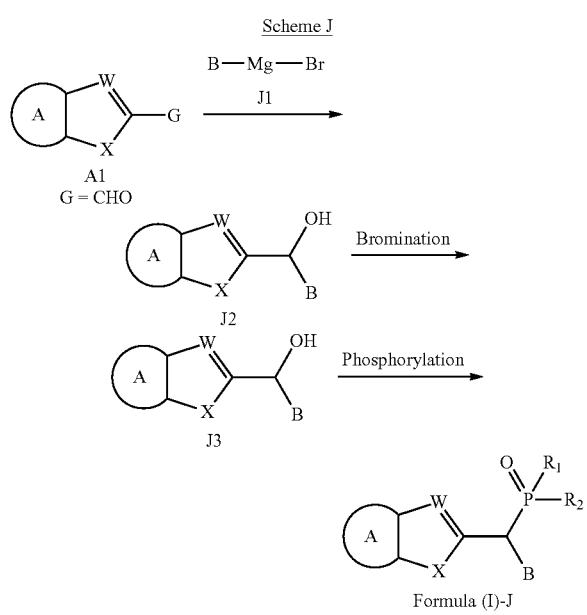

A compound of formula A1 wherein G is an aldehyde may be treated with a B-substituted Grignard reagent of formula J1 to form the alcohol of formula J2. Treatment of the alcohol with a brominating agent such as phosphorus tribromide or the like affords a compound of formula J3, which may be phosphorylated according to the methods described herein to form a compound of Formula (I)-J.

Scheme K illustrates the preparation of compounds of Formula (I) wherein $R_3$ is fluoro, $R_1$ and $R_2$ are $C_{1-6}$alkoxy, and D is d-1 or d-2.

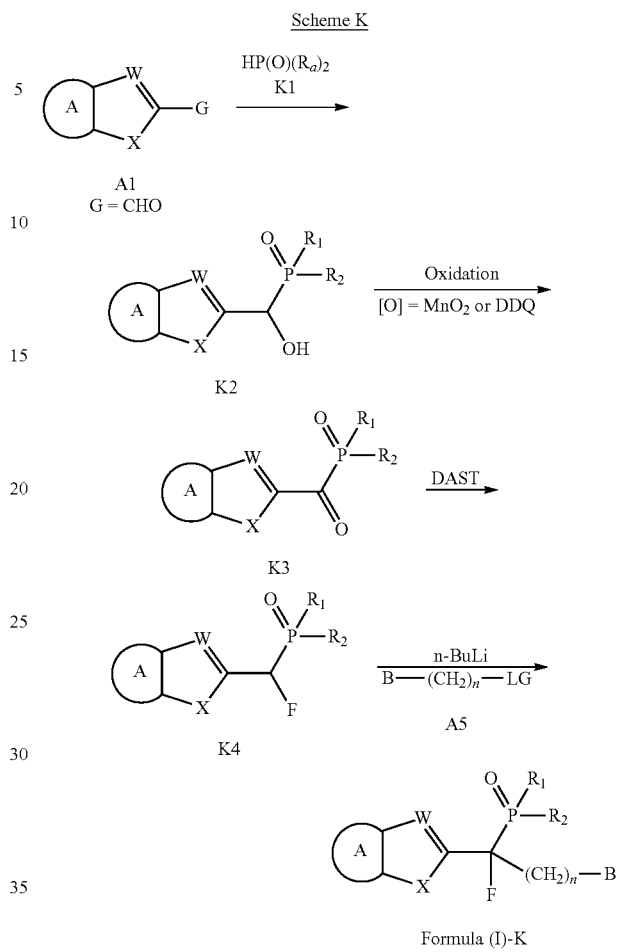

$R_a = R_1$ or $R_2$

A compound of formula A1 wherein G is an aldehyde may be treated with a phosphorylating agent of formula K1 to form an alcohol of formula K2. The alcohol of formula K2 may be oxidized with an appropriate oxidizing agent, such as manganese (IV) oxide or DDQ, to form the corresponding carbonyl compound of formula K3. Treatment of a compound of formula K3 with DAST ((diethylamino)sulfur trifluoride) affords the fluorinated compound of formula K4. Treatment of a compound of formula K4 with an organometallic base such as n-butyllitihium, followed by alkylation with a compound of formula A5 provides a compound of formula (I)-K.

Scheme L describes the preparation of compounds of the present invention wherein $R_1$ and $R_2$ are $C_{1-6}$alkoxy, $R_3$ is hydroxy, and D is d-1 or d-2.

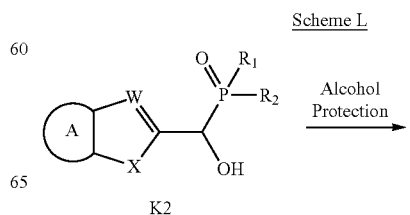

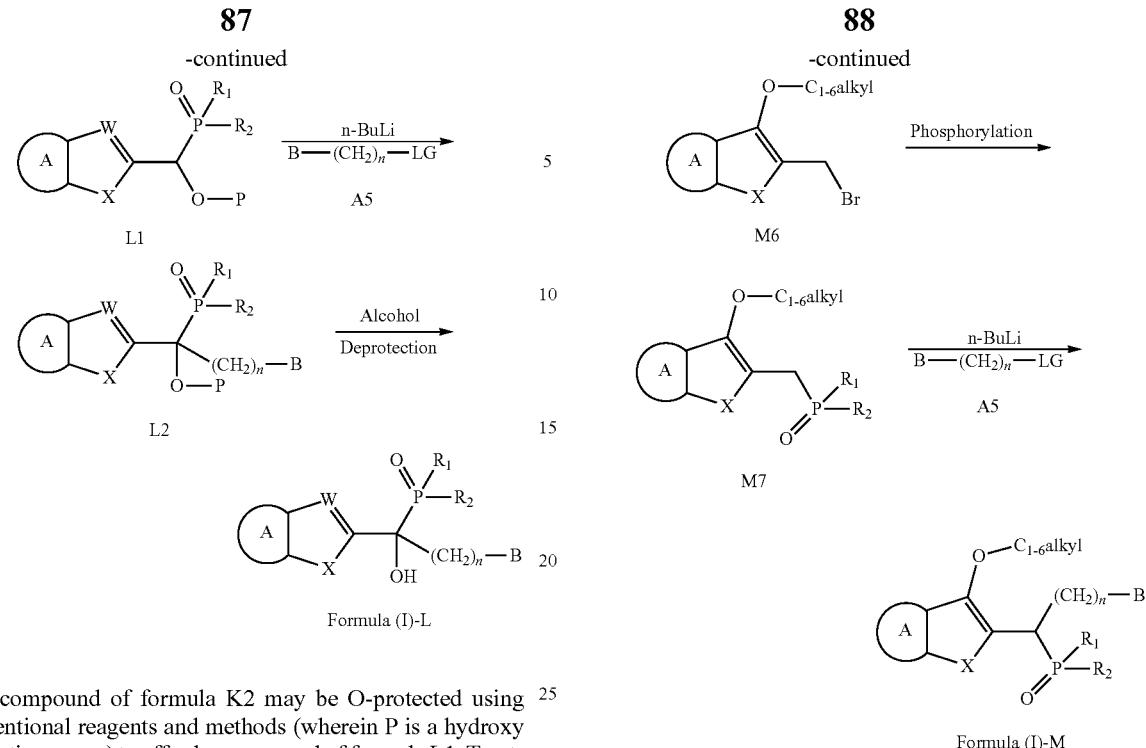

A compound of formula K2 may be O-protected using conventional reagents and methods (wherein P is a hydroxy protecting group) to afford a compound of formula L1. Treatment of a compound of formula L1 with an organometallic base followed by alkylation with a compound of formula A5 provides a compound of formula L2. Removal of hydroxy-protecting group P may be achieved using conventional methods to afford a compound of Formula (I)-L.

Scheme M describes the preparation of certain compounds of Formula (I) wherein W is $C(R_4)$ and $R_4$ is $C_{1-6}$alkoxy, X is O, S, or N—$R_6$, and ring A is benzo. D is d-1 or d-2.

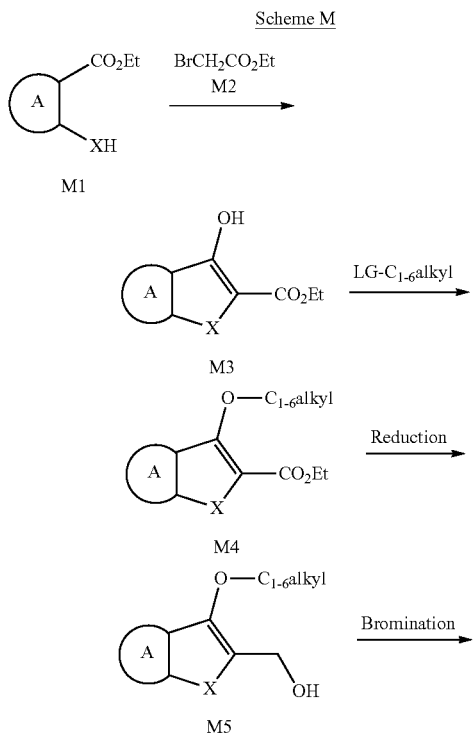

A compound of formula M1 may be cyclized with a compound of formula M2 to form a fused ring system of formula M3. The hydroxy substituent of M3 may be alkylated with a standard alkylating agent (wherein LG is defined herein) to form an $R_4$— alkoxy substituent of formula M4. Reduction of the ester group of a compound of formula M4 using a borane complex, lithium aluminum hydride, or the like, provides a primary alcohol of formula M5 which may be converted to its corresponding bromide using reagents and methods taught herein. The bromide may then be phosphorylated and then alkylated with a compound of formula A5 to form a compound of Formula (I)-M.

Scheme N describes the preparation of certain intermediates to prepare compounds of Formula (I) wherein W is $C(R_4)$ and $R_4$ is $C_{1-6}$alkoxy, X is O, S, or N—$R_6$, and ring A is pyrido. D is d-1 or d-2.

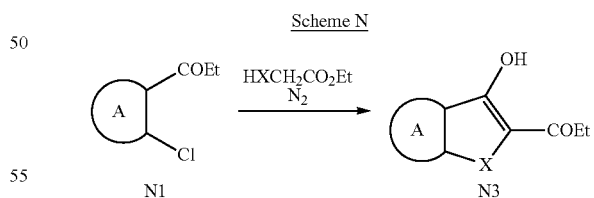

A compound of formula N1 may be cyclized with a compound of formula N2 (wherein X is S, O, or N—$R_6$) to form a fused ring system of formula N3. A compound of formula N3 may be further elaborated to a compound of Formula (I) using the synthetic sequence described for compounds of formula M3.

Scheme P describes the preparation of certain compounds of Formula (I) wherein $R_4$ is bromo or chloro, X is N—H (wherein $R_6$ is H), and ring A is benzo. D is d-1 or d-2.

89

Scheme P

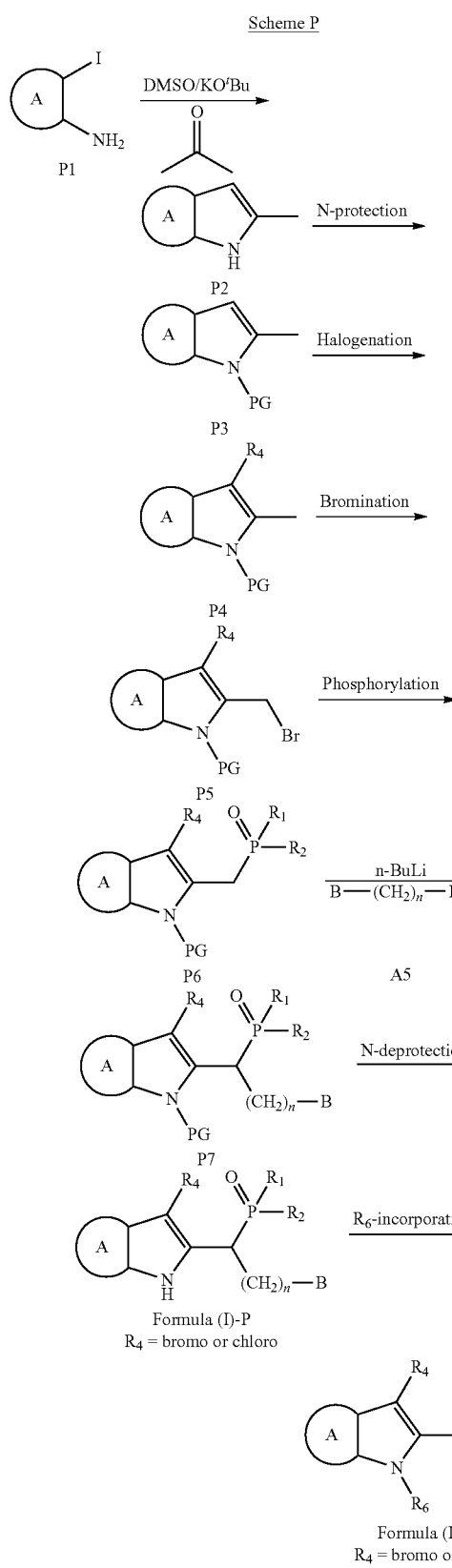

90 tected using a standard nitrogen protecting group (PG) to give a compound of formula P3. The 3-position of the indole may be chlorinated or brominated using N-chlorosuccinimide or N-bromosuccinimide, respectively, to give a compound of formula P4 (wherein $R_4$ is chloro or bromo). The methyl group of a compound of formula P4 may be converted to its methyl bromide using a brominating agent such as N-bromosuccinimide to afford a compound of formula P5 that is readily phosphorylated, according to the methods described herein, to give a compound of formula P6. Alkylation with a compound of formula A5 yields a compound of formula P7, which, upon removal of the nitrogen protecting group PG, affords a compound of Formula (I)-P. The indole amino group (wherein X=NH) may be substituted with other $R_6$ substituents of the present invention using conventional synthetic methods and reagents to provide compounds of Formula (I)-P1. For example, an alkyl halide, allyl bromide, acid chloride, or sulfonyl chloride may be used for the installation of the respective $R_6$ groups. Arylation of the indole amine may be achieved by nucleophilic aromatic displacement to afford compounds wherein $R_6$ is phenyl. Treatment of the indole amine with a strong base such as sodium hydride, followed by the addition of a fluoro-substituted pyridinyl will afford a compound of Formula (I) wherein $R_6$ is pyridinyl.

Scheme Q describes the preparation of certain compounds of Formula (I) wherein W is C($R_4$), X is O, S, or N—$R_6$, and ring A is benzo substituted with aminocarbonyl, ($C_{1-2}$alkyl) aminocarbonyl, or di($C_{1-2}$alkyl)aminocarbonyl. In Scheme Q, D is d-1 or d-2, and $R_{30}$ and $R_{31}$ are hydrogen or $C_{1-2}$alkyl.

Scheme Q

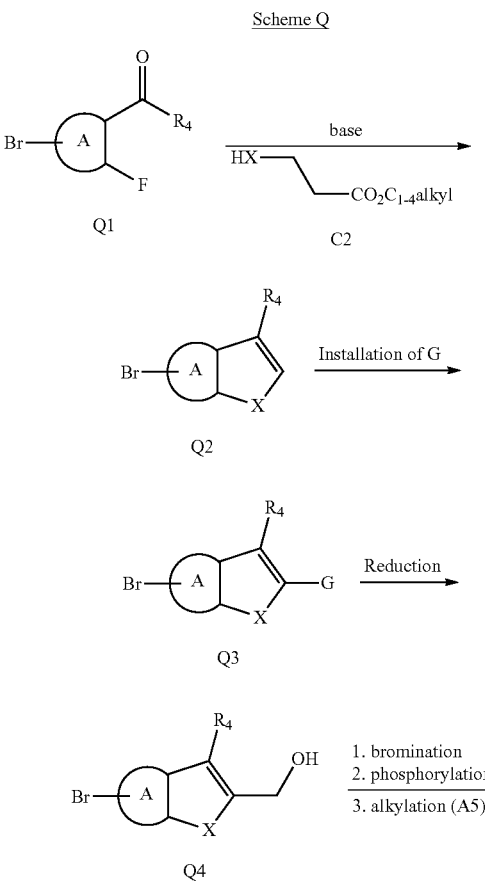

A compound of formula P1 may be treated with DMSO, potassium t-butoxide, and acetone to form a 2-methyl substituted indole of formula P2. The indole nitrogen may be pro- -continued

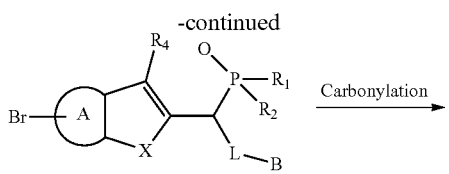

Q5

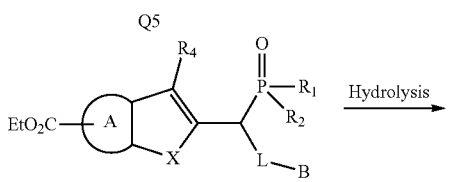

Q6

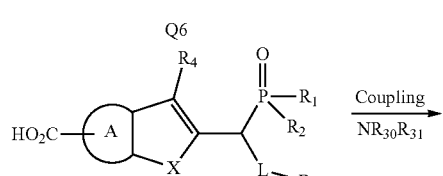

Q7

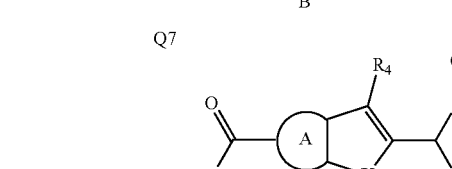

Formula (I)-Q

A compound of formula Q1 may be cyclized with a compound of formula C2 to form a fused ring system of formula Q2. Using chemistry described herein in Scheme B, a compound of formula Q2 can be converted to a compound of formula Q3. Reduction of substituent G of a compound of formula Q3 using a hydride source, borane complex, lithium aluminum hydride, or the like, provides a primary alcohol of formula Q4. A compound of formula Q4 may be converted to its corresponding bromide using reagents and methods taught herein. The bromide may then be phosphorylated and subsequently alkylated with a compound of formula A5 to form a compound of formula Q5. Carbonylation of a compound of formula Q5 to afford a compound of formula Q6 may be achieved using a palladium source, such as dichlorobis(triphenylphosphine)palladium (II), carbon monoxide, and a suitable alcoholic solvent, such as ethanol or methanol. Subsequent hydrolysis of the ester of a compound of formula Q6 may be achieved using known methods in the scientific literature to afford a compound of formula Q7, which can be coupled with an amine of formula HNR$_{30}$R$_{31}$ using known methods in the scientific literature to afford a compound of Formula (I)-Q.

Scheme R describes the preparation of certain compounds of Formula (I) wherein W is C(R$_4$) and R$_4$ is a C$_{1-6}$alkoxycarbonyl substituent, X is O, S, or N—R$_6$, and ring A is benzo or pyrido. D is d-1 or d-2.

Scheme R

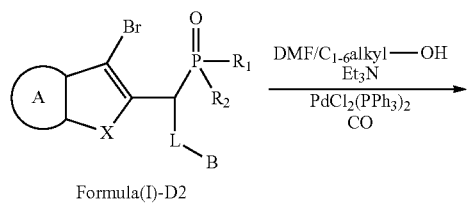

Formula(I)-D2

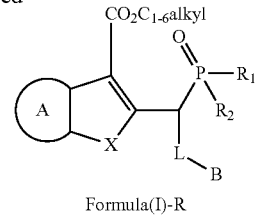

Formula(I)-R

Carbonylation of a compound of Formula (I)-D2 to afford a compound of formula Formula (I)-R may be achieved using a palladium source, such as dichlorobis(triphenylphosphine) palladium (II), carbon monoxide, and a suitable alcoholic solvent (C$_{1-6}$alkyl-OH).

Scheme S describes the preparation of certain compounds of Formula (I)-S wherein W is C(R$_4$), wherein R$_4$ is cyano, X is O, S, or N—R$_6$, and ring A is a benzo or pyrido. D is d-1 or d-2.

Scheme S

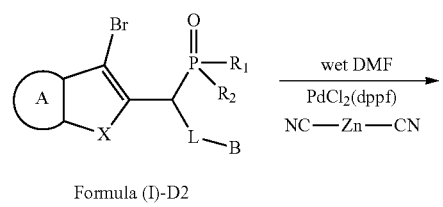

Formula (I)-D2

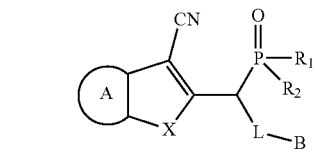

Formula (I)-S

Cyanation of a compound of Formula (I)-D2 to afford a compound of formula Formula (I)-S may be achieved using a cyanide source, such as zinc cyanide, copper (I) cyanide, or sodium cyanide, and an appropriate solvent, such as dimethylformamide, N-methylpyrrolidine, or dimethylacetamide (DMA).

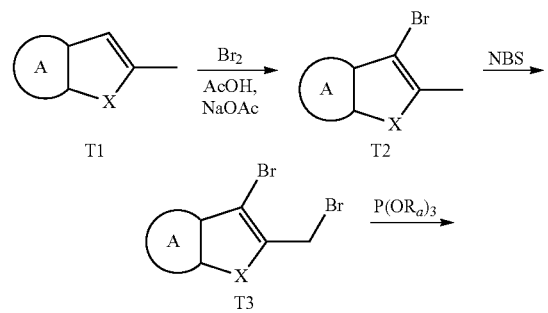

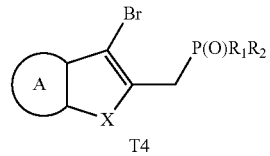

T4

Scheme T illustrates the preparation of intermediate T3 wherein W is C(R$_4$), R$_4$ is bromo, X is O, S, or N-PG, and ring A is a benzo or pyrido. D is d-1 or d-2.

A 2-methyl substituted compound of formula T1 may be treated with bromine and sodium acetate in acetic acid to form a compound of formula T2 wherein $R_4$ is bromo. The 2-methyl substituent of a compound of formula T2 may be converted to its corresponding 2-methyl bromide T3 using N-bromosuccinimide. Compounds of formula T3 may be converted to certain compounds of Formula (I) using analogous chemistry to that described for compounds of formula A3 to compounds of Formula (I).

Alternatively, a compound of formula T3 may be phosphonylated to the corresponding compound of formula T4 according to the conditions described in Scheme A for the conversion of a compound of formula A3 to a compound of formula A4. Subsequently, a compound of formula T4 may be taken to form compounds of Formula (I) using potassium t-butoxide in THF/diethyl ether at about 55° C. in place of the reaction conditions described in Scheme A for the conversion of a compound of formula A4 to a compound of formula Formula (I)-A.

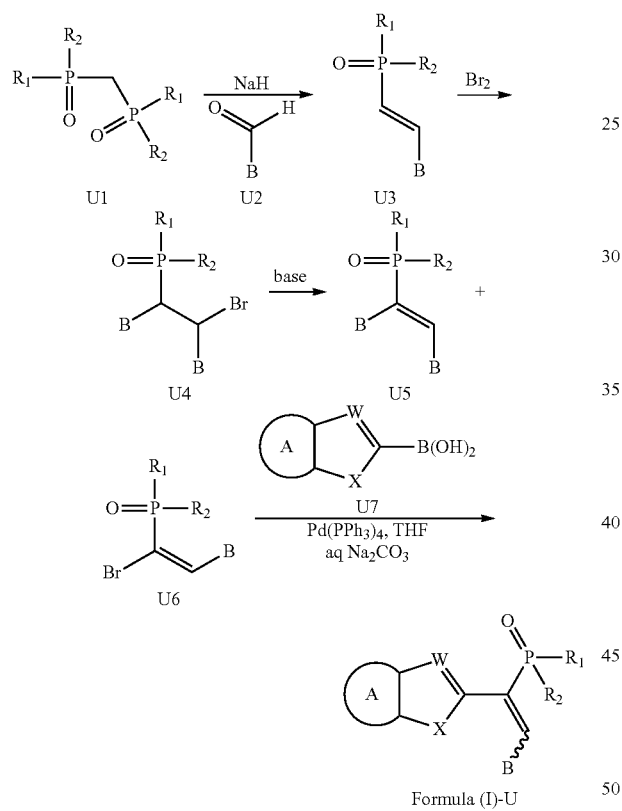

Scheme U illustrates the synthesis of compounds of Formula (I) wherein L is =CH— and $R_3$ is absent; W is $C(R_4)$; $R_4$ is as described herein; X is O, S, or N—$R_6$; and ring A is a benzo or pyrido. D is d-1 or d-2 and $R_1$ and $R_2$ are each $C_{1-8}$alkoxy.

To a solution of compound U1 under basic conditions is added an aldehyde of formula U2. Upon heating, a compound of formula U3 is formed, and the resulting alkenyl functionality may be brominated using bromine under acidic conditions to form a dibromide of formula U4. Upon addition of a base such as a tertiary amine, a mixture of alkenes of formulae U5 and U6 may be prepared. The alkene may then be coupled with a boronic acid of formula U7 in the presence of a transition metal catalyst, under basic conditions, to form a compound of Formula (I)-U Compounds of Formula (I) may be prepared enantioselectively by reaction of a compound of formula VI with a compound of formula A5 in the presence of the chiral catalyst (R,R)-2,6-bis(3,4,5-trifluorophenyl)-3,3',5,5'-tetrahydro-4,4'-spirobi[dinaphtho[2,1-c:1',2'-e]azepin]-4-ium bromide or (S,S)-2,6-bis(3,4,5-trifluorophenyl)-3,3',5,5'-tetrahydro-4,4'-spirobi[dinaphtho[2,1-c:1',2'-e]azepin]-4-ium bromide, under basic conditions to form the appropriate chiral product of formula (I)-V.

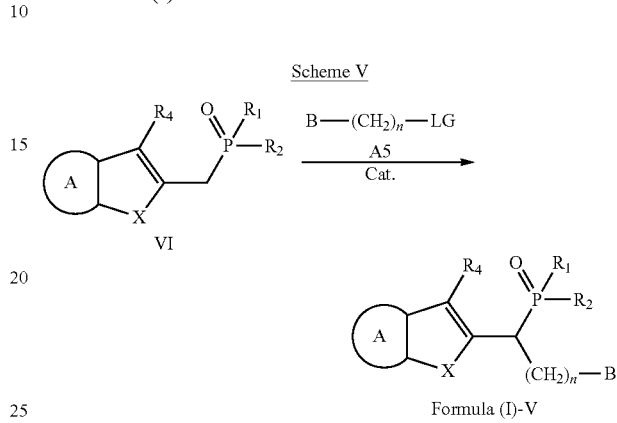

SPECIFIC EXAMPLES

Example 1

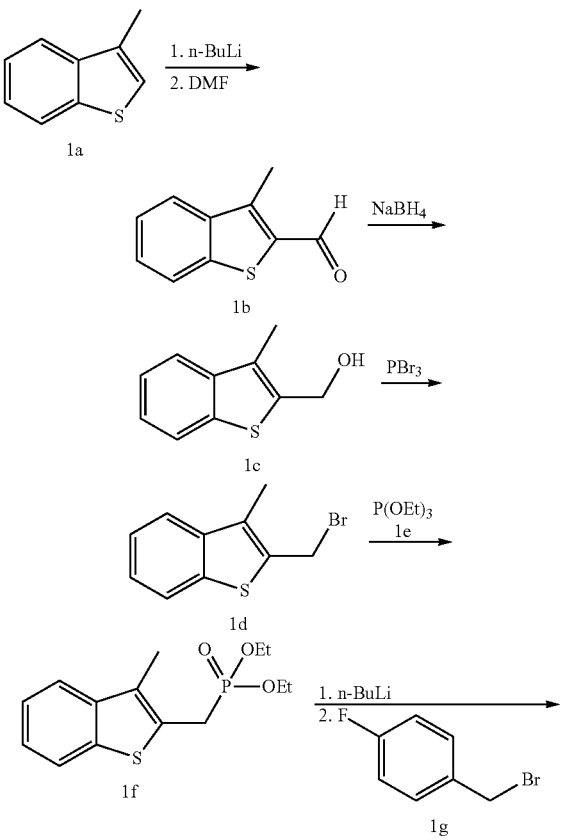

-continued

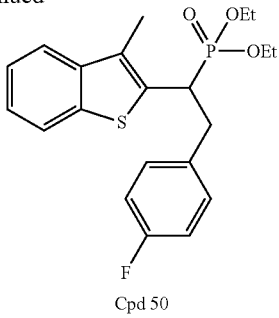

Cpd 50

A. 3-Methyl-benzo[b]thiophene-2-carboxyaldehyde. To a solution of 3-methyl-benzo[b]thiophene (Compound 1a) (4.87 g; 30.1 mmol) in anhydrous THF (50 mL), cooled to −69° C., was added a solution of 2.5 M n-butyllithium in hexanes (14.4 mL; 36.0 mmol), dropwise. The reaction was allowed to stir at −69° C. for 1 h, to which was then added anhydrous DMF (5.0 mL; 64.5 mmol), dropwise. The reaction was allowed to warm to ambient temperature, and was then refluxed for 1 h. At that time, the reaction was cooled, diluted with EtOAc, washed sequentially with $H_2O$ and brine, and dried over $Na_2SO_4$. The mixture was filtered and the solvent evaporated under reduced pressure to afford Compound 1b. $^1$H-NMR (300 MHz, DMSO-$d_6$): δ 10.34 (s, 1H), 7.85-7.90 (m, 2H), 7.42-7.53 (m, 2H), 2.79 (s, 3H).

B. (3-Methyl-benzo[b]thiophene-2-yl)-methanol. To a stirred solution of Compound 1b (2.3 g; 13.0 mmol) in MeOH (30 mL) was added sodium borohydride (1.0 g; 26.4 mol), in three equal portions, at ambient temperature. The reaction mixture was stirred for 18 h at room temperature, and then the solvent was evaporated in vacuo. The resultant residue was partitioned between EtOAc and $H_2O$, and the layers were separated. The organic phase was washed sequentially with $H_2O$ and brine, and dried over $Na_2SO_4$. The mixture was filtered and the solvent removed under reduced pressure to afford Compound 1c. $^1$H-NMR (300 MHz, DMSO-$d_6$): δ 8.08-8.10 (d, 1H), 7.89-7.91 (d, 1H), 7.49-7.59 (m, 2H), 5.72-5.75 (t, 1H), 4.92-4.94 (d, 2H), 2.53 (s, 3H).

C. 2-Bromomethyl-3-methyl-benzo[b]thiophene. To Compound 1c (2.19 g, 12.3 mmol) dissolved in anhydrous ether (40 mL) was added phosphorous tribromide (0.583 mL; 18.4 mmol) dropwise at ambient temperature. The reaction was stirred at ambient temperature for 1 h, diluted with EtOAc, washed sequentially with saturated $NaHCO_3$, $H_2O$, and brine, and then dried over $Na_2SO_4$. The mixture was filtered and the filtrate was evaporated under reduced pressure to afford Compound 1d. (Note: material is unstable and is used immediately in next step.)

D. (3-Methyl-benzo[b]thiophen-2-ylmethyl)-phosphonic acid diethyl ester. To a solution of Compound 1d (2.76 g; 11.5 mmol) in toluene (15 mL) was added triethyl phosphite, Compound 1e (2.2 mL; 12.6 mmol), and the reaction was refluxed for 18 h. The reaction mixture was cooled, concentrated under reduced pressure and the resultant residue was purified by flash column chromatography ($SiO_2$), eluting with a hexanes-EtOAc gradient to afford of Compound 1f. $^1$H-NMR (300 MHz, $CDCl_3$): δ 7.75-7.77 (d, 1H), 7.62-7.64 (d, 1H), 7.27-7.37 (m, 2H), 4.04-4.14 (q, 4H), 3.38-3.44 (d, 2H), 2.36-2.37 (d, 3H), 1.25-1.36 (t, 6H); LC/MS: $C_{14}H_{19}O_3PS$: m/z 299.0 (M+1).

E. Cpd 50: [2-(4-Fluoro-phenyl)-1-(3-methyl-benzo[b] thiophene-2-yl)-ethyl]-phosphonic acid diethyl ester. To a solution of Compound 1f (0.2 g; 0.671 mmol) in THF (3.0 mL) cooled to −70° C., was added a 2.5 M solution of n-butyllithium in hexanes (0.332 mL; 0.805 mmol), dropwise. The reaction mixture was allowed to stir at −70° C. for 30 min, to which was then added a solution of Compound 1g (0.092 mL; 0.739 mmol) in THF (0.7 mL), dropwise. The reaction mixture was allowed to slowly warm to ambient temperature, and stirred for an additional 30 min before quenching with a solution of saturated aqueous $NH_4Cl$ (1.0 mL). The mixture was diluted with EtOAc, washed with $H_2O$, then brine, and dried over $Na_2SO_4$. The mixture was then filtered, and the filtrate was concentrated under reduced pressure. The resulting residue was purified by reverse-phase semi-prep HPLC eluting with a 55% to 75% MeCN—$H_2O$ gradient to afford Compound 50. $^1$H-NMR (300 MHz, $CDCl_3$): δ 7.77-7.79 (m, 1H), 7.53-7.55 (m, 1H), 7.28-7.35 (m, 2H), 6.96-7.01 (m, 2H), 6.78-6.84 (m, 2H), 4.10-4.19 (m, 3H), 3.91-4.09 (m, 1H), 3.77-3.86 (m, 1H), 3.46-3.53 (m, 1H), 3.08-3.16 (m, 1H), 2.00-2.01 (d, 3H), 1.29-1.33 (t, 3H), 1.22-1.25 (t, 3H); LC/MS: $C_{21}H_{24}FO_3PS$: m/z 406.8 (M+1).

Following the procedure described above for Example 1 and substituting the appropriate reagents, starting materials and purification methods known to those skilled in the art, the following compounds of the present invention were prepared:

| Cpd | MS Observed | MS Calc'd |
|---|---|---|
| 1 | 452.9 | 452.1 |
| 4 | 452.9 | 422.1 |
| 7 | 406.8 | 406.1 |
| 9 | 409.8 | 408.1 |
| 10 | 424.8 | 424.1 |
| 11 | 437.1 | 436.2 |
| 14 | 424.8 | 424.1 |
| 17 | 424.8 | 424.1 |
| 18 | 402.9 | 402.1 |
| 21 | 458.7 | 456.0 |
| 22 | 406.8 | 406.1 |
| 23 | 440.7 | 440.1 |
| 25 | 440.1 | 439.1 |
| 26 | 402.9 | 402.1 |
| 27 | 440.7 | 440.1 |
| 28 | 458.7 | 458.1 |
| 31 | 474.8 | 474.1 |
| 32 | 418.8 | 418.1 |
| 35 | 458.7 | 456.0 |
| 37 | 474.8 | 474.1 |
| 39 | 442.8 | 442.1 |
| 40 | 468.7 | 466.0 |
| 46 | 438.9 | 438.1 |
| 47 | 458.7 | 456.0 |
| 48 | 422.9 | 422.1 |
| 49 | 490.8 | 490.1 |
| 50 | 406.8 | 406.1 |
| 51 | 392.9 | 392.1 |
| 52 | 456.7 | 456.1 |
| 53 | 508.8 | 508.2 |
| 54 | 456.7 | 456.0 |
| 55 | 472.8 | 472.1 |
| 56 | 474.8 | 474.1 |
| 57 | 472.8 | 472.1 |
| 58 | 461.1 | 460.1 |
| 59 | 456.7 | 456.1 |
| 60 | 454.8 | 454.1 |
| 61 | 472.8 | 472.1 |
| 62 | 467.2 | 466.2 |
| 63 | 438.9 | 438.1 |
| 66 | 468.7 | 466.0 |
| 67 | 474.8 | 474.1 |
| 68 | 442.8 | 442.1 |
| 69 | 470.9 | 470.1 |
| 70 | 453.8 | 452.0 |
| 71 | 466.8 | 466.1 |
| 73 | 508.8 | 508.1 |

| Cpd | MS Observed | MS Calc'd |
|---|---|---|
| 74 | 374.9 | 374.1 |
| 75 | 411.0 | 410.1 |
| 76 | 474.8 | 474.0 |
| 78 | 442.6 | 442.0 |
| 80 | 393.9 | 392.1 |
| 81 | 490.8 | 490.1 |
| 83 | 424.8 | 424.1 |
| 85 | 410.9 | 408.1 |
| 87 | 377.0 | 376.1 |
| 89 | 388.8 | 388.1 |
| 90 | 430.8 | 430.1 |
| 91 | 456.7 | 456.1 |
| 92 | 487.0 | 486.1 |
| 95 | 444.7 | 442.0 |
| 96 | 510.8 | 510.1 |
| 98 | 426.7 | 426.1 |
| 99 | 490.8 | 490.1 |
| 100 | 444.7 | 442.0 |
| 101 | 532.8 | 532.2 |
| 102 | 442.8 | 442.1 |
| 112 | 452.7 | 452.1 |
| 113 | 524.7 | 524.1 |
| 115 | 464.9 | 464.2 |
| 120 | 423.1 | 422.1 |
| 121 | 439.0 | 438.1 |
| 122 | 439.0 | 438.1 |
| 125 | 489.1 | 488.1 |
| 126 | 523.0 | 522.1 |
| 133 | 421.2 | 420.1 |
| 134 | 437.1 | 436.1 |
| 202 | 455.1 | 454.42 |
| 265 | 394.35 | 395.1 |

Cpd 9: [2-(3,4-Difluoro-phenyl)-1-(3-methyl-benzofuran-2-yl)-ethyl]-phosphonic acid diethyl ester. Compound 9 was prepared according to the method of Example 1, substituting 3-methyl-benzofuran for Compound 1a of Step A. $^1$H-NMR (300 MHz, DMSO-$d_6$): δ 7.43-7.48 (m, 2H), 7.14-7.32 (m, 4H), 6.96-6.99 (m, 1H), 3.92-4.10 (m, 5H), 3.26-3.30 (t, 2H), 2.02-2.03 (d, 3H), 1.21-1.24 (t, 3H), 1.12-1.15 (t, 3H); LC/MS: $C_{21}H_{23}F_2O_4P$: m/z 409.8 (M+1).

Cpd 14: [2-(3,4-Difluoro-phenyl)-1-(3-methyl-benzo[b]thiophen-2-yl)-ethyl]-phosphonic acid diethyl ester. Compound 14 was prepared according to the method of Example 1, substituting 3,4-difluorobenzyl bromide for Compound 1g in Step E. $^1$H-NMR (300 MHz, CDCl$_3$): δ 7.76-7.78 (m, 1H), 7.54-7.56 (m, 1H), 7.28-7.35 (m, 2H), 6.86-6.93 (m, 2H), 6.73-6.76 (m, 1H), 4.03-4.18 (m, 3H), 3.89-4.01 (m, 1H), 3.74-3.88 (m, 1H), 3.45-3.51 (m, 1H), 3.08-3.16 (m, 1H), 2.07 (s, 3H), 1.30-1.33 (t, 3H), 1.18-1.22 (t, 3H); LC/MS: $C_{21}H_{23}F_2O_3PS$: m/z 424.8 (M+).

Cpd 25: [1-Benzothiazol-2-yl-2-(3,4-difluoro-phenyl)-ethyl]-phosphonic acid diisopropyl ester. Compound 25 was prepared according to the method of Example 1, substituting benzothiazole-2-carbaldehyde for Compound 1b of Step B, and substituting 3,4-difluorobenzyl bromide for Compound 1g in Step E. $^1$H-NMR (300 MHz, DMSO-$d_6$): δ 8.02-8.04 (t, 1H), 7.91-7.93 (d, 1H), 7.29-7.59 (m, 3H), 7.12-7.29 (m, 1H), 6.88-7.12 (m, 1H), 4.10-4.97 (m, 3H), 3.24-3.52 (m, 2H), 1.12-1.38 (m, 9H), 1.00-1.12 (m, 3H); LC/MS: $C_{21}H_{24}F_2NO_3PS$: m/z 440.1 (M+1).

Cpd 53: [2-(3,4-Difluoro-phenyl)-1-(3-methyl-benzo[b]thiophen-2-yl)-ethyl]-phosphonic acid bis-(2,2-dimethyl-propyl) ester. Compound 53 was prepared according to the method of Example 1, substituting tri-neopentyl phosphite for Compound 1e of Step D, and substituting 3,4-difluorobenzyl bromide for Compound 1g in Step E. $^1$H-NMR (300 MHz, CD$_3$OD): δ 7.79-7.81 (m, 1H), 7.57-7.59 (m, 1H), 7.30-7.33 (m, 2H), 7.00-7.02 (m, 1H), 6.72-6.93 (m, 1H), 3.92-4.23 (m, 1H), 3.69-3.75 (m, 3H), 3.54-3.57 (m, 1H), 3.42-3.53 (m, 1H), 2.78-3.21 (m, 1H), 2.08-2.09 (d, 3H), 0.865-0.933 (m, 18H); LC/MS: $C_{27}H_{35}F_2O_3PS$: m/z 508.8 (M+).

Cpd 62: 2-(3,4-Difluoro-phenyl)-[1-(3,5-dimethyl-benzo[b]thiophen-2-yl)-ethyl]-phosphonic acid diisopropyl ester. Compound 62 was prepared according to the method of Example 1, substituting 3,5-dimethyl-benzo[b]thiophene for Compound 1a of Step A; substituting triisopropyl phosphite for Compound 1e of Step D; and substituting 3,4-difluorobenzyl bromide for Compound 1g in Step E. $^1$H-NMR (300 MHz, CDCl$_3$): δ 7.64-7.66 (d, 1H), 7.32 (s, 1H), 7.12-7.14 (d, 1H), 6.82-6.91 (m, 2H), 6.69-6.72 (m, 1H), 4.72-4.77 (m, 1H), 4.60-4.65 (m, 1H), 3.66-3.75 (m, 1H), 3.41-3.44 (m, 1H), 3.06-3.11 (m, 1H), 2.44 (s, 3H), 2.29-2.30 (d, 3H), 1.29-1.32 (m 9H), 1.02-1.04 (d, 3H); LC/MS: $C_{24}H_{29}F_2O_3PS$: m/z 467.2 (M+1).

Cpd 63: [1-Benzo[b]thiophen-2-yl-2-(3,4-difluoro-phenyl)-ethyl]-phosphonic acid diisopropyl ester. Compound 63 was prepared according to the method of Example 1, substituting benzo[b]thiophene-2-carbaldehyde for Compound 1b of Step B; substituting triisopropyl phosphite for Compound 1e of Step D; and substituting 3,4-difluorobenzyl bromide for Compound 1g in Step E. $^1$H-NMR (300 MHz, DMSO-$d_6$): δ 7.84-7.86 (m, 1H), 7.70-7.72 (m, 1H), 7.16-7.32 (m, 5H), 6.72-7.10 (m, 1H), 4.61-4.65 (m, 1H), 4.47-4.51 (m, 1H), 3.90-4.23 (m, 1H), 3.20-3.49 (m, 1H), 2.92-3.20 (m, 1H), 1.20-1.27 (m, 9H), 1.01-1.03 (d, 3H); LC/MS: $C_{22}H_{25}F_2O_3PS$: m/z 438.9 (M+1).

Cpd 78: [1-Benzo[b]thiophen-2-yl-2-(3,4-dichloro-phenyl)-ethyl]-phosphonic acid diethyl ester. Compound 78 was prepared according to the method of Example 1, substituting benzo[b]thiophene for Compound 1a of Step A, and substituting 3,4-dichlorobenzyl bromide for Compound 1g in Step E. $^1$H-NMR (300 MHz, DMSO-$d_6$): δ 7.85-7.87 (d, 1H), 7.71-7.73 (d, 1H), 7.55-7.56 (d, 1H), 7.40-7.42 (d, 1H), 7.19-7.32 (m, 4H), 4.18-4.28 (m, 1H), 3.87-4.09 (m, 4H), 3.32-3.45 (m, 1H), 3.10-3.19 (m, 1H), 1.21-1.24 (t, 3H), 1.10-1.14 (t, 3H); LC/MS: $C_{20}H_{21}Cl_2O_3PS$: m/z 442.6 (M+1).

Cpd 87: [1-Benzofuran-2-yl-2-(4-fluoro-phenyl)-ethyl]-phosphonic acid diethyl ester. Compound 87 was prepared according to the method of Example 1, substituting benzofuran-2-carbaldehyde for Compound 1b of Step B. $^1$H-NMR (300 MHz, DMSO-$d_6$): δ 7.48-7.53 (m, 2H), 7.11-7.25 (m, 4H), 6.97-7.01 (t, 2H), 6.73-6.74 (d, 1H), 4.00-4.10 (m, 5H), 3.19-3.31 (m, 2H), 1.21-1.24 (t, 3H), 1.12-1.16 (t, 3H); LC/MS: $C_{20}H_{22}FO_4P$: m/z 377.0 (M+1).

Cpd 92: [1-(5-Chloro-3-methyl-benzo[b]thiophen-2-O-2-(3,4-difluoro-phenyl)-ethyl]-phosphonic acid diisopropyl ester. Compound 92 was prepared according to the method of Example 1, substituting 5-chloro-3-methyl-benzo[b]thiophene for Compound 1a of Step A; substituting triisopropyl phosphite for Compound 1e of Step D; and substituting 3,4-difluorobenzyl bromide for Compound 1g in Step E. $^1$H-NMR (300 MHz, DMSO-$d_6$): δ 7.89-7.91 (d, 1H), 7.67-7.68 (d, 1H), 7.14-7.32 (m, 3H), 6.95-6.98 (m, 1H), 4.63-4.68 (m, 1H), 4.48-4.53 (m, 1H), 4.09-4.18 (m, 1H), 3.34-3.39 (m, 1H), 2.99-3.05 (m, 1H), 2.10-2.11 (d, 3H), 1.24-1.27 (m 6H), 1.20-1.22 (d, 3H), 0.962-0.977 (d, 3H); LC/MS: $C_{23}H_{26}ClF_2O_3PS$: m/z 487.0 (M+1).

Cpd 101: [2-(3,4-Difluoro-phenyl)-1-(3-methyl-benzo[b]thiophen-2-yl)-ethy]-phosphonic acid dicyclohexyl ester. Compound 101 was prepared according to the method of Example 1, substituting tricyclohexyl phosphite for Compound 1e of Step D, and substituting 3,4-difluorobenzyl bromide for Compound 1g in Step E. $^1$H-NMR (300 MHz, DMSO-$d_6$): δ 7.84-7.86 (m, 1H), 7.58-7.61 (m, 1H), 7.24-7.33 (m, 3H), 7.13-7.20 (m, 1H), 6.95-6.97 (m, 1H), 4.30-4.40 (m, 2H), 4.09-4.14 (m, 1H), 3.37-3.39 (m, 1H), 2.82-3.10 (m, 1H), 2.10-2.11 (d, 3H), 1.80 (m, 3H), 1.15-1.64 (m, 18H); LC/MS: $C_{29}H_{35}F_2O_3PS$: m/z 532.8 (M+).

Example 2

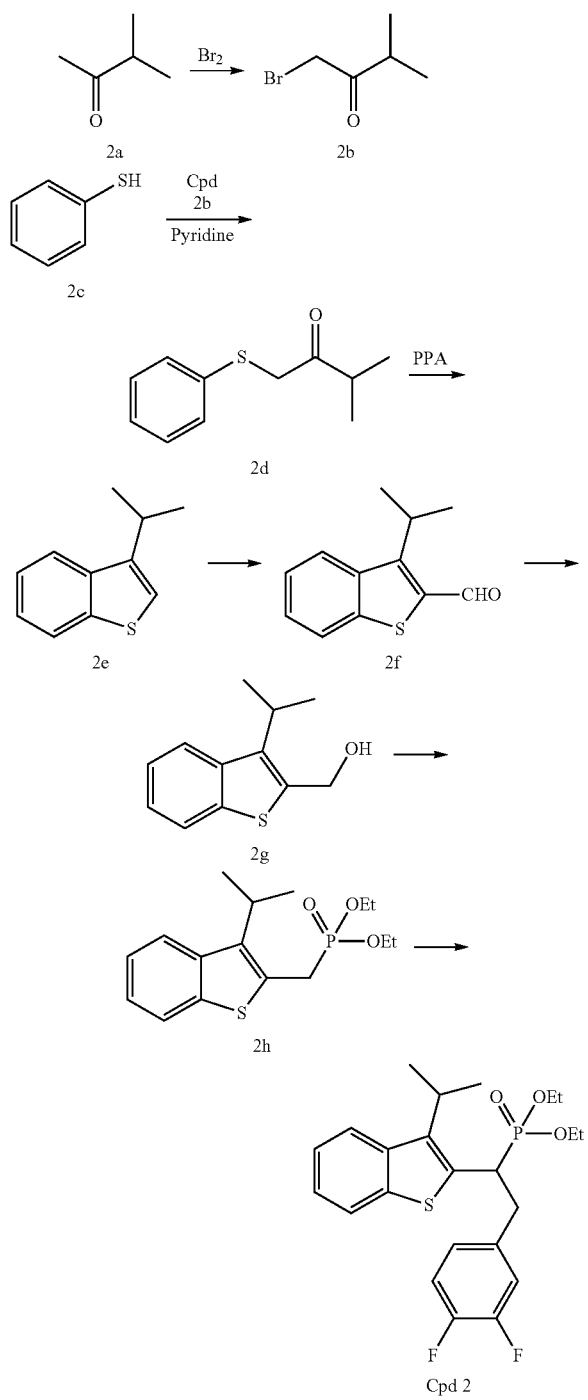

A. 1-Bromo-3-methyl-butan-2-one. To a solution of 3-methyl-2-butanone (6.0 g; 69.7 mmol), dissolved in MeOH (40 mL), cooled to 0° C., was added bromine (3.56 mL; 69.7 mmol), at a rate such that the internal temperature did not exceed 10° C. The reaction was allowed to stir for 45 min at 5-10° C., to which was then added $H_2O$ (20 mL) and the reaction was stirred for an additional 18 h at ambient temperature. Water was added to the reaction mixture, which was then extracted with diethyl ether. The combined ether extracts were washed sequentially with 10% aq. $NaHCO_3$, $H_2O$, and brine, dried over $Na_2SO_4$, filtered, and the filtrate was evaporated under reduced pressure to afford Compound 2b. $^1$H-NMR (300 MHz, $CDCl_3$): δ 3.98 (s, 2H), 2.95-3.02 (m, 1H), 1.10-1.17 (d, 6H).

B. 3-Methyl-1-phenylsulfanyl-butan-2-one. To a solution of thiophenol (2c) (4.44 mL; 43.4 mmol) in diethyl ether (29 mL) was added pyridine (17.2 mL; 0.21 mol), followed by the dropwise addition of a solution of Compound 2b (7.18 g; 43.5 mmol) in diethyl ether (15 mL), at ambient temperature, and the reaction was stirred for 72 h. The reaction was diluted with EtOAc, washed with 2N HCl, $H_2O$, brine, dried over $Na_2SO_4$, filtered and the solvent evaporated under reduced pressure. The crude residue was purified by flash column chromatography ($SiO_2$) eluting with a heptane-EtOAc gradient to afford Compound 2d. $^1$H-NMR (300 MHz, $CDCl_3$): δ 7.18-7.35 (m, 5H), 3.75 (s, 2H), 2.90-2.97 (m, 1H), 1.09-1.10 (d, 6H).

C. 3-Isopropyl-benzo[b]thiophene. To a hot solution (136° C.) of PPA (8.2 g) in chlorobenzene (50 mL) is added a solution of Compound 2d (4.34 g; 22.4 mmol) in chlorobenzene (35 mL). The reaction was stirred at 136° C. for 18 h, cooled to ambient temperature, diluted with EtOAc, quenched with $H_2O$, and the EtOAc layer was washed with $H_2O$, brine, dried over $Na_2SO_4$, filtered and the solvent evaporated under reduced pressure. The crude residue was purified by flash column chromatography ($SiO_2$), eluting with a heptane-EtOAc gradient to afford Compound 2e. $^1$H-NMR (300 MHz, DMSO-$d_6$): δ 7.95-7.97 (m, 1H), 7.83-7.85 (m, 1H), 7.33-7.43 (m, 2H), 3.26-3.31 (m, 1H), 1.31-1.33 (d, 6H); LC/MS: $C_{16}H_{22}NO_3PS$: m/z 328.0 (M+1).

D. 3-Isopropyl-benzo[b]thiophene-2-carboxaldehyde. Compound 2f was prepared following the method described in Example 1, Step A, substituting Compound 2e for Compound 1a.

E. (3-Isopropyl-benzo[b]thiophen-2-yl)-methanol. Compound 2g was prepared following the method described in Example 1, Step B, substituting Compound 2f for Compound 1b. Purification by flash column chromatography ($SiO_2$), eluting with a heptane-EtOAc gradient, afforded Compound 2g. $^1$H-NMR (300 MHz, DMSO-$d_6$): 7.85-7.88 (m, 1H), 7.26-7.34 (m, 1H), 5.61-5.64 (t, 1H), 4.76-4.77 (d, 1H), 3.38-3.42 (m, 1H), 1.35-1.37 (d, 6H).

F. (3-Isopropyl-benzo[b]thiophen-2-ylmethyl)-phosphonic acid diethyl ester. Compound 2h was prepared following the method described in Example 1, Steps C and D, substituting Compound 2g for Compound 1c. Purification by flash column chromatography ($SiO_2$), eluting with a heptane-EtOAc gradient, afforded Compound 2h. $^1$H-NMR (300 MHz, $CD_3OD$): δ 7.93-7.95 (d, 1H), 7.75-7.77 (d, 1H), 7.25-7.30 (m, 2H), 4.05-4.13 (m, 4H), 3.51-3.56 (d, 2H), 3.43-3.47 (m, 1H), 1.46-1.48 (d, 6H), 1.27-1.31 (t, 6H); LC/MS: $C_{16}H_{23}O_3PS$: m/z 326.9 (M+1).

Cpd 2: [2-(3,4-Difluoro-phenyl)-1-(3-isopropyl-benzo[b]thiophene-2-yl)-ethyl]-phosphonic acid diethyl ester. Compound 2 was prepared following the method described in Example 1, Step E substituting Compound 2h for Compound 1f, and substituting 3,4-difluorobenzyl bromide for Compound 1g. $^1$H-NMR (300 MHz, DMSO-$d_6$): δ 7.82-7.88 (m, 2H), 7.16-7.29 (m, 4H), 6.81-7.06 (m, 5H), 3.90-4.11 (m, 5H), 3.14-3.54 (m, 2H), 2.85-3.14 (m, 1H), 0.97-1.31 (m, 12H); LC/MS: $C_{23}H_{27}F_2O_3PS$: m/z 452.9 (M+1).

Following the procedure described above for Example 2 and substituting the appropriate reagents, starting materials and purification methods known to those skilled in the art, the following compounds of the present invention were prepared:

| Cpd | MS Observed | MS Calc'd |
|---|---|---|
| 19 | 480.7 | 480.2 |

Example 3

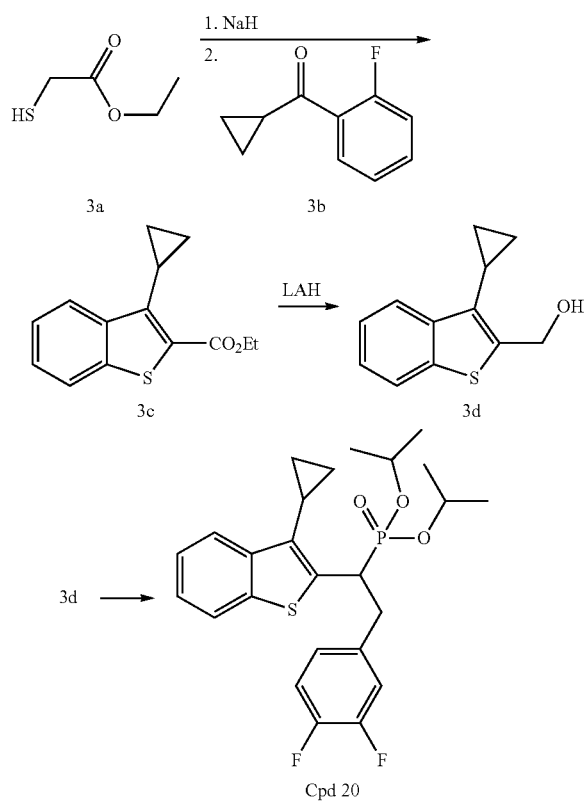

A. 3-Cyclopropyl-benzo[b]thiophene-2-carboxylic acid ethyl ester. To a suspension of 60% NaH (0.26 g; 7.74 mmol) in THF (10 mL), at ambient temperature, was added ethyl thioglycolate (Compound 3a) (0.86 g; 7.14 mmol) dropwise, and the reaction was stirred at ambient temperature for 30 min. Cyclopropyl-(2-fluoro-phenyl)-methanone (Compound 3b) (0.98 g; 5.96 mmol) was added in one-portion. The reaction was allowed to reflux for 18 h, then cooled, diluted with EtOAc, washed sequentially with 1N NaOH, H$_2$O, and brine, dried over Na$_2$SO$_4$, filtered, and the filtrate was concentrated under reduced pressure. The crude residue was purified by flash column chromatography (SiO$_2$), eluting with a heptane-EtOAc gradient to afford 0.484 g (33%) of Compound 3c. $^1$H-NMR (300 MHz, DMSO-d$_6$): δ 7.99-8.05 (m, 2H), 7.64-7.75 (m, 1H), 7.32-7.54 (m, 2H), 4.31-4.37 (q, 2H), 2.36-2.51 (m, 1H), 1.32-1.36 (t, 3H), 1.08-1.16 (m, 4H); LC/MS: C$_{14}$H$_{14}$O$_2$S: m/z 247.1 (M+1).

B. (3-Cyclopropyl-benzo[b]thiophen-2-yl)-methanol. To a solution of 1M lithium aluminum hydride-THF (23 mL; 23 mmol), cooled to 0° C., was added a solution of Compound 3c (1.88 g; 7.65 mmol) in THF (25.mL) dropwise, to maintain the internal temperature between 0-5° C. The reaction was allowed to stir an additional 1 h at 0° C. The reaction was quenched with saturated NH$_4$Cl, to which was added 3N NaOH. The layers were separated and the organic phase washed sequentially with H$_2$O and brine, dried over Na$_2$SO$_4$, filtered, and the filtrate was concentrated under reduced pressure to afford Compound 3d. $^1$H-NMR (300 MHz, DMSO-d$_6$): δ 3.55-3.74 (m, 2H), 7.34-7.38 (m, 1H), 7.27-7.31 (m, 1H), 5.57-5.60 (t, 1H), 4.83-4.85 (m, 2H), 1.75-1.81 (m, 1H), 0.965-0.996 (m, 2H), 0.581-0.620 (m, 2H).

C. Cpd 20: [1-(3-Cyclopropyl-benzo[b]thiophene-2-yl)-2-(3,4-difluoro-phenyl)-ethyl]-phosphonic acid diisopropyl ester. Compound 20 was prepared following the methods described in Example 1, substituting Compound 3d for Compound 1c in Step C, substituting triisopropyl phosphite for Compound 1e in Step D, and substituting 3,4-difluorobenzyl bromide for Compound 1g in Step E. $^1$H-NMR (300 MHz, CDCl$_3$): δ 7.83-7.85 (m, 1H), 7.76-7.78 (m, 1H), 7.26-7.33 (m, 2H), 6.84-6.91 (m, 2H), 6.70-6.73 (m, 1H), 4.73-4.78 (m, 1H), 4.62-4.66 (m, 1H), 4.14-4.24 (m, 1H), 3.41-3.48 (m, 1H), 3.03-3.11 (m, 1H), 1.24-1.36 (m, 10H), 0.840-0.976 (m, 5H), 0.644-0.681 (m, 1H), 0.49-0.82 (m, 1H); LC/MS C$_{26}$H$_{29}$F$_2$O$_3$PS: m/z 479.1 (M+1).

Following the procedure described above for Example 3 and substituting the appropriate reagents, starting materials and purification methods known to those skilled in the art, the following compounds of the present invention were prepared:

| Cpd | MS Observed | MS Calc'd |
|---|---|---|
| 5 | 479.1 | 478.2 |
| 20 | 479.1 | 478.2 |
| 29 | 451.1 | 450.1 |
| 38 | 507.1 | 506.2 |
| 41 | 465.1 | 464.1 |
| 45 | 443.1 | 442.1 |
| 65 | 459.0 | 458.1 |
| 82 | 455.1 | 454.1 |
| 84 | 493.0 | 492.1 |
| 116 | 493.0 | 492.1 |
| 117 | 513.2 | 512.1 |
| 119 | 493.2 | 492.2 |
| 129 | 465.1 | 480.2 |

Cpd 41: [1-(3-Cyclobutyl-benzo[b]thiophen-2-yl)-2-(3,4-difluoro-phenyl)-ethyl]-phosphonic acid diethyl ester. Compound 41 was prepared following the method described in Example 3, substituting cyclobutyl-(2-fluoro-phenyl)-methanone for Compound 3b of Step A. $^1$H NMR (300 MHz, CD$_3$OD): δ 7.93-7.95 (m, 1H), 7.79-7.81 (m, 1H), 7.26-7.33 (m, 2H), 6.94-7.04 (m, 2H), 6.82-6.85 (m, 1H), 3.90-4.20 (m, 5H), 3.68 (m, 1H), 3.39-3.47 (m, 1H), 3.03-3.25 (m, 1H), 2.54-2.59 (m, 1H), 2.30-2.37 (m, 1H), 1.94-2.13 (m, 3H), 1.32-1.36 (t, 3H), 1.14-1.17 (t, 3H); LC/MS: C$_{24}$H$_{27}$F$_2$O$_3$PS: m/z 465.1 (M+1).

Cpd 45: [2-(3,4-Difluoro-phenyl)-1-(5-fluoro-3-methyl-benzo[b]thiophen-2-yl)-ethyl]-phosphonic acid diethyl ester. Compound 45 was prepared following the method described in Example 3, substituting 1-(2,5-difluoro-phenyl)ethanone for Compound 3b of Step A. $^1$H NMR (300 MHz, DMSO-d$_6$): δ 7.87-7.91 (m, 1H), 7.42-7.45 (m, 1H), 7.31-

7.36 (m, 1H), 7.14-7.22 (m, 2H), 7.00-7.01 (m, 1H), 4.20-4.30 (m, 1H), 4.03-4.08 (m, 2H), 3.87-3.99 (m, 2H), 3.35-3.40 (m, 1H), 3.01-3.08 (m, 1H), 2.12-2.13 (m, 3H), 1.22-1.26 (t, 3H), 1.09-1.12 (t, 3H); LC/MS $C_{21}H_{22}F_3O_3PS$: m/z 443.1 (M+1).

Cpd 65: [1-(4-Chloro-3-methyl-benzo[b]thiophen-2-yl)-2-(3,4-difluoro-phenyl)-ethyl]-phosphonic acid diethyl ester. Compound 65 was prepared following the method described in Example 3, substituting 1-(2-chloro-6-fluoro-phenyl)-ethanone for Compound 3b of Step A. $^1$H NMR (300 MHz, DMSO-$d_6$): δ 7.85-7.87 (m, 1H), 7.33-7.38 (m, 2H), 7.17-7.27 (m, 2H), 7.01 (m, 1H), 4.04-4.11 (m, 1H), 3.91-3.95 (m, 2H), 3.91-3.94 (m, 2H), 3.03-3.10 (m, 1H), 2.43-2.49 (d, 3H), 1.23-1.26 (t, 3H), 1.10-1.14 (t, 3H); LC/MS: $C_{21}H_{22}ClF_2O_3PS$: m/z 459.0 (M+1).

Cpd 82: [2-(3,4-Difluoro-phenyl)-1-[6-methoxy-3-methyl-benzo[b]thiophene-2-yl)-ethyl]-phosphonic acid diethyl ester. Compound 82 was prepared following the method described in Example 3, substituting 1-(2-fluoro-4-methoxy-phenyl)-ethanone for Compound 3b of Step A. $^1$H NMR (300 MHz, CD$_3$OD): δ 7.45-7.47 (d, 1H), 7.34-7.35 (m, 1H), 6.87-7.03 (m, 4H), 3.90-4.17 (m, 5H), 3.83 (s, 3H), 3.37-3.59 (m, 1H), 2.91-3.16 (m, 1H), 2.03-2.04 (m, 3H), 1.31-1.35 (t, 3H), 1.15-1.19 (t, 3H); LC/MS: $C_{22}H_{25}F_2O_4PS$: m/z 455.1 (M+1).

Cpd 84: [2-(3,4-Difluoro-phenyl)-(3-methyl)-4-trifluoromethyl-benzo[b]thiophen-2-yl)-ethyl]-phosphonic acid diethyl ester. Compound 84 was prepared following the method described in Example 3, substituting 1-(2-fluoro-6-trifluoromethyl-phenyl)-ethanone for Compound 3b of Step A. $^1$H NMR (300 MHz, DMSO-$d_6$): δ 8.14-8.40 (m, 1H), 7.63-8.02 (m, 1H), 7.41-7.62 (m, 1H), 7.26-7.41 (m, 1H), 7.11-7.26 (m, 1H), 6.89-7.11 (m, 1H), 4.26-4.58 (m, 1H), 4.02-4.22 (m, 2H), 3.74-4.02 (m, 2H), 3.38-3.58 (m, 1H), 3.04-3.16 (m, 1H), 2.07-2.30 (s, 3H), 1.15-1.38 (t, 3H), 1.03-1.15 (t, 3H); LC/MS: $C_{22}H_{22}F_5O_3PS$: m/z 493.0 (M+1).

Cpd 117: [1-(6-Chloro-3-cyclopentyl-benzo[b]thiophen-2-yl)-2-(3,4-difluoro-phenyl)-ethyl]-phosphonic acid diethyl ester. Compound 117 was prepared following the method described in Example 3, substituting (4-chloro-2-fluoro-phenyl)-cyclopentyl-methanone for Compound 3b of Step A. $^1$H NMR (300 MHz, CD$_3$OD) δ 7.85 (m, 1H), 7.63-7.65 (m, 1H), 7.25-7.28 (m, 1H), 7.00-7.04 (m, 2H), 6.83-6.99 (m, 1H), 3.92-4.21 (m, 5H), 3.42-3.48 (m, 1H), 3.04-3.24 (m, 2H), 1.62-1.94 (m, 7H), 1.15-1.36 (m, 7H); LC/MS: $C_{25}H_{28}ClF_2O_3PS$: m/z 513.2 (M+1).

Cpd 119: [1-(3-Cyclohexyl-benzo[b]thiophen-2-yl)-2-(3,4-difluoro-phenyl)-ethyl]-phosphonic acid diethyl ester. Compound 119 was prepared following the method described in Example 3, substituting cyclohexyl-(2-fluoro-phenyl)-methanone for Compound 3b of Step A. $^1$H NMR (300 MHz, CD$_3$OD): δ 7.89-7.91 (m, 1H), 7.78-7.81 (m, 1H), 7.25-7.29 (m, 2H), 6.96-7.05 (m, 2H), 6.83-6.86 (m, 1H), 3.92-4.21 (m, 5H), 3.43-3.49 (m, 1H), 3.07-3.11 (m, 1H), 2.45 (m, 1H), 1.15-1.85 (m, 17H); LC/MS: $C_{26}H_{31}F_2O_3PS$: m/z 493.2 (M+1).

Cpd 129: [2-(3,4-Difluoro-phenyl)-1-[3-(2,2-dimethyl-propyl)-benzo[b]thiophen-2-yl)-ethyl]-phosphonic acid diethyl ester. Compound 129 was prepared following the method described in Example 3, substituting 1-(2-fluoro-phenyl)-3,3-dimethyl-butan-1-one for Compound 3b of Step A. $^1$H NMR (300 MHz, CD$_3$OD): δ 7.93-7.95 (m, 1H), 7.79-7.81 (m, 1H), 7.26-7.33 (m, 2H), 6.94-7.04 (m, 2H), 6.82-6.85 (m, 1H), 3.90-4.20 (m, 5H), 3.68 (m, 1H), 3.39-3.47 (m, 1H), 3.03-3.25 (m, 1H), 2.54-2.59 (m, 1H), 2.30-2.37 (m, 1H), 1.94-2.13 (m, 3H), 1.32-1.36 (t, 3H), 1.14-1.17 (t, 3H); LC/MS: $C_{24}H_{27}F_2O_3PS$: m/z 465.1 (M+1).

Example 4

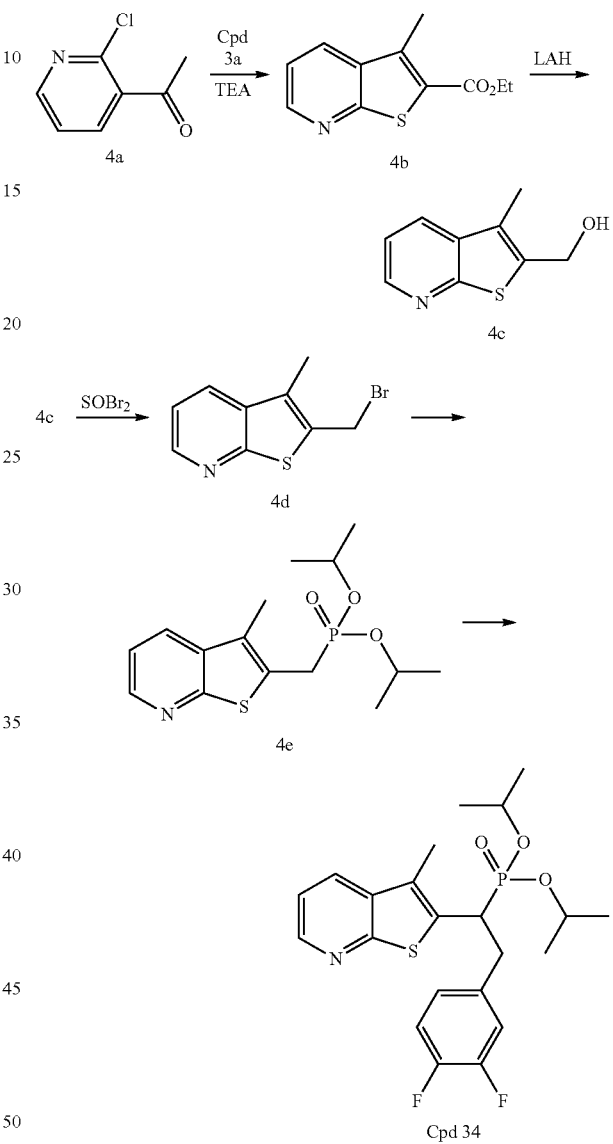

A. 3-Methyl-thieno[2,3-b]pyridine-2-carboxlic acid ethyl ester. To a solution of Compound 4a (0.637 g; 4.1 mmol), dissolved in MeCN (3.0 mL), at ambient temperature, is added TEA (0.743 mL; 5.3 mmol), followed by Compound 3a (0.542 g; 4.5 mmol) and the reaction was heated under microwave radiation at 180° C. for 20 min. The crude reaction was diluted with EtOAc, washed sequentially with 3N NaOH, H$_2$O, and brine, dried over Na$_2$SO$_4$, filtered and the filtrate was concentrated under reduced pressure. The crude residue was purified by flash column chromatography (SiO$_2$), eluting with a heptane-EtOAc gradient to afford Compound 4b. $^1$H-NMR (300 MHz, DMSO-$d_6$): δ 8.72-8.74 (m, 1H), 8.28-8.42 (m, 1H), 7.36-7.67 (m, 1H), 4.21-4.49 (q, 2H), 1.21-1.36 (t, 3H); LC/MS: $C_{11}H_{11}NO_2S$: m/z 222.0 (M+1).

B. (3-Methyl-thieno[2,3-b]pyridin-2-yl)-methanol. To a solution 1.0 M LAH in THF (8.6 mL), cooled to 0° C., was added a solution of Compound 4b (0.632 g; 2.85 mmol), dissolved in THF (10 mL), dropwise, and the reaction was stirred at 0° C. for 2 h. The reaction was quenched with $H_2O$, extracted with EtOAc, and the organic phase was washed sequentially with $H_2O$ and brine, dried over $Na_2SO_4$, filtered and the filtrate was concentrated under reduced pressure to afford Compound 4c.

C. 2-Bromomethyl-3-methyl-thieno[2,3-b]pyridine. To a solution of Compound 4c (0.210 g; 1.17 mmol), in DCE (3.0 mL), was added thionyl bromide (0.182 mL; 2.34 mmol) at ambient temperature. The reaction was refluxed for 3 h, cooled, diluted with EtOAc, and washed sequentially with 10% $NaHCO_3$, $H_2O$, and brine. The organic phase was dried over $Na_2SO_4$, filtered, and the filtrate was concentrated under reduced pressure to afford Compound 4d.

D. (3-Methyl-thieno[2,3-b]pyridin-2-ylmethyl)-phosphonic acid diisopropyl ester. To a solution of Compound 4d in toluene (9.0 mL) was added triisopropyl phosphite (0.731 mL; 3.51 mmol) and the reaction was refluxed for 18 h. The reaction was cooled, concentrated under reduced pressure and the crude residue was purified by reverse-phase semi-prep HPLC, eluting with a 25-45% MeCN—$H_2O$ gradient, to afford Compound 4e. $^1$H-NMR (300 MHz, DMSO-$d_6$): δ 8.48-8.50 (m, 1H), 8.08-8.11 (m, 1H), 7.39-7.43 (m, 1H), 4.55-4.60 (m, 2H), 3.48-3.53 (d, 2H), 2.23 (s, 3H), 2.46-2.50 (d, 3H), 1.86-1.93 (d, 3H); LC/MS: $C_{15}1-1_{22}NO_3PS$: m/z 328.0 (M+1).

E. Cpd 34: [2-(3,4-Difluoro-phenyl)-1-(3-methyl-thieno[2,3-b]pyridin-2-yl)-ethyl]-phosphonic acid diisopropyl ester. Compound 34 was prepared following the methods described in Example 1, Step E substituting Compound 4e for Compound 1f, and substituting 3,4-difluorobenzyl bromide for Compound 1g. $^1$H-NMR (300 MHz, DMSO-$d_6$): δ 9.27-9.28 (m, 1H), 8.81-8.83 (m, 1H), 8.13-8.19 (m, 2H), 7.97-8.02 (m, 1H), 7.81-7.83 (m, 1H), 5.46-5.50 (m, 1H), 5.34-5.38 (m, 1H), 4.94-5.02 (m, 1H), 4.17-4.22 (m, 3H), 3.81-3.88 (m, 1H), 2.94-2.95 (d, 3H), 2.04-2.09 (m, 9H), 1.82-1.83 (m, 3H); LC/MS: $C_{22}H_{26}F_2NO_3PS$: m/z 454.1 (M+1).

Following the procedure described above for Example 4 and substituting the appropriate reagents, starting materials and purification methods known to those skilled in the art, the following compounds of the present invention were prepared:

| Cpd | MS Observed | MS Calc'd |
|---|---|---|
| 3 | 443.1 | 442.1 |
| 8 | 443.1 | 442.1 |
| 16 | 443.1 | 442.1 |
| 34 | 454.1 | 453.1 |
| 43 | 507.1 | 506.1 |
| 131 | 412.0 | 411.1 |

Cpd 3: [2-(3,4-Difluoro-phenyl)-1-(4-fluoro-3-methyl-benzo[b]-thiophene-2-yl)-ethyl]-phosphonic acid diethyl ester. Compound 3 was prepared following the method described in Example 4, substituting 1-(2,6-difluoro-phenyl) ethanone for Compound 4a of Step A. $^1$H NMR (300 MHz, $CDCl_3$): δ 7.50-7.52 (d, 1H), 7.18-7.23 (m, 1H), 6.86-6.97 (m, 3H), 6.75-6.78 (m, 1H), 3.92-4.17 (m, 4H), 3.74-3.84 (m, 1H), 3.45-3.51 (m, 1H), 3.05-3.13 (m, 1H), 2.22-2.24 (m, 3H), 1.31-1.35 (t, 3H), 1.20-1.24 (t, 3H); LC/MS $C_{21}H_{22}F_3O_3PS$: m/z 443.1 (M+1).

Cpd 8: [2-(3,4-Difluoro-phenyl)-1-(7-fluoro-3-methyl-benzo[b-]thiophene-2-yl)-ethyl]-phosphonic acid diethyl ester. Compound 8 was prepared following the method described in Example 4, substituting 1-(2,3-difluoro-phenyl) ethanone for Compound 4a of Step A. $^1$H NMR (300 MHz, $CDCl_3$): δ 7.44-7.49 (m, 2H), 7.05-7.10 (m, 1H), 6.84-6.95 (m, 2H), 6.73-6.76 (m, 1H), 3.93-4.17 (m, 4H), 3.72-3.81 (m, 1H), 3.43-3.50 (m, 1H), 3.04-3.13 (m, 1H), 2.03-2.04 (d, 3H), 1.30-1.34 (t, 3H), 1.20-1.24 (t, 3H); LC/MS $C_{21}H_{22}F_3O_3PS$: m/z 443.1 (M+1).

Cpd 16: [2-(3,4-Difluoro-phenyl)-1-(6-fluoro-3-methyl-benzo[b]-thiophene-2-yl)-ethyl]-phosphonic acid diethyl ester. Compound 16 was prepared following the method described in Example 4, substituting 1-(2,4-difluoro-phenyl)-ethanone for Compound 4a of Step A. $^1$H NMR (300 MHz, $CDCl_3$): δ 7.28-7.25 (m, 2H), 6.85-7.03 (m, 3H), 6.74-6.77 (m, 1H), 3.98-4.17 (m, 4H), 3.76-3.86 (m, 1H), 3.47-3.53 (m, 1H), 3.07-3.15 (m, 1H), 2.06-2.07 (d, 3H), 1.30-1.33 (t, 3H), 1.24-1.27 (t, 3H); LC/MS $C_{21}H_{22}F_3O_3PS$: m/z 443.1 (M+1).

Cpd 43: [2-(3,4-Difluoro-phenyl)-1-(3-trifluoromethyl-benzo[b]-thiophene-2-yl)-ethyl]-phosphonic acid diisopropyl ester. Compound 43 was prepared following the method described in Example 4, substituting 2,2,2-trifluoro-1-(2-fluoro-phenyl)-ethanone for Compound 4a of Step A. $^1$H NMR (300 MHz, $CDCl_3$): δ 7.79-7.81 (m, 2H), 7.37-7.41 (m, 2H), 6.85-6.96 (m, 2H), 6.74-6.77 (m, 1H), 4.74-4.79 (m, 1H), 4.62-4.66 (m, 1H), 4.22-4.28 (m, 1H), 3.49-3.55 (m, 1H), 3.09-3.16 (m, 1H), 1.29-1.34 (m, 9H), 1.01-1.03 (d, 3H); LC/MS $C_{23}H_{24}F_5O_3PS$: m/z 507.1 (M+1).

Example 5

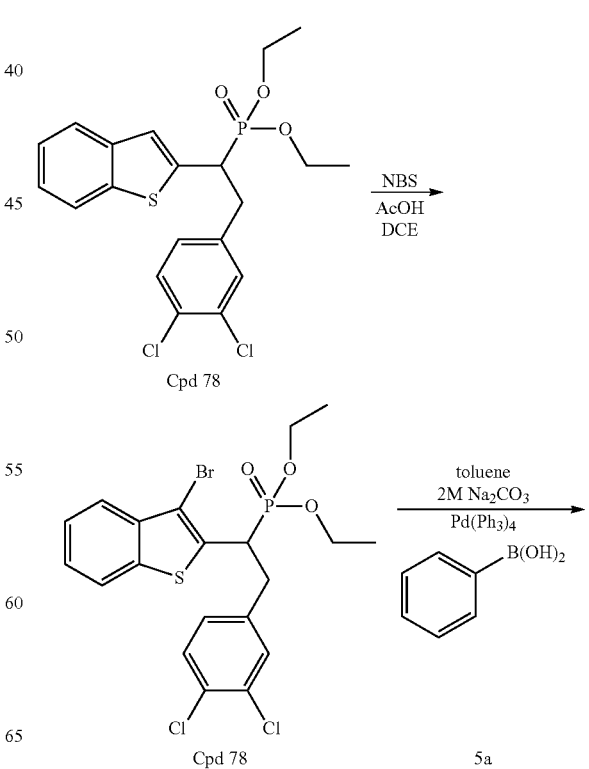

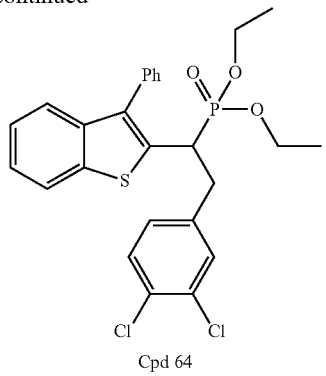

Cpd 64

A. Cpd 24: [1-(3-Bromo-benzo[b]thiophen-2-yl)-2-(3,4-dichloro-phenyl)-ethyl]-phosphonic acid diethyl ester. To a solution of Compound 78 of Example 1 (0.36 g; 0.814 mmol) in DCE (4.3 mL) was added AcOH (4.3 mL) followed by N-bromosuccinimide (0.188 g; 1.05 mmol) and the reaction was refluxed for 18 h. The reaction was cooled, diluted with EtOAc, and washed with H$_2$O and brine. The organic phase was dried over Na$_2$SO$_4$, filtered, and the filtrate was concentrated under reduced pressure. The crude residue was purified by reverse-phase semi-prep HPLC eluting with a 65% to 85% MeCN/H$_2$O gradient to afford Compound 24. $^1$H NMR (300 MHz, CDCl$_3$): δ 7.75-7.77 (t, 1H), 7.68-7.70 (m, 1H), 7.34-7.42 (m, 2H), 7.18-7.24 (m, 2H), 6.89-6.92 (m, 1H), 3.91-4.23 (m, 5H), 3.49-3.55 (m, 1H), 3.09-3.18 (m, 1H), 1.30-1.33 (t, 3H), 1.20-1.23 (t, 3H); LC/MS C$_{20}$H$_{20}$BrCl$_2$O$_3$PS: m/z 522.6 (M−1).

B. Cpd 64: [2-(3,4-Dichloro-phenyl)-1-(3-phenyl-benzo[b]thiophen-2-yl)-ethyl]-phosphonic acid diethyl ester. To a solution of Compound 24 (0.266 g; 0.509 mmol), in toluene (2.5 mL) was added 2M aqueous Na$_2$CO$_3$ (1.0 mL), phenylboronic acid (Compound 5a) (0.124 g; 1.01 mmol) and palladium triphenylphosphine (0.005 g; 0.004 mmol) and the reaction was refluxed for 16 h. At that time, the reaction was cooled, diluted with EtOAc, and washed with H$_2$O and brine. The organic phase was dried over Na$_2$SO$_4$, filtered, and the filtrate was concentrated under reduced pressure. The crude residue was purified by reverse-phase semi-prep HPLC eluting with a 70% to 90% MeCN/H$_2$O gradient to afford Compound 64. $^1$H NMR (300 MHz, CDCl$_3$): δ 7.82-7.84 (d, 1H), 7.23-7.46 (m, 7H), 7.09-7.11 (d, 2H), 6.90-6.91 (d, 1H), 6.65-6.67 (m, 1H), 6.41-6.42 (m, 1H), 4.01-4.20 (m, 4H), 3.72-3.81 (m, 1H), 3.02-3.35 (m, 2H), 1.32-1.35 (t, 3H), 1.24-1.28 (t, 3H); LC/MS C$_{26}$H$_{25}$Cl$_2$O$_3$PS: m/z 518.7 (M+).

Following the procedure described above for Example 5 and substituting the appropriate reagents, starting materials and purification methods known to those skilled in the art, the following compounds of the present invention were prepared:

| Cpd | MS Observed | MS Calc'd |
|---|---|---|
| 12 | 472.8 | 472.1 |
| 15 | 518.7 | 516.0 |
| 24 | 522.6 | 519.9 |
| 64 | 518.7 | 518.1 |
| 93 | 596.5 | 593.9 |
| 124 | 501.1 | 500.1 |
| 127 | 491.1 | 488.0 |
| 143 | 518.7 | 517/519 |
| 144 | 518.7 | 519.0 |
| 166 | 515.83 | 516.9 |
| 192 | 501.0 | 499.38 |
| 193 | 517.0 | 517.37 |
| 194 | 519.0 | 517.37 |
| 195 | 603.0 | 601.83 |
| 196 | 501.0 | 499.37 |
| 197 | 501.0 | 499.37 |
| 198 | 579.0 | 578.27 |
| 199 | 579.0 | 578.27 |
| 200 | 579.0 | 578.27 |
| 205 | 521.1 | 519.29 |
| 206 | 493.0 | 491.24 |
| 266 | 473.0/475.0 | 473.25 |
| 267 | 533.0/535.0 | 533.8 |

Cpd 12: [1-(3-Chloro-benzo[b]thiophen-2-yl)-2-(3,4-difluoro-phenyl)-ethyl]-phosphonic acid diisopropyl ester. Compound 12 was prepared from Compound 63 (prepared according to Example 1) following the method described in Example 5 and substituting N-bromosuccinimide with N-chlorosuccinimide. $^1$H NMR (300 MHz, DMSO-d$_6$): δ 7.99-8.01 (t, 1H), 7.63-7.65 (m, 1H), 7.42-7.45 (m, 2H), 7.17-7.20 (m, 2H), 6.79-7.05 (m, 1H), 4.67-4.69 (m, 1H), 4.50-4.52 (m, 1H), 3.95-4.28 (m, 1H), 3.25-3.56 (m, 1H), 2.89-3.21 (m, 1H), 1.27-1.28 (d, 6H), 1.22-1.23 (d, 3H), 1.00-1.01 (d, 3H); LC/MS C$_{22}$H$_{24}$ClF$_2$O$_3$PS: m/z 472.8 (M+1).

Cpd 15: [1-(3-Bromo-benzo[b]thiophen-2-yl)-2-(3,4-difluoro-phenyl)-ethyl]-phosphonic acid diisopropyl ester; and Cpd 93: [1-Bromo-1-(3-bromo-benzo[b]thiophen-2-O-2-(3,4-difluoro-phenyl)-ethyl]-phosphonic acid diisopropyl ester. Compound 15 was prepared from Compound 63 (prepared according to Example 1) following the method described in Example 5. $^1$H NMR (300 MHz, DMSO-d$_6$): δ 7.99-8.02 (m, 1H), 7.61-7.63 (m, 1H), 7.42-7.47 (m, 2H), 7.15-7.25 (m, 2H), 6.93-6.94 (m, 1H), 4.66-4.71 (m, 1H), 4.48-4.53 (m, 1H), 4.05-4.12 (m, 1H), 3.34-3.43 (m, 1H), 2.89-3.13 (m, 1H), 1.27-1.29 (d, 6H), 1.21-1.23 (d, 3H), 0.980-0.995 (d, 3H); LC/MS C$_{22}$H$_{24}$BrF$_2$O$_3$PS: m/z 518.7 (M+1).

Cpd 93 was isolated as a by-product during the purification of Compound 15. $^1$H NMR (300 MHz, DMSO-d$_6$): δ 8.09-8.11 (m, 1H), 7.73-7.79 (m, 2H), 7.46-7.56 (m, 4H), 5.65-5.69 (m, 1H), 4.57-4.66 (m, 1H), 4.25-4.37 (m, 2H), 1.06-1.09 (d, 6H), 0.915-0.930 (d, 3H), 0.765-0.780 (d, 3H); LC/MS C$_{22}$H$_{23}$Br$_2$F$_2$O$_3$PS: m/z 596.5 (M+1).

Cpd 127: [1-(3-Bromo-benzo[b]thiophen-2-yl)-2-(3,4-difluoro-phenyl)-ethyl]-phosphonic acid dethyl ester. Compound 127 was prepared from Compound 75 (which was prepared according to Example 1) following the method described in Example 5. $^1$H NMR (300 MHz, DMSO-d$_6$): δ 7.99-8.01 (m, 1H), 7.62-7.64 (m, 1H), 7.41-7.48 (m, 2H), 7.16-7.32 (m, 2H), 6.94-6.98 (m, 1H), 3.90-4.26 (m, 5H), 3.41-3.47 (m, 1H), 3.06-3.14 (m, 1H), 1.25-1.28 (t, 3H), 1.09-1.13 (t, 3H); LC/MS C$_{20}$H$_{20}$BrF$_2$O$_3$PS: m/z 491.1 (M+1).

Example 6

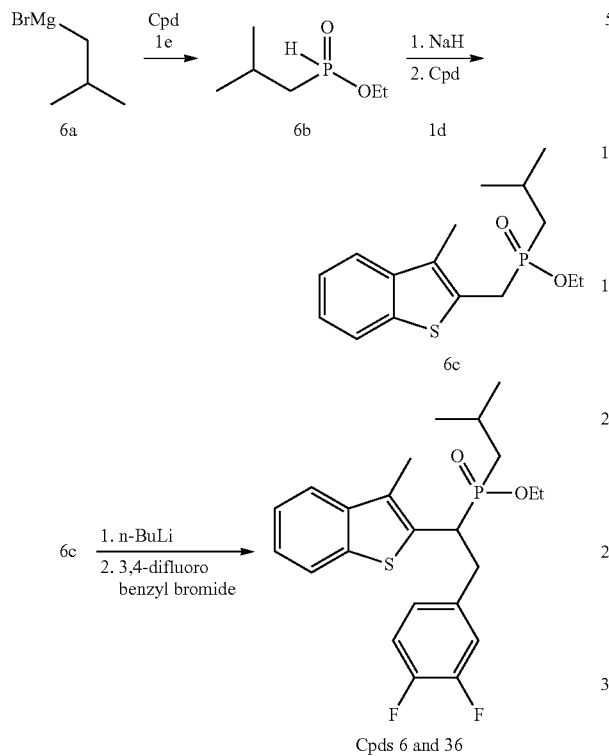

Cpds 6 and 36

A. Isobutyl-phosphinic acid ethyl ester. To a solution of 2.0 M isobutyl magnesium bromide (Compound 6a) in ether (10 mL; 20 mmol), under nitrogen, was added triethyl phosphite (Compound 1e, 4.2 mL; 24.1 mmol), dropwise at ambient temperature, and the reaction was stirred for 6 h at ambient temperature. The crude mixture was diluted with EtOAc, washed with $H_2O$ and brine, dried over $Na_2SO_4$, filtered, and the filtrate was evaporated under reduced pressure. The crude residue was purified by flash column chromatography ($SiO_2$), eluting with a heptane-EtOAc gradient (stain with Ninhydrin) to afford Compound 6b. $^1$H NMR (300 MHz, $CDCl_3$): δ 7.81-7.82 (m, 0.5H, P—H), 6.49-6.50 (m, 0.5H, P—H), 4.01-4.21 (m, 2H), 2.09-2.18 (m, 1H), 1.66-1.74 (m, 2H), 1.34-1.38 (m, 3H), 1.03-1.07 (d, 6H).

B. Isobutyl-(3-methyl-benzo[b]thiophen-2-ylmethyl)-phosphinic acid ethyl ester. To a suspension of 60% NaH (0.208 g; 5.21 mmol) in toluene (20 mL), cooled to 0° C., was added a solution of Compound 6b (0.837 g; 5.57 mmol) in toluene (5 mL), dropwise. The reaction mixture was stirred at 0° C. for 30 min, to which was added a solution of Compound 1d (0.662 g; 3.71 mmol) in toluene (5 mL), dropwise. The reaction was refluxed for 3 h, cooled, diluted with EtOAc, washed with $H_2O$ and brine, dried over $Na_2SO_4$, filtered, and the filtrate was evaporated under reduced pressure. The crude residue was purified by reverse-phase semi-prep HPLC eluting with a 50% to 70% MeCN—$H_2O$ gradient to afford Compound 6c. $^1$H NMR (300 MHz, DMSO-$d_6$): δ 7.87-7.89 (d, 1H), 7.68-7.70 (d, 1H), 7.30-7.39 (m, 2H), 3.89-3.99 (m, 2H), 3.46-3.51 (m, 2H), 2.32-2.33 (d, 3H), 1.97-2.00 (m, 1H), 1.63-1.68 (m, 2H), 1.16-1.20 (t, 3H), 0.965-0.982 (d, 6H); LC/MS $C_{16}H_{23}O_2PS$: m/z 311.0 (M-F).

C. Cpds 6 and 36: [2-(3,4-Difluoro-phenyl)-1-(3-methyl-benzo[b]thiophene-2-yl)-ethyl]-isobutyl-phosphonic acid ethyl ester. Compounds 6 and 36 were prepared following the method described in Example 1, Step E, substituting Compound 6c for Compound 1f, and substituting 3,4-difluorobenzyl bromide for Compound 1g. The mixture of compounds were purified and separated by reverse-phase semi-prep HPLC (J-sphere, ODS-H80 column; 100×30 mm I.D.; S-4 μM) eluting with a 60% to 80% MeCN—$H_2O$ gradient to afford diastereomers.

Cpd 6: faster-eluting peak; $^1$H NMR (300 MHz, DMSO-$d_6$): δ 7.85-7.87 (m, 1H), 7.59-7.61 (m, 1H), 7.27-7.32 (m, 3H), 7.16-7.18 (m, 1H), 6.82-7.06 (m, 1H), 4.06-4.13 (m, 3H), 3.23-3.33 (m, 1H), 2.86-3.09 (m, 1H), 2.10-2.11 (d, 3H), 1.76-1.99 (m, 1H), 1.59-1.65 (m, 2H), 1.26-1.30 (t, 3H), 0.900-0.933 (t, 6H); LC/MS $C_{23}H_{27}F_2O_2PS$: m/z 436.8 (M+).

Cpd 36: slower-eluting peak; $^1$H NMR (300 MHz, DMSO-$d_6$): δ 7.85-7.87 (m, 1H), 7.59-7.61 (m, 1H), 7.26-7.34 (m, 3H), 7.14-7.21 (m, 1H), 6.96-6.97 (m, 1H), 4.08-4.14 (m, 3H), 3.89-3.95 (m, 1H), 3.71-3.77 (m, 1H), 3.33 (m, 1H), 2.92-3.09 (m, 1H), 2.11-2.12 (d, 3H), 2.01-2.03 (m, 1H), 1.68-1.73 (m, 2H), 1.06-1.09 (t, 3H), 0.976-0.992 (t, 6H); LC/MS $C_{23}H_{27}F_2O_2PS$: m/z 436.8 (M+).

Following the procedure described above for Example 6 and substituting the appropriate reagents, starting materials and purification methods known to those skilled in the art, the following compounds of the present invention were prepared:

Cpds 135 and 136: [2-(3,4-Difluoro-phenyl)-1-(3-methyl-benzo[b]thiophene-2-yl)-ethyl]-[3-(4-methoxy-phenyl)-propyl]-phosphonic acid ethyl ester. Compounds 135 and 136 were prepared by the method described in Example 6, substituting [3-(4-methoxy-phenyl)-propyl]-(3-methyl-benzo[b]thiophen-2-ylmethyl)-phosphinic acid ethyl ester (prepared according to the procedures described in United States patent application US 20050176769) for Compound 6c in Step C. The diastereomers were separated by reverse-phase semi-prep HPLC (J-sphere, ODS-H80 column; 100×30 mm I.D.; S-4 μM) eluting with a 60% to 80% MeCN—$H_2O$ gradient.

Cpd 135: faster-eluting peak; $^1$H NMR (300 MHz, DMSO-$d_6$): δ 7.84-7.86 (m, 1H), 7.59-7.61 (d, 1H), 7.30-7.34 (m, 3H), 7.15-7.18 (m, 1H), 6.88-6.90 (m, 3H), 6.68-6.70 (m, 2H), 4.04-4.11 (m, 3H), 3.66 (s, 3H), 2.84-3.08 (m, 3H), 2.43-2.49 (m, 1H), 2.08-2.09 (d, 3H), 1.61-1.63 (m, 4H), 1.24-1.28 (t, 3H); LC/MS $C_{29}H_{31}F_2O_3PS$: m/z 528.7 (M+).

Cpd 136: slower-eluting peak; $^1$H NMR (300 MHz, DMSO-$d_6$): δ7.72-8.06 (m, 1H), 7.47-7.72 (m, 1H), 7.29-7.31 (m, 3H), 7.09-7.23 (m, 1H), 7.00-7.02 (m, 3H), 6.75-6.77 (m, 2H), 3.98-4.30 (m, 1H), 3.85-3.98 (m, 1H), 3.56-3.85 (m, 4H), 3.17 (m, 1H), 2.81-3.09 (m, 1H), 2.28-2.32 (m, 1H), 2.10-2.11 (d, 3H), 1.72-1.73 (m, 4H), 1.07-1.11 (t, 3H); LC/MS $C_{29}H_{31}F_2O_3PS$: m/z 528.7 (M+).

Cpd 30 and 106: [2-(3,4-Difluoro-phenyl)-1-(3-methyl-benzo[b]thiophene-2-yl)-ethyl]-methyl-phosphonic acid ethyl ester. Compounds 30 and 106 were prepared by the method described in Example 6, substituting methyl-phosphinic acid ethyl ester for Compound 6b in Step B. Diastereomers 30 and 106 were separated by flash column chromatography ($SiO_2$), eluting with a heptane-EtOAc gradient.

Cpd 30: faster-eluting peak; $^1$H NMR (300 MHz, $CD_3OD$): δ 7.78-7.81 (m, 1H), 7.58-7.60 (m, 1H), 7.28-7.35 (m, 2H), 6.96-7.06 (m, 2H), 6.86-6.89 (m, 1H), 3.93-4.12 (m, 4H), 3.47-3.53 (m, 1H), 3.03-3.11 (m, 1H), 2.08-2.09 (d, 3H), 1.54-1.57 (d, 3H), 1.24-1.28 (t, 3H); LC/MS $C_{20}H_{21}F_2O_2PS$: m/z 394.8 (M+).

Cpd 106: slower-eluting peak; LC/MS $C_{20}H_{21}F_2O_2PS$: m/z 394.8 (M+).

Example 7

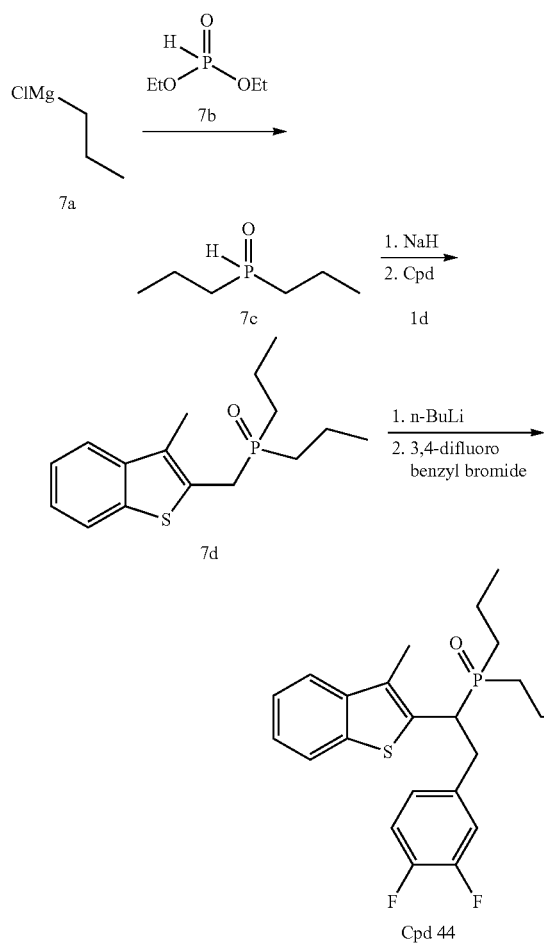

A. 1-Propylphosphinoyl-propane. To a solution of 2.0 M propyl magnesium chloride (7a) in diethyl ether (58 mL; 116 mmol), under nitrogen and cooled in an ice-bath, was added diethyl phosphate (7b) (5.0 mL; 39 mmol), dropwise at a rate to maintain temperature between 20-30° C. The reaction was allowed to stir at ambient temperature for 1 h, to which was added a cold solution of $K_2CO_3$ (16.0 g; 116 mmol) in $H_2O$ (20 mL), dropwise. The resultant mixture was filtered, washed with EtOH (4×100 mL), and the EtOH washes were combined and concentrated under reduced pressure. The resultant residue was taken up in diethyl ether, and a solid was removed by filtration. The filtrate was concentrated under reduced pressure to afford Compound 7c. $^1$H NMR (300 MHz, DMSO-$d_6$): δ 7.28 (m, 0.5H, P—H), 6.18 (m, 0.5H, P—H), 1.68-1.76 (m, 4H), 1.48-1.59 (m, 4H), 0.972-1.00 (t, 6H).

B. 2-(Dipropyl-phosphinoylmethyl)-3-methylbenzo[b]thiophene. The title Compound 7d was prepared following the method described in Example 6, Step B substituting Compound 7c for Compound 6b. $^1$H NMR (300 MHz, CDCl$_3$): δ 7.76-7.78 (d, 1H), 7.64-7.66 (d, 1H), 7.32-7.42 (m, 2H), 3.52-3.55 (d, 2H), 2.37-2.38 (d, 3H), 1.77-1.87 (m, 4H), 1.62-1.74 (m, 4H), 1.03-1.07 (m, 6H), 0.965-0.982 (d, 6H); LC/MS $C_{16}H_{23}OPS$: m/z 295.1 (M+).

C. Cpd 44: 2-[2-(3,4-Difluoro-phenyl)-1-(dipropyl-phosphinoyl)-ethyl]-3-methyl-benzo[b]thiophene. Compound 44 was prepared following the method described in Example 6, Step C substituting Compound 7d for Compound 6c. $^1$H NMR (300 MHz, CDCl$_3$): δ 7.78-7.81 (m, 1H), 7.54-7.57 (m, 2H), 7.32-7.38 (m, 2H), 6.82-6.93 (m, 2H), 6.71-6.74 (m, 1H), 3.67-3.75 (m, 8H), 0.998-1.03 (m, 6H); LC/MS $C_{23}H_{27}F_2OPS$: m/z 421.1 (M+1).

Cpd 42: 2-[(3,4-Difluoro-benzyloxy)-(dipropyl-phosphinoyl-methyl]-3-methyl-benzo[b]thiophene. Compound 42 was isolated as a by-product during the synthesis of Compound 44. $^1$H NMR (300 MHz, CDCl$_3$): δ 7.81-7.83 (d, 1H), 7.70-7.72 (d, 1H), 7.35-7.43 (m, 2H), 7.12-7.19 (m, 2H), 7.00-7.03 (m, 1H), 5.23-5.26 (d, 1H), 4.70-4.73 (d, 1H), 4.35-4.37 (d, 1H), 2.40-2.41 (d, 3H), 1.70-1.92 (m, 5H), 1.51-1.61 (m, 3H), 1.03-1.07 (t, 3H), 0.962-1.00 (t, 3H); LC/MS $C_{23}H_{27}F_2O_2PS$: m/z 437.1 (M+1).

Following the procedure described above for Example 7 and substituting the appropriate reagents, starting materials and purification methods known to those skilled in the art, the following compounds of the present invention were prepared:

| Cpd | MS Observed | MS Calc'd |
| --- | --- | --- |
| 13 | 464.1 | 464.2 |
| 33 | 449.2 | 448.2 |
| 42 | 437.1 | 436.1 |
| 44 | 421.1 | 420.1 |
| 123 | 499.0 | 496.1 |
| 203 | 515.1 | 513.43 |
| 204 | 531.0 | 529.42 |

Cpd 33: 2-[2-(3,4-Difluoro-phenyl)-1-(diisobutyl-phosphinoyl)-ethyl]-3-methyl-benzo[b]thiophene. Compound 33 was prepared following the method described in Example 7, Step A substituting Compound 6a for Compound 7a. $^1$H NMR (300 MHz, DMSO-$d_6$): δ 7.86-7.88 (m, 1H), 7.58-7.60 (m, 1H), 7.13-7.34 (m, 4H), 6.92-6.95 (m, 1H), 3.95-3.96 (m, 1H), 3.39-3.42 (m, 1H), 3.01-3.02 (m, 1H), 2.08-2.12 (m, 4H), 1.72-1.98 (m, 3H), 1.50-1.55 (m, 2H), 1.05-1.07 (d, 6H), 0.867-0.884 (d, 3H), 0.817-0.833 (d, 3H); LC/MS $C_{25}H_{31}F_2OPS$: m/z 449.2 (M+1).

Cpd 13: 2-[(3,4-Difluoro-benzyloxy)-(diisobutyl-phosphinoyl)-methyl]-3-methyl-benzo[b]thiophene. Compound 13 was isolated as a by-product during the synthesis of Compound 33. $^1$H NMR (300 MHz, DMSO-$d_6$): δ 7.95-7.97 (m, 1H), 7.77-7.79 (d, 1H), 7.36-7.49 (m, 4H), 7.17-7.21 (m, 1H), 5.31-5.34 (d, 1H), 4.60-4.63 (d, 1H), 4.45-4.48 (d, 1H), 2.38-2.39 (d, 3H), 1.75-1.80 (m, 2H), 1.59-1.73 (m, 4H), 1.00-1.01 (d, 3H), 0.954-0.970 (d, 3H), 0.901-0.923 (m, 6H); LC/MS $C_{25}H_{31}F_2O_2PS$: m/z 464.1 (M+1).

Example 8

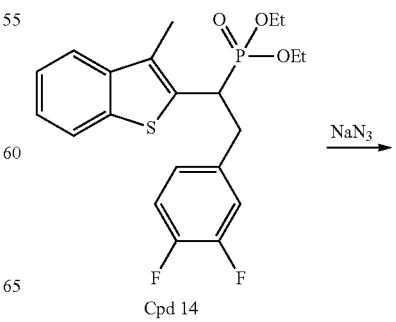

Cpd 14

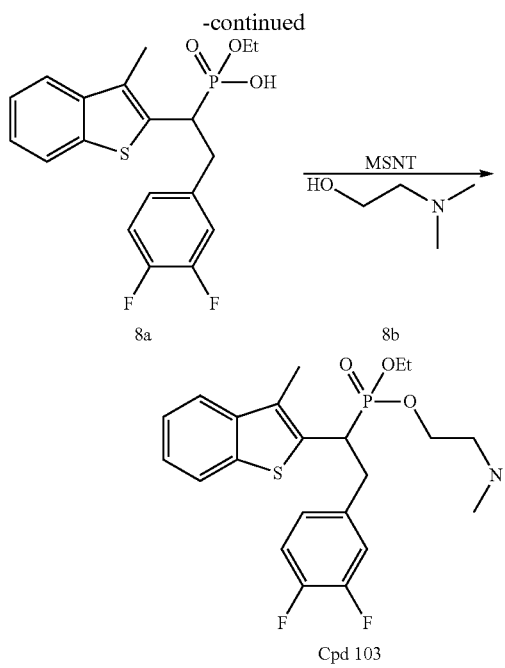

Cpd 103

A. [2-(3,4-Difluoro-phenyl)-1-(3-methyl-benzo[b] thiophen-2-yl)-ethyl]-phosphonic acid monoethyl ester. To a solution of Compound 14 of Example 1 (0.309 g; 0.728 mmol) in DMF (20 mL), was added NaN$_3$ (0.331 g; 5.09 mmol), in one-portion, at ambient temperature. The reaction was stirred at 100° C. for 18 h, cooled, diluted with EtOAc, sequentially washed with 1N HCl, H$_2$O, and brine. The organic phase was dried over Na$_2$SO$_4$, filtered, and the filtrate was concentrated under reduced pressure. The crude residue was purified by reverse-phase semi-prep HPLC eluting with a 40% to 60% MeCN:H$_2$O gradient to afford Compound 8a. $^1$H NMR (300 MHz, CD$_3$OD): δ 7.77-7.79 (m, 1H), 7.56-7.58 (m, 1H), 7.25-7.33 (m, 2H), 6.95-7.01 (m, 2H), 6.83-6.86 (m, 1H), 3.86-4.10 (m, 3H), 3.45-3.51 (m, 1H), 3.05-3.13 (m, 1H), 2.05-2.06 (d, 3H), 1.22-1.25 (t, 3H); LC/MS C$_{19}$H$_{19}$F$_2$O$_3$PS: m/z 396.7 (M+).

B. Cpd 103: [2-(3,4-Difluoro-phenyl)-1-(3-methyl-benzo [b]thiophen-2-yl)-ethyl]-phosphonic acid 2-dimethylamino-ethyl ester ethyl ester. To a solution of Compound 8a (0.131 g; 0.463 mmol) in pyridine (4.0 mL), was added MSNT (0.822 g; 2.77 mmol), in one portion, at ambient temperature, followed by the addition of dimethylaminoethanol (Compound 8b) (0.103 mL; 1.02 mmol) and the reaction was stirred for 48 h at ambient temperature. An additional 2.0 equivalents of Compound 8b were added to the reaction mixture, and the solution was stirred for an additional 72 h at ambient temperature. The reaction was diluted with EtOAc, washed sequentially with 1N HCl, H$_2$O, and brine. The organic phase was dried over Na$_2$SO$_4$, filtered, and the filtrate was concentrated under reduced pressure. The crude residue was purified by reverse-phase semi-prep HPLC eluting with a 30% to 50% MeCN:H$_2$O gradient to afford Compound 103. $^1$H NMR (300 MHz, CD$_3$OD): δ 7.79-7.83 (m, 1H), 7.59-7.63 (m, 1H), 7.31-7.37 (m, 2H), 6.97-7.08 (m, 2H), 6.87-6.90 (m, 1H), 4.41-4.45 (m, 1H), 4.01-4.33 (m, 43.24-3.34 (m, 2H), 3.12-3.28 (m, 2H), 2.92 (s, 3H), 2.75 (s, 3H), 2.10-2.11 (d, 3H), 1.37-1.41 (t, 3H) 1.17-1.20 (m, 3H); LC/MS C$_{23}$H$_{28}$F$_2$NO$_3$PS: m/z 467.9 (M+).

Example 9

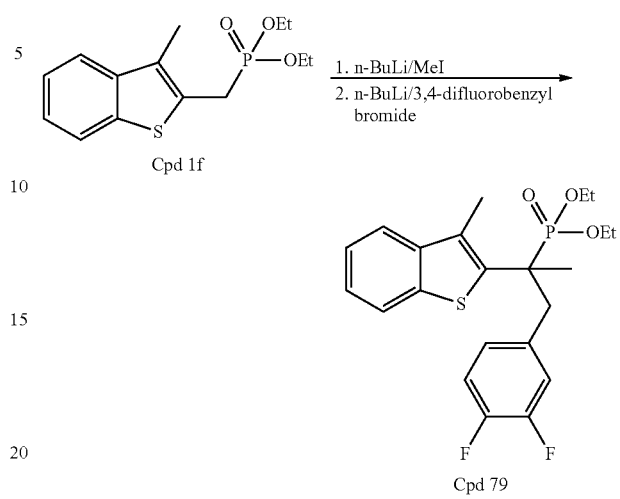

Cpd 79: [2-(3,4-Difluoro-phenyl)-1-methyl-1-(3-methyl-benzo[b]-thiophen-2-yl)-ethyl]-phosphonic acid diethyl ester. To a solution of Compound 1f (0.100 g; 0.336 mmol) in THF (1.0 mL), cooled to −78° C., was added a solution of 2.5 M n-butyllithium-hexanes (0.175 mL; 0.438 mmol), dropwise. The solution was allowed to stir at −70° C. for 30 min. At that time, a solution of iodomethane (0.072 g; 0.507 mmol) in THF (0.5 mL) was added. The reaction was allowed to stir for 30 min at −70° C. At that time, another 1.3 equivalents of 2.5 M n-butyllithium in hexanes (0.175 mL) was added dropwise, followed by the dropwise addition of a solution of 3,4-difluorobenzyl bromide (0.139 g; 0.671 mmol) in THF (1.0 mL). The reaction was allowed to warm to ambient temperature and stirred for 18 h. The reaction was quenched with saturated aqueous NH$_4$Cl, diluted with EtOAc, and washed with H$_2$O and brine. The organic phase was dried over Na$_2$SO$_4$, filtered, and the filtrate was concentrated under reduced pressure. The crude residue was purified by reverse-phase semi-prep HPLC, eluting with a 45% to 65% MeCN: H$_2$O gradient to afford Compound 79. $^1$H NMR (300 MHz, CD$_3$OD): δ 7.75-7.79 (t, 1H), 7.32-7.42 (m, 2H), 6.97-7.04 (m, 1H), 6.85-6.90 (m, 1H), 6.77-6.80 (m, 1H), 4.10-4.16 (m, 2H), 3.87-3.96 (m, 2H), 3.63-3.69 (m, 1H), 3.15-3.20 (m, 1H), 2.77-2.78 (d, 3H), 1.63-1.67 (d, 3H), 1.28-1.35 (t, 3H), 1.06-1.10 (t, 3H); LC/MS C$_{22}$H$_{25}$F$_2$O$_3$PS: m/z 438.7 (M+).

Example 10

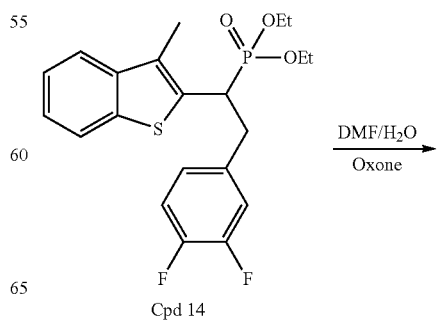

Cpd 14

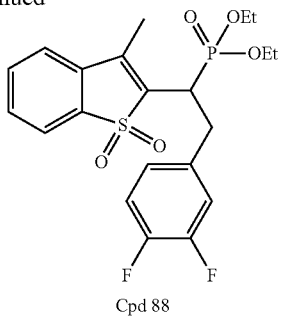

Cpd 88

Cpd 88: [2-(3,4-Difluoro-phenyl)-1-(3-methyl-1,1-dioxo-1H-1%⁶-benzo-[b]thiophen-2-yl)-ethyl]-phosphonic acid diethyl ester. To a solution of Compound 14 of Example 1 (0.136 g; 0.320 mmol) in DMF (3.5 mL) and $H_2O$ (1.7 mL), was added oxone (1.18 g; 1.92 mmol), in one portion, at ambient temperature. The reaction was stirred for 18 h at ambient temperature, at which time the reaction mixture was diluted with EtOAc, and washed with $H_2O$ and brine. The organic phase was dried over $Na_2SO_4$, filtered, and the filtrate was concentrated under reduced pressure. The crude residue was purified by reverse-phase semi-prep HPLC, eluting with a 40% to 60% MeCN:$H_2O$ gradient to afford Compound 88. $^1$H NMR (300 MHz, DMSO-$d_6$): δ 7.76-7.78 (m, 1H), 7.57-7.72 (m, 3H), 7.35-7.40 (m, 1H), 7.21-7.28 (m, 1H), 7.07-7.09 (m, 1H), 3.99-4.11 (m, 4H), 3.41 (m, 1H), 3.24-3.29 (m, 2H), 2.27 (s, 3H), 1.22-1.25 (t, 3H), 1.15-1.18 (t, 3H); LC/MS $C_{21}H_{23}F_2O_5PS$: m/z 456.7 (M+).

Following the procedure described above for Example 10 and substituting the appropriate reagents, starting materials and purification methods known to those skilled in the art, the following compounds of the present invention were prepared:

| Cpd | MS Observed | MS Calc'd |
|---|---|---|
| 118 | 440.9 | 440.1 |

Example 11

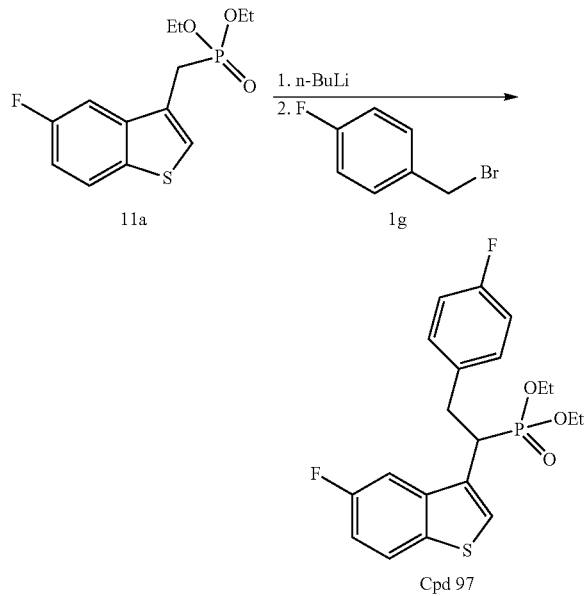

Cpd 97: [1-(5-Fluoro-benzo[b]thiophene-3-yl)-2-(4-fluoro-phenyl)-ethyl]-phosphonic acid diethyl ester. To a solution of Compound 11a (prepared according to the procedures described in United States patent application US 20050176769) (0.38 g; 1.26 mmol) in THF (2.0 mL) at −70° C. was added a 1.6 M solution of n-butyllithium in hexanes (1.0 mL; 1.6 mmol), dropwise. The reaction mixture was allowed to stir at −70° C. for 30 min, to which was then added a solution of Compound 1g (0.2 mL; 1.6 mmol) in THF (0.7 mL), dropwise. The reaction mixture was allowed to slowly warm to ambient temperature, and stirred for an additional 30 min before quenching with a solution of saturated aqueous $NH_4Cl$ (1.0 mL). The mixture was diluted with EtOAc, washed with $H_2O$ and then brine. The organic phase was dried over $Na_2SO_4$, filtered, and the filtrate was concentrated under reduced pressure. The resulting residue was purified by reverse-phase semi-prep HPLC, eluting with a 55% to 75% MeCN—$H_2O$ gradient to afford Compound 97. $^1$H-NMR (300 MHz, CDCl$_3$): δ 7.70-7.73 (m, 1H), 7.58-7.59 (m, 1H), 7.27-7.30 (m, 2H), 6.96-7.09 (m, 3H), 6.76-6.82 (m, 2H), 4.03-4.13 (m, 2H), 3.83-3.91 (m, 1H), 3.47-3.69 (m, 3H), 3.19-3.28 (m, 1H), 1.26-1.29 (t, 3H), 0.955-0.990 (t, 3H); LC/MS: $C_{20}H_{21}F_2O_3PS$: m/z 410.9 (M+).

Following the procedure described above for Example 11 and substituting the appropriate reagents, starting materials and purification methods known to those skilled in the art, the following compounds of the present invention were prepared:

| Cpd | MS Observed | MS Calc'd |
|---|---|---|
| 86 | 393.9 | 392.1 |
| 97 | 410.9 | 410.1 |
| 108 | 485.9 | 485.1 |

Example 12

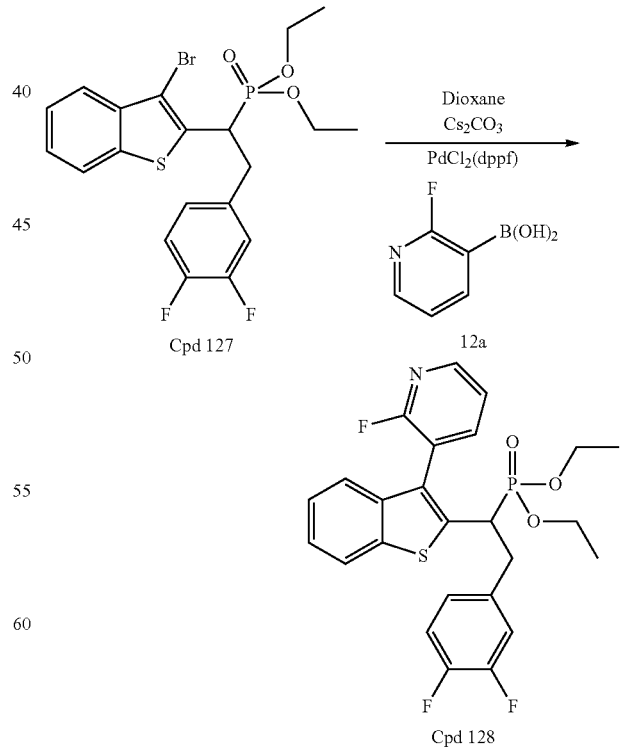

Cpd 128: {2-(3,4-Difluoro-phenyl)-1-[3-(2-fluoro-pyridin-3-yl)-benzo[b]thiophen-2-yl]ethyl}-phosphonic acid diethyl ester. To Compound 127 (prepared according to Example 5) (0.061 g; 0.125 mmol) in a microwave vessel purged with nitrogen was added Compound 12a (0.045 g; 0.319 mmol), dioxane (3.0 mL), Cs$_2$CO$_3$ (0.081 g; 0.249 mmol), and PdCl$_2$(dppf) (0.012 g; 0.016 mmol). The reaction mixture was purged with nitrogen and heated under microwave radiation for 30 minutes at 180° C. The reaction mixture was diluted with EtOAc, and washed with H$_2$O and brine. The organic phase was dried over Na$_2$SO$_4$, filtered, and the filtrate was concentrated reduced pressure. The crude reaction mixture was purified by reverse-phase semi-prep HPLC eluting with a 55% to 75% MeCN/H$_2$O gradient to afford Compound 128. LC/MS C$_{25}$H$_{23}$F$_3$NO$_3$PS: m/z 506.1 (M+1).

Following the procedure described above for Example 12 and substituting the appropriate reagents, starting materials and purification methods known to those skilled in the art, the following compounds of the present invention were prepared:

Cpd 130: {2-(3,4-Difluoro-phenyl)-1-[3-(6-fluoro-pyridin-3-yl)-benzo[b]thiophen-2-yl]-ethyl}-phosphonic acid diethyl ester. Compound 130 was prepared from Compound 127 (prepared according to Example 5) following the method described in Example 12, substituting 2-fluoropyridyl-5-boronic acid for Compound 12a. $^1$H NMR (300 MHz, DMSO-d$_6$): δ 8.01-8.03 (m, 1H), 6.99-7.40 (m, 7H), 6.73-6.75 (m, 1H), 4.00-4.13 (m, 4H), 3.26-3.31 (m, 1H), 2.98-3.07 (m, 1H), 1.26-1.29 (t, 3H), 1.14-1.17 (t, 3H); LC/MS C$_{25}$H$_{23}$F$_3$NO$_3$PS: m/z 506.1 (M+1).

Cpd 132: 1-[(3-Bromo-thieno[2,3-b]pyridin-2-yl)-2-(3,4-difluoro-phenyl)-ethyl]-phosphonic acid diethyl ester. Compound 132 was prepared from Compound 13a following the methods described in Example 4, Steps A and B, substituting 2-chloro-3-pyridinecarboxaldehyde for Compound 4a; and following the method described in Example 5, Step A, substituting Compound 13d for Compound 78. $^1$H NMR (300 MHz, CD$_3$OD): δ 8.54-8.56 (m, 1H), 8.02-8.04 (m, 1H), 7.46-7.49 (m, 1H), 6.98-7.13 (m, 3H), 4.04-4.34 (m, 5H), 3.50-3.56 (m, 1H), 3.11-3.19 (m, 1H), 1.33-1.36 (t, 3H), 1.22-1.26 (t, 3H); LC/MS C$_{19}$H$_{19}$BrF$_2$NO$_3$PS: m/z 492.0 (M+1).

Following the procedure described above for Example 13 and substituting the appropriate reagents, starting materials and purification methods known to those skilled in the art, the following compound of the present invention was prepared:

| Cpd | MS Observed | MS Calc'd |
|---|---|---|
| 207 | 520.0 | 518.36 |

Example 14

Example 13

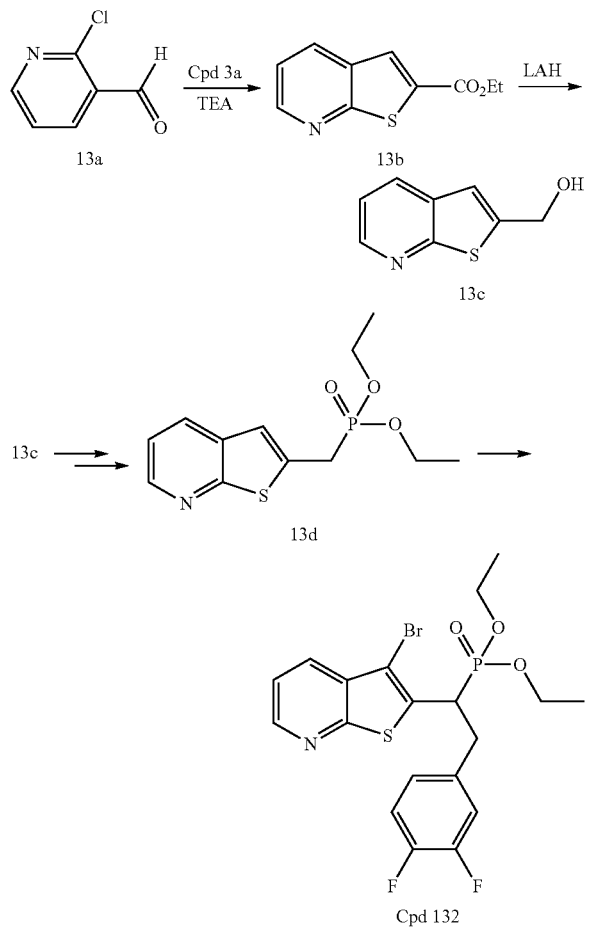

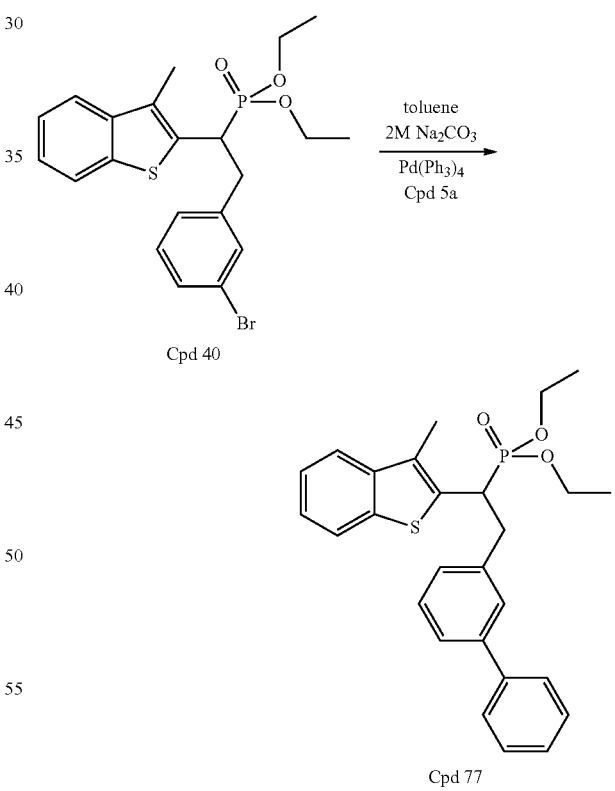

Cpd 77: [2-(Biphenyl-3-yl-1-(3-methyl-benzo[b]thiophen-2-yl)-ethyl]-phosphonic acid diethyl ester. To a solution of Compound 40 of Example 1 (0.111 g; 0.237 mmol), in toluene (1.0 mL) was added 2M aqueous Na$_2$CO$_3$ (0.474 mL; 0.948 mmol), phenyl-boronic acid (Compound 5a) (0.058 g; 0.475 mmol) and palladium triphenylphosphine (0.0065 g; 0.0043 mmol) and the reaction was refluxed for 18 h. At that time, the reaction was cooled, diluted with EtOAc, and washed with H₂O and brine. The organic phase was dried over Na₂SO₄, filtered, and the filtrate was concentrated under reduced pressure. The crude residue was purified by reverse-phase semi-prep HPLC eluting with a 60% to 80% MeCN/H₂O gradient to afford Compound 77. $^1$H NMR (300 MHz, CD₃OD): δ 7.82-7.86 (m, 1H), 7.52-7.56 (m, 1H), 7.30-7.34 (m, 3H), 7.09-7.24 (m, 5H), 3.94-4.23 (m, 5H), 3.48-3.54 (m, 1H), 3.11-3.20 (m, 1H), 1.94-1.95 (d, 3H), 1.33-1.37 (t, 3H), 1.18-1.21 (t, 3H); LC/MS $C_{27}H_{29}O_3PS$: m/z 464.9 (M+).

Following the procedure described above for Example 14 and substituting the appropriate reagents, starting materials and purification methods known to those skilled in the art, the following compounds of the present invention were prepared:

Cpd 72: [1-(3-Methyl-benzo[b]thiophen-2-yl)-2-(3-pyridin-4-yl-phenyl)-ethyl]-phosphonic acid diethyl ester. Compound 72 was prepared from Compound 40 (prepared according to Example 1) following the method described in Example 14, Step A and substituting 4-pyridyl boronic acid for Compound 5a. $^1$H NMR (300 MHz, CD₃OD): δ 8.50-8.60 (m, 2H), 7.82-7.86 (m, 2H), 7.40-7.54 (m, 3H), 7.25-7.35 (m, 5H), 4.15-4.23 (m, 2H), 3.95-4.12 (m, 2H), 3.53-3.69 (m, 1H), 3.12-3.25 (m, 3H), 1.97 (s, 3H), 1.34-1.37 (t, 3H), 1.18-1.22 (t, 3H); LC/MS $C_{26}H_{28}NO_3PS$: m/z 465.8 (M+).

Example 15

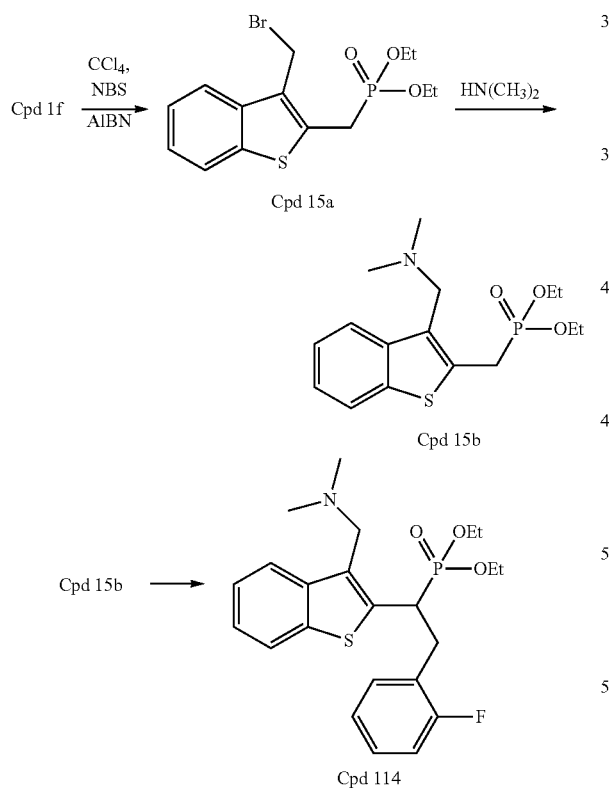

A. (3-Bromomethyl-benzo[b]thiophen-2-ylmethyl)-phosphonic acid diethyl ester. To a solution of Compound 1f of Example 1 (0.215 g; 0.721 mmol) in CCl₄ (3.0 mL) was added N-bromosuccinimide (0.133 g; 0.747 mmol) followed by 2,2'-azobisisobutyronitrile (0.018 g; 0.109 mmol) and the reaction refluxed for 18 h under irradiation. The reaction was cooled, diluted with EtOAc, and washed with H₂O and brine. The organic phase was dried over Na₂SO₄, filtered, and the filtrate was concentrated under reduced pressure. The crude residue was purified by flash column chromatography (SiO₂) eluting with a heptane-EtOAc gradient to afford Compound 15a. $^1$H NMR (300 MHz, CDCl₃): δ 7.77-7.80 (m, 2H), 7.33-7.45 (m, 2H), 4.77-4.80 (s, 2H), 4.06-4.14 (m, 4H), 3.28-3.52 (d, 2H), 1.28-1.32 (t, 6H).

B. [1-(3-Dimethylaminomethyl-benzo[b]thiophen-2-ylmethyl)-phosphonic acid diethyl ester. To a solution of Compound 15a (0.139 g; 0.368 mmol) in MeOH (2.0 mL) was added a 2M solution of dimethylamine in methanol (5.0 mL) and the reaction was heated at 65° C. in a pressure tube. The reaction was cooled, diluted with EtOAc, and washed with 10% NaOH, H₂O and brine. The organic phase was dried over Na₂SO₄, filtered, and the filtrate was concentrated under reduced pressure. The crude residue was purified by flash column chromatography (SiO₂), eluting with a heptane-EtOAc gradient to afford Compound 15b. LC/MS $C_{16}H_{24}NO_3PS$: m/z 341.9 (M+).

C. Cpd 114: [1-(3-Dimethylaminomethyl-benzo[b]thiophen-2-yl)-2-(2-fluoro-phenyl)-ethyl]-phosphonic acid diethyl ester. Compound 114 was prepared following the method described in Example 1, Step E substituting Compound 15b for Compound 1f and 2-fluorobenzyl bromide for Compound 1g. LC/MS $C_{23}H_{29}FNO_3PS$: m/z 449.9 (M+1).

Example 16

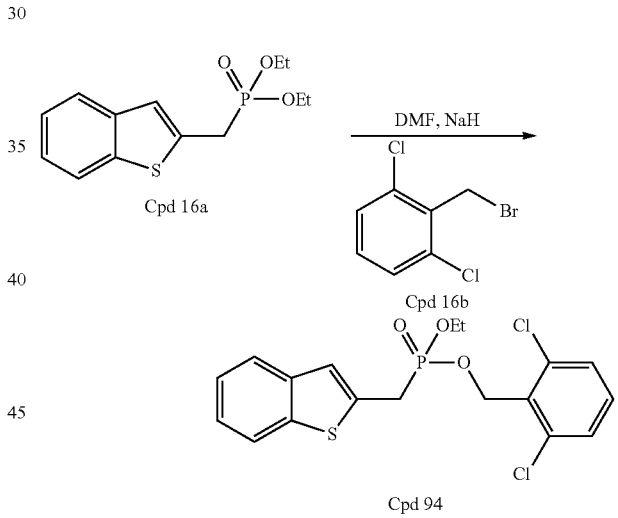

A. Cpd 94: Benzo[b]thiophen-2-ylmethyl-phosphonic acid 2,6-dichloro-benzyl ester ethyl ester. To a solution of Compound 16a of Example 1 (0.138 g, 0.484 mmol) in DMF (1.0 mL) was added 60% NaH (0.019 g; 0.726 mmol) and the suspension was stirred at ambient temperature for 1 h. 2,6-Dichlorobenzyl bromide (Compound 16b) (0.127 g; 0.532 mmol) was added in one-portion and the suspension was stirred at ambient temperature for 18 h. The reaction was diluted with EtOAc, and washed with H₂O and brine. The organic phase was dried over Na₂SO₄, filtered, and the filtrate was concentrated under reduced pressure. The crude residue was purified by reverse-phase semi-prep HPLC eluting with a 55% to 75% MeCN:H₂O gradient to afford Compound 94. $^1$H NMR (300 MHz, CD₃OD): δ 7.75-7.77 (m, 1H), 7.67-7.69 (m, 1H), 7.21-7.41 (m, 6H), 5.32-5.41 (m, 2H), 4.10-4.17 (m, 2H), 3.59-3.64 (d, 2H), 1.26-1.30 (t, 3H); LC/MS $C_{18}H_{17}Cl_2O_3PS$: m/z 416.7 (M+1).

Following the procedure described above for Example 16 and substituting the appropriate reagents, starting materials and purification methods known to those skilled in the art, the following compounds of the present invention were prepared:

| Cpd | MS Observed | MS Calc'd |
|---|---|---|
| 94 | 416.7 | 414.0 |
| 104 | 360.9 | 360.1 |
| 105 | 380.9 | 380.0 |
| 107 | 364.8 | 364.1 |
| 109 | 364.8 | 364.1 |
| 110 | 426.7 | 424.0 |
| 111 | 347.0 | 346.1 |

Cpd 104: Benzo[b]thiophen-2-ylmethyl-phosphonic acid ethyl ester 2-methyl-benzyl ester. Compound 104 was prepared following the method described in Example 16, Step A substituting 2-methylbenzyl bromide for Compound 16b. $^1$H NMR (300 MHz, CD$_3$OD): δ 7.76-7.78 (m, 1H), 7.67-7.69 (m, 1H), 7.11-7.33 (m, 7H), 5.09-5.17 (m, 2H), 4.81-4.88 (m, 2H), 4.00-4.08 (m, 2H), 2.21-2.32 (s, 3H), 1.21-1.25 (t, 3H); LC/MS C$_{19}$H$_{21}$O$_3$PS: m/z 360.9 (M+).

Cpd 109: Benzo[b]thiophen-2-ylmethyl-phosphonic acid ethyl ester 2-fluoro-benzyl ester. Compound 109 was prepared following the method described in Example 16, Step A substituting 2-fluorobenzyl bromide for Compound 16b. $^1$H NMR (300 MHz, CD$_3$OD): δ 7.76-7.78 (m, 1H), 7.67-7.69 (m, 1H), 7.28-7.40 (m, 4H), 7.18-7.19 (m, 1H), 7.07-7.12 (m, 2H), 5.12-5.15 (m, 2H), 4.03-4.11 (m, 2H), 3.57-3.62 (d, 2H), 1.23-1.27 (t, 3H); LC/MS C$_{18}$H$_{18}$FO$_3$PS: m/z 364.8 (M+).

Example 17

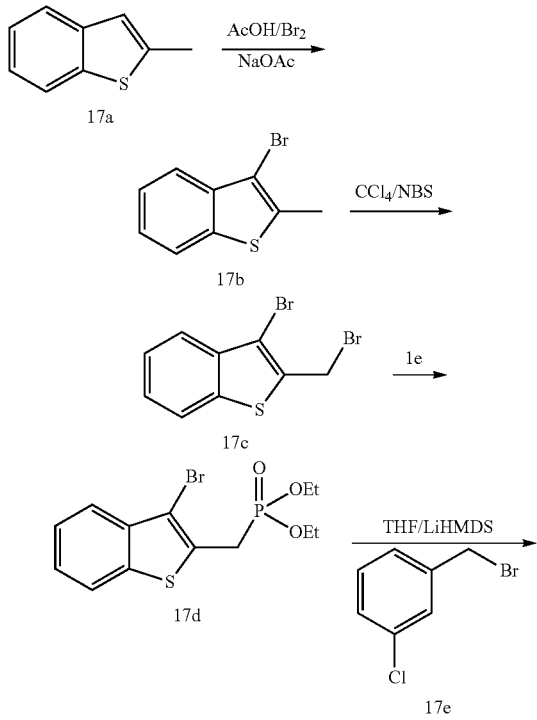

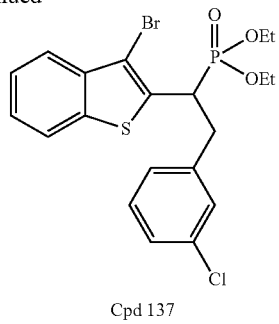

Cpd 137

A. 3-Bromo-2-methyl-benzo[b]thiophene. To a mixture of Compound 17a (10.0 g; 67.4 mmol) and anhydrous NaOAc (6.74 g; 82.2 mmol), in AcOH (100 mL), at ambient temperature, was added Br$_2$, drop-wise, and the reaction mixture was stirred at ambient temperature for 1 h. The reaction mixture was poured into H$_2$O, extracted with CHCl$_3$ several times, and the combined extracts were washed sequentially with H$_2$O, 1N NaOH, H$_2$O, and dried over Na$_2$SO$_4$. The mixture was filtered and the solvent evaporated under reduced pressure to afford Compound 17b. $^1$H NMR (400 MHz, DMSO-d$_6$): δ 7.95-7.97 (m, 1H), 7.64-7.67 (m, 1H), 7.46-7.50 (m, 1H), 7.39-7.43 (m, 1H), 2.52 (s, 3H). LC/MS C$_9$H$_7$BrS: m/z 227.0 (M+).

B. 3-Bromo-2-bromomethyl-benzo[b]thiophene. To a solution of Compound 17b (15.6 g; 69 mmol) in CCl$_4$ (200 mL) was added N-bromosuccinimide (14.7 g; 83 mmol) and the reaction was refluxed for 24 h. The reaction was cooled and then concentrated under reduced pressure. The resultant residue was purified by flash column chromatography (SiO$_2$) eluting with a heptane-EtOAc gradient to afford Compound 17c.

C. (3-Bromo-benzo[b]thiophen-2-ylmethyl)-phosphonic acid diethyl ester. To a solution of Compound 17c (22.0 g; 72 mmol) in toluene (100 mL) was added triethyl phosphite, Compound 1e (38.0 mL; 216.0 mmol) and the reaction was refluxed for 24 h. The reaction mixture was cooled, concentrated under reduced pressure and the resultant residue was purified by flash column chromatography (SiO$_2$), eluting with a hexanes-EtOAc gradient to afford of Compound 17d. $^1$H-NMR (400 MHz, CDCl$_3$): δ 8.00-8.02 (d, 1H), 7.70-7.72 (d, 1H), 7.45-7.52 (m, 2H), 3.98-4.00 (q, 4H), 3.62-3.68 (d, 2H), 1.19-1.24 (t, 6H); LC/MS: C$_{13}$H$_{16}$BrO$_3$PS: m/z 365.0 (M+1).

D. Cpd 137: [1-(3-Bromo-benzo[b]thiophene-2-yl)-2-(3-chloro-phenyl)-ethyl]-phosphonic acid diethyl ester. To a solution of Compound 17d (0.188 g; 0.518 mmol) in THF (2.0 mL) cooled to −70° C., was added a 1.0 M solution of lithium bis(trimethylsilyl)amide in THF (0.673 mL; 0.673 mmol), drop-wise. The reaction mixture was allowed to stir at −70° C. for 30 min, to which was then added a solution of Compound 17e (0.138 g; 0.673 mmol) in THF (1.0 mL), dropwise. The reaction mixture was allowed to slowly warm to ambient temperature, and stirred for an additional 18 h before quenching with a solution of saturated aqueous NH$_4$Cl (1.0 mL). The mixture was diluted with EtOAc, washed with H$_2$O, brine, and dried over Na$_2$SO$_4$. The mixture was then filtered, and the filtrate was concentrated under reduced pressure. The resulting residue was purified by reverse-phase semi-prep HPLC eluting with a 55% to 75% MeCN—H$_2$O gradient to afford Compound 137. $^1$H-NMR (400 MHz, CDCl$_3$): δ 8.00-8.02 (m, 1H), 7.60-7.64 (m, 2H), 7.41-7.51 (m, 4H), 4.21-4.30 (m, 1H), 4.08-4.15 (m, 2H), 3.91-4.03 (m, 2H), 3.49-3.55 (m, 1H), 3.16-3.25 (m, 1H), 1.24-1.27 (t, 3H), 1.09-1.13 (t, 3H); LC/MS: $C_{20}H_{21}BrClO_3PS$: m/z 489.0 (M+1).

Following the procedure described above for Example 17 and substituting the appropriate reagents, starting materials and purification methods known to those skilled in the art, the following compounds of the present invention were prepared:

| Cpd | MS Observed | MS Calc'd |
|---|---|---|
| 137 | 489.0 | 487.7 |
| 138 | 541.0 | 539.3 |
| 139 | 557.0 | 555.8 |
| 140 | 539.0 | 539.3 |
| 141 | 523.0 | 521.3 |
| 142 | 540.9 | 539.3 |
| 143 | 507.0 | 505.8 |
| 144 | 541.0 | 539.3 |
| 145 | 539.0 | 537.3 |
| 146 | 540.9 | 539.3 |
| 147 | 489.0 | 487.8 |
| 148 | 557.0 | 555.8 |
| 149 | 540.9 | 571.8 |
| 150 | 572.9 | 539.3 |
| 151 | 557.0 | 555.8 |
| 152 | 553.0 | 551.4 |
| 153 | 555.0 | 553.4 |
| 154 | 523.0 | 521.3 |
| 155 | 537.0 | 537.3 |
| 156 | 503.0 | 501.4 |
| 157 | 531.0 | 529.4 |
| 158 | 503.0 | 501.4 |
| 159 | 531.0 | 529.4 |
| 160 | 557.0 | 555.3 |
| 161 | 585.0 | 583.4 |
| 162 | 503.0 | 501.4 |
| 163 | 531.0 | 529.4 |
| 164 | 537.0 | 535.8 |
| 165 | 565.0 | 563.9 |
| 167 | 539.0 | 539.3 |
| 168 | 523.0 | 522.9 |
| 169 | 523.0 | 522.9 |
| 170 | 505.0 | 504.9 |
| 171 | 573.2 | 572.9 |
| 172 | 523.0 | 522.9 |
| 173 | 505.0 | 504.9 |
| 174 | 523.0 | 522.9 |
| 175 | 505.0 | 504.9 |
| 176 | 535.2 | 534.9 |
| 177 | 539.1 | 539.3 |
| 178 | 539.1 | 539.3 |
| 179 | 437.1 | 436.9 |
| 180 | 471.1 | 471.3 |
| 181 | 471.1 | 471.3 |
| 182 | 515.1 | 515.8 |
| 183 | 505.0 | 505.8 |
| 184 | 555.0 | 555.3 |
| 185 | 489.0 | 489.3 |
| 186 | 489.0 | 489.3 |
| 187 | 521.1 | 520.9 |
| 188 | 523.0 | 522.9 |
| 189 | 461.0 | 461.3 |
| 190 | 533.0 | 533.8 |
| 191 | 523.1 | 522.9 |
| 201 | 461.0 | 461.2 |
| 234 | 519.0 | 517.3 |
| 235 | 519.0 | 517.3 |
| 236 | 537.0 | 537.3 |
| 237 | 537.1 | 537.3 |
| 238 | 471.1 | 470.1 |
| 239 | 471.1 | 470.1 |
| 240 | 471.0 | 470.1 |
| 241 | 567.0/569.0 | 567.4 |
| 242 | 567.0/569.0 | 567.4 |
| 243 | 567.0/569.0 | 567.4 |
| 244 | 504.0 | 504.9 |
| 245 | 538.0 | 538.9 |
| 246 | 552.0 | 552.9 |
| 247 | 498.0 | 498.9 |
| 248 | 532.0 | 532.9 |
| 249 | 566.0 | 567.0 |
| 250 | 580.9 | 580.0 |
| 251 | 526.9 | 526.0 |
| 252 | 559 | 558.0 |
| 253 | 489 | 488.1 |
| 254 | 545.0 (M + Na+) | 522.1 |
| 255 | 537.0 | 536.1 |
| 256 | 483.1 | 482.1 |
| 257 | 486.9 | 486.0 |
| 258 | 504.9 | 504.0 |
| 259 | 504.8 | 504.0 |
| 260 | 520.9 | 520.0 |
| 261 | 588.9 | 588.0 |
| 262 | 584.8 | 584.0 |
| 263 | 612.7 | 612.0 |
| 264 | 568.9 | 568.1 |
| 268 | 583.0/585.0 | 583.8 |
| 269 | 445.0/443.0 | 443.3 |
| 270 | 493.0/495.0 | 492.8 |
| 271 | 527.0/529.0 | 527.3 |
| 272 | 461.0/463.0 | 461.3 |
| 273 | 495.0 | 494.8 |
| 274 | 511.0/513.0 | 511.3 |
| 275 | 486.9/489.0 | 487.7 |
| 276 | 461.0/463.0 | 461.3 |
| 277 | 493.0/495.0 | 492.8 |
| 278 | 495.0/497.0 | 494.8 |
| 279 | 477.0/479.1 | 476.8 |
| 280 | 511.0/513.0 | 511.3 |
| 281 | 495.0/497.0 | 494.8 |
| 282 | 545.0/547.0 | 544.8 |
| 283 | 509.0/511.0 | 508.9 |
| 284 | 427.0/429.0 | 426.8 |
| 285 | 477.0/479.0 | 476.8 |
| 286 | 495.0/497.1 | 494.8 |
| 287 | 511.0/513.0 | 511.3 |
| 288 | 515.0/516.9 | 515.8 |
| 289 | 567.0/569.0 | 567.3 |
| 290 | 443.0/445.0 | 443.3 |
| 291 | 495.0/497.0 | 494.8 |
| 292 | 507.0/509.1 | 506.9 |
| 293 | 443.0/445.0 | 443.3 |
| 294 | 495.0/497.0 | 494.8 |
| 295 | 533.0/534.9 | 532.2 |
| 296 | 509.0/511.0 | 508.9 |
| 297 | 461.0/463.0 | 461.3 |
| 298 | 495.0/497.0 | 494.8 |
| 299 | 455.0/457.0 | 454.9 |
| 300 | 541.0/543.0 | 540.9 |
| 301 | 521.0/523.0 | 520.9 |
| 302 | 489.0/491.1 | 489.3 |
| 303 | 489.0/491.0 | 489.3 |
| 304 | 537.0/539.1 | 537.0 |
| 305 | 461.0/463.0 | 461.3 |
| 306 | 455.1/457.0 | 454.9 |
| 307 | 507.0/504.9 | 505.7 |
| 308 | 534.9/533.0 | 533.8 |
| 309 | 480.0/478.0 | 478.3 |
| 310 | 520.0/518.0 | 518.4 |
| 311 | 521.0/519.0 | 519.3 |
| 312 | 477.9/480.0 | 478.3 |
| 313 | 511.0/513.0 | 511.3 |
| 314 | 485.0/483.0 | 483.3 |
| 315 | 500.0/498.0 | 498.3 |
| 317 | 511.0/513.0 | 511.4 |
| 319 | 513.0/515.0 | 513.3 |
| 320 | 483.0/485.0 | 483.3 |
| 321 | 483.0/485.0 | 483.3 |
| 326 | 579.0/581.0 | 579.4 |

| Cpd | MS Observed | MS Calc'd |
|---|---|---|
| 335 | 567.0/569.0 | 567.38 |
| 336 | 551.0/549.0 | 549.39 |

Cpd 155: [1-(3-Bromo-benzo[b]thiophen-2-yl)-2-(4-trifluoromethoxy-phenyl)-ethyl]-phosphonic acid diethyl ester. Compound 155 was prepared according to the method of Example 17, substituting 4-trifluoromethoxy benzyl bromide for Compound 17e of Step D. $^1$H-NMR (400 MHz, DMSO-d$_6$): δ 7.76-7.79 (m, 1H), 7.67-7.70 (m, 1H), 7.35-7.44 (m, 2H), 7.12 (d, 2H), 7.00 (d, 2H), 3.92-4.28 (m, 5H), 3.52-3.60 (m, 1H), 3.12-3.24 (m, 1H), 1.31 (t, 3H), 1.23 (t, 3H); LC/MS C$_{21}$H$_{21}$BrF$_3$O$_4$PS: m/z 537.0 (M+1).

Cpd 241: [1-(3-Bromo-benzo[b]thiophen-2-yl)-2-(4-fluoro-3-trifluoromethyl-phenyl)-ethyl]-phosphonic acid diisopropyl ester. Compound 241 was prepared according to the method of Example 17, substituting 4-fluoro-3-trifluoromethyl benzyl bromide for Compound 17e of Step D. $^1$H NMR (300 MHz, DMSO-d$_6$): δ 7.99-8.02 (m, 1H), 7.61-7.63 (m, 1H), 7.40-7.59 (m, 4H), 7.25-7.32 (m, 1H), 4.65-4.74 (m, 1H), 4.43-4.63 (m, 1H), 4.09-4.22 (m, 1H), 3.45-3.53 (m, 1H), 3.00-3.21 (m, 1H), 1.27-1.33 (d, 6H), 1.14-1.23 (d, 3H), 0.98-1.08 (d, 3H); LC/MS C$_{23}$H$_{24}$BrF$_4$O$_3$PS: m/z 567.0/569.0 (M/M+2).

Cpd 238: [1-(3-Bromo-benzo[b]thiophen-2-yl)-2-(4-fluoro-phenyl)-ethyl]-phosphonic acid diethyl ester. Compound 238 was prepared according to the method of Example 17, substituting 4-fluoro benzyl bromide for Compound 17e of Step D. $^1$H NMR (400 MHz, DMSO-d$_6$): δ 8.05-7.97 (m, 1H), 7.66-7.58 (m, 1H), 7.50-7.39 (m, 2H), 7.17 (dd, 2H), 6.98 (t, 2H), 4.23-3.84 (m, 5H), 3.50-3.38 (m, 1H), 3.15-3.01 (m, 1H), 1.26 (t, 3H), 1.11 (t, 3H); LC/MS C$_{20}$H$_{21}$BrFO$_3$PS: m/z 471.1 (M+1); Anal. Calcd for C$_{20}$H$_{21}$BrFO$_3$PS; C, 50.97; H, 4.50. Found: C, 51.01; H, 4.54.

Cpd 234: (S)-[1-(3-Bromo-benzo[b]thiophen-2-yl)-2-(3,4-difluoro-phenyl)-ethyl]-phosphonic acid diisopropyl ester; and Cpd 235: (R)-[1-(3-Bromo-benzo[b]thiophen-2-yl)-2-(3,4-difluoro-phenyl)-ethyl]-phosphonic acid diisopropyl ester. Compound 15 was separated by chiral chromatography using a Chiralpak AD column (1000 g; 1000 Å; 10 μM; 34 cm×80 mm; λ=254 nM) eluting with heptane-EtOH to afford Compound 234 and Compound 235.

Cpd 234: $^1$H NMR (300 MHz, DMSO-d$_6$): δ7.99-8.02 (m, 1H), 7.61-7.63 (m, 1H), 7.42-7.45 (m, 2H), 7.17-7.22 (m, 2H), 6.69-7.05 (m, 1H), 4.59-4.83 (m, 1H), 4.34-4.53 (m, 1H), 3.90-4.15 (m, 1H), 3.34-3.43 (m, 1H), 2.87-3.13 (m, 1H), 1.27-1.29 (d, 6H), 1.21-1.23 (d, 3H), 0.980-0.995 (d, 3H); LC/MS C$_{22}$H$_{24}$BrF$_2$O$_3$PS: m/z 517.0/519.0 (M+1); Anal. Calcd for C$_{22}$H$_{24}$BrF$_2$O$_3$PS; C, 51.07; H, 4.68; F, 7.34; P, 5.99. Found: C, 50.7; H, 4.84; F, 7.12; P, 5.71. [α]D$^{25}$+89.8° (c 1.04, MeOH).

Cpd 235: $^1$H NMR (300 MHz, DMSO-d$_6$): δ8.00-8.02 (m, 1H), 7.61-7.63 (m, 1H), 7.40-7.47 (m, 2H), 7.15-7.26 (m, 2H), 6.92-6.94 (m, 1H), 4.64-4.72 (m, 1H), 4.46-4.54 (m, 1H), 4.04-4.14 (m, 1H), 3.35-3.45 (m, 1H), 3.02-3.11 (m, 1H), 1.27-1.29 (d, 6H), 1.21-1.23 (d, 3H), 0.978-0.993 (d, 3H); LC/MS C$_{22}$H$_{24}$BrF$_2$O$_3$PS: m/z 519.0 (M+1); [α]$_D^{25}$ −93.3° (c 1.05, MeOH).

Cpd 242: (S)-[1-(3-Bromo-benzo[b]thiophen-2-yl)-2-(4-fluoro-3-trifluoromethyl-phenyl)-ethyl]-phosphonic acid diisopropyl ester; and Cpd 243: (R)-[1-(3-Bromo-benzo[b]thiophen-2-yl)-2-(4-fluoro-3-trifluoromethyl-phenyl)-ethyl]-phosphonic acid diisopropyl ester. Compound 241 was separated by chiral chromatography using a Chiralpak AD column (500 g; 1000 Å; 20 μM; 17 cm×80 mm; λ=220 nM) eluting with 95:5 heptane-EtOH to afford Compound 242 and Compound 243.

Cpd 242: $^1$H NMR (400 MHz, CDCl$_3$): δ 7.76-7.78 (m, 1H), 7.65-7.67 (m, 1H), 7.32-7.45 (m, 3H), 7.17-7.22 (m, 1H), 6.90-6.95 (m, 1H), 4.78-4.85 (m, 1H), 4.63-4.69 (m, 1H), 4.08-4.18 (m, 1H), 3.53-3.55 (m, 1H), 3.14-3.17 (m, 1H), 1.33-1.41 (m, 9H), 1.01-1.18 (d, 3H); LC/MS C$_{23}$H$_{24}$BrF$_4$O$_3$PS: m/z 567.0/569.0 (M/M+2); Anal. Calcd for C$_{23}$H$_{24}$BrF$_4$O$_3$PS; C, 48.69; H, 4.26; F, 13.39. Found: C, 47.95; H, 4.07; F, 13.45. (0.5 eq H$_2$O); [α]$_D^{25}$ +94.6° (c 1.03, MeOH).

Cpd 243: $^1$H NMR (400 MHz, CDCl$_3$): δ 7.76-7.78 (m, 1H), 7.65-7.67 (m, 1H), 7.31-7.38 (m, 3H), 7.17-7.26 (m, 1H), 6.90-6.95 (m, 1H), 4.80-4.85 (m, 1H), 4.66-4.79 (m, 1H), 4.11-4.19 (m, 1H), 3.53-3.55 (m, 1H), 3.14-3.17 (m, 1H), 1.33-1.41 (m, 9H), 1.10-1.18 (d, 3H); LC/MS C$_{23}$H$_{24}$BrF$_4$O$_3$PS: m/z 567.0/569.0 (M/M+2); [α]$_D^{25}$ −96.9° (c 1.02, MeOH).

Cpd 239: (S)-[1-(3-Bromo-benzo[b]thiophen-2-yl)-2-(4-fluoro-phenyl)-ethyl]-phosphonic acid diisopropyl ester; and Cpd 240: (R)-[1-(3-Bromo-benzo[b]thiophen-2-yl)-2-(4-fluoro-phenyl)-ethyl]-phosphonic acid diisopropyl ester. Compound 238 was separated by chiral chromatography using a OS-A column (1000 g; 1000 Å; 10 μM; 34 cm×80 mm; λ=254 nM) eluting with hetpante-EtOH (80:20) to afford Compound 239 and Compound 240.

Cpd 239: $^1$H NMR (300 MHz, DMSO-d$_6$): 8.04-7.96 (m, 1H), 7.65-7.58 (m, 1H), 7.49-7.39 (m, 2H), 7.17 (dd, 2H), 6.98 (t, 2H), 4.23-3.85 (m, 5H), 3.50-3.38 (m, 1H), 3.14-3.00 (m, 1H), 1.26 (t, 3H), 1.11 (t, 3H); LC/MS C$_{20}$H$_{21}$BrFO$_3$PS: m/z 471.0 (M+1); [α]D+110.1° (c 1.00, MeOH).

Cpd 240: LC/MS C$_{20}$H$_{21}$BrFO$_3$PS: m/z 471.0 (M+1); [α]$_D^{25}$ −111.1° (c 1.00, MeOH).

Cpd 236: (S)-[1-(3-Bromo-benzo[b]thiophen-2-yl)-2-(4-trifluoromethoxy-phenyl)-ethyl]-phosphonic acid diisopropyl ester; and Cpd 237: (R)-[1-(3-Bromo-benzo[b]thiophen-2-yl)-2-(4-trifluoromethoxy-phenyl)-ethyl]-phosphonic acid diisopropyl ester. Compound 155 was separated by chiral chromatography using a Chiralpak AS column (1000 g; 1000 Å; 10 μM; 34 cm×80 mm; λ=254 nM) eluting with acetonitrile (100%) to afford Compound 236 and Compound 237.

Cpd 236: $^1$H NMR (300 MHz, CDCl$_3$): δ 7.76-7.79 (m, 1H), 7.66-7.69 (m, 1H), 7.34-7.43 (m, 2H), 7.10-7.13 (m, 2H), 6.99 (d, 2H), 3.90-4.25 (m, 5H), 3.52-3.60 (m, 1H), 3.13-3.24 (m, 1H), 1.31 (t, 3H), 1.22 (t, 3H); LC/MS C$_{21}$H$_{21}$BrF$_3$O$_4$PS: m/z 537 (M+1); Anal. Calcd for C$_{21}$H$_{21}$BrF$_3$O$_4$PS; C, 46.94; H, 3.94; Br, 14.87; F, 10.61; P, 5.76; S, 5.97. Found: C, 46.56; H, 3.82; Br, 14.96; F, 10.35; P, 5.95; S, 5.35. [α]$_D^{25}$ +92.7° (c 1.04, MeOH).

Cpd 237: $^1$H NMR (300 MHz, CDCl$_3$): δ 7.76-7.79 (m, 1H), 7.67-7.70 (m, 1H), 7.34-7.43 (m, 2H), 7.10-7.13 (m, 2H), 6.99 (d, 2H), 3.90-4.25 (m, 5H), 3.53-3.62 (m, 1H), 3.13-3.24 (m, 1H), 1.31 (t, 3H), 1.22 (t, 3H); LC/MS C$_{21}$H$_{21}$BrF$_3$O$_4$PS: m/z 537.1 (M+1); [α]$_D^{25}$ −93.7° (c 1.05, MeOH).

Example 18

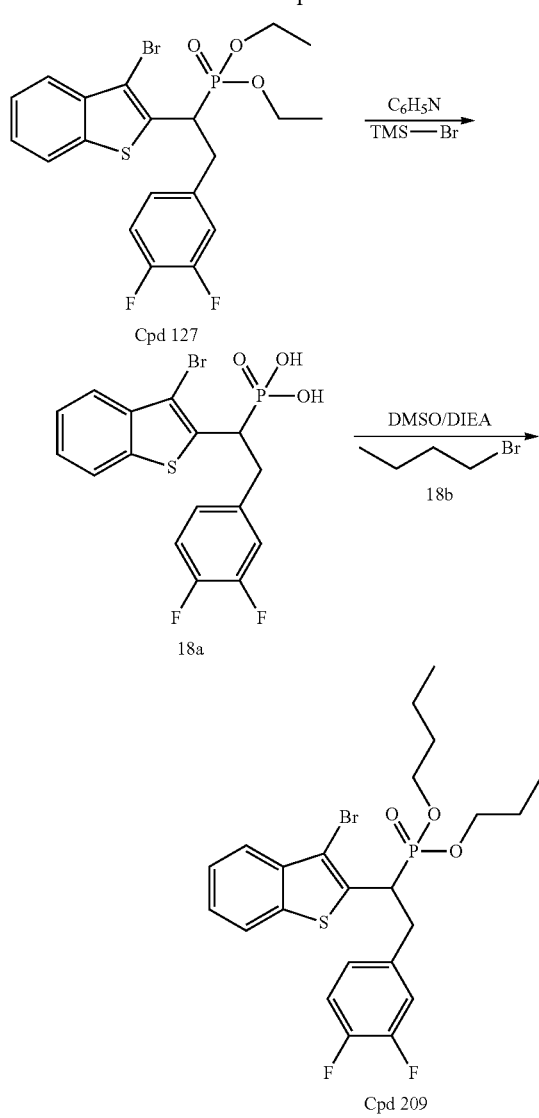

A. [1-(3-Bromo-benzo[b]thiophen-2-yl)-2-(3,4-difluoro-phenyl)-ethyl]-phosphonic acid. To a solution of Compound 127 of Example 5 (1.25 g; 2.55 mmol) in pyridine (8.0 mL), at ambient temperature, was added trimethylsilyl bromide, dropwise, in 3 equal portions (0.55 mL; 4.23 mmol), at 15 minute intervals. The reaction was stirred at ambient temperature for 72 h, diluted with EtOAc, sequentially washed with 1N HCl, H$_2$O, and brine. The organic phase was dried over Na$_2$SO$_4$, filtered, and the filtrate was concentrated under reduced pressure to afford Compound 18a. $^1$H NMR (400 MHz, DMSO-d$_6$): δ 11.42-11.46 (m, 1H), 7.95-7.97 (m, 1H), 7.57-7.59 (m, 1H), 7.37-7.45 (m, 2H), 7.10-7.21 (m 2H), 6.86-6.89 (m, 1H), 3.88-3.97 (m, 1H), 3.16-3.56 (m, 1H), 2.97-3.05 (m, 1H).

B. Cpd 209: [1-(3-Bromo-benzo[b]thiophen-2-yl)-2-(3,4-difluoro-phenyl)-ethyl]-phosphonic acid dibutyl ester. To a solution of Compound 18a (0.050 g; 0.116 mmol) in DMSO (0.5 mL), was added DIEA (0.101 mL; 0.582 mmol), followed by 1-bromobutane (Compound 18b), and the reaction was heated at 100° C. for 10 min under microwave irradiation. The crude material was purified by reverse-phase semi-prep HPLC eluting with a 70% to 90% MeCN:H$_2$O gradient to afford Compound 209. $^1$H NMR (400 MHz, CD$_3$OD): δ 7.86-7.88 (m, 1H), 7.66-7.68 (m, 1H), 7.38-7.45 (m, 2H), 6.97-7.07 (m, 2H), 6.87-6.90 (m, 1H), 4.21-4.30 (m, 1H), 3.90-4.05 (m, 4H), 3.45-3.52 (m, 1H), 3.09-3.18 (m, 1H), 1.61-1.68 (m, 2H), 1.22-1.52 (m, 6H), 0.890-0.933 (t, 3H), 0.755-0.792 (t, 3H); LC/MS C$_{24}$H$_{28}$BrF$_2$O$_3$PS: m/z 547.0 (M+1).

Following the procedure described above for Example 18 and substituting the appropriate reagents, starting materials and purification methods known to those skilled in the art, the following compounds of the present invention were prepared:

| Cpd | MS Observed | MS Calc'd |
| --- | --- | --- |
| 209 | 547.0 | 545.42 |
| 210 | 639.0 | 637.48 |
| 211 | 575.1 | 573.47 |
| 212 | 576.9 | 577.33 |
| 213 | 627.0 (+Na) | 605.39 |

Cpd 212: {[1-(3-Bromo-benzo[b]thiophen-2-yl)-2-(3,4-difluoro-phenyl)-ethyl]-methoxycarbonylmethoxy-phosphinoyloxy}-acetic acid methyl ester. Compound 212 was prepared according to the method of Example 18, substituting toluene for DMSO and bromo acetic-acid methyl ester for 1-bromobutane of Step B, and heating the reaction for 150° C. for 20 min. $^1$H NMR (400 MHz, CD$_3$OD): δ 7.86-7.88 (m, 1H), 7.66-7.68 (m, 1H), 7.40-7.44 (m, 2H), 6.91-7.01 (m, 3H), 4.49-4.83 (m, 5H), 3.71-3.80 (m, 7H), 3.29 (m, 1H); LC/MS: C$_{22}$H$_{20}$BrF$_2$O$_7$PS: m/z 576.9 (M+1).

Example 19

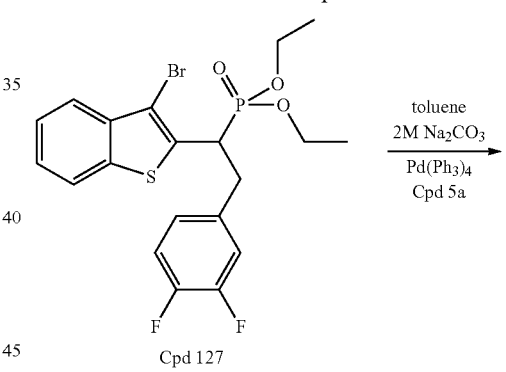

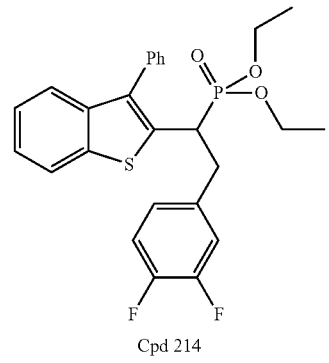

Cpd 214: [2-(3,4-Difluoro-phenyl)-1-(3-phenyl-benzo[b]thiophen-2-yl)-ethyl]-phosphonic acid diethyl ester. To a solution of Compound 127 of Example 5 (0.045 g; 0.093 mmol), in toluene (1.0 mL) was added 2M aqueous Na$_2$CO$_3$ (0.186 mL), phenyl-boronic acid (Compound 5a) (0.023 g; 0.186 mmol) and Pd(Ph$_3$)$_4$ (0.0034 g; 0.0029 mmol) and the reaction was heated under microwave irradiation at 150° C. for 10 min. At that time, the reaction was cooled, diluted with EtOAc, and washed with H₂O and brine. The organic phase was dried over Na₂SO₄, filtered, and the filtrate was concentrated under reduced pressure. The crude residue was purified by reverse-phase semi-prep HPLC eluting with a 60% to 80% MeCN/H₂O gradient to afford Compound 214. ¹H NMR (400 MHz, DMSO-d₆): δ 7.99-8.01 (d, 1H), 7.10-7.53 (m, 8H), 6.81-6.87 (m, 1H), 6.66-6.67 (m, 1H), 6.50 (bs, 1H), 3.92-4.10 (m, 4H), 3.59-3.72 (m, 1H), 3.23-3.28 (m, 1H), 2.99-3.06 (m, 1H), 1.24-1.28 (t, 3H), 1.12-1.15 (t, 3H); LC/MS C$_{26}$H$_{26}$F$_2$O$_3$PS: m/z 487.0 (M+1).

Following the procedure described above for Example 19 and substituting the appropriate reagents, starting materials and purification methods known to those skilled in the art, the following compounds of the present invention were prepared:

| Cpd | MS Observed | MS Calc'd |
|-----|-------------|-----------|
| 214 | 487.0 | 486.51 |
| 215 | 503.1 | 502.51 |
| 216 | 505.0 | 504.50 |
| 217 | 505.0 | 504.50 |
| 218 | 530.0 | 529.54 |
| 219 | 545.1 | 544.55 |
| 220 | 505.0 | 504.50 |

Cpd 217: {2-(3,4-Difluoro-phenyl)-1-[3-(3-fluoro-phenyl)-benzo[b]thiophen-2-yl)-ethyl]-phosphonic acid diethyl ester. Compound 217 was prepared according to the method of Example 19, substituting 1,1'-bis(di-tertbutylphosphino) ferrocene palladium dichloride (PdCl₂(dbpf)) for palladium triphenylphosphine; dioxane for toluene; and heating under microwave irradiation at 110° C. for 10 min in Step A. LC/MS: C$_{26}$H$_{24}$F$_3$O$_3$PS: m/z 505.0 (M+1).

Example 20

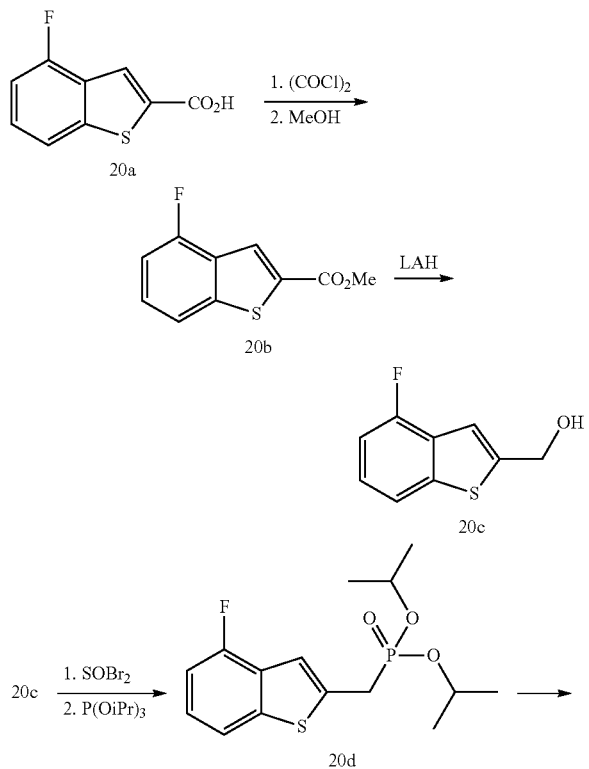

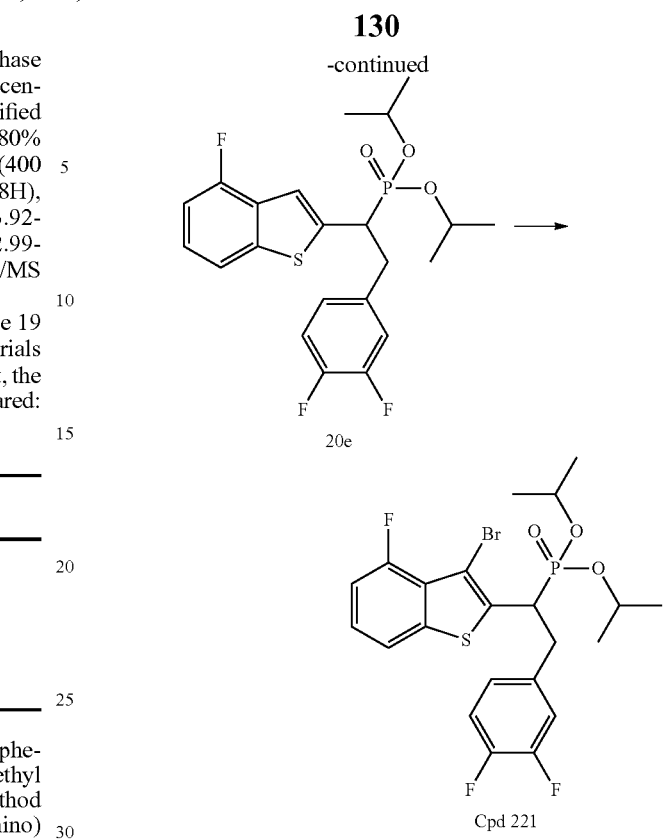

A. 4-Fluoro-benzo[b]thiophene-2-carboxlic acid methyl ester. To a suspension of Compound 20a (5.0 g; 25.4 mmol) in CH₂Cl₂ (20 mL), at ambient temperature was added oxalyl chloride (2.44 mL; 28 mmol), followed by catalytic DMF (0.1 mL) and the reaction was allowed to stir at ambient temperature for 18 h. Methanol (20 mL) was added to the reaction mixture, dropwise, and the reaction was allowed to stir an additional 18 h at ambient temperature. The solvent was evaporated under reduced pressure and the crude residue purified by flash column chromatography (SiO₂) eluting with a heptane-EtOAc gradient to afford Compound 20b. ¹H-NMR (400 MHz, DMSO-d₆): δ 8.14 (s, 1H), 7.93-7.95 (m, 1H), 7.55-7.61 (m, 1H), 7.29-7.33 (m, 1H), 3.91 (s, 3H).

B. (4-Fluoro-benzo[b]thiophen-2-yl)-methanol. To a solution 1.0 M LAH in THF (37.5 mL), cooled to 0° C., was added a solution of Compound 20b (2.63 g; 12.5 mmol), dissolved in THF (15 mL), dropwise, and the reaction was stirred at 0° C. for 1 h. The reaction was quenched with H₂O, extracted with EtOAc, and the organic phase was washed sequentially with H₂O and brine, dried over Na₂SO₄, filtered and the filtrate was concentrated under reduced pressure. The crude residue was purified by flash column chromatography (SiO₂) eluting with a heptane-EtOAc gradient to afford Compound 20c. ¹H-NMR (400 MHz, DMSO-d₆): δ 8.14 (s, 1H), 7.76-7.78 (d, 1H), 7.30-7.35 (m, 2H), 7.13-7.18 (m, 1H), 5.73-5.76 (t, 1H), 4.76-4.77 (q, 2H); LC/MS: C$_9$H$_7$FOS: m/z 165.0 ((M+1)-H₂O).

C. (4-Fluoro-benzo[b]thiophen-2-ylmethyl)-phosphonic acid diisopropyl ester. To a solution of Compound 20c (0.71 g; 3.81 mmol), in diethyl ether (6.5 mL), was added phosphorous tribromide (0.181 mL; 2.42 mmol) at ambient temperature and the reaction was stirred for 1 h. The reaction was diluted with EtOAc, washed with 10% saturated NaHCO₃ (2×), H₂O, brine, dried over Na₂SO₄, filtered, and the filtrate was concentrated under reduced pressure to afford the bromomethyl intermediate. This crude material was dissolved in toluene (5 mL), to which was added triisopropyl phosphite (2.63 mL; 11.44 mmol) and the reaction was refluxed for 72 h. The reaction was cooled, the solvent evaporated under reduced pressure and the crude residue purified by flash column chromatography (SiO$_2$) eluting with a heptane-EtOAc gradient, then by reverse-phase semi-prep HPLC, eluting with a 50-70% MeCN—H$_2$O gradient, to afford Compound 20d. $^1$H-NMR (400 MHz, DMSO-d$_6$): δ 7.76-7.78 (d, 1H), 7.32-7.35 (m, 2H), 7.13-7.18 (m, 1H), 4.56-4.61 (m, 2H), 3.58-3.64 (d, 2H), 1.23-1.25 (d, 3H), 1.18-1.19 (d, 3H); LC/MS: C$_{16}$H$_{20}$FO$_3$PS: m/z 331.0 (M+1).

D. Cpd 20e: [2-(3,4-Difluoro-phenyl)-1-(4-fluoro-benzo[b]thiophen-2-yl)-ethyl]-phosphonic acid diisopropyl ester. Compound 20e was prepared following the methods described in Example 1, Step E substituting Compound 20d for Compound 1f, substituting lithium bis(trimethylsilyl)amide for n-butyllithium, and substituting 3,4-difluorobenzyl bromide for Compound 1g. $^1$H-NMR (400 MHz, CD$_3$OD): δ 7.58-7.60 (m, 1H), 7.24-7.29 (m, 2H), 6.89-7.09 (m, 4H), 4.71-4.76 (m, 1H), 4.57-4.62 (m, 1H), 3.83-3.93 (m, 1H), 3.42-3.48 (m, 1H), 3.08-3.17 (m, 1H), 1.29-1.35 (m, 9H), 1.09-1.11 (d, 3H); LC/MS: C$_{22}$H$_{24}$F$_3$O$_3$PS: m/z 457.0 (M+1).

E. Cpd 221: [1-(3-Bromo-4-fluoro-benzo[b]thiophen-2-yl)-2-(3,4-difluoro-phenyl)-ethyl]-phosphonic acid diisopropyl ester. Compound 221 was prepared following the methods described in Example 5, Step A substituting Compound 20e for Compound 1f. $^1$H-NMR (400 MHz, DMSO-d$_6$): δ 7.87-7.89 (m, 1H), 7.39-7.44 (m, 1H), 7.18-7.27 (m, 4H), 6.93-6.94 (m, 1H), 4.66-4.71 (m, 1H), 4.49-4.53 (m, 1H), 4.06-4.16 (m, 1H), 3.40-3.41 (m, 1H), 3.04-3.08 (m, 1H), 1.21-1.30 (m, 9H), 1.01-1.02 (d, 3H); LC/MS: C$_{22}$H$_{23}$BrF$_3$O$_3$PS: m/z 537.0 (M+1).

Following the procedure described above for Example 20 and substituting the appropriate reagents, starting materials and purification methods known to those skilled in the art, the following compounds of the present invention were prepared:

| Cpd | MS Observed | MS Calc'd |
| --- | --- | --- |
| 221 | 537.0 | 535.36 |
| 222 | 587.0 | 585.36 |
| 223 | 558.92 | 557.31 |
| 224 | 507.0 | 507.31 |

Example 21

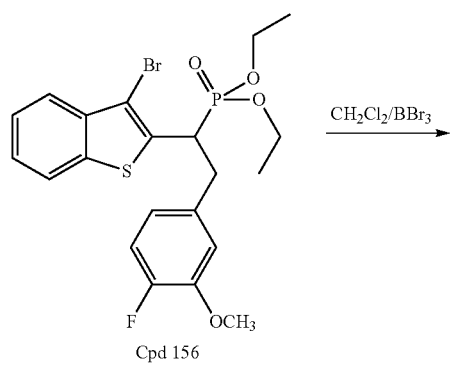

Cpd 156

CH$_2$Cl$_2$/BBr$_3$ →

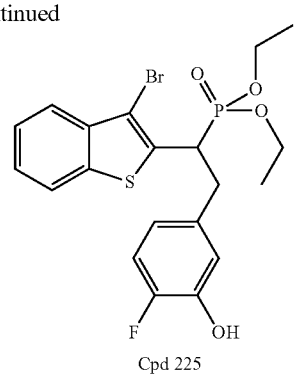

Cpd 225

A. Cpd 225: [1-(3-Bromo-benzo[b]thiophen-2-yl)-2-(4-fluoro-3-hydroxy-phenyl)-ethyl]-phosphonic acid diethyl ester. To a solution of Compound 156, prepared in Example 17 (0.118 g; 0.235 mmol) in CH$_2$Cl$_2$ (10 mL), cooled to −40° C., was added a 1.0M solution of boron tribromide in CH$_2$Cl$_2$ (1.4 mL; 1.41 mmol), drop-wise, and the reaction was allowed to warm to 5° C. over 2 h. The reaction mixture was quenched with saturated NaHCO$_3$, diluted with CH$_2$Cl$_2$, washed with H$_2$O, dried over Na$_2$SO$_4$, filtered, and the filtrate removed under reduced pressure. The crude residue was purified by flash column chromatography (SiO$_2$) eluting with a heptane-EtOAc gradient to afford Compound 225. $^1$H-NMR (400 MHz, DMSO-d$_6$): δ 9.79 (s, 1H), 7.99-8.01 (m, 1H), 7.62-7.64 (m, 1H), 7.42-7.46 (m, 2H), 6.86-6.89 (m, 1H), 6.69-6.71 (m, 1H), 6.37-6.59 (m, 1H), 4.07-4.11 (m, 5H), 2.80-3.12 (m, 1H), 1.24-1.27 (t, 3H), 1.08-1.12 (t, 3H); LC/MS: C$_{20}$H$_{21}$BrFO$_4$PS: m/z 489.0 (M+1).

Following the procedure described above for Example 21 and substituting the appropriate reagents, starting materials and purification methods known to those skilled in the art, the following compounds of the present invention were prepared:

| Cpd | MS Observed | MS Calc'd |
| --- | --- | --- |
| 225 | 489.0 | 487.32 |
| 226 | 489.0 | 487.32 |
| 227 | 517.0 | 515.37 |
| 228 | 543.0 | 541.29 |
| 229 | 571.0 | 569.35 |
| 230 | 517.0 | 515.37 |
| 231 | 522.9 | 521.77 |
| 232 | 549.82 | 551.0 |
| 233 | 537.33 | 539.0 |
| 316 | 471.0/469.0 | 469.3 |
| 322 | 485.0/486.9 | 485.3 |
| 323 | 469.0/471.0 | 469.3 |
| 324 | 469.0/471.0 | 469.3 |
| 325 | 497.0/499.0 | 497.4 |

Example 22

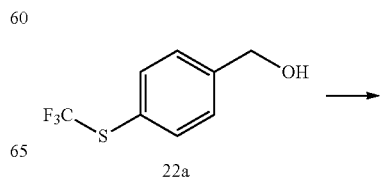

22a

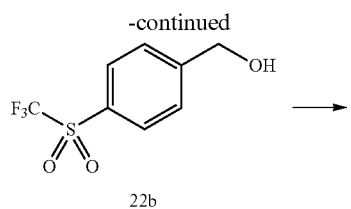

22b

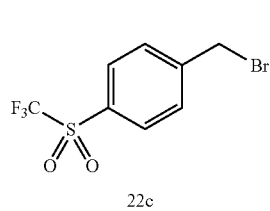

22c

A. (4-Trifluoromethanesulfonyl-phenyl)-methanol. To a solution of Compound 22a (2.08 g, 10.0 mmol) in trifluoroacetic acid (25 mL) was added 30% $H_2O_2$ (5 mL) and the reaction was stirred 5 days. The reaction mixture was diluted with ice-water (125 mL), 10% Pd/C (0.225 g) was added, and allowed to stir 18 h. The reaction mixture was extracted with diethyl ether (3×50 mL), the combined organics washed with saturated $NaHCO_3$ (4×50 mL), and treated with solid $NaHCO_3$ until neutralized. The layers were separated, the organic phase treated with 10% $Na_2SO_3$ (50 mL), washed with brine (50 mL), dried over $Na_2SO_4$ filtered, and evaporated in vacuo to afford Compound 22b. $^1$H-NMR (400 MHz, DMSO-$d_6$): δ 8.10 (d, 2H), 7.80 (d, 2H), 5.62 (br s, 1H), 4.70 (s, 2H).

B. 1-Bromo-4-trifluoromethanesulfonyl-benzene. To a solution of Compound 22b (2.178 g, 9.05 mmol) in diethyl ether (25 mL) was added $PBr_3$ (1.3 mL, 13.7 mmol) and the reaction was stirred under nitrogen atmosphere for 3 days. The reaction mixture was diluted with diethyl ether (100 mL), washed with water (2×50 mL), saturated $NaHCO_3$ (50 mL), brine (50 mL), dried over $Na_2SO_4$, filtered and the filtrate evaporated under reduced pressure to afford Compound 22c. $^1$H-NMR (400 MHz, CDCl$_3$): 8.03 (d, 2H), 7.69 (d, 2H), 4.53 (s, 2H).

Example 23

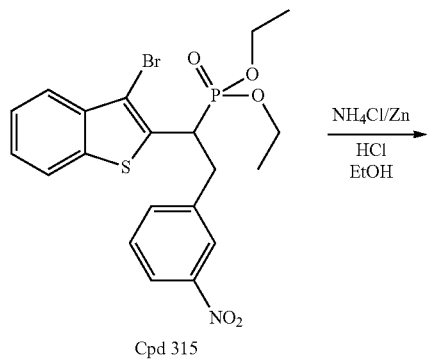

Cpd 315

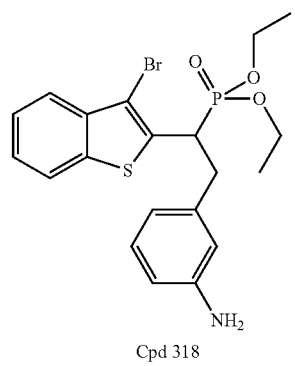

Cpd 318

Cpd 318: [2-(3-Amino-phenyl)-1-(3-bromo-benzo[b]thiophen-2-yl)-ethyl]-phosphonic acid diethyl ester. To a solution of Compound 315 (prepared according to the method in Example 17), (0.5 g; 1.0 mmol) in ethanol (20 mL) was added ammonium chloride (0.1 g; 2.0 mmol), aqueous 1 N HCl (20 mL; 20.0 mmol), and zinc dust (0.30 g; 4.6 mmol), and the reaction was stirred at ambient temperature for 48 h. The reaction was cooled, neutralized with the dropwise addition of sat'd $NaHCO_3$ and extracted with ethyl acetate. The organic phase was washed with brine, dried over $Na_2SO_4$, filtered, and the filtrate was concentrated under reduced pressure. The crude residue was purified by reverse-phase semi-prep HPLC eluting with a 20-40% MeCN/$H_2O$ gradient to afford Compound 318. $^1$H NMR (300 MHz, CDCl$_3$): δ 7.72-7.78 (m, 1H), 7.65-7.70 (m, 1H), 7.30-7.40 (m, 2H), 7.08-7.18 (m, 2H), 6.90-7.00 (m, 2H), 4.14-4.28 (m, 1H), 3.88-4.08 (m, 4H), 3.40-3.52 (m, 1H), 3.10-3.22 (m, 1H), 1.14-1.22 (m, 6H); LC/MS $C_{20}1-1_{23}BrNO_3PS$: m/z 468.0/470.0 (M/M+2).

Example 24

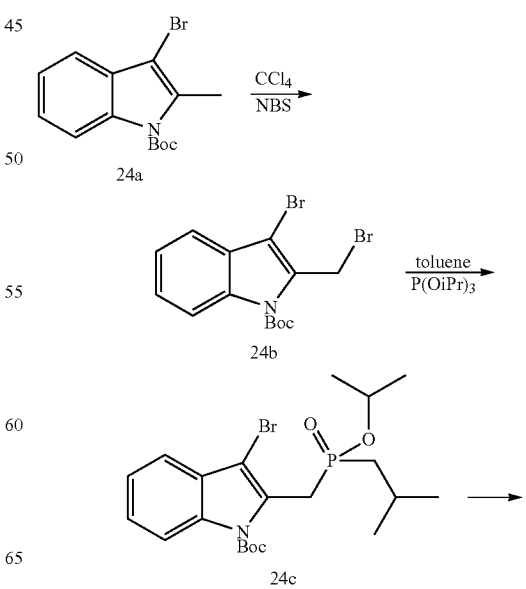

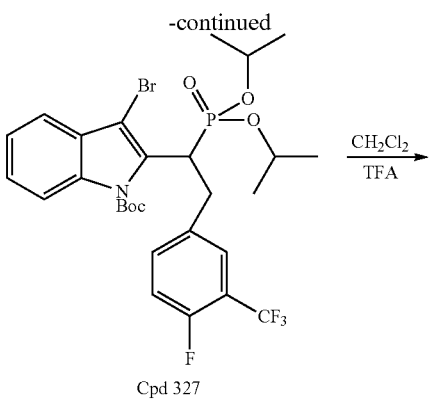

Cpd 327

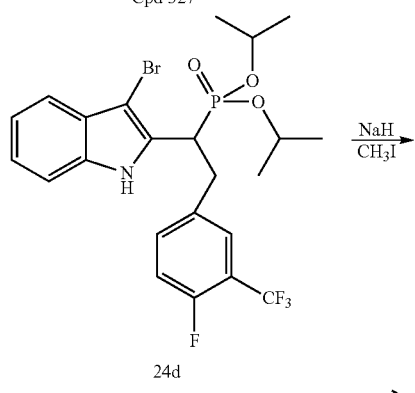

24d

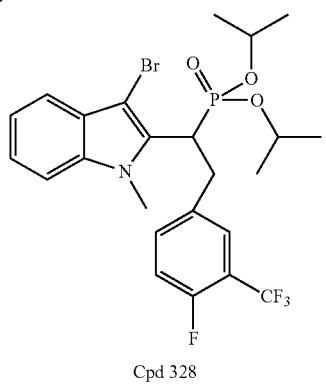

Cpd 328

A. 3-Bromo-2-bromomethyl-indole-1-carboxylic acid tert-butyl ester. To a solution of 3-bromo-2-methyl-indole-1-carboxylic acid tert-butyl ester (Compound 24a) (1.07 g; 3.45 mmol) in carbon tetrachloride (10 mL), at ambient temperature, was added n-bromosuccinimide (0.737 g; 4.13 mmol) and the reaction was refluxed for 72 h. The solution was cooled, diluted with $CH_2Cl_2$, washed with $H_2O$, dried over $Na_2SO_4$, filtered, and the solvent evaporated under reduced pressure to afford Compound 24b, which was used as is in Step B. $^1$H NMR (400 MHz, $CDCl_3$): δ 8.31 (d, 1H), 7.62-7.76 (m, 1H), 7.47-7.62 (m, 1H), 7.36-7.46 (m, 1H), 5.07 (s, 2H), 1.73 (s, 9H).

B. 3-Bromo-2-(diisopropoxy-phosphorylmethyl)-indole-1-carboxylic acid tert-butyl ester. To a solution of Compound 24b (1.64 g; 3.45 mmol) in toluene (10 mL) was added triisopropyl phosphite (1.39 mL; 10.3 mmol) and the reaction was refluxed for 24 h. The reaction mixture was cooled, concentrated under reduced pressure and the resultant residue was purified by flash column chromatography ($SiO_2$), eluting with a hexanes-EtOAc gradient, followed by reverse-phase semi-prep HPLC eluting with a 50% to 70% $MeCN$—$H_2O$ gradient to afford Compound 24c. $^1$H-NMR (400 MHz, DMSO-$d_6$): δ 8.06-8.08 (d, 1H), 7.19-7.64 (m, 3H), 4.51-4.53 (m, 2H), 3.75-3.80 (d, 2H), 1.66 (s, 9H), 1.20-1.21 (d, 6H), 1.09-1.10 (d, 6H); LC/MS: $C_{20}H_{29}BrNO_5P$: m/z 476.1 (M+1).

C. Cpd 327: 3-Bromo-2-[1-(diisopropoxy-phosphoryl)-2-(4-fluoro-3-trifluoromethyl-phenyl)-ethyl]-indole-1-carboxylic acid tert-butyl ester. To a solution of Compound 24c (1.08 g; 2.27 mmol) in THF (10.0 mL) cooled to −70° C., was added a 1.0 M solution of lithium bis(trimethylsilyl)amide in THF (2.50 mL; 2.50 mmol), drop-wise. The reaction mixture was allowed to stir at −70° C. for 30 min, to which was then added a solution of 4-fluoro-3-trifluoromethyl benzyl bromide (0.758 g; 2.95 mmol) in THF (10.0 mL), dropwise. The reaction mixture was allowed to slowly warm to ambient temperature, and stirred for an additional 18 h before quenching with a solution of saturated aqueous $NH_4Cl$ (1.0 mL). The mixture was diluted with EtOAc, washed with $H_2O$, brine, and dried over $Na_2SO_4$. The mixture was then filtered, and the filtrate was concentrated under reduced pressure. The resulting residue was purified by flash column chromatography ($SiO_2$) eluting with a heptane-EtOAc gradient, followed by purification by reverse-phase semi-prep HPLC eluting with a 70% to 90% $MeCN$—$H_2O$ gradient to afford Compound 327. $^1$H-NMR (400 MHz, DMSO-$d_6$): δ 7.89-7.92 (m, 1H), 7.53-7.67 (m, 2H), 7.24-7.44 (m, 4H), 5.19-5.53 (m, 1H), 4.52-4.62 (m, 2H), 4.33-4.53 (m, 1H), 3.78-4.07 (m, 1H), 3.34-3.57 (m, 1H), 1.62 (s, 9H), 1.15-1.22 (m, 9H), 0.81-0.83 (d, 3H); LC/MS: $C_{28}H_{33}BrF_4NO_6P$: m/z 652.0 (M+1).

D. [1-(3-Bromo-1H-indol-2-yl)-2-(4-fluoro-3-trifluoromethyl-phenyl)-ethyl]-phosphonic acid diisopropyl ester. To a solution of Compound 327 (1.06 g; 1.63 mmol) in $CH_2Cl_2$ (0.5 mL) at ambient temperature was added trifluoroacetic acid (0.5 mL) and the reaction was allowed to stir for 30 min. The reaction mixture was washed with 3N NaOH, extracted with EtOAc, the organic phase washed with $H_2O$, brine, dried over $Na_2SO_4$, filtered, and the solvent evaporated under reduced pressure to afford Compound 24d. LC/MS: $C_{23}H_{25}BrF_4NO_3P$: m/z 552.0 (M+1).

E. Cpd 328: [1-(3-Bromo-1-methyl-1H-indol-2-yl)-2-(4-fluoro-3-trifluoromethyl-phenyl)-ethyl]-phosphonic acid diisopropyl ester. To a solution of Compound 24d (25.4 mg; 0.046 mmol) in DMF (0.5 mL) at ambient temperature was added 60% NaH (2.5 mg; 0.060 mmol) and the suspension was allowed to stir for 30 min. Iodomethane (0.004 mL; 0.055 mmol) was added drop-wise and the reaction was allowed to stir at ambient temperature for 18 h. The mixture was quenched with 3N NaOH, extracted with EtOAc, the organic extract washed with $H_2O$, brine, dried over $Na_2SO_4$, filtered, and the solvent evaporated under reduced pressure. The crude residue was purified by flash column chromatography ($SiO_2$) eluting with a heptane-EtOAc gradient to afford Compound 328. LC/MS: $C_{24}H_{27}BrF_4NO_3P$: m/z 564.0 (M+).

Following the procedure described above for Example 24 and substituting the appropriate reagents, starting materials and purification methods known to those skilled in the art, the following compounds of the present invention were prepared:

| Cpd | MS Observed | MS Calc'd |
|---|---|---|
| 329 | 592.41 | 592.0 |
| 330 | 628.0/630.0 | 627.05 |
| 331 | 591.0 | 592.08 |
| 332 | 656.1/658.0 | 656.4 |

Cpd 330: [1-(3-Bromo-1-methanesulfonly-1H-indol-2-yl)-2-(4-fluoro-3-trifluoromethyl-phenyl)-ethyl]-phosphonic acid diisopropyl ester. Compound 330 was prepared according to the method of Example 24, substituting methane sulfonyl chloride for iodomethane in Step E. $^1$H-NMR (400 MHz, DMSO-$d_6$): δ 7.87-7.89 (m, 1H), 7.53-7.58 (m, 2H), 7.39-7.46 (m, 4H), 5.02-5.11 (m, 1H), 4.57-4.66 (m, 2H), 3.82-3.85 (m, 1H), 3.53-3.60 (m, 1H), 3.32-3.37 (m, 3H), 1.19-1.31 (m, 9H), 1.03-1.05 (m, 3H); LC/MS: $C_{24}H_{27}BrF_4NO_5PS$: m/z 628.0/630.0 (M+/M+2).

Example 25

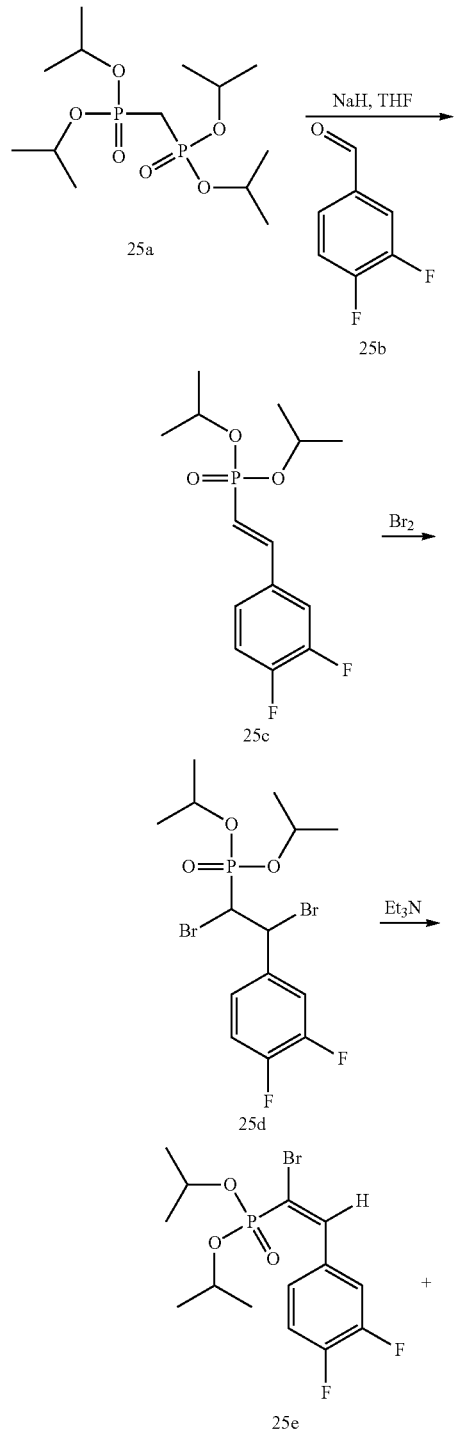

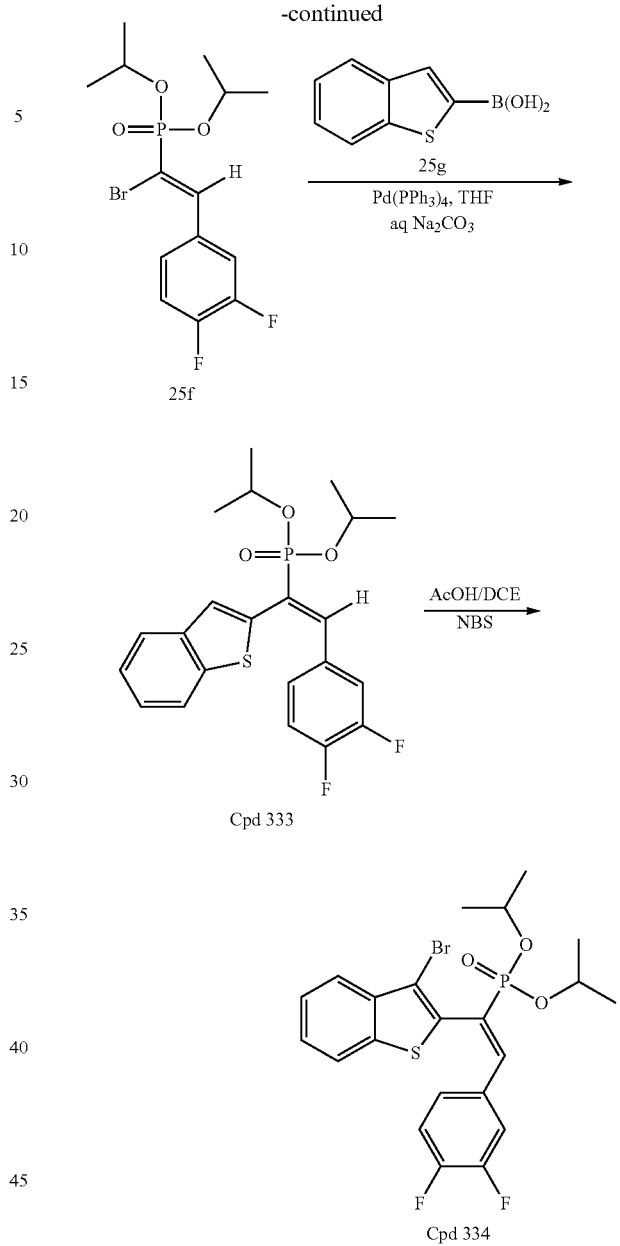

A. (E)-[2-(3,4-Difluoro-phenyl)-vinyl]-phosphonic acid diisopropyl ester. To a suspension of 60% NaH (0.35 g, 8.7 mmol) in THF (8.7 mL), at ambient temperature, was added drop-wise diisopropyl methylenediphosphonate (Compound 25a) (3.0 g, 8.7 mmol) with a small amount of THF to complete the transfer. The addition was completed in 5 min, and a small rise in temperature was noted (up from 18° C. to 25° C.). The reaction was stirred for a minimum of 25 min, and as long as 1 hr. A solution of 3,4-difluorobenzaldehyde (Compound 25b) (0.96 mL, 8.7 mmol) in THF (1 mL) was added over 3 min. The internal reaction temperature rose to 45° C., and 1 hr at 55° C. The reaction was cooled to room temperature, quenched with $H_2O$ (10 mL), extracted with ether (2×10 mL), ethyl acetate (1×10 mL) and the combined organics were dried over $Na_2SO_4$, filtered, and the solvent evaporated under reduced pressure to afford a crude oil. The resulting residue was purified by flash column chromatography ($SiO_2$) eluting with ethyl acetate-CH$_2$Cl$_2$ to afford Compound 25c. $^1$H-NMR (300 MHz, CDCl$_3$): δ 7.41-7.11 (m, 4H), 6.18 (t, J=16 Hz, 1H), 4.72 (m, 2H), 1.37 (d, 6H), 1.32 (d, 6H).

B. [1,2-Dibromo-2-(3,4-difluoro-phenyl)-ethyl]phosphonic acid diisopropyl ester. To a solution of Compound 25c (1.76 g, 5.78 mmol) in carbon tetrachloride (20 mL), cooled to 0° C., was added bromine (0.16 mL; 3.11 mmol) and the mixture was stirred at ambient temperature for 1 h. The reaction was cooled to 0° C., sat'd sodium thiosulfate (20 mL) was added, the layers separated, and the aqueous phase extracted with CH$_2$Cl$_2$ (2×20 mL). The extracts were combined, dried over MgSO$_4$, filtered, and the solvent evaporated under reduced pressure. The crude residue was purified by flash column chromatography (SiO$_2$) eluting with EtOAc-CH$_2$Cl$_2$ to afford Compound 25d was as a mixture (1.7/1) of isomers. LC/MS: C$_{14}$H$_{19}$Br$_2$F$_2$O$_3$P: m/z 463/465/467.0 (M+1, 1:2:1 isotope ratio).

C. (E)-[1-Bromo-2-(3,4-difluoro-phenyl)-vinyl]phosphonic acid diisopropyl ester (Cpd 25e) and (Z)-[1-bromo-2-(3,4-difluoro-phenyl)-vinyl]-phosphonic acid diisopropyl ester. To a solution of Compound 25d (1.67 g; 3.59 mmol) in CH$_2$Cl$_2$ (30 mL), cooled to 0 to 5° C. (ice bath), was added triethylamine (1.0 mL; 7.2 mmol) and the mixture was warmed to 40° C. for 3 h. The reaction mixture was cooled to 7° C., to which was added 1N HCl (20 mL) and the aqueous layer was extracted with CH$_2$Cl$_2$ (2×10 mL). The combined extracts were washed with brine (1×20 mL), dried over MgSO$_4$, filtered, and the solvent evaporated under reduced pressure. The crude oil was purified by flash column chromatography (SiO$_2$) eluting with EtOAc-CH$_2$Cl$_2$ to afford Compound 25e (first eluent) and Compound 25f (second eluent).

Cpd 25e: $^1$H-NMR (400 MHz, CDCl$_3$): δ 7.71 (d, J=37 Hz, H—P coupling, E-trans, 1H), 7.47 (m, 1H), 7.22 (m, 1H), 7.13 (m, 1H), 4.72 (m, 2H), 1.31 (d, 6H), 1.27 (d, 6H).

Cpd 25f: $^1$H-NMR (400 MHz, CDCl$_3$): δ 7.95 (d, J=37 Hz, H—P coupling, Z-cis, 1H), 7.82 (m, 1H), 7.48 (br d, 1H), 7.19 (m, 1H), 4.73 (m, 2H), 1.27 (d, 6H), 1.24 (d, 6H); $^{19}$F-NMR (376 MHz, CDCl$_3$): δ −133.7, −136.4 ppm; $^{31}$P-NMR (162 MHz, CDCl$_3$): δ 7.63 ppm. LCMS: C$_{14}$H$_{18}$BrF$_2$O$_3$P: m/z 384/386 (M+1).

(Upon storing at room temperature, Compound 25e isomerized to Compound 25f).

D. Cpd 333: (E)-[1-Benzo[b]thiophen-2-yl-2-(3,4-difluoro-phenyl)-vinyl]-phosphonic acid diisopropyl ester. To a solution of Compound 25e (759 mg, 1.98 mmol) in DME (23 mL), purged with argon gas for 15 min, was added Pd(Ph$_3$P)$_4$ (114 mg, 0.1 mmol). The reaction mixture was stirred at ambient temperature for 30 min, to which was added benzo[b]thiophen-2-ylboronic acid (423 mg, 2.38 mmol), sodium carbonate (210 mg, 1.98 mmol) and H$_2$O (4.5 mL). The reaction was heated to 70° C. for 2 h, cooled to 45° C., and brine (25 mL) was added. The mixture was extracted with ethyl acetate (25 mL), and the aqueous layer extracted with additional ethyl acetate (2×15 mL). The combined organics were washed with brine (25 mL), dried over MgSO$_4$, filtered and the solvent removed under reduced pressure. The brown oil was purified by flash column chromatography (SiO$_2$) eluting with heptane-EtOAc to afford Compound 333. $^1$H-NMR (400 MHz, CDCl$_3$): δ 7.76 (m, 2H), 7.66 (d, J=24 Hz, 1H), 7.51-7.30 (m, 2H), 7.10-6.96 (m, 3H), 7.47 (m, 2H), 1.34 (d, 6H), 1.28 (d, 6H); $^{31}$P-NMR (162 MHz, CDCl$_3$): δ 16.24 ppm. HPLC: 11.256 min, 94.4%. Elem. Anal: Calc for C$_{22}$H$_{23}$SF$_2$O$_3$P: C, 60.54; H, 5.31; F, 8.71. found: C, 60.54; H, 5.25; F, 9.06. LCMS: C$_{22}$H$_{23}$F$_2$O$_3$PS: m/z 437 (M+1); mp 93.5-95° C.

E. Cpd 334: (E)-[1-(3-Bromo-benzo[b]thiophen-2-yl)-2-(3,4-difluoro-phenyl)-vinyl]-phosphonic acid diisopropyl ester. To a solution of Cpd 333 (52.4 mg, 0.120 mmol) in DCE (0.5 mL) and AcOH (0.5 mL) was added N-bromosuccinimide (32 mg; 0.180 mmol) and the reaction was refluxed for 24 h. The reaction was cooled, concentrated under reduced pressure and the resultant residue was purified by reverse-phase semi-prep HPLC eluting with a 60% to 80% MeCN—H$_2$O gradient to afford Compound 334. $^1$H-NMR (400 MHz, DMSO-d$_6$): δ 8.10-8.14 (m, 1H), 7.71-7.78 (m, 2H), 7.50-7.59 (m, 2H), 7.27-7.39 (m, 2H), 7.04-7.06 (m, 1H), 1.14-1.31 (m, 12H); LCMS: C$_{22}$H$_{22}$BrF$_2$O$_3$PS: m/z 517.0 (M+2).

Example 26

An Alternate Route to Compounds of the Present Invention is Presented Herein

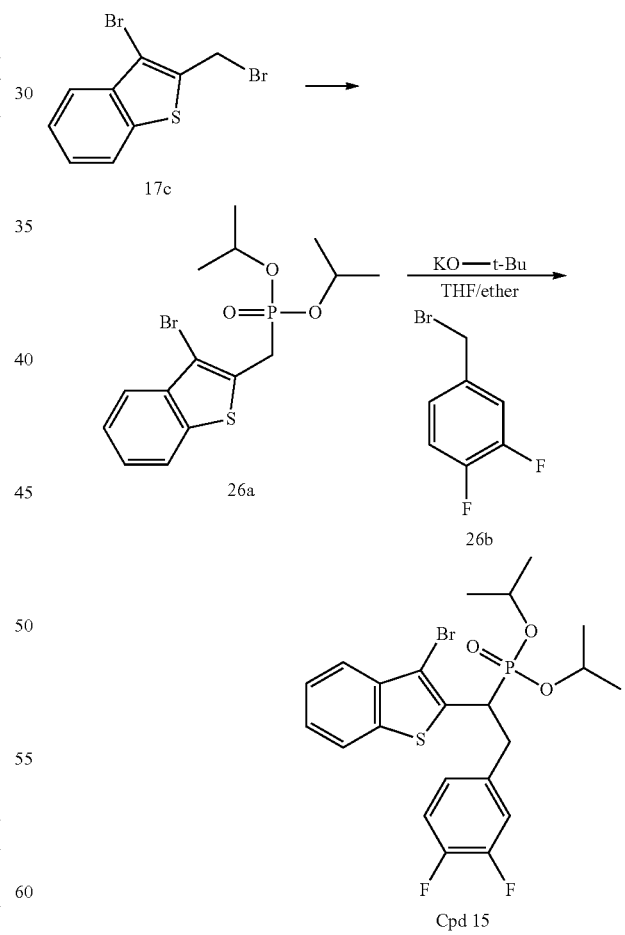

A. (3-Bromo-benzo[b]thiophen-2-ylmethyl)-phosphonic acid diisopropyl ester. A mixture of Cpd 17c (100 g, 326.8 mmol) and triisopropyl phosphite (76.7 mL, 326.8 mmol) were heated at 55° C. for 2 h. Upon cooling, some of Cpd 26a precipitated and was isolated by filtration. The filtrate was evaporated under reduced pressure. The filtered solids and filtrates were each separately purified by flash column chromatography (SiO$_2$) using a heptane-EtOAc gradient. The desired fractions were combined and slurried in heptane (100 mL) with sonication, filtered, and washed with heptane (3×20 mL). The solid was first air-dried before being transferred to dry in a vacuum oven at 40° C. (20 mm). The desired Compound 26a was obtained as a white solid.

B. Cpd 15: [1-(3-Bromo-benzo[b]thiophen-2-yl)-2-(3,4-difluoro-phenyl)-ethyl]-phosphonic acid diisopropyl ester. To a solution of Compound 26a (72 g, 184.0 mmol) in diethyl ether (1.44 L) was added 1M potassium tert-butoxide in THF (202.4 mL, 202.4 mmol) and the reaction was stirred at ambient temperature for 15 minutes. To the resulting brown suspension was added 3,4-difluorobenzyl bromide (23.6 mL, 184.0 mmol), dropwise, at ambient temperature, and the reaction was stirred for 16 h. The reaction mixture was poured into saturated aqueous ammonium chloride (3000 mL), extracted with EtOAc (2×2500 mL), and the combined organic extracts were dried over MgSO$_4$, filtered, rinsed with EtOAc (3×50 mL) and the solvent evaporated under reduced pressure. The resulting residue was purified by flash column chromatography (SiO$_2$), eluting with a heptane-EtOAc gradient to afford Compound 15.

Example 27

An Enantioselective Route to Compounds of the Present Invention

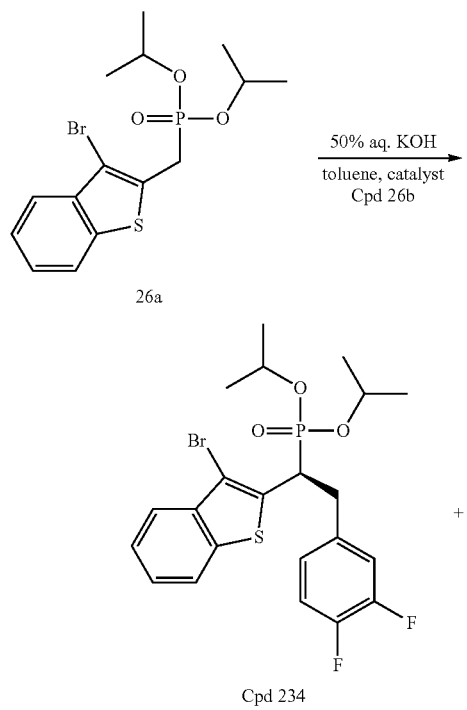

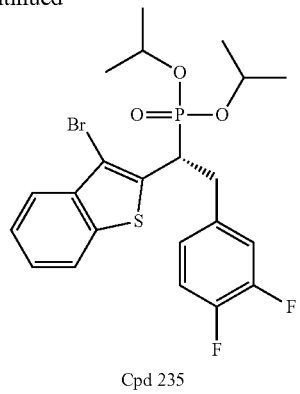

Cpd 235

A. Cpd 235: (R)-(3-Bromo-benzo[b]thiophen-2-ylmethyl)-phosphonic acid diisopropyl ester. To a 5 mL vial with a small stir bar was added Compound 26a (80 mg, 0.20 mmol) in toluene (1.2 mL), (R,R)-2,6-bis(3,4,5-trifluorophenyl)-3,3',5,5'-tetrahydro-4,4'-spirobi[dinaphtho[2,1-c:1',2'-e]azepin]-4-ium bromide (5 mg, 0.005 mmol) and 50% KOH (291 mg KOH in 0.29 mL H$_2$O) and the reaction mixture was stirred vigorously at 0° C. Compound 26b (28 µL, 0.22 mmol) was added via syringe over 1 min, and vigorously stirred for at 0° C. for 3.5 hr. An additional portion of Compound 26b (14 µL, 0.11 mmol) was added, and the reaction stirred at ambient temperature for 60 h. The reaction was worked up by separation of the toluene layer, and neutralization of the aqueous layer by addition of HCl (1N, 1 mL). The aqueous layer was extracted with CH$_2$Cl$_2$ (3×1 mL), and the combined organic layers were dried over Na$_2$SO$_4$, filtered and the solvent evaporated under reduced pressure. The crude residue was purified by flash column chromatography (SiO$_2$) eluting with an EtOAc-CH$_2$Cl$_2$ gradient to afford Compound 235. The enantiomeric excess was determined using a Chiralpak AD column (20% IPA hex, 254 nm). The (S)-isomer (Compound 234) eluted at 5.74 min, 13.9%, and the (R)-isomer (Compound 235) eluted at 7.61 min, 81.5%. The (Y)ee was 68%.

B. Cpd 234: (S)-(3-Bromo-benzo[b]thiophen-2-ylmethyl)-phosphonic acid diisopropyl ester. To a 5 mL vial equipped with a small stir bar was added Compound 26a (80 mg, 0.20 mmol), toluene (1.2 mL), (S,S)-2,6-bis(3,4,5-trifluorophenyl)-3,3',5,5'-tetrahydro-4,4'-spirobi[dinaphtho[2,1-c:1',2'-e]azepin]-4-ium bromide (5 mg, 0.005 mmol) and 50% KOH (291 mg KOH in 0.29 mL water) and the reaction mixture was stirred vigorously at 0° C. Compound 26b (28 µL, 0.22 mmol) was added dropwise via syringe over 30 sec, and assay of the reaction was performed at 30 min using chiral HPLC. The analysis revealed the ratios by HPLC (normalized to 100) to be 20.9% of the Compound 234, 2.6% of the Compound 235, and 74.6% of Compound 26a remaining. The % ee was calculated to be 77%.

Absolute Stereochemistry Determination

The absolute stereochemistry of Compound 234 was determined using Vibrational Circular Dichroism techniques (VCD; BioTools, Inc.). The comparison of the experimental VCD data with ab initio DFT calculations conclude that the assignment of the absolute stereochemistry of Compound 234 was (S). By analogy, the absolute stereochemistry of Compound 236, Compound 239, and Compound 242 were assigned (S)-stereochemistry, and Compound 235, Compound 237, Compound 240 and Compound 243 were assigned (R)-stereochemistry.

Using the methods described in the schemes and specific examples, and adaptations thereof, compounds of Formula (Ia) wherein $R_3$ is H, shown in Table 1, were prepared.

TABLE 1

Formula (Ia)

| Cpd | A | W | $R_4$ | X | $R_1$ | $R_2$ | L | B |
|---|---|---|---|---|---|---|---|---|
| 1 | benzo | $C(R_4)$ | methyl | S | isopropyloxy | isopropyloxy | $CH_2$ | 3,4-difluoro-phenyl |
| 2 | benzo | $C(R_4)$ | i-propyl | S | ethoxy | ethoxy | $CH_2$ | 3,4-difluoro-phenyl |
| 3 | 4-fluoro-benzo | $C(R_4)$ | methyl | S | ethoxy | ethoxy | $CH_2$ | 3,4-difluoro-phenyl |
| 4 | benzo | $C(R_4)$ | methyl | S | ethoxy | ethoxy | $CH_2$ | 3-chloro-phenyl |
| 5 | benzo | $C(R_4)$ | cyclopentyl | S | ethoxy | ethoxy | $CH_2$ | 3,4-difluoro-phenyl |
| Diast. 6 | benzo | $C(R_4)$ | methyl | S | ethoxy | isobutyl | $CH_2$ | 3,4-difluoro-phenyl |
| 7 | benzo | $C(R_4)$ | methyl | S | ethoxy | ethoxy | $CH_2$ | 3-fluoro-phenyl |
| 8 | 7-fluoro-benzo | $C(R_4)$ | methyl | S | ethoxy | ethoxy | $CH_2$ | 3,4-difluoro-phenyl |
| 9 | benzo | $C(R_4)$ | methyl | O | ethoxy | ethoxy | $CH_2$ | 3,4-difluoro-phenyl |
| 10 | benzo | $C(R_4)$ | methyl | S | ethoxy | ethoxy | $CH_2$ | 2,3-difluoro-phenyl |
| 11 | benzo | $C(R_4)$ | methyl | O | isopropyloxy | isopropyloxy | $CH_2$ | 3,4-difluoro-phenyl |
| 12 | benzo | $C(R_4)$ | chloro | S | isopropyloxy | isopropyloxy | $CH_2$ | 3,4-difluoro-phenyl |
| 13 | benzo | $C(R_4)$ | methyl | S | isobutyl | isobutyl | $OCH_2$ | 3,4-difluoro-phenyl |
| 14 | benzo | $C(R_4)$ | methyl | S | ethoxy | ethoxy | $CH_2$ | 3,4-difluoro-phenyl |
| 15 | benzo | $C(R_4)$ | bromo | S | isopropyloxy | isopropyloxy | $CH_2$ | 3,4-difluoro-phenyl |
| 16 | 6-fluoro-benzo | $C(R_4)$ | methyl | S | ethoxy | ethoxy | $CH_2$ | 3,4-difluoro-phenyl |
| 17 | benzo | $C(R_4)$ | methyl | S | ethoxy | ethoxy | $CH_2$ | 3,5-difluoro-phenyl |
| 18 | benzo | $C(R_4)$ | methyl | S | ethoxy | ethoxy | $CH_2$ | 3-methyl-phenyl |
| 19 | benzo | $C(R_4)$ | i-propyl | S | isopropyloxy | isopropyloxy | $CH_2$ | 3,4-difluoro-phenyl |
| 20 | benzo | $C(R_4)$ | cyclopropyl | S | isopropyloxy | isopropyloxy | $CH_2$ | 3,4-difluoro-phenyl |
| 21 | benzo | $C(R_4)$ | methyl | S | ethoxy | ethoxy | $CH_2$ | 3,4-dichloro-phenyl |
| 22 | benzo | $C(R_4)$ | methyl | S | ethoxy | ethoxy | $CH_2$ | 2-fluoro-phenyl |
| 23 | benzo | $C(R_4)$ | methyl | S | ethoxy | ethoxy | $CH_2$ | 2-fluoro-3-chloro-phenyl |
| 24 | benzo | $C(R_4)$ | bromo | S | ethoxy | ethoxy | $CH_2$ | 3,4-dichloro-phenyl |
| 25 | benzo | N | na | S | isopropyloxy | isopropyloxy | $CH_2$ | 3,4-difluoro-phenyl |
| 26 | benzo | $C(R_4)$ | methyl | S | ethoxy | ethoxy | $CH_2$ | 2-methyl-phenyl |
| 27 | benzo | $C(R_4)$ | methyl | S | ethoxy | ethoxy | $CH_2$ | 2-chloro-4-fluoro-phenyl |
| 28 | benzo | $C(R_4)$ | methyl | S | ethoxy | ethoxy | $CH_2$ | 2-chloro-3,5-difluoro-phenyl |
| 29 | benzo | $C(R_4)$ | cyclopropyl | S | ethoxy | ethoxy | $CH_2$ | 3,4-difluoro-phenyl |
| Diast. 30 | benzo | $C(R_4)$ | methyl | S | ethoxy | methyl | $CH_2$ | 3,4-difluoro-phenyl |

TABLE 1-continued

Formula (Ia)

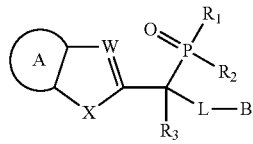

| Cpd | A | W | R₄ | X | R₁ | R₂ | L | B |
|---|---|---|---|---|---|---|---|---|
| 31 | benzo | C(R₄) | methyl | S | ethoxy | ethoxy | CH₂ | 3-trifluoro-methyl-4-fluoro-phenyl |
| 32 | benzo | C(R₄) | methyl | S | ethoxy | ethoxy | CH₂ | 3-methoxy-phenyl |
| 33 | benzo | C(R₄) | methyl | S | isobutyl | isobutyl | CH₂ | 3,4-difluoro-phenyl |
| 34 | (2,3-b)pyridin-2-yl | C(R₄) | methyl | S | isopropyloxy | isopropyloxy | CH₂ | 3,4-difluoro-phenyl |
| 35 | benzo | C(R₄) | methyl | S | ethoxy | ethoxy | CH₂ | 2,3-dichloro-phenyl |
| Diast. 36 | benzo | C(R₄) | methyl | S | ethoxy | isobutyl | CH₂ | 3,4-difluoro-phenyl |
| 37 | benzo | C(R₄) | methyl | S | ethoxy | ethoxy | CH₂ | 2-fluoro-3-trifluoro-methyl-phenyl |
| 38 | benzo | C(R₄) | cyclopentyl | S | isopropyloxy | isopropyloxy | CH₂ | 3,4-difluoro-phenyl |
| 39 | benzo | C(R₄) | H | S | ethoxy | ethoxy | CH₂ | 3-trifluoro-methyl-phenyl |
| 40 | benzo | C(R₄) | methyl | S | ethoxy | ethoxy | CH₂ | 3-bromo-phenyl |
| 41 | benzo | C(R₄) | cyclobutyl | S | ethoxy | ethoxy | CH₂ | 3,4-difluoro-phenyl |
| 42 | benzo | C(R₄) | methyl | S | n-propyl | n-propyl | OCH₂ | 3,4-difluoro-phenyl |
| 43 | benzo | C(R₄) | trifluoromethyl | S | isopropyloxy | isopropyloxy | CH₂ | 3,4-difluoro-phenyl |
| 44 | benzo | C(R₄) | methyl | S | n-propyl | n-propyl | CH₂ | 3,4-difluoro-phenyl |
| 45 | 5-fluoro-benzo | C(R₄) | methyl | S | ethoxy | ethoxy | CH₂ | 3,4-difluoro-phenyl |
| 46 | benzo | C(R₄) | methyl | S | ethoxy | ethoxy | CH₂ | naphthalen-2-yl |
| 47 | benzo | C(R₄) | methyl | S | ethoxy | ethoxy | CH₂ | 2,5-dichloro-phenyl |
| 48 | benzo | C(R₄) | methyl | S | ethoxy | ethoxy | CH₂ | 2-chloro-phenyl |
| 49 | benzo | C(R₄) | methyl | S | ethoxy | ethoxy | CH₂ | 3-trifluoromethyl-4-chloro-phenyl |
| 50 | benzo | C(R₄) | methyl | S | ethoxy | ethoxy | CH₂ | 4-fluoro-phenyl |
| 51 | benzo | C(R₄) | H | S | ethoxy | ethoxy | CH₂ | 4-fluoro-phenyl |
| 52 | benzo | C(R₄) | methyl | S | ethoxy | ethoxy | CH₂ | 3-trifluoromethyl-phenyl |
| 53 | benzo | C(R₄) | methyl | S | 2,2-dimethyl-propyl | 2,2-dimethyl-propyl | CH₂ | 3,4-difluoro-phenyl |
| 54 | benzo | C(R₄) | methyl | S | ethoxy | ethoxy | CH₂ | 2,6-dichloro-phenyl |
| 55 | benzo | C(R₄) | methyl | S | ethoxy | ethoxy | CH₂ | 4-trifluoromethoxy-phenyl |
| 56 | benzo | C(R₄) | methyl | S | ethoxy | ethoxy | CH₂ | 3-fluoro-5-trifluoromethyl-phenyl |
| 57 | benzo | C(R₄) | methyl | S | ethoxy | ethoxy | CH₂ | 3-trifluoromethoxy-phenyl |

TABLE 1-continued

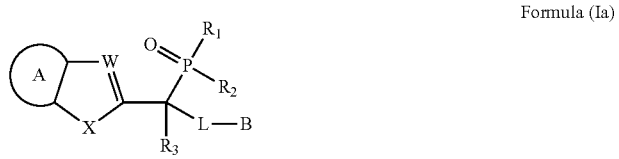

Formula (Ia)

| Cpd | A | W | $R_4$ | X | $R_1$ | $R_2$ | L | B |
|---|---|---|---|---|---|---|---|---|
| 58 | benzo | C($R_4$) | H | S | ethoxy | ethoxy | $CH_2$ | 3-fluoro-4-trifluoromethyl-phenyl |
| 59 | benzo | C($R_4$) | methyl | S | ethoxy | ethoxy | $CH_2$ | 2-trifluoromethyl-phenyl |
| 60 | benzo | C($R_4$) | methyl | S | ethoxy | ethoxy | $CH_2$ | 2-fluoro-3-methyl-6-chloro-phenyl |
| 61 | benzo | C($R_4$) | methyl | S | ethoxy | ethoxy | $CH_2$ | 2-trifluoromethoxy-phenyl |
| 62 | 5-methyl-benzo | C($R_4$) | methyl | S | isopropyloxy | isopropyloxy | $CH_2$ | 3,4-difluoro-phenyl |
| 63 | benzo | C($R_4$) | H | S | isopropyloxy | isopropyloxy | $CH_2$ | 3,4-difluoro-phenyl |
| 64 | benzo | C($R_4$) | phenyl | S | ethoxy | ethoxy | $CH_2$ | 3,4-dichloro-phenyl |
| 65 | 4-chloro-benzo | C($R_4$) | methyl | S | ethoxy | ethoxy | $CH_2$ | 3,4-dichloro-phenyl |
| 66 | benzo | C($R_4$) | methyl | S | ethoxy | ethoxy | $CH_2$ | 2-bromo-phenyl |
| 67 | benzo | C($R_4$) | methyl | S | ethoxy | ethoxy | $CH_2$ | 2-fluoro-5-trifluoromethyl-phenyl |
| 68 | benzo | C($R_4$) | H | S | ethoxy | ethoxy | $CH_2$ | 4-trifluoromethyl-phenyl |
| 69 | benzo | C($R_4$) | H | S | isopropyloxy | isopropyloxy | $CH_2$ | 3-trifluoromethyl-phenyl |
| 70 | benzo | C($R_4$) | H | S | ethoxy | ethoxy | $CH_2$ | 4-bromo-phenyl |
| 71 | benzo | C($R_4$) | methyl | S | ethoxy | ethoxy | $CH_2$ | 5-chloro-benzo[1,3]dioxol-6-yl |
| 72 | benzo | C($R_4$) | methyl | S | ethoxy | ethoxy | $CH_2$ | 3-(pyridin-4-yl)-phenyl |
| 73 | benzo | C($R_4$) | methyl | S | ethoxy | ethoxy | $CH_2$ | 2-fluoro-3-chloro-5-trifluoromethyl-phenyl |
| 74 | benzo | C($R_4$) | H | S | ethoxy | ethoxy | $CH_2$ | phenyl |
| 75 | benzo | C($R_4$) | H | S | ethoxy | ethoxy | $CH_2$ | 3,4-difluoro-phenyl |
| 76 | benzo | C($R_4$) | methyl | S | ethoxy | ethoxy | $CH_2$ | 2,4-dichloro-5-fluoro-phenyl |
| 77 | benzo | C($R_4$) | methyl | S | ethoxy | ethoxy | $CH_2$ | 3-biphenyl |
| 78 | benzo | C($R_4$) | H | S | ethoxy | ethoxy | $CH_2$ | 3,4-dichloro-phenyl |
| 80 | benzo | C($R_4$) | H | S | ethoxy | ethoxy | $CH_2$ | 2-fluoro-phenyl |
| 81 | benzo | C($R_4$) | methyl | S | ethoxy | ethoxy | $CH_2$ | 2-chloro-3-trifluoromethyl-phenyl |
| 82 | 6-methoxy-benzo | C($R_4$) | methyl | S | ethoxy | ethoxy | $CH_2$ | 3,4-difluoro-phenyl |
| 83 | benzo | C($R_4$) | H | S | ethoxy | ethoxy | $CH_2$ | naphthalen-2-yl |
| 84 | 4-trifluoromethyl-benzo | C($R_4$) | methyl | S | ethoxy | ethoxy | $CH_2$ | 3,4-difluoro-phenyl |

TABLE 1-continued

Formula (Ia)

| Cpd | A | W | $R_4$ | X | $R_1$ | $R_2$ | L | B |
|---|---|---|---|---|---|---|---|---|
| 85 | benzo | $C(R_4)$ | H | S | ethoxy | ethoxy | $CH_2$ | 2-chloro-phenyl |
| 87 | benzo | $C(R_4)$ | H | O | ethoxy | ethoxy | $CH_2$ | 4-fluoro-phenyl |
| 88 | benzo | $C(R_4)$ | methyl | $SO_2$ | ethoxy | ethoxy | $CH_2$ | 3,4-difluoro-phenyl |
| 89 | benzo | $C(R_4)$ | H | S | ethoxy | ethoxy | $CH_2$ | 2-methyl-phenyl |
| 90 | benzo | $C(R_4)$ | H | S | ethoxy | ethoxy | $CH_2$ | benzo-thiophen-2-yl |
| 91 | benzo | $C(R_4)$ | methyl | S | ethoxy | ethoxy | $CH_2$ | 4-trifluoro methyl-phenyl |
| 92 | 5-chloro-benzo | $C(R_4)$ | methyl | S | isopropyloxy | isopropyloxy | $CH_2$ | 3,4-difluoro-phenyl |
| 94 | benzo | $C(R_4)$ | H | S | ethoxy | 2,6-dichloro-phenyl methoxy | absent | H |
| 95 | benzo | $C(R_4)$ | H | S | ethoxy | ethoxy | $CH_2$ | 2,6-dichloro-phenyl |
| 96 | benzo | $C(R_4)$ | H | S | ethoxy | ethoxy | $CH_2$ | 3,5-trifluoro methyl-phenyl |
| 98 | benzo | $C(R_4)$ | H | S | ethoxy | ethoxy | $CH_2$ | 2-chloro-4-fluoro-phenyl |
| 99 | benzo | $C(R_4)$ | methyl | S | ethoxy | ethoxy | $CH_2$ | 2-chloro-5-trifluoro methyl-phenyl |
| 100 | benzo | $C(R_4)$ | H | S | ethoxy | ethoxy | $CH_2$ | 2,3-dichloro-phenyl |
| 101 | benzo | $C(R_4)$ | methyl | S | cyclohexyloxy | cyclohexyloxy | $CH_2$ | 3,4-difluoro-phenyl |
| 102 | benzo | $C(R_4)$ | H | S | ethoxy | ethoxy | $CH_2$ | 2-trifluoro methyl-phenyl |
| 103 | benzo | $C(R_4)$ | methyl | S | ethoxy | 2-(N,N-dimethyl amino)-ethoxy | $CH_2$ | 3,4-difluoro-phenyl |
| 104 | benzo | $C(R_4)$ | H | S | ethoxy | 2-methyl-phenyl-methoxy | absent | H |
| 105 | benzo | $C(R_4)$ | H | S | ethoxy | 2-chloro-phenyl methoxy | absent | H |
| Diast. 106 | benzo | $C(R_4)$ | methyl | S | ethoxy | methyl | $CH_2$ | 3,4-difluoro-phenyl |
| 107 | benzo | $C(R_4)$ | H | S | ethoxy | 4-fluoro-phenyl methoxy | absent | H |
| 109 | benzo | $C(R_4)$ | H | S | ethoxy | 2-fluoro-phenyl methoxy | absent | H |
| 110 | benzo | $C(R_4)$ | H | S | ethoxy | 2-bromo-phenyl methoxy | absent | H |
| 111 | benzo | $C(R_4)$ | H | S | ethoxy | phenylmethoxy | absent | H |
| 112 | benzo | $C(R_4)$ | H | S | ethoxy | ethoxy | $CH_2$ | 5-chloro-benzo[1,3]dioxol-6-yl |
| 113 | benzo | $C(R_4)$ | methyl | S | ethoxy | ethoxy | $CH_2$ | 2,5-di-trifluoro methyl-phenyl |

TABLE 1-continued

Formula (Ia)

| Cpd | A | W | R4 | X | R1 | R2 | L | B |
|---|---|---|---|---|---|---|---|---|
| 114 | benzo | C(R4) | N,N-dimethyl-aminomethyl | S | ethoxy | ethoxy | CH2 | 2-fluoro-phenyl |
| 115 | benzo | C(R4) | methyl | S | ethoxy | ethoxy | CH2 | 2-biphenyl |
| 116 | 7-trifluoromethyl-benzo | C(R4) | methyl | S | ethoxy | ethoxy | CH2 | 3,4-difluoro-phenyl |
| 117 | 6-chloro-benzo | C(R4) | cyclopentyl | S | ethoxy | ethoxy | CH2 | 3,4-difluoro-phenyl |
| 118 | benzo | C(R4) | methyl | S(O) | ethoxy | ethoxy | CH2 | 3,4-difluoro-phenyl |
| 119 | benzo | C(R4) | cyclohexyl | S | ethoxy | ethoxy | CH2 | 3,4-difluoro-phenyl |
| 120 | benzo | C(R4) | H | O | isopropyloxy | isopropyloxy | CH2 | 3,4-difluoro-phenyl |
| 121 | benzo | C(R4) | H | S | isopropyloxy | isopropyloxy | CH2 | 3,5-difluoro-phenyl |
| 122 | benzo | C(R4) | H | S | isopropyloxy | isopropyloxy | CH2 | 2,3-difluoro-phenyl |
| 123 | benzo | C(R4) | bromo | O | s-butyl | s-butyl | CH2 | 3,4-difluoro-phenyl |
| 124 | benzo | C(R4) | bromo | O | isopropyloxy | isopropyloxy | CH2 | 3,4-difluoro-phenyl |
| 125 | benzo | C(R4) | H | S | isopropyloxy | isopropyloxy | CH2 | 3-trifluoromethyl-4-fluoro-phenyl |
| 126 | benzo | C(R4) | H | S | isopropyloxy | isopropyloxy | CH2 | 2-fluoro-3-chloro-5-trifluoromethyl-phenyl |
| 127 | benzo | C(R4) | bromo | S | ethoxy | ethoxy | CH2 | 3,4-difluoro-phenyl |
| 128 | benzo | C(R4) | 2-fluoro-pyridin-3-yl | S | ethoxy | ethoxy | CH2 | 3,4-difluoro-phenyl |
| 129 | benzo | C(R4) | 2,2-dimethyl-propyl | S | ethoxy | ethoxy | CH2 | 3,4-difluoro-phenyl |
| 130 | benzo | C(R4) | 2-fluoro-pyridin-5-yl | S | ethoxy | ethoxy | CH2 | 3,4-difluoro-phenyl |
| 131 | (2,3-b)pyridin-2-yl | C(R4) | H | S | ethoxy | ethoxy | CH2 | 3,4-difluoro-phenyl |
| 132 | (2,3-b)pyridin-2-yl | C(R4) | bromo | S | ethoxy | ethoxy | CH2 | 3,4-difluoro-phenyl |
| 133 | benzo | C(R4) | H | S | isopropyloxy | isopropyloxy | CH2 | 3-fluoro-phenyl |
| 134 | benzo | C(R4) | H | S | isopropyloxy | isopropyloxy | CH2 | 3-chloro-phenyl |
| Diast. 135 | benzo | C(R4) | methyl | S | ethoxy | 3-(4-methoxy-phenyl)-propyl | CH2 | 3,4-difluoro-phenyl |
| Diast. 136 | benzo | C(R4) | methyl | S | ethoxy | 3-(4-methoxy-phenyl)-propyl | CH2 | 3,4-difluoro-phenyl |
| 137 | benzo | C(R4) | bromo | S | ethoxy | ethoxy | CH2 | 3-chloro-phenyl |
| 138 | benzo | C(R4) | bromo | S | ethoxy | ethoxy | CH2 | 4-fluoro-3-trimethyl-phenyl |

TABLE 1-continued

Formula (Ia)

| Cpd | A | W | R₄ | X | R₁ | R₂ | L | B |
|---|---|---|---|---|---|---|---|---|
| 139 | benzo | C(R₄) | bromo | S | ethoxy | ethoxy | CH₂ | 4-chloro-3-trifluoromethyl-phenyl |
| 140 | benzo | C(R₄) | bromo | S | ethoxy | ethoxy | CH₂ | 3-fluoro-5-trifluoromethyl-phenyl |
| 141 | benzo | C(R₄) | bromo | S | ethoxy | ethoxy | CH₂ | 3-trifluoromethyl-phenyl |
| 142 | benzo | C(R₄) | bromo | S | ethoxy | ethoxy | CH₂ | 2-fluoro-3-trifluoromethyl-phenyl |
| 143 | benzo | C(R₄) | bromo | S | ethoxy | ethoxy | CH₂ | 2-fluoro-3-chloro-phenyl |
| 144 | benzo | C(R₄) | bromo | S | ethoxy | ethoxy | CH₂ | 3-fluoro-4-trifluoromethyl-phenyl |
| 145 | benzo | C(R₄) | bromo | S | ethoxy | ethoxy | CH₂ | 3-trifluoromethoxy-phenyl |
| 146 | benzo | C(R₄) | bromo | S | ethoxy | ethoxy | CH₂ | 2-fluoro-5-trifluoromethyl-phenyl |
| 147 | benzo | C(R₄) | bromo | S | ethoxy | ethoxy | CH₂ | 2-chloro-phenyl |
| 148 | benzo | C(R₄) | bromo | S | ethoxy | ethoxy | CH₂ | 2-chloro-5-trifluoromethyl-phenyl |
| 149 | benzo | C(R₄) | bromo | S | ethoxy | ethoxy | CH₂ | 3-chloro-4-trifluoromethoxy-phenyl |
| 150 | benzo | C(R₄) | bromo | S | ethoxy | ethoxy | CH₂ | 2-fluoro-4-trifluoromethyl-phenyl |
| 151 | benzo | C(R₄) | bromo | S | ethoxy | ethoxy | CH₂ | 2-chloro-3-trifluoromethyl-phenyl |
| 152 | benzo | C(R₄) | bromo | S | ethoxy | ethoxy | CH₂ | 3-trifluoromethyl-4-methoxy-phenyl |
| 153 | benzo | C(R₄) | bromo | S | ethoxy | ethoxy | CH₂ | 4-trifluoromethylthio-phenyl |
| 154 | benzo | C(R₄) | bromo | S | ethoxy | ethoxy | CH₂ | 4-trifluoromethyl-phenyl |
| 155 | benzo | C(R₄) | bromo | S | ethoxy | ethoxy | CH₂ | 4-trifluoromethoxy-phenyl |
| 156 | benzo | C(R₄) | bromo | S | ethoxy | ethoxy | CH₂ | 3-methoxy-4-fluoro-phenyl |
| 157 | benzo | C(R₄) | bromo | S | isopropyloxy | isopropyloxy | CH₂ | 3-methoxy-4-fluoro-phenyl |
| 158 | benzo | C(R₄) | bromo | S | ethoxy | ethoxy | CH₂ | 3-fluoro-4-methoxy-phenyl |

TABLE 1-continued

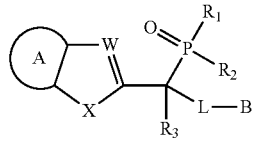

Formula (Ia)

| Cpd | A | W | $R_4$ | X | $R_1$ | $R_2$ | L | B |
|---|---|---|---|---|---|---|---|---|
| 159 | benzo | $C(R_4)$ | bromo | S | isopropyloxy | isopropyloxy | $CH_2$ | 3-fluoro-4-methoxy-phenyl |
| 160 | benzo | $C(R_4)$ | bromo | S | ethoxy | ethoxy | $CH_2$ | 2,3,5,6-tetrafluoro-4-methoxy-phenyl |
| 161 | benzo | $C(R_4)$ | bromo | S | isopropyloxy | isopropyloxy | $CH_2$ | 2,3,5,6-tetrafluoro-4-methoxy-phenyl |
| 162 | benzo | $C(R_4)$ | bromo | S | ethoxy | ethoxy | $CH_2$ | 2-fluoro-3-methoxy-phenyl |
| 163 | benzo | $C(R_4)$ | bromo | S | isopropyloxy | isopropyloxy | $CH_2$ | 2-fluoro-4-methoxy-phenyl |
| 164 | benzo | $C(R_4)$ | bromo | S | ethoxy | ethoxy | $CH_2$ | 2-fluoro-4-chloro-5-methoxy-phenyl |
| 165 | benzo | $C(R_4)$ | bromo | S | isopropyloxy | isopropyloxy | $CH_2$ | 2-fluoro-4-chloro-5-methoxy-phenyl |
| 166 | benzo | $C(R_4)$ | bromo | S | isopropyloxy | isopropyloxy | $CH_2$ | 3-chloro-phenyl |
| 167 | benzo | $C(R_4)$ | chloro | S | isopropyloxy | isopropyloxy | $CH_2$ | 3-trifluoromethyl-4-chloro-phenyl |
| 168 | benzo | $C(R_4)$ | chloro | S | isopropyloxy | isopropyloxy | $CH_2$ | 2-fluoro-3-trifluoromethyl-phenyl |
| 169 | benzo | $C(R_4)$ | chloro | S | isopropyloxy | isopropyloxy | $CH_2$ | 3-fluoro-5-trifluoromethyl-phenyl |
| 170 | benzo | $C(R_4)$ | chloro | S | isopropyloxy | isopropyloxy | $CH_2$ | 3-trifluoromethyl-phenyl |
| 171 | benzo | $C(R_4)$ | chloro | S | isopropyloxy | isopropyloxy | $CH_2$ | 3,5-di-trifluoromethyl-phenyl |
| 172 | benzo | $C(R_4)$ | chloro | S | isopropyloxy | isopropyloxy | $CH_2$ | 2-fluoro-5-trifluoromethyl-phenyl |
| 173 | benzo | $C(R_4)$ | chloro | S | isopropyloxy | isopropyloxy | $CH_2$ | 2-trifluoromethyl-phenyl |
| 174 | benzo | $C(R_4)$ | chloro | S | isopropyloxy | isopropyloxy | $CH_2$ | 3-fluoro-4-trifluoromethyl-phenyl |
| 175 | benzo | $C(R_4)$ | chloro | S | isopropyloxy | isopropyloxy | $CH_2$ | 4-trifluoromethyl-phenyl |
| 176 | benzo | $C(R_4)$ | chloro | S | isopropyloxy | isopropyloxy | $CH_2$ | 3-trifluoromethyl-4-methoxy-phenyl |
| 177 | benzo | $C(R_4)$ | chloro | S | isopropyloxy | isopropyloxy | $CH_2$ | 2-chloro-3-trifluoromethyl-phenyl |

TABLE 1-continued

Formula (Ia)

| Cpd | A | W | R$_4$ | X | R$_1$ | R$_2$ | L | B |
|---|---|---|---|---|---|---|---|---|
| 178 | benzo | C(R$_4$) | chloro | S | isopropyloxy | isopropyloxy | CH$_2$ | 2-chloro-5-trifluoromethyl-phenyl |
| 179 | benzo | C(R$_4$) | chloro | S | isopropyloxy | isopropyloxy | CH$_2$ | phenyl |
| 180 | benzo | C(R$_4$) | chloro | S | isopropyloxy | isopropyloxy | CH$_2$ | 3-chloro-phenyl |
| 181 | benzo | C(R$_4$) | chloro | S | isopropyloxy | isopropyloxy | CH$_2$ | 4-chloro-phenyl |
| 182 | benzo | C(R$_4$) | chloro | S | isopropyloxy | isopropyloxy | CH$_2$ | 3-bromo-phenyl |
| 183 | benzo | C(R$_4$) | chloro | S | isopropyloxy | isopropyloxy | CH$_2$ | 2,6-dichloro-phenyl |
| 184 | benzo | C(R$_4$) | chloro | S | isopropyloxy | isopropyloxy | CH$_2$ | 3-chloro-4-trifluoromethoxy-phenyl |
| 185 | benzo | C(R$_4$) | chloro | S | isopropyloxy | isopropyloxy | CH$_2$ | 2-fluoro-3-chloro-phenyl |
| 186 | benzo | C(R$_4$) | chloro | S | isopropyloxy | isopropyloxy | CH$_2$ | 3-chloro-5-fluoro-phenyl |
| 187 | benzo | C(R$_4$) | chloro | S | isopropyloxy | isopropyloxy | CH$_2$ | 4-trifluoromethoxy-phenyl |
| 188 | benzo | C(R$_4$) | chloro | S | isopropyloxy | isopropyloxy | CH$_2$ | 3-trifluoromethyl-4-fluoro-phenyl |
| 189 | benzo | C(R$_4$) | chloro | S | isopropyloxy | isopropyloxy | CH$_2$ | 3-fluoro-4-chloro-phenyl |
| 190 | benzo | C(R$_4$) | bromo | S | isopropyloxy | isopropyloxy | CH$_2$ | 3-fluoro-4-chloro-phenyl |
| 191 | benzo | C(R$_4$) | chloro | S | isopropyloxy | isopropyloxy | CH$_2$ | 2-fluoro-4-trifluoromethyl-phenyl |
| 192 | benzo | C(R$_4$) | bromo | S | isopropyloxy | isopropyloxy | CH$_2$ | 3-fluoro-phenyl |
| 193 | benzo | C(R$_4$) | bromo | S | isopropyloxy | isopropyloxy | CH$_2$ | 3,5-difluoro-phenyl |
| 194 | benzo | C(R$_4$) | bromo | S | isopropyloxy | isopropyloxy | CH$_2$ | 2,3-difluoro-phenyl |
| 195 | benzo | C(R$_4$) | bromo | S | isopropyloxy | isopropyloxy | CH$_2$ | 2-fluoro-3-chloro-5-trifluoromethyl-phenyl |
| 196 | benzo | C(R$_4$) | bromo | S | isopropyloxy | isopropyloxy | CH$_2$ | 2-fluoro-phenyl |
| 197 | benzo | C(R$_4$) | bromo | S | isopropyloxy | isopropyloxy | CH$_2$ | 4-fluoro-phenyl |
| 198 | 4-bromo-benzo | C(R$_4$) | bromo | S | isopropyloxy | isopropyloxy | CH$_2$ | 2-fluoro-phenyl |
| 199 | 6-bromo-benzyl | C(R$_4$) | bromo | S | isopropyloxy | isopropyloxy | CH$_2$ | 2-fluoro-phenyl |
| 200 | 6-bromo-benzyl | C(R$_4$) | bromo | S | isopropyloxy | isopropyloxy | CH$_2$ | 4-fluoro-phenyl |
| 201 | benzo | C(R$_4$) | bromo | S | methoxy | methoxy | CH$_2$ | 3,4-difluoro-phenyl |
| 202 | 4-fluoro-benzo | C(R$_4$) | methyl | O | isopropyloxy | isopropyloxy | CH$_2$ | 3,4-difluoro-phenyl |
| 203 | benzo | C(R$_4$) | bromo | S | s-butyl | s-butyl | CH$_2$ | 3,4-difluoro-phenyl |
| 204 | benzo | C(R$_4$) | bromo | S | s-butyl | s-butyl | OCH$_2$ | 3,4-difluoro-phenyl |

TABLE 1-continued

Formula (Ia)

| Cpd | A | W | R4 | X | R1 | R2 | L | B |
|---|---|---|---|---|---|---|---|---|
| 205 | 4-fluoro-benzo | C(R4) | bromo | O | Isopropyloxy | isopropyloxy | CH2 | 3,4-difluoro-phenyl |
| 206 | 4-fluoro-benzo | C(R4) | bromo | O | ethoxy | ethoxy | CH2 | 3,4-difluoro-phenyl |
| 207 | (2,3-b)pyridin-2-yl | C(R4) | bromo | S | Isopropyloxy | isopropyloxy | CH2 | 3,4-difluoro-phenyl |
| 208 | benzo | C(R4) | thien-3-yl | S | ethoxy | ethoxy | CH2 | 3,4-difluoro-phenyl |
| 209 | benzo | C(R4) | bromo | S | n-butyloxy | n-butyloxy | CH2 | 3,4-difluoro-phenyl |
| 210 | benzo | C(R4) | bromo | S | 2-(2-methoxy-ethoxy)-ethoxy | 2-(2-methoxy-ethoxy)-ethoxy | CH2 | 3,4-difluoro-phenyl |
| 211 | benzo | C(R4) | bromo | S | 3-methyl-butoxy | 3-methyl-butoxy | CH2 | 3,4-difluoro-phenyl |
| 212 | benzo | C(R4) | bromo | S | methoxy carbony-methoxy | methoxy carbony-methoxy | CH2 | 3,4-difluoro-phenyl |
| 213 | benzo | C(R4) | bromo | S | 2-acetoxy-ethoxy | 2-acetoxy-ethoxy | CH2 | 3,4-difluoro-phenyl |
| 214 | benzo | C(R4) | phenyl | S | ethoxy | ethoxy | CH2 | 3,4-difluoro-phenyl |
| 215 | benzo | C(R4) | 2-hydroxy-phenyl | S | ethoxy | ethoxy | CH2 | 3,4-difluoro-phenyl |
| 216 | benzo | C(R4) | 2-fluoro-phenyl | S | ethoxy | ethoxy | CH2 | 3,4-difluoro-phenyl |
| 217 | benzo | C(R4) | 3-fluoro-phenyl | S | ethoxy | ethoxy | CH2 | 3,4-difluoro-phenyl |
| 218 | benzo | C(R4) | 3-amino carbonyl-phenyl | S | ethoxy | ethoxy | CH2 | 3,4-difluoro-phenyl |
| 219 | benzo | C(R4) | 3-methoxy carbonyl-phenyl | S | ethoxy | ethoxy | CH2 | 3,4-difluoro-phenyl |
| 220 | benzo | C(R4) | 4-fluoro-phenyl | S | ethoxy | ethoxy | CH2 | 3,4-difluoro-phenyl |
| 221 | 4-fluoro-benzo | C(R4) | bromo | S | isopropyloxy | isopropyloxy | CH2 | 3,4-difluoro-phenyl |
| 222 | 4-fluoro-benzo | C(R4) | bromo | S | isopropyloxy | isopropyloxy | CH2 | 3-trifluoro methyl-4-fluoro-phenyl |
| 223 | 4-fluoro-benzo | C(R4) | bromo | S | ethoxy | ethoxy | CH2 | 3-trifluoro methyl-4-fluoro-phenyl |
| 224 | 4-fluoro-benzo | C(R4) | bromo | S | ethoxy | ethoxy | CH2 | 3,4-difluoro-phenyl |
| 225 | benzo | C(R4) | bromo | S | ethoxy | ethoxy | CH2 | 3-hydroxy-4-fluoro-phenyl |
| 226 | benzo | C(R4) | bromo | S | ethoxy | ethoxy | CH2 | 3-fluoro-4-hydroxy-phenyl |
| 227 | benzo | C(R4) | bromo | S | isopropyloxy | isopropyloxy | CH2 | 3-fluoro-4-hydroxy-phenyl |
| 228 | benzo | C(R4) | bromo | S | ethoxy | ethoxy | CH2 | 2,3,5,6-tetrafluoro-4-hydroxy-phenyl |
| 229 | benzo | C(R4) | bromo | S | isopropyloxy | isopropyloxy | CH2 | 2,3,5,6-tetrafluoro-4-hydroxy-phenyl |

TABLE 1-continued

Formula (Ia)

| Cpd | A | W | $R_4$ | X | $R_1$ | $R_2$ | L | B |
|---|---|---|---|---|---|---|---|---|
| 230 | benzo | $C(R_4)$ | bromo | S | isopropyloxy | isopropyloxy | $CH_2$ | 2-fluoro-3-hydroxy-phenyl |
| 231 | benzo | $C(R_4)$ | bromo | S | ethoxy | ethoxy | $CH_2$ | 2-fluoro-4-chloro-5-hydroxy-phenyl |
| 232 | benzo | $C(R_4)$ | bromo | S | isopropyloxy | isopropyloxy | $CH_2$ | 2-fluoro-4-chloro-5-hydroxy-phenyl |
| 233 | benzo | $C(R_4)$ | bromo | S | ethoxy | ethoxy | $CH_2$ | 3-trifluoromethyl-4-hydroxy-phenyl |
| Enant. A 234 | benzo | $C(R_4)$ | bromo | S | isopropyloxy | isopropyloxy | $CH_2$ | 3,4-difluoro-phenyl |
| Enant. B 235 | benzo | $C(R_4)$ | bromo | S | isopropyloxy | isopropyloxy | $CH_2$ | 3,4-difluoro-phenyl |
| Enant. A 236 | benzo | $C(R_4)$ | bromo | S | ethoxy | ethoxy | $CH_2$ | 4-trifluoromethoxy-phenyl |
| Enant. B 237 | benzo | $C(R_4)$ | bromo | S | ethoxy | ethoxy | $CH_2$ | 4-trifluoromethoxy-phenyl |
| 238 | benzo | $C(R_4)$ | bromo | S | ethoxy | ethoxy | $CH_2$ | 4-fluoro-phenyl |
| Enant. A 239 | benzo | $C(R_4)$ | bromo | S | ethoxy | ethoxy | $CH_2$ | 4-fluoro-phenyl |
| Enant. B 240 | benzo | $C(R_4)$ | bromo | S | ethoxy | ethoxy | $CH_2$ | 4-fluoro-phenyl |
| 241 | benzo | $C(R_4)$ | bromo | S | isopropyloxy | isopropyloxy | $CH_2$ | 3-trifluoromethyl-4-fluoro-phenyl |
| Enant. A 242 | benzo | $C(R_4)$ | bromo | S | isopropyloxy | isopropyloxy | $CH_2$ | 3-trifluoromethyl-4-fluoro-phenyl |
| Enant. B 243 | benzo | $C(R_4)$ | bromo | S | isopropyloxy | isopropyloxy | $CH_2$ | 3-trifluoromethyl-4-fluoro-phenyl |
| 244 | benzo | $C(R_4)$ | bromo | S | ethoxy | ethoxy | $CH_2$ | 3-chloro-4-fluoro-phenyl |
| 245 | benzo | $C(R_4)$ | bromo | S | ethoxy | ethoxy | $CH_2$ | 2-trifluoromethyl-4-fluoro-phenyl |
| 246 | benzo | $C(R_4)$ | bromo | S | ethoxy | ethoxy | $CH_2$ | 3-trimethylthio-phenyl |
| 247 | benzo | $C(R_4)$ | bromo | S | ethoxy | ethoxy | $CH_2$ | 4-methylthio-phenyl |
| 248 | benzo | $C(R_4)$ | bromo | S | isopropyloxy | isopropyloxy | $CH_2$ | 3-chloro-4-fluoro-phenyl |
| 249 | benzo | $C(R_4)$ | bromo | S | isopropyloxy | isopropyloxy | $CH_2$ | 2-trifluoromethyl-4-fluoro-phenyl |
| 250 | benzo | $C(R_4)$ | bromo | S | isopropyloxy | isopropyloxy | $CH_2$ | 3-trifluoromethylthio-phenyl |

TABLE 1-continued

Formula (Ia)

| Cpd | A | W | R4 | X | R1 | R2 | L | B |
|---|---|---|---|---|---|---|---|---|
| 251 | benzo | C(R4) | bromo | S | isopropyloxy | isopropyloxy | CH2 | 4-methylthio-phenyl |
| 252 | benzo | C(R4) | bromo | S | isopropyloxy | isopropyloxy | CH2 | 4-methyl sulfonyl-phenyl |
| 253 | benzo | C(R4) | chloro | S | isopropyloxy | isopropyloxy | CH2 | 3-chloro-4-fluoro-phenyl |
| 254 | benzo | C(R4) | chloro | S | isopropyloxy | isopropyloxy | CH2 | 2-trifluoro-methyl-4-fluoro-phenyl |
| 255 | benzo | C(R4) | chloro | S | isopropyloxy | isopropyloxy | CH2 | 3-trifluoro methylthio-phenyl |
| 256 | benzo | C(R4) | chloro | S | isopropyloxy | isopropyloxy | CH2 | 4-methyl thio-phenyl |
| 257 | benzo | C(R4) | bromo | S | ethoxy | ethoxy | CH2 | 4-chloro-phenyl |
| 258 | benzo | C(R4) | bromo | S | ethoxy | ethoxy | CH2 | 3-fluoro-4-chloro-phenyl |
| 259 | benzo | C(R4) | bromo | S | ethoxy | ethoxy | CH2 | 3-chloro-5-fluoro-phenyl |
| 260 | benzo | C(R4) | bromo | S | ethoxy | ethoxy | CH2 | 2-trifluoro methyl-phenyl |
| 261 | benzo | C(R4) | bromo | S | ethoxy | ethoxy | CH2 | 3,5-di-trifluoro-methyl-phenyl |
| 262 | benzo | C(R4) | bromo | S | ethoxy | ethoxy | CH2 | 4-trifluoro methyl sulfonyl-phenyl |
| 263 | benzo | C(R4) | bromo | S | isopropyloxy | isopropyloxy | CH2 | 4-trifluoro methyl sulfonyl-phenyl |
| 264 | benzo | C(R4) | chloro | S | isopropyloxy | isopropyloxy | CH2 | 4-trifluoro methyl sulfonyl-phenyl |
| 265 | benzo | C(R4) | H | O | ethoxy | ethoxy | CH2 | 3,4-difluoro-phenyl |
| 266 | benzo | C(R4) | bromo | O | ethoxy | ethoxy | CH2 | 3,4-difluoro-phenyl |
| 267 | benzo | C(R4) | bromo | S | isopropyloxy | isopropyloxy | CH2 | 3-chloro-2-fluoro-phenyl |
| 268 | benzo | C(R4) | bromo | S | isopropyloxy | isopropyloxy | CH2 | 2-chloro-3-trifluoro methyl-phenyl |
| 269 | benzo | C(R4) | chloro | S | ethoxy | ethoxy | CH2 | 2-chloro-phenyl |
| 270 | benzo | C(R4) | chloro | S | ethoxy | ethoxy | CH2 | 3-trifluoro methoxy-phenyl |
| 271 | benzo | C(R4) | chloro | S | ethoxy | ethoxy | CH2 | 3-chloro-4-trifluoro methoxy-phenyl |
| 272 | benzo | C(R4) | chloro | S | ethoxy | ethoxy | CH2 | 3-chloro-2-fluoro-phenyl |

TABLE 1-continued

Formula (Ia)

| Cpd | A | W | R$_4$ | X | R$_1$ | R$_2$ | L | B |
|---|---|---|---|---|---|---|---|---|
| 273 | benzo | C(R$_4$) | chloro | S | ethoxy | ethoxy | CH$_2$ | 3-fluoro-4-trifluoromethyl-phenyl |
| 274 | benzo | C(R$_4$) | chloro | S | ethoxy | ethoxy | CH$_2$ | 2-chloro-5-trifluoromethyl-phenyl |
| 275 | benzo | C(R$_4$) | chloro | S | ethoxy | ethoxy | CH$_2$ | 3-bromo-phenyl |
| 276 | benzo | C(R$_4$) | chloro | S | ethoxy | ethoxy | CH$_2$ | 3-chloro-5-fluoro-phenyl |
| 277 | benzo | C(R$_4$) | chloro | S | ethoxy | ethoxy | CH$_2$ | 4-trifluoromethoxy-phenyl |
| 278 | benzo | C(R$_4$) | chloro | S | ethoxy | ethoxy | CH$_2$ | 3-fluoro-5-trifluoromethyl-phenyl |
| 279 | benzo | C(R$_4$) | chloro | S | ethoxy | ethoxy | CH$_2$ | 2-trifluoromethyl-phenyl |
| 280 | benzo | C(R$_4$) | chloro | S | ethoxy | ethoxy | CH$_2$ | 2-chloro-3-trifluoromethyl-phenyl |
| 281 | benzo | C(R$_4$) | chloro | S | ethoxy | ethoxy | CH$_2$ | 2-fluoro-3-trifluoromethyl-phenyl |
| 282 | benzo | C(R$_4$) | chloro | S | ethoxy | ethoxy | CH$_2$ | 3,5-di-trifluoromethyl-phenyl |
| 283 | benzo | C(R$_4$) | chloro | S | ethoxy | ethoxy | CH$_2$ | 4-trifluoromethylthio-phenyl |
| 284 | benzo | C(R$_4$) | chloro | S | ethoxy | ethoxy | CH$_2$ | 4-fluoro-phenyl |
| 285 | benzo | C(R$_4$) | chloro | S | ethoxy | ethoxy | CH$_2$ | 4-trifluoromethyl-phenyl |
| 286 | benzo | C(R$_4$) | chloro | S | ethoxy | ethoxy | CH$_2$ | 2-fluoro-5-trifluoromethyl-phenyl |
| 287 | benzo | C(R$_4$) | chloro | S | ethoxy | ethoxy | CH$_2$ | 4-chloro-3-trifluoromethyl-phenyl |
| 288 | benzo | C(R$_4$) | bromo | S | isopropyloxy | isopropyloxy | CH$_2$ | 4-chloro-phenyl |
| 289 | benzo | C(R$_4$) | bromo | S | isopropyloxy | isopropyloxy | CH$_2$ | 2-fluoro-4-trifluoromethyl-phenyl |
| 290 | benzo | C(R$_4$) | chloro | S | ethoxy | ethoxy | CH$_2$ | 3-chloro-phenyl |
| 291 | benzo | C(R$_4$) | chloro | S | ethoxy | ethoxy | CH$_2$ | 2-fluoro-4-trifluoromethyl-phenyl |
| 292 | benzo | C(R$_4$) | chloro | S | ethoxy | ethoxy | CH$_2$ | 4-methoxy-3-trifluoromethyl-phenyl |
| 293 | benzo | C(R$_4$) | chloro | S | ethoxy | ethoxy | CH$_2$ | 4-chloro-phenyl |

TABLE 1-continued

Formula (Ia)

| Cpd | A | W | R$_4$ | X | R$_1$ | R$_2$ | L | B |
|---|---|---|---|---|---|---|---|---|
| 294 | benzo | C(R$_4$) | chloro | S | ethoxy | ethoxy | CH$_2$ | 4-fluoro-3-trifluoromethyl-phenyl |
| 295 | benzo | C(R$_4$) | bromo | S | ethoxy | ethoxy | CH$_2$ | 3-bromo-phenyl |
| 296 | benzo | C(R$_4$) | chloro | S | ethoxy | ethoxy | CH$_2$ | 3-trifluoromethylthio-phenyl |
| 297 | benzo | C(R$_4$) | chloro | S | ethoxy | ethoxy | CH$_2$ | 3-chloro-4-fluoro-phenyl |
| 298 | benzo | C(R$_4$) | chloro | S | ethoxy | ethoxy | CH$_2$ | 4-fluoro-3-trifluoromethyl-phenyl |
| 299 | benzo | C(R$_4$) | chloro | S | ethoxy | ethoxy | CH$_2$ | 4-methylthio-phenyl |
| 300 | benzo | C(R$_4$) | chloro | S | ethoxy | ethoxy | CH$_2$ | 4-trifluoromethylsulfonyl-phenyl |
| 301 | benzo | C(R$_4$) | chloro | S | isopropyloxy | isopropyloxy | CH$_2$ | 3-trifluoromethoxy-phenyl |
| 302 | benzo | C(R$_4$) | chloro | S | isopropyloxy | isopropyloxy | CH$_2$ | 4-chloro-3-fluoro-phenyl |
| 303 | benzo | C(R$_4$) | chloro | S | isopropyloxy | isopropyloxy | CH$_2$ | 5-chloro-2-fluoro-phenyl |
| 304 | benzo | C(R$_4$) | chloro | S | isopropyloxy | isopropyloxy | CH$_2$ | 4-trifluoromethylthio-phenyl |
| 305 | benzo | C(R$_4$) | chloro | S | ethoxy | ethoxy | CH$_2$ | 5-chloro-2-fluoro-phenyl |
| 306 | benzo | C(R$_4$) | chloro | S | isopropyloxy | isopropyloxy | CH$_2$ | 4-fluoro-phenyl |
| 307 | benzo | C(R$_4$) | bromo | S | ethoxy | ethoxy | CH$_2$ | 5-chloro-2-fluoro-phenyl |
| 308 | benzo | C(R$_4$) | bromo | S | isopropyloxy | isopropyloxy | CH$_2$ | 5-chloro-2-fluoro-phenyl |
| 309 | benzo | C(R$_4$) | bromo | S | ethoxy | ethoxy | CH$_2$ | 3-cyano-phenyl |
| 310 | benzo | C(R$_4$) | bromo | S | ethoxy | ethoxy | CH$_2$ | 3-pyrrol-1-yl-phenyl |
| 311 | benzo | C(R$_4$) | bromo | S | ethoxy | ethoxy | CH$_2$ | 4-difluoromethoxy-phenyl |
| 312 | benzo | C(R$_4$) | bromo | S | ethoxy | ethoxy | CH$_2$ | 4-cyano-phenyl |
| 313 | benzo | C(R$_4$) | bromo | S | ethoxy | ethoxy | CH$_2$ | 3-methoxycarbonyl-phenyl |
| 314 | benzo | C(R$_4$) | bromo | S | ethoxy | ethoxy | CH$_2$ | 3-methoxy-phenyl |
| 315 | benzo | C(R$_4$) | bromo | S | ethoxy | ethoxy | CH$_2$ | 3-nitro-phenyl |
| 316 | benzo | C(R$_4$) | bromo | S | ethoxy | ethoxy | CH$_2$ | 3-hydroxy-phenyl |

TABLE 1-continued

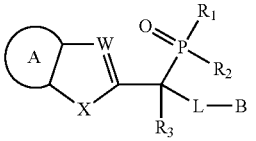

Formula (Ia)

| Cpd | A | W | $R_4$ | X | $R_1$ | $R_2$ | L | B |
|---|---|---|---|---|---|---|---|---|
| 317 | benzo | $C(R_4)$ | bromo | S | isopropyloxy | isopropyloxy | $CH_2$ | 3-methoxy-phenyl |
| 318 | benzo | $C(R_4)$ | bromo | S | ethoxy | ethoxy | $CH_2$ | 3-amino-phenyl |
| 319 | benzo | $C(R_4)$ | bromo | S | ethoxy | ethoxy | $CH_2$ | 3,5-dimethoxy-phenyl |
| 320 | benzo | $C(R_4)$ | bromo | S | ethoxy | ethoxy | $CH_2$ | 2-methoxy-phenyl |
| 321 | benzo | $C(R_4)$ | bromo | S | ethoxy | ethoxy | $CH_2$ | 4-methoxy-phenyl |
| 322 | benzo | $C(R_4)$ | bromo | S | ethoxy | ethoxy | $CH_2$ | 3,5-dihydroxy-phenyl |
| 323 | benzo | $C(R_4)$ | bromo | S | ethoxy | ethoxy | $CH_2$ | 2-hydroxy-phenyl |
| 324 | benzo | $C(R_4)$ | bromo | S | ethoxy | ethoxy | $CH_2$ | 4-hydroxy-phenyl |
| 325 | benzo | $C(R_4)$ | bromo | S | isopropyloxy | isopropyloxy | $CH_2$ | 3-hydroxy-phenyl |
| 326 | benzo | $C(R_4)$ | bromo | S | isopropyloxy | isopropyloxy | $CH_2$ | 4-methoxy-3-trifluoromethyl-phenyl |
| 327 | benzo | $C(R_4)$ | bromo | N(t-butoxy carbonyl) | isopropyloxy | isopropyloxy | $CH_2$ | 4-fluoro-3-trifluoromethyl-phenyl |
| 328 | benzo | $C(R_4)$ | bromo | N(MeI) | isopropyloxy | isopropyloxy | $CH_2$ | 4-fluoro-3-trifluoromethyl-phenyl |
| 329 | 3-trifluoromethyl-4-fluoro-benzo | $C(R_4)$ | bromo | N(n-propyl) | isopropyloxy | isopropyloxy | $CH_2$ | 4-fluoro-3-trifluoromethyl-phenyl |
| 330 | 3-trifluoromethyl-4-fluoro-benzo | $C(R_4)$ | bromo | N(methane sulfonyl) | isopropyloxy | isopropyloxy | $CH_2$ | 4-fluoro-3-trifluoromethyl-phenyl |
| 331 | benzo | $C(R_4)$ | bromo | N(methyl carbonyl) | isopropyloxy | isopropyloxy | $CH_2$ | 4-fluoro-3-trifluoromethyl-phenyl |
| 332 | benzo | $C(R_4)$ | bromo | N(n-propyl sulfonyl) | isopropyloxy | isopropyloxy | $CH_2$ | 4-fluoro-3-trifluoromethyl-phenyl |
| 333 | benzo | $C(R_4)$ | H | S | isopropyloxy | isopropyloxy | CH | 3,4-difluoro-phenyl |
| 334 | benzo | $C(R_4)$ | bromo | S | isopropyloxy | isopropyloxy | CH | 3,4-difluoro-phenyl |
| 335 | benzo | $C(R_4)$ | bromo | S | isopropyloxy | isopropyloxy | $CH_2$ | 2-fluoro-5-trifluoromethyl-phenyl |
| 336 | benzo | $C(R_4)$ | bromo | S | isopropyloxy | isopropyloxy | $CH_2$ | 4-trifluoromethyl-phenyl |

Using the methods described in the schemes and specific examples, and adaptations thereof, compounds of Formula (Ia), shown in Table 2, were prepared.

TABLE 2

Formula (Ia)

| Cpd | A | W | $R_4$ | X | $R_1$ | $R_2$ | $R_3$ | L | B |
|---|---|---|---|---|---|---|---|---|---|
| 79 | benzo | $C(R_4)$ | methyl | S | ethoxy | ethoxy | $CH_3$ | $CH_2$ | 3,4-difluoro-phenyl |
| 93 | benzo | $C(R_4)$ | bromo | S | isopropyl oxy | isopropyl oxy | bromo | $CH_2$ | 3,4-difluoro-phenyl |

Using the methods described in the schemes and specific examples, and adaptations thereof, compounds of Formula (Ib) wherein $R_3$ is H, shown in Table 3, were prepared.

TABLE 3

Formula (Ib)

| Cpd | A | W | $R_4$ | X | $R_1$ | $R_2$ | L | B |
|---|---|---|---|---|---|---|---|---|
| 86 | benzo | na | H | S | ethoxy | ethoxy | $CH_2$ | 2-fluoro-phenyl |
| 97 | 5-fluoro-benzo | na | H | S | ethoxy | ethoxy | $CH_2$ | 4-fluoro-phenyl |
| 108 | 5-chloro-benzo | na | H | N(phenyl) | ethoxy | ethoxy | $CH_2$ | 4-fluoro-phenyl |

Biological Examples

Example 1

In Vitro Canine TRPM8 Functional Assay

The functional activity of compounds of Formula (I) was determined by measuring changes in intracellular calcium concentration using a $Ca^{2+}$-sensitive fluorescent dye. The changes in fluorescent signal were monitored by a fluorescence plate reader, either a FLIPR™ (Molecular Devices) or FDSS (Hamamatsu). Increases in intracellular $Ca^{2+}$ concentration were readily detected upon activation with icilin.

HEK293 cells stably expressing canine TRPM8 were routinely grown as monolayers in Dulbecco's minimum essential medium supplemented with 10% FBS, 1 mM L-glutamine, 100 units/mL penicillin, 100 ug/mL streptomycin and 400 μg/mL G418. Cells were maintained in 5% $CO_2$ at 37° C. At 24 hrs prior to assay, cells were seeded in clear-base poly-D-lysine coated 384-well plates (BD Biosciences, NJ, USA) at a density of 5,000 cells per well in culture medium and grown overnight in 5% $CO_2$ at 37° C. On assay day, growth media was removed and cells were loaded with Calcium 3 Dye (Molecular Devices) for 35 min at 37° C., under 5% $CO_2$ and then for 25 min at room temperature and atmosphere. Subsequently, cells were tested for agonist-induced increases in intracellular $Ca^{2+}$ levels using FLIPR™ or FDSS. Cells were challenged with a compound of Formula (I) (at varying concentrations) and intracellular $Ca^{2+}$ was measured for 5 min prior to the addition of icilin to all wells to achieve a final concentration which produces approximately an 80% maximal response. $EC_{50}$ or $IC_{50}$ values for compounds of the present invention were determined from eight-point dose-response studies and represent the concentration of compound required to elicit or inhibit 50% of the maximal response, respectively.

Maximal fluorescence intensity (FI) achieved upon addition of icilin was exported from the FLIPR or FDSS software and further analyzed using GraphPad Prism 3.02 (Graph Pad Software Inc., CA, U.S.A.). Basal FI was subtracted prior to normalizing data to percent of maximal response. Curves were generated using the average of quadruplicate wells for each data point, were analyzed using nonlinear regression of either sigmoidal dose response or sigmoidal dose response (variable slope). Finally, the $EC_{50}$ and $IC_{50}$ values were calculated with the best-fit dose curve determined by GraphPad Prism. The resultant data are displayed in Table 4.

TABLE 4

| | | TRPM8 Screening | | | | |
|---|---|---|---|---|---|---|
| Cpd No. | Conc | % I (10 μM) | % I (5 μM) | % I (1 μM) | % I (0.5 μM) | IC50 (μM) |
| 1 | 1 | | | 100, 101 | | 0.0020, 0.0013, 0.069 |
| 2 | 1 | | | 100 | 0.0040, 0.015, 0.017 | 0.0040, 0.015, 0.017 |
| 3 | 1 | | | 100 | | 0.012, 0.051 |
| 4 | 1 | | | 100 | | 0.022 |
| 5 | 1 | | | 100 | | 0.026 |
| 6 | 1 | | | 100 | | 0.028 |
| 7 | 1 | | | 100 | | 0.031 |
| 8 | 1 | | | 100 | | 0.037 |
| 9 | 1 | | | 100 | | 0.041 |
| 10 | 1 | | | 100 | | 0.043 |
| 11 | 1 | | | 99, 103 | | 0.043, 0.047 |
| 12 | 1 | | | 100 | | 0.043, 0.13 |
| 13 | 1 | | | 100 | | 0.046 |
| 14 | 1 | | | 100, 101, 102 | | 0.047, 0.080 |
| 15 | 1 | | | 99, 100, 103 | | 0.029, 0.048, 0.105 |
| 16 | 1 | | | 100 | | 0.057, 0.064 |
| 17 | 1 | | | 100 | | 0.058 |

TABLE 4-continued

TRPM8 Screening

| Cpd No. | Conc | % I (10 μM) | % I (5 μM) | % I (1 μM) | % I (0.5 μM) | IC50 (μM) |
|---|---|---|---|---|---|---|
| 18 | 1 | | | 100 | | 0.065 |
| 19 | 1 | | | 100 | | 0.068 |
| 20 | 1 | | | 100 | | 0.070 |
| 21 | 1 | | | 100 | | 0.088 |
| 22 | 1 | | | 100, 100 | | 0.090, 0.101, 0.152 |
| 23 | 1 | | | 100 | | 0.096 |
| 24 | 1 | | | 100 | | 0.107 |
| 25 | 1 | | | 101 | | 0.12, 0.19 |
| 26 | 1 | | | 100 | | 0.108 |
| 27 | 1 | | | 99 | | 0.110 |
| 28 | 1 | | | 100 | | 0.110 |
| 29 | 1 | | | 100 | | 0.116 |
| 30 | 1 | | | 100, 99 | | 0.12, 0.20 |
| 31 | 1 | | | 100 | | 0.12 |
| 32 | 1 | | | 100 | | 0.121 |
| 33 | 1 | | | 101 | | 0.123 |
| 34 | 1 | | | 100, 101, 101 | | 0.12, 0.15, 0.20 |
| 35 | 1 | | | 100 | | 0.125 |
| 36 | 1 | | | 100 | | 0.126 |
| 37 | 1 | | | 100 | | 0.127 |
| 38 | 1 | | | 99 | | 0.14 |
| 39 | 1 | | | 100 | | 0.141 |
| 40 | 1 | | | 100 | | 0.145 |
| 41 | 1 | | | 100 | | 0.146 |
| 42 | 1 | | | 100, 100 | | 0.15, 0.14 |
| 43 | 1 | | | 100 | | 0.16 |
| 44 | 1 | | | 100, 100 | | 0.16, 0.17 |
| 45 | 1 | | | 100 | | 0.164 |
| 46 | 1 | | | 99 | | 0.167 |
| 47 | 1 | | | 100 | | 0.167 |
| 48 | 1 | | | 100 | | 0.169 |
| 49 | 1 | | | 100 | | 0.171 |
| 50 | 1 | | | 99 | | 0.184 |
| 51 | 5 | | | 101, 101 | | 0.20, 0.30 |
| 52 | 1 | | | 99 | | 0.22, 0.056 |
| 53 | 1 | | | 100, 97 | | 0.22, 0.26 |
| 54 | 1 | | | 100 | | 0.23 |
| 55 | 1 | | | 100 | | 0.24 |
| 56 | 1 | | | 103 | | 0.24 |
| 57 | 1 | | | 100 | | 0.26 |
| 58 | 1 | | | 100 | | 0.27 |
| 59 | 1 | | | 99 | | 0.27 |
| 60 | 1 | | | 100 | | 0.28 |
| 61 | 1 | | | 100 | | 0.28 |
| 62 | 1 | | | 95 | | 0.29 |
| 63 | 1 | | | 100 | | 0.30 |
| 64 | 1 | | | 64 | | 0.30 |
| 65 | 1 | | | 100 | | 0.30 |
| 66 | 1 | | | 100 | | 0.33 |
| 67 | 1 | | | 100 | | 0.33 |
| 68 | 1 | | | 96 | | 0.34 |
| 69 | 1 | | | 99 | | 0.35 |
| 70 | 1 & 5 | | 99 | 82 | | 0.35 |
| 71 | 1 | | | 98 | | 0.36 |
| 72 | 1 | | | 99 | | 0.36 |
| 73 | 1 | | | 100 | | 0.36 |
| 74 | 1 | | | 92 | | 0.38 |
| 75 | 1 | | | 100 | | 0.39 |
| 76 | 1 | | | 100 | | 0.40 |
| 77 | 1 | | | 98 | | 0.41 |
| 78 | 1 | | | 95 | | 0.43 |
| 79 | 1 | | | 88 | | 0.43 |
| 80 | 1 & 5 | | 100 | 93 | | 0.43 |
| 81 | 1 | | | 100, 87 | | 0.44, 0.61 |
| 82 | 1 | | | 87 | | 0.44 |
| 83 | 1 | | | 84 | | 0.45 |
| 84 | 1 | | | 97 | | 0.46 |
| 85 | 1 & 5 | | 100 | 90 | | 0.48 |
| 86 | 5 | | | 101 | | 0.50 |
| 87 | 1 | | | 93 | | 0.50 |
| 88 | 1 | | | 80, 89 | | 0.50, 0.54 |
| 89 | 1 & 5 | | 100 | 91 | | 0.52 |
| 90 | 1 | | | 89 | | 0.54 |
| 91 | 1 | | | 100 | | 0.57, 0.16 |
| 92 | 1 | | | 91 | | 0.58 |
| 93 | 1 | | | 80 | | 0.58 |
| 94 | 1 & 5 | | 98 | 79 | | 0.60 |
| 95 | 1 & 5 | | 100 | 89 | | 0.60 |
| 96 | 1 | | | 92 | | 0.64 |
| 97 | 5 | | 100 | | | 0.70 |
| 98 | 1 | | | 79 | | 0.71 |
| 99 | 1 | | | 100 | | 0.72 |
| 100 | 1 | | | 82 | | 0.73 |
| 101 | 1 | | | 55 | | 0.75 |
| 102 | 1 | | | 86 | | 0.75 |
| 103 | 1 | | | 60 | | 0.93 |
| 104 | 1 & 5 | | 99 | 53 | | 0.96 |
| 105 | 1 & 5 | | 100 | 48 | | 1.01 |
| 106 | 1 | | | 32 | | 1.26 |
| 107 | 5 | | 99 | | | 1.30 |
| 108 | 5 | | 86 | | | 1.40 |
| 109 | 1 & 5 | | 98 | 17 | | 1.47 |
| 110 | 1 & 5 | | 96 | 11 | | 2.32 |
| 111 | 1 | | | 14 | | — |
| 112 | 1 | | | 42 | | — |
| 113 | 1 | | | 25 | | — |
| 114 | 1 | | | 15 | | — |
| 115 | 1 | | | 69 | | — |
| 116 | 1 | | | 64 | | — |
| 117 | 1 | | | 28 | | — |
| 118 | 1 | | | 23 | | — |
| 119 | 1 | | | 95 | | 0.35 |
| 120 | 1 | | | 102 | | 0.39 |
| 121 | 1 | | | 103 | | 0.35 |
| 122 | 1 | | | 102 | | 0.35 |
| 123 | 1 | | | 103 | | 0.28 |
| 124 | 1 | | | 103 | | 0.049 |
| 125 | 1 | | | 103 | | 0.39 |
| 126 | 1 | | | 100 | | 0.41 |
| 127 | 1 | | | 100 | | 0.052 |
| 128 | 1 | | | 100 | | 0.020 |
| 129 | 1 | | | 102 | | 0.27 |
| 130 | 1 | | | 100 | | 0.11 |
| 131 | 1 | | | 28 | | — |
| 132 | 1 | | | 102 | | 0.11 |
| 133 | 1 | | | 101 | | 0.34 |
| 134 | 1 | | | 101 | | 0.34 |
| Diast. A, 135 | | | | 90 | | 0.41 |
| Diast. B, 136 | | | | 91 | | 0.42 |
| 137 | 0.5 | | | | 102 | 0.024 |
| 138 | 0.5 | | | | 102 | 0.044 |
| 139 | 0.5 | | | | 102 | 0.06 |
| 140 | 0.5 | | | | 102 | 0.056 |
| 141 | 0.5 | | | | 100 | 0.051 |
| 142 | 0.5 | | | | 101 | 0.054 |
| 143 | 0.5 | | | | 101 | 0.067 |
| 144 | 0.5 | | | | 101 | 0.058 |
| 145 | 0.5 | | | | 103, 102 | 0.119, 0.116 |
| 146 | 0.5 | | | | 103 | 0.100 |
| 147 | 0.5 | | | | 103 | 0.125 |
| 148 | 0.5 | | | | 103 | 0.172 |
| 149 | 0.5 | | | | 103 | 0.060 |
| 150 | 0.5 | | | | 103 | 0.090 |
| 151 | 0.5 | | | | 103 | 0.120 |
| 152 | 0.5 | | | | 102, 92 | 0.054, 0.050 |
| 153 | 0.5 | | | | 103 | 0.043 |
| 154 | 0.5 | | | | 103 | 0.027 |
| 155 | 0.5 | | | | 104, 101, 102 | 0.046, 0.12, 0.09 |
| 156 | 0.5 | | | | 103, 98 | 0.015, 0.032 |

TABLE 4-continued

TRPM8 Screening

| Cpd No. | Conc | % I (10 μM) | % I (5 μM) | % I (1 μM) | % I (0.5 μM) | IC50 (μM) |
|---|---|---|---|---|---|---|
| 157 | 0.5 | | | | 103, 98 | 0.003, 0.017 |
| 158 | 0.5 | | | | 101 | 0.059 |
| 159 | 0.5 | | | | 103 | 0.036 |
| 160 | 0.5 | | | | 87 | 0.060 |
| 161 | 0.5 | | | | 103 | 0.019 |
| 162 | 0.5 | | | | 103 | 0.032 |
| 163 | 0.5 | | | | 103 | 0.020 |
| 164 | 0.5 | | | | 94 | 0.082 |
| 165 | 0.5 | | | | 102 | 0.086 |
| 166 | 0.5 | | | 103 | 102 | 0.018, 0.014 |
| 167 | 0.5 | | | | 104 | 0.097 |
| 168 | 0.5 | | | | 104 | 0.076 |
| 169 | 0.5 | | | | 104 | 0.096 |
| 170 | 0.5 | | | | 103 | 0.073 |
| 171 | 0.5 | | | | 95 | 0.221 |
| 172 | 0.5 | | | | 104 | 0.105 |
| 173 | 0.5 | | | | 103 | 0.140 |
| 174 | 0.5 | | | | 104 | 0.089 |
| 175 | 0.5 | | | | 104 | 0.072 |
| 176 | 0.5 | | | | 104 | 0.131 |
| 177 | 0.5 | | | | 96 | 0.139 |
| 178 | 0.5 | | | | 79 | 0.355 |
| 179 | 0.5 | | | | 103 | 0.068 |
| 180 | 0.5 | | | | 103 | 0.075 |
| 181 | 0.5 | | | | 103 | 0.112 |
| 182 | 0.5 | | | | 104 | 0.075 |
| 183 | 0.5 | | | | 103 | 0.131 |
| 184 | 0.5 | | | | 104 | 0.057 |
| 185 | 0.5 | | | | 103 | 0.071 |
| 186 | 0.5 | | | | 104 | 0.051 |
| 187 | 0.5 | | | | 103 | 0.062 |
| 188 | 0.5 | | | | 103 | 0.064 |
| 189 | 0.5 | | | | 103 | 0.122 |
| 190 | 0.5 | | | | 104 | 0.102 |
| 191 | 0.5 | | | | 104 | 0.125 |
| 192 | 0.5 | | | 103 | | 0.038 |
| 193 | 0.5 | | | 103 | | 0.059 |
| 194 | 0.5 | | | 103 | | 0.041 |
| 195 | 0.5 | | | 103 | | 0.061 |
| 196 | 0.5 | | | 100 | | 0.048 |
| 197 | 0.5 | | | 100 | 102 | 0.045, 0.020 |
| 198 | 0.5 | | | 98 | | 0.357 |
| 199 | 0.5 | | | 81 | | |
| 200 | 0.5 | | | 81 | | |
| 201 | 0.5 | | | 100 | | 0.133 |
| 202 | 0.5 | | | 103 | | 0.053 |
| 203 | 0.5 | | | 96 | | 0.457 |
| 204 | 0.5 | | | 100 | | 0.092 |
| 205 | 0.5 | | | 101 | | 0.050 |
| 206 | 0.5 | | | 100 | | 0.098 |
| 207 | 0.5 | | | | 99 | 0.051 |
| 208 | 0.5 | | | | 104 | 0.104 |
| 209 | 0.5 | | | | 104 | 0.071 |
| 210 | 0.5 | | | | 62 | |
| 211 | 0.5 | | | | 97 | 0.095 |
| 212 | 0.5 | | | | 102 | 0.119 |
| 213 | 0.5 | | | | 100 | 0.202 |
| 214 | 0.5 | | | | 101 | 0.08 |
| 215 | 0.5 | | | | 101 | 0.085 |
| 216 | 0.5 | | | | 100 | 0.126 |
| 217 | 0.5 | | | | 100 | 0.142 |
| 218 | 0.5 | | | | 79 | 0.483 |
| 219 | 0.5 | | | | 68 | |
| 220 | 0.5 | | | | 101 | 0.207 |
| 221 | 0.5 | | | | 102 | 0.032 |
| 222 | 0.5 | | | | 103 | 0.033 |
| 223 | 0.5 | | | | 102 | 0.052 |
| 224 | 0.5 | | | | 102 | 0.044 |
| 225 | 0.5 | | | | 103 | 0.027 |
| 226 | 0.5 | | | | 34 | |
| 227 | 0.5 | | | | 52 | |
| 228 | 0.5 | | | | 94 | 0.129 |
| 229 | 0.5 | | | | 95 | 0.156 |
| 230 | 0.5 | | | | 97 | 0.01 |
| 231 | 0.5 | | | | 98 | 0.122 |
| 232 | 0.5 | | | | 99 | 0.063 |
| 233 | 0.5 | | | | 70 | |
| 234 | 0.5 | | | | 104 | 0.029 |
| 235 | 0.5 | | | | 93, 56 | 0.253 |
| 236 | 0.5 | | | | 103, 103 | 0.122, 0.099, 0.035, 0.124 |
| 237 | 0.5 | | | | 96, 70 | 0.307, 0.338, 0.147, 0.121 |
| 238 | 0.5 | | | | 104 | 0.044 |
| 239 | 0.5 | | | | 103, 103 | 0.037, 0.027, 0.031 |
| 240 | 0.5 | | | | 98, 77 | 0.225, 0.057 |
| 241 | 0.5 | | | 103 | 102 | 0.038 |
| 242 | 0.5 | | | | 103 | 0.009 |
| 243 | 0.5 | | | | 80, 64 | 0.089 |
| 244 | 0.5 | | | | 103 | 0.028 |
| 245 | 0.5 | | | | 103 | 0.124 |
| 246 | 0.5 | | | | 104 | 0.102 |
| 247 | 0.5 | | | | 103 | 0.121 |
| 248 | 0.5 | | | | 104 | 0.021 |
| 249 | 0.5 | | | | 103 | 0.054 |
| 250 | 0.5 | | | | 103 | 0.048 |
| 251 | 0.5 | | | | 103 | 0.045 |
| 252 | 0.5 | | | | 44 | |
| 253 | 0.5 | | | | 103 | 0.034 |
| 254 | 0.5 | | | | 103 | 0.079 |
| 255 | 0.5 | | | | 103 | 0.058 |
| 256 | 0.5 | | | | 103 | 0.056 |
| 257 | 0.5 | | | | 101 | 0.026 |
| 258 | 0.5 | | | | 102 | 0.045 |
| 259 | 0.5 | | | | 103 | 0.023 |
| 260 | 0.5 | | | | 103 | 0.077, 0.056 |
| 261 | 0.5 | | | | 102 | 0.073, 0.077 |
| 262 | 0.5 | | | | 103 | 0.066 |
| 263 | 0.5 | | | | 103 | 0.022 |
| 264 | 0.5 | | | | 103 | 0.029 |
| 265 | 1 | | | 95 | | 0.409 |
| 266 | 1 | | | 103 | | 0.051 |
| 267 | 1 | | | 101, 102 | | 0.047, 0.029 |
| 268 | 0.5 | | | | 104 | 0.034 |
| 269 | 0.5 | | | | 102 | 0.162 |
| 270 | 0.5 | | | | 102 | 0.202 |
| 271 | 0.5 | | | | 103 | 0.104 |
| 272 | 0.5 | | | | 103 | 0.114 |
| 273 | 0.5 | | | | 103 | 0.116 |
| 274 | 0.5 | | | | 95 | 0.301 |
| 275 | 0.5 | | | | 103 | 0.104 |
| 276 | 0.5 | | | | 103 | 0.114 |
| 277 | 0.5 | | | | 103 | 0.116 |
| 278 | 0.5 | | | | 103 | 0.159 |
| 279 | 0.5 | | | | 97 | 0.291 |
| 280 | 0.5 | | | | 101 | 0.227 |
| 281 | 0.5 | | | | 102 | 0.131 |
| 282 | 0.5 | | | | 100 | 0.235 |
| 283 | 0.5 | | | | 103 | 0.125 |
| 284 | 0.5 | | | | 103, 102 | 0.079, 0.065 |
| 285 | 0.5 | | | | 103 | 0.125 |
| 286 | 0.5 | | | | 102 | 0.127 |
| 287 | 0.5 | | | | 103 | 0.124 |
| 288 | 0.5 | | | | 103 | 0.065 |
| 289 | 0.5 | | | | 103 | 0.051 |
| 290 | 0.5 | | | | 103 | 0.115 |
| 291 | 0.5 | | | | 103 | 0.156 |
| 292 | 0.5 | | | | 99 | 0.216 |
| 293 | 0.5 | | | | 103 | 0.156 |
| 294 | 0.5 | | | | 103 | 0.118 |
| 295 | 0.5 | | | | 102, 103 | 0.031, 0.016 |
| 296 | 0.5 | | | | 102 | 0.137 |
| 297 | 0.5 | | | | 103 | 0.040 |
| 298 | 0.5 | | | | 99 | 0.085 |
| 299 | 0.5 | | | | 101 | 0.141 |
| 300 | 0.5 | | | | 103 | 0.089 |
| 301 | 0.5 | | | | 102 | 0.054 |

TABLE 4-continued

TRPM8 Screening

| Cpd No. | Conc | % I (10 µM) | % I (5 µM) | % I (1 µM) | % I (0.5 µM) | IC50 (µM) |
|---|---|---|---|---|---|---|
| 302 | 0.5 | | | | 103 | 0.079 |
| 303 | 0.5 | | | | 102 | 0.049 |
| 304 | 0.5 | | | | 102 | 0.028 |
| 305 | 0.5 | | | | 102 | 0.070 |
| 306 | 0.5 | | | | 101, 102 | 0.066, 0.031 |
| 307 | 0.5 | | | | 103 | 0.026 |
| 308 | 0.5 | | | | 103 | 0.017 |
| 309 | 0.5 | | | | 103 | 0.088 |
| 310 | 0.5 | | | | 102 | 0.042 |
| 311 | 0.5 | | | | 102 | 0.053 |
| 312 | 0.5 | | | | 102 | 0.089 |
| 313 | 0.5 | | | | 102 | 0.083 |
| 314 | 0.5 | | | | 103, 104 | 0.029, 0.021 |
| 315 | 0.5 | | | | 103 | 0.041 |
| 316 | 0.5 | | | | 103, 104 | 0.032, 0.020 |
| 317 | 0.5 | | | | 102 | 0.021 |
| 318 | 0.5 | | | | 100 | 0.211 |
| 319 | 0.5 | | | | 103 | 0.026 |
| 320 | 0.5 | | | | 103 | 0.028 |
| 321 | 0.5 | | | | 102 | 0.043 |
| 322 | 0.5 | | | | 45 | |
| 323 | 0.5 | | | | 104 | 0.009 |
| 324 | 0.5 | | | | 54 | |
| 325 | 0.5 | | | | 97 | 0.010 |
| 326 | 0.5 | | | | 103, 102 | 0.086, 0.051 |
| 327 | 0.5 | | | | 44 | |
| 328 | 0.5 | | | | 102 | 0.193 |
| 329 | 0.5 | | | | 100 | 0.177 |
| 330 | 0.5 | | | | 103 | 0.137 |
| 331 | 0.5 | | | | 101 | 0.152 |
| 332 | 0.5 | | | | 72 | |
| 333 | 0.5 | | | | 95 | 0.176 |
| 334 | 0.5 | | | | 97 | 0.110 |
| 335 | 0.5 | | | | 102 | 0.035 |
| 336 | 0.5 | | | | 102 | 0.043 |

In Vivo Models

Example 2

Inhibition of Icilin-induced Behaviors in Rodents

Icilin was initially developed as a "super-cooling" compound by Delmar Chemicals Ltd. Subsequently it was shown to be one of the most potent known agonists of TRPM8 (McKemy D D, et al. Nature 2002, 416(6876): 52-8), having an $EC_{50}$=0.2 µM in stimulating calcium ion influx into TRPM8 transfected cells (Behrendt H J et al. Brit J Pharmacol 2004, 141(4): 737-45). Initial in vivo testing of icilin showed it to cause "wet-dog" shakes in rats. Similar shaking or jumping behavior was also evident in mice, rabbits, cats, dogs and monkeys. In humans, icilin produced a sensation of coolness on contact with mucous membranes, cold prickling when 0.1 mg was dropped on the tongue and coldness in the mouth, pharynx and chest lasting 30-60 minutes when 5-10 mg was ingested orally (Wei E T, Seid D A, J Pharm Pharmacol. 1983, 35, 110). The inhibition of icilin-induced shaking behaviors in rodents provides evidence for the utility of TRPM8 antagonists of Formula (I) in modulating TRPM8-mediated effects in vivo.

Example 2a

Inhibition of Icilin-induced "wet-dog" Shakes in Rats

Male Sprague Dawley rats (275-500 g, Charles River Labs, n=4-6/treatment) were administered icilin in PEG-400 at 1.0 mg/kg, i.p. Spontaneous "wet-dog" shakes were counted in 2 minute bins over 30 minutes post-icilin. Selected compounds of Formula (I) were administered i.p. 15 minutes before icilin to assess their ability to inhibit (relative to vehicle pretreatment) this spontaneous "wet-dog" shake (WDS) phenomena. Percent inhibition was calculated as follows: % Inhibition= [1−(treatment WDS count/vehicle WDS count)]×100. The resultant data are shown in Table 5.

TABLE 5

| Cpd | Dose (mg/kg) | Route | Pre icilin | % Inhibition | ED50 mg/kg |
|---|---|---|---|---|---|
| 1 | 30 | i.p. | 15' | 22.6 | |
| 2 | 30 | i.p. | 15' | 88.9 | |
| 14 | 30 | i.p. | 15' | 73.1 | |
| 15 | 30 | i.p. | 15' | 71.1 | |
| 34 | 30 | i.p. | 15' | 28.8 | |
| 42 | 30 | i.p. | 15' | 70.6 | |
| 53 | 30 | i.p. | 15' | 65.6 | |
| 234 | 10 | p.o. | 15' | 14.2 | |
| 234 | 30 | p.o. | 15' | 68.0 | |
| 234 | 100 | p.o. | 15' | 92.9 | 24.3 |

Example 2b

Reversal of Icilin-induced Behaviors in Rats

Compounds of Formula (I) capable of inhibiting the onset of icilin-induced "wet-dog" shaking behavior may be further assessed for their ability to reverse an existing icilin-induced "wet-dog" shaking behavior. In this paradigm, icilin-induced shaking was counted for 10 minutes followed by administration of a compound of Formula (I). The diminution of shaking behavior is represented as a percent inhibition relative to icilin-induced shakes in the absence of test compound administration, as described by the following formula: % Inhibition=[1−(WDS count following test compound dose/WDS count prior to test compound dose)]×100. The resultant data are shown in Table 6.

TABLE 6

| Cpd | Dose (mg/kg) | Route | Post-icilin | % Inhibition | ED50 mg/kg |
|---|---|---|---|---|---|
| 14 | 30 | i.p. | 14' | 93.6 | |
| 234 | 10 | p.o. | 1 h | 24.4 | |
| 234 | 30 | p.o. | 1 h | 56.1 | |
| 234 | 100 | p.o. | 1 h | 75.1 | 28.5 |
| 236 | 30 | p.o. | 1 h | 36.8 | |
| 239 | 30 | p.o. | 1 h | 48.4 | |
| 242 | 30 | p.o. | 1 h | 79.9 | |

Example 3

In Vivo Model for of Chronic Inflammatory Pain Complete Freund's Adjuvant (CFA)-induced Hyperalgesia Intraplantar injection of Complete Freund's Adjuvant (CFA) in rodents results in a long-lasting inflammatory reaction, characterized by a pronounced hypersensitivity to both thermal and mechanical stimuli. This hypersensitivity peaks between 24-72 hours following injection and can last for several weeks. To assess whether test compounds of Formula (I) reverse established hypersensitivity, a 100 µL intraplantar injection of CFA (suspended in a 1:1 emulsion of saline and heat-killed *Mycobacterium tuberculosis* in mineral oil) was injected into a single hind paw of Sprague-Dawley rats (typically males ranging from 150-350 g). This paradigm also may be conducted with a multiple dosing or a prophylactic dosing regime designed to alter the course of hyperalgesia development. This test predicts the analgesic, anti-allodynic and anti-hyperalgesic effect of numerous effective clinical agents, including NSAIDS such as acetaminophen, aspirin and ibuprofen, and opioids such as morphine.

Example 3a

CFA-induced Paw Radiant Heat Hypersensitivity

Each rat was placed in a test chamber on a warm glass surface and allowed to acclimate for approximately 10 minutes. A radiant thermal stimulus (beam of light) was then focused through the glass onto the plantar surface of each hind paw in turn. The thermal stimulus was automatically shut off by a photoelectric relay when the paw was moved or when the cut-off time was reached (20 seconds for radiant heat at ~5 Amps). An initial (baseline) response latency to the thermal stimulus was recorded for each animal prior to the injection of CFA. Twenty-four hours following intraplantar CFA injection, the response latency of the animal to the thermal stimulus was then re-evaluated and compared to the animal's baseline response time. Only rats that exhibited at least a 25% reduction in response latency (i.e. hyperalgesia) were included in further analysis. Immediately following the post-CFA latency assessment, test compound or vehicle (usually Solutol, hydroxypropyl methylcellulose, hydroxypropyl beta-cyclodextrin or PEG-400) was administered i.p. or p.o. to rats. Post-compound treatment withdrawal latencies were assessed at fixed time intervals, typically 30, 60 and 120 minutes. The percent reversal (% R) of hypersenstivitiy was calculated according to the following formula:

% Reversal=(Treatment Response−CFA Response)/
(Baseline Response−CFA Response)×100.

Resultant data are shown in Table 7.

TABLE 7

| Cpd | Dose (mg/kg) | Route | % Reversal | Time | $ED_{50}$ |
|---|---|---|---|---|---|
| 2 | 30 | i.p. | 74 | 1 h | |
| 5 | 30 | i.p. | 38 | 30' | |
| 12 | 30 | i.p. | 105 | 1 h | |
| 14 | 30 | i.p | 40 | 30', 1 h, 2 h | |
| 14 | 30 | i.p. | 63 | 1 h | 20.7 |
| | 30 | p.o. | 47 | 2 h | — |
| 15 | 30 | i.p. | 95 | 1 h | |
| | 30 | p.o. | 82 | 1 h | |
| 53 | 30 | i.p. | 77 | 30' | |
| | 30 | p.o. | 44 | 2 h | |
| 127 | 30 | p.o. | 88 | 1 | 5.2 |
| 137 | 30 | p.o. | 34 | 1 | |
| 155 | 30 | p.o. | 138 | 1 | |
| 190 | 30 | p.o. | 45 | 1 | |
| 197 | 30 | p.o. | 23 | 2 | |
| 234 | 30 | p.o. | 56 | 2 | 6.6 |
| | 30 | p.o. | 75 | 1 | |
| 235 | 30 | p.o. | 45 | 1 | |
| 236 | 30 | p.o. | 25 | 2 | |
| 238 | 30 | p.o. | 56 | 2 | |
| 239 | 30 | p.o. | 36 | 2 | |
| 241 | 30 | p.o. | 72 | 1 | |
| 244 | 30 | p.o. | 45 | 2 | |
| 298 | 30 | p.o. | 20 | 1 | |
| 299 | 30 | p.o. | 23 | 1 | |
| 335 | 30 | p.o. | 0 | 1 | |
| 336 | 30 | p.o. | 64 | 1 | |

A 3-point dose-response study in the CFA-induced Paw Radiant Heat model, using a 10% solutol vehicle, was obtained. A dose-dependent reversal of hyperalgesia was observed, with an oral $ED_{50}$ of 11.4 mg/kg and 5.2 mg/kg for Compounds 15 and 127, respectively, at the 1 h time point.

Example 3a

CFA-induced Paw Cold Hypersensitivity

Prior to intraplantar CFA injection mice were placed individually in elevated observation chambers having wire mesh floors. Through the mesh floor a series of three applications of acetone (0.04 mL/application) was sprayed onto the bottom of the paw using a multidose syringe device. A positive response took the form of an abrupt withdrawal and licking of the paw. The cumulative duration of licking was recorded for each of the three trials which were then averaged to give the individual's response. Twenty-four hours following CFA injection acetone licking durations were markedly elevated implying a hypersensitivity to cooling. A test compound of Formula (I) was assessed for its ability to return acetone-evoked paw licking durations to pre-CFA levels (typically near zero) following systemic administration. Percent inhibition was calculated % Inhibition=[1−(treatment licking duration/vehicle licking duration)]×100. The resultant data are displayed in

TABLE 8

| Cpd | Dose (mg/kg) | Route | % I | Time |
|---|---|---|---|---|
| 242 | 60 | p.o. | 84 | 30' |

Example 4

Chemically-induced Abdominal Irritant Models of Visceral Pain

A chemical irritant (such as acetic acid, kaolin, bradykinin, phenyl-p-(benzo) quinine, bromo-acetylcholine, or zymosan) is injected in mice intraperitoneally, causing a contraction of the abdominal musculature, which is characterized by an elongation of the body extending through to the hind limbs. The number of such responses is quantitated and is reduced by pretreatment of analgesic agents, thus forming the basis for a screening test (Collier H O et al. Br J Pharmacol Chemother 1968, 32(2): 295-310). This type of abdmonial irritant test has been used to predict the analgesic effect of numerous clinically effective agents, the potency of which in the abdominal irritant test parallels the magnitude of the dose needed in the relief of clinical pain.

One modification of the chemically-induced abdmonial irritant model of visceral pain is to pretreat animals with agents known to induce inflammatory responses following intraperitoneal injection (such as LPS, zymosan, or thioglycolate). A small intraperitoneal dose of such an inflammogen, administered hours or days before the acute chemical irritant challenge, has been shown to increase the number of abdominal contractions observed (Ribeiro R A, et al. Eur J Pharmacol 2000, 387(1): 111-8). While some analgesic agents are effective at mitigating acute viscerochemical nociception, others, particularly those dependent upon receptor induction are more effective at preventing or reversing the enhancement of behavioral responses caused by a preconditioning inflammatory stimulus. Because of the up-regulation of the TRPM8 receptor in inflammation, TRPM8 antagonists that are effective at reducing the mean number of contractions are predicted to provide antiinflammatory action in human clinical use.

The ability of compounds of Formula (I) to mitigate chemical irritant—induced abodominal contractions following a pre-conditioning inflammatory stimulus were studied. Thioglycolate (3%, w/v, 2-3 mL i.p.) was injected into male CD1 mice (20-40 g, Charles River Labs), at a maximum dosage volume of 80 mL/kg, to induce peritoneal inflammation. Following a twenty-four hour pre-inflammation period these mice were dosed orally with a compound of Formula (I) (30 mg/kg; n=10) or vehicle (HPMC with 2% Tween80; n=9) and then one hour later subjected to an abdominal irritant challenge of acetic acid (1%, 10 mL/kg, i.p.). Immediately following injection of acetic acid, mice were placed individually in glass bell jars (approximately 15 cm in diameter) for counting of abdominal contractions over the next 15 minutes. The total number of abdominal contractions was summed for each treatment group and employed in the following formula to calculate Percent Inhibition (% I):

% I=[1−(test compound contractions/vehicle contractions)]×100.

The resultant data are displayed in Table 9.

TABLE 9

Acetic acid graded abdominal irritant test with a 24-hour thioglycolate pretreatment.

| Cpd | Dose (mg/kg) | Route | % I | Time |
|---|---|---|---|---|
| 15 | 30 | p.o. | 33 | 1 h |

Example 5

In Vivo Models of Neuropathic Pain

The sciatic nerve is the major sensorimotor innervation of the (hind) leg and foot. Injury to the sciatic nerve or its constituent spinal nerves often results in pain-related behaviors. In rats and mice, tight ligation of the L5 spinal nerve with silk suture, partial tight ligation of the sciatic nerve with silk suture or loose ligation of the sciatic nerve with chromic gut suture each result in behaviors reminiscent of neuropathic pain in humans. These lesions (one per animal) were performed surgically in anesthetized rodents. Both the spinal nerve and sciatic nerve lesions result in allodynia, a painful response to normally innocuous stimuli, and hyperalgesia, an exaggerated response to normally noxious stimuli. It is important to note that both of these pain-related behaviors were evoked by the testing procedures and that normal use of the paw (e.g., walking) was relatively uncompromised, apart from occasional "guarding" of the paw. Subsequent to the surgery, the subjects' behaviors, such as grooming, feeding, and weight gain, were normal, except for hypersensitivity (as defined above) of the affected paw.

In addition to induction by nerve damage resulting from accidental trauma or surgical procedures, neuropathic pain can also be induced by diabetes (Fox, A et al., Pain 81:307-316, 1999) or by treatment with chemotherapeutic agents, such as paclitaxel or vincristine (Yaksh, T L et al., Pain 93:69-76, 2001).

Agents that attenuate neuropathic pain in the clinic also are effective in rodent neuropathic pain models. These agents include the recently approved Cymbalta (Duloxetine, Iyengar, S., et al., JPET 2004 311:576-584), morphine (Suzuki, R et al., Pain 1999 80:215-228) and gabapentin (Hunter, J C et al., Eur J Pharmacol. 1997 324:153-160). The dual TRPV1/TRPM8 receptor antagonist BCTC reduced mechanical hyperalgesia and tactile allodynia in the chronic constriction injury rodent neuropathic pain model (Pomonis, J D et al., JPET. 2003 306:387-393; Behrendt, H et al., Brit J. Pharm. 2004 141:737). Cold allodynia is a particularly debilitating symptom of neuropathic pain conditions (Jorum E et al. Pain. 2003 101: 229-235).

Example 5a

Chronic Constriction Injury (CCI)-induced Model of Neuropathic Pain—Acetone-induced Hypersensitivity In male SD rats (175-325 g), four loose ligatures of 4-0 chromic gut were surgically placed around the left sciatic nerve under inhalation anesthesia as described by Bennet et al (Bennett G J, Xie Y K. Pain 1988, 33(1): 87-107). Seven to 21 days following sciatic chronic constriction injury (CCI) surgery, the subjects were placed in elevated observation chambers having wire mesh floors. Through the mesh floor a series of five applications of acetone (0.05 mL/application) was sprayed onto the bottom of the paw using a multidose syringe device. A positive response took the form of an abrupt withdrawal or lifting of the paw. The percentage of positive responses from the five trials represented the individual's overall response that was then averaged over the entire treatment group. A test compound of Formula (I) was assessed for its ability to return acetone response frequencies to pre-lesion levels (typically zero) following systemic administration. An ascending dose response relationship (as in Table 10 below) was generated by addition of successive doses of test compound followed by re-assessment of behavior. The number of positive responses following administration of test compound was taken as a percentage of the number of positive responses prior to test compound treatment. The resultant data are displayed in Table 10.

TABLE 10

| Cpd No. | Dose (mg/kg) | Route | preRx | % of Allodynic Baseline | ED50 (mg/kg) |
|---|---|---|---|---|---|
| 14 | 10 | | | 47.7 | |
| | 30 | | | 31.8 | |
| | 100 | s.c. | 20' | 40.9 | |
| 234 | 3 | p.o. | 1 hr | 16.7 | |
| | 10 | | | 51.7 | |
| | 30 | | | 59.6 | |
| | 100 | | | 83.1 | |
| | 3 | p.o. | 2 hr | 10.0 | |
| | 30 | | | 56.7 | |
| | 100 | | | 93.3 | |
| | | p.o. | 1 hr | | 14.8 |
| 235 | 30 | p.o. | 1 hr | 34.3 | |
| 236 | 30 | p.o. | 4 hr | 28.6 | |
| | 100 | | | 68.8 | |
| 239 | 30 | p.o. | 1 hr | 29.4 | |
| 242 | 30 | i.p. | 2 hr | 63.3 | |
| | 3 | p.o. | 3 hr | 15.0 | |
| | 10 | | | 30.0 | |
| | 30 | | | 66.7 | |
| | 100 | | | 86.7 | |
| | | p.o. | 3 hr | | 18.0 |

Example 5b

Chronic Constriction Injury (CCI)-induced Model of Neuropathic Pain—Cold Plate-induced Hypersensitivity In male SD rats (175-325 g), four loose ligatures of 4-0 chromic gut were surgically placed around the left sciatic nerve under inhalation anesthesia as described by Bennet et al (Bennett G J, Xie Y K. Pain 1988, 33(1): 87-107). Seven to 21 days following sciatic chronic constriction injury (CCI) surgery, the subjects were placed onto a commercial cold plate device cooled by peltier elements such that the surface temperature was held at 1° C. Each subject underwent a 6 minute conditioning period followed by a 3 minute assessment period during which the total duration of hind paw lifting was recorded. This procedure was repeated at several intervals prior to and following systemic drug administration. Test compounds of Formula (I) were assessed for their ability to return duration of paw lifting back to pre-lesion levels. The duration of paw lifting during the 3 minute test period following administration of test compound was taken as a percentage of the duration of paw lifting during the 3 minute test period prior to test compound treatment. The resultant data are displayed in Table 11.

TABLE 11

| Cpd | Dose (mg/kg) | Route | Post dose | % of Allodynic Baseline |
|---|---|---|---|---|
| 14 | 30 | i.p. | 60' | 79.6 |
|  |  | p.o. | 60' | 68.5 |
|  |  | p.o. | 120' | 61.8 |

Example 6

Inflammatory Agent-Induced Models of Pyresis/Antipyresis

Compounds of Formula (I) can be tested in animal models of pyresis, according to previously documented and validated methods, such as those described by Kozak et al (Kozak W, Fraifeld V. Front Biosci 2004, 9: 3339-55). Fever is a frequent accompaniment of inflammatory disease. Animal models make use of the pyretic properties of yeast and other inflammatory agents, injecting a yeast suspension or other agent subcutaneously (Tomazetti J et al. J Neurosci Methods 2005, 147(1): 29-35); Van Miert A S, Van Duin C T. Eur J Pharmacol 1977, 44(3): 197-204). For example, Male Wistar rats (75-100 g) can be housed in groups of four to a cage at controlled temperature (23±1° C.) with a 12 h light:12 h dark cycle (lights on at 07:00 h) and with standard lab chow and tap water ad libitum. All measured temperatures can be taken between 08:00 and 19:00 h. Each animal can be used in only one study. Rectal temperature (TR) can be measured by inserting a lubricated thermistor probe (external diameter: 3 mm) 2.8 cm into the rectum of the animal. The probe can be linked to a digital device, which displayed the temperature at the tip of the probe with a 0.1° C. precision and logs the values over time.

Immediately after measuring the initial basal rectal temperature, the animals can be injected with commercially available dried baker yeast (*Saccharomyces cerevisiae*) suspended in pyrogen-free 0.9% NaCl (0.05-0.25 g/kg, i.p.) or 0.9% NaCl (10 ml/kg). TR changes can be recorded every hour up to 12 h, and expressed as the difference from the basal value. Since it has been previously reported that handling and temperature measuring-related stress alter rectal temperature, these animals can be habituated to the injection and measuring procedure for 2 days before experiments are carried out. In these sessions, the animals can be subjected to the same temperature measuring procedure described above, and can be injected intraperitoneally (i.p.) with 0.9% NaCl (10 ml/kg).

To assess the effect of potential antipyretic compounds on basal rectal temperature study animals can have their TR measured for 4 h, and after the fourth TR measurement they can be subcutaneously (s.c.) injected with vehicle (such as 10% Solutol in sterile water 5 ml/kg) or a compound of Formula (I) prepared in vehicle. TR can then be recorded every hour up to 8 h after the compound injections. To assess the effect of a compound of Formula (I) on baker yeast-induced hyperthermia, study animals can have their basal TR measured and then be injected with a pyrogenic dose of baker yeast (for example, 0.135 g/kg). TR changes can be recorded every hour up to 4 h, when potential antipyretics agents such as those of Formula (I) are administered. Rectal temperature can then be monitored over the following 8 h. Basal rectal temperature and changes in rectal temperature can be expressed as means±S.E.M. of the differences from TR at 07:00 h. Data can be analyzed by two-way analysis of variance (ANOVA), with time of measures treated as within subject factor, depending on the experimental design. Post hoc analysis can be carried out by the F-test for simple effect and the Student-Newman-Keuls test, when appropriate. A value of $P<0.05$ would be considered statistically significant.

The modification of the subsequent pyretic response by therapeutic agents can also be monitored by rectal telemetry or other measurements of body temperature. Several clinically relevant agents such as acetaminophen, aspirin and ibuprofen, reduce fever in these models.

Example 7

CFA-Induced Model of Rheumatoid Arthritis

Compounds of Formula (I) can be tested in animal models of rheumatoid arthritis, according to previously documented and validated methods, such as those described by Nagakura et al (Nagakura Y, et al. J Pharmacol Exp Ther 2003, 306(2): 490-7). For example, arthritis can be induced by the CFA inoculation in the rats (Male Lewis rats150-225 g; Charles River). Briefly, 100 mg of *Mycobacterium butyricum* (Difco, Detroit, Mich.) can be thoroughly mixed with 20 mL of paraffin oil. Then mixture can be autoclaved for 20 min at 120° C. Each rat can be injected in the right footpad (hind paw) with the mixture in a 0.1-mL volume under inhalation anesthesia. The rats serving as controls can be injected with 0.1 mL of saline. Pain and other disease development parameters can be measured in the CFA- or saline-treated rats just before inoculation and up to 28 days post-inoculation. The measurement for pain parameters can be conducted for both mechanical and thermal (hot or cold) endpoints. The measurement of mechanical allodynia can be performed using the von Frey hairs (Semmes-Weinstein Monofilaments, Stoelting Co., IL) wherein the rats can be habituated to wire mesh bottom cages before the start of the experiment. Static allodynia can be tested in the unrestrained rats by touching the plantar surface of the hind paw with von Frey hairs in ascending order of force (1.2, 1.5, 2.0, 3.6, 5.5, 8.5, 12, 15, 29, and 76 g) for up to 6 s or until a paw withdrawal response can be elicited. The lowest amount of force required to elicit a response can be recorded as the withdrawal threshold in log g. Thermal hyperalgesia can be assessed using the radiant heat test wherein a mobile radiant heat source can be located under a glass surface upon which the rat is placed. The beam of light can be focused on the hind paw, and the paw withdrawal latencies are defined as the time taken by the rat to remove its hind paw from the heat source. The measurement of joint hyperalgesia can be performed by a modification of the previously reported method (Rupniak N M J et al. Pain. 1997, 71:89-97). The torso of each rat can be held from the back with the left palm, and the bending and extension (one after the other and five times in each direction) of the ankle within its limits of range of motion can be performed with the right fingers. The total number of vocalizations emitted after the manipulation (the bending and extension, five times in each direction) can be recorded for each paw (the maximum score is 10 for each paw).

The scoring of mobility can be performed by modifying the evaluation scale reported by Butler et al. (Butler S H et al 1992 Pain 48:73-81): score 6, walks normally; score 5, walks being protective toward the ipsilateral hind paw (touches the ipsilateral hind paw fully on the floor); score 4, walks being protective toward the ipsilateral hind paw (touches only the toe of the ipsilateral hind paw on the floor); score 3, walks being protective toward both hind paws (touches the contralateral hind paw fully on the floor); score 2, walks being protective toward both hind paws (touches only the toe of the contralateral hind paw on the floor); score1, crawls only using the fore paws; and score 0, does not move. Paw volumes can be measured by volume displacement of electrolyte solution in a commercially available plethysmometer device. The hind paw can be immersed to the junction of the hairy skin, and the volumes can be read on a digital display. The scoring of joint stiffness can be performed as follows: the body of rats can be held from the back with the left palm, and the bending and extension (once in each direction) of the ankle within its limits of range of motion can be performed with the right fingers. It can be confirmed beforehand that there is no restriction of ankle joint movement in the bending and extension manipulations in naive rats, and the scoring can be performed according to the evaluation scale reported by Butler et al. (1992): score 2, there are restrictions of full range of movement of the ankle in both bending and extension; score 1, there is a restriction of full range of movement of the ankle in bending or extension; and score 0, no restriction. The measurements for paw volume and joint stiffness can be conducted for both hind paws.

Compounds of Formula (I) can be assessed for antihyperalgesic efficacy as follows: thirty-two rats (eight rats per dose and four doses per compound) that are treated with the CFA and another eight rats as naive controls can be used for each drug evaluation. The analgesic effects can be evaluated on post-inoculation day 9, when mechanical allodynia, thermal hyperalgesia, joint hyperalgesia, and joint stiffness in the ipsilateral paw reached almost the maximum, although those parameters in the contralateral paw changed only slightly and the systemic disturbance shown by the change of mobility score is small. On the day before evaluation, body weight, mechanical allodynia, thermal hyperalgesia, and joint hyperalgesia can be measured for the 32 rats that are to be used for compound evaluation. The rats are allocated to four groups (eight rats per group) such that the differences in the averages of those parameters among the groups became small. All the analgesic effect evaluations and behavioral observations can be carried out by the observer who is blind to the drug treatment.

Data can be expressed as the mean+/−S.E.M. The time-course curves for mechanical allodynia, thermal hyperalgesia, joint hyperalgesia, body weight, and paw volume can be subjected to two-way repeated measures analysis of variance with post hoc t test. In experiments for evaluation of a compound of Formula (I), the difference in scores between the vehicle-treated and naive control groups can be analyzed by Student's t test to confirm significant changes in the pain parameters in the ipsilateral paw. The analgesic effects can be analyzed by Dunnett's t test, and in each case the drug-treated groups can be compared with the vehicle-treated group. In each statistical analysis, the comparison can be conducted for paws on the corresponding side. $P<0.05$ is considered statistically significant.

Example 8

In Vivo Model for Arthritis: Inflammogen-Induced Hyperalgesia of the Knee Joint

Compounds of Formula (I) can be tested in animal models of osteoarthritis, according to previously documented and validated methods, such as those described by Sluka et al (Sluka K A, Westlund K N. Pain 1993, 55(3): 367-77). For example, male Sprague-Dawley rats (Harlan, Indianapolis, Ind.) weighing 225 to 350 g can be briefly anesthetized with vaporized halothane and then injected with a mixture of 3% carrageenan and 3% kaolin (100 µL in 0.9% sterile saline) into the joint cavity of one knee. After the injection, the animals can be returned to their cages until the time of testing. For behavioral testing animals can be placed in individual clear plastic cages on top of an elevated wire mesh surface that restricted movement. The animals should be allowed to acclimate for approximately 1 hour before testing. Von Frey filaments, as described above, can then be used to test for enhanced responses to mechanical stimuli. The filaments can be successively applied through the wire mesh perpendicularly to the plantar surface in between the pads of the third and fourth phalanges. The response threshold to mechanical stimuli can be determined before inflammation of the knee joint; 4 hours after inflammation to confirm the development of hyperalgesia; immediately after the administration of test compound such as those of Formula (I) i.e. 5 hours after inflammation; and at 8, 12, and 24 hours after inflammation.

The Kruskal-Wallis test, a nonparametric test, can be used to analyze the effects for frequency, intensity, and group for response to mechanical stimuli at baseline, 4 hours after inflammation, and after compound treatment (5 hours, 8 hours, 12 hours, and 24 hours after inflammation). Further post hoc testing between groups can be executed by using the Mann-Whitney signed rank test. The data can be presented as median with 25th and 75th percentiles. Significance is $P \leq 0.05$.

Additionally, the gait of the animal or other pain-related behavior can be scored as the dependent measure of the painful effect of the arthritis on the animal's activity (Hallas B, Lehman S, Bosak A, et al. J Am Osteopath Assoc 1997, 97(4): 207-14). The effect of test drug on the animal's normal behavior can be quantified from zero, meaning no response, to three for incapacitating impairment. Effective analgesic treatment includes the clinically used indomethacin (Motta A F, et al. Life Sci 2003, 73(15): 1995-2004).

Example 9

Sarcoma Cell-Induced Models of Bone Cancer Pain

Compounds of Formula (I) can be tested in animal models of bone cancer pain, according to previously documented and validated methods, such as those described in the scientific literature (El Mouedden M, Meert T F. Pharmacol Biochem Behav 2005, 82(1): 109-19; Ghilardi J R, et al. J Neurosci 2005, 25(12): 3126-31). In preparation for cell inoculation and tumor induction, osteolytic murine sarcoma cells (NCTC 2472, American Type Culture Collection (ATCC), Rockville, Md., USA) can be cultured in NCTC 135 medium (Invitrogen) containing 10% horse serum (Gibco) and passaged 2 times weekly according to ATCC guidelines. For their administration, cells can be detached by scraping and then centrifuged at 1000×g. The pellet can be suspended in fresh NCTC 135 medium ($2.5 \times 10^6$ cells/20 µL) and then used for intramedullary femur inoculation. Male C3H/HeNCrI mice (25-30 g, Charles River Labs) can be used in such experiments. After induction of general anesthesia with xylazine (10 mg/kg i.p.) and ketamine (100 mg/kg i.p.) the left hind paw can be shaved and disinfected with povidone-iodine followed by 70% ethanol. A superficial incision of 1 cm can then be made over the knee overlaying the patella. The patellar ligament can then be cut, exposing the condyles of the distal femur. A 23-gauge needle can be inserted at the level of the intercondylar notch and the intramedullary canal of the femur to create a cavity for injection of the cells. Twenty microliters of media (sham animals) or media containing tumor cells (approximately $2.5 \times 10^6$ cells) can then be injected into the bone cavity using a syringe. To prevent leakage of cells outside the bone, the injection site can be sealed with dental acrylic and the wound closed with skin stitches.

Pain behaviors can be evaluated in separate groups (n=6) of sham and bone tumor mice with confirmed hyperalgesia as assessed by spontaneous lifting behavior. Animals can be behaviorally tested during a 3-week period prior to and after tumor inoculation. Body weight of the mice can be recorded throughout the experimental period to help monitor general health status. To measure the spontaneous lifting, the animals can be habituated in a transparent acrylic cylinder of 20 cm diameter put on an horizontal surface and thereafter observed during 4 min for spontaneous lifting behavior of the left hind paw. After spontaneous lifting behavior assessment, animals can be immediately placed on a mouse rotarod (e.g. ENV-575M\, Med Associates Inc., GA, USA) at a speed of 16 rpm for 2 min wherein limb-use during forced ambulation is scored: 4=normal; 3=limping; 2=partial non-use of left hind paw; 1=substantial non-use of left hind paw; 0=non-use of left hind paw. Assessment of cold allodynia may be made by exposing the ipsilateral hind paw of the mouse to 5 repeated applications of acetone (20 µL) and quantifying the lift/licking frequency and/or duration. Post-mortem evaluation of bone destruction can be assessed by ACT processing followed by scanning using a system such as the Skyscan 1076 microtomograph system for small animal imaging (Skyscan 1076\, Skyscan, Aartselaar, Belgium). Measured histomorphometry parameters of bone destruction can be subsequently correlated with behavioral endpoints.

The antihyperalgesic, antiallodynic and disease modifying effects of compounds such as those of Formula (I) can be tested in this murine model of bone cancer pain in separate groups (n=6 per dose group). Animals with confirmed hyperalgesia, as assessed by spontaneous or acetone-evoked lifting, can be behaviorally tested, for example, on days 15 and 22 after distal femur tumor inoculation before and 1 h after systemic administration of vehicle (e.g. 10% Solutol in sterile water) or a compound of Formula (I). The statistical analysis can be performed by one-way ANOVA to compare behavioral measurements and bone parameters among the experimental groups. To compare behavioral measurements and bone parameters between sham and tumor-bearing animals, a Mann-Whitney U test can be used. Results are considered statistically significant at $P<0.05$ (two-tailed). Data are expressed as mean+/−S.E.M.

Bone cancer causes intense pain in humans, mimicked in animal models of bone cancer pain in rodents such as that described above. Analgesic treatments that are effective in this model include COX-2 inhibitors (Sabino M A, Ghilardi J R, Jongen J L, et al. Cancer Res 2002, 62(24): 7343-9) and high doses of morphine (Luger N M et al. Pain. 2002, 99(3): 397-406), agents used clinically for pain relief in patients experiencing bone cancer pain.

Example 10

Respiratory Irritant-induced Models of Cough

Compounds of Formula (I) can be tested in animal models of antitussive activity, according to previously documented and validated methods, such as those described by: Tanaka, M. and Maruyama, K. J. Pharmacol. Sci. 2005, 99(1), 77-82; Trevisani, M. et al., Throax 2004, 59(9), 769-72; and Hall, E. et al., J. Med. Microbiol. 1999, 48: 95-98. Testing is conducted in transparent ventilated chambers with a constant airflow of 400 mL/min. The tussive agent (citric acid 0.25 M or capsaicin 30 mM) can be nebulised via a miniultrasonic nebuliser with an output of 0.4 mL/min. The appearance of cough can be detected by means of a tie clip microphone and confirmed by the characteristic posture of the animal. The cough sounds can be recorded and digitally stored. A blinded observer subsequently counts the number of elicited cough efforts. In some cases, animals can be sensitized by pre-exposure to certain agents such as ovalbumin. A test compound can be administered to at the peak of irritant-induced cough to evaluate the antitussive effects of the compound. In addition, prophylactic or multiple dosing regimes can be utilized to evaluate the test compound for modulation of the onset and duration of irritant-induced cough. Variations of these tests predict the antitussive effects of effective clinical agents, including NMDA antagonists such as dextrorphan and dextromethorphan, opioids such as codeine, beta 2 agonists such as salbutamol and antimuscarinics such as ipratropium (Bolser, D. C. et al., Eur. J. Pharmacol. 1995, 277(2-3), 159-64; Braga, P. C. Drugs Exper. Clin. Res. 1994, 20, 199-203).

Example 11

Chemical Irritant-induced Models of Itch, Contact Dermatitis, Eczema and Other Manifestations of Dermal Allergy, Hypersensitivity and/or Inflammation Compounds of Formula (I) can be tested in animal models of contact dermatitis or itch, according to previously documented and validated methods, such as those described in the scientific literature (Saint-Mezard P et al. Eur J Dermatol. 2004, 14(5): 284-95; Thomsen J. S., et al. J. Exp Dermatol. 2002, 11(4): 370-5; Weisshaar E, et al. Arch Dermatol Res 1998, 290(6): 306-11; Wille J J, et al. Skin Pharmacol Appl Skin Physiol. 1999, 12(1-2): 18-27). Mice (or species such as guinea pig or rat) can be sensitized with 25 mL of 0.5% dinitrofluorobenzene solution (DNFB diluted 4:1 in acetone: olive oil immediately before application or other haptens, such as 12-myristate-13 acetate, picryl chloride, oxazolone, capsaicin, arachidonic acid, lactic acid, trans-retinoic acid or sodium lauryl sulfate) painted to the shaved dorsal skin or untreated (controls). Five days later, 10 mL of 0.2% DNFB a nonirritant dose) can be applied onto both sides of the right ear and the same amount of solvent alone onto the left ear. Ear thickness can be monitored daily using a caliper. Compounds of Formula (I) can be administered at the peak of inflammation to evaluate the anti-allergy activity of compounds. In addition, prophylactic or multiple dosing regimes can be utilized to evaluate the test compound for modulation of the onset and duration of anti-allergy activity. Variations of these tests can predict the anti-allergy and itch activity of effective clinical agents. The ability of these models to predict the therapeutic effect of compounds in human dermal conditions is supported by the cross-species ability of serotonin to induce itch (Weisshaar E, Gollnick H. Skin Therapy Lett 2000, 5(5): 1-2,5). Additionally, for the contact sensitizing property of commercially important drugs and the ability of ion channel modulators to prevent and treat skin sensitization in these models, see Kydonieus A, et al., Proceedings of the International Symposium on Controlled Release of Bioactive Materials 24th:23-24, 1997.

Example 12

Chemical Irritant-induced Models of Rhinitis and Other Manifestations of Nasal Hypersensitivity and/or Inflammation Compounds of Formula (I) can be tested in animal models of rhinitis, according to previously documented and validated methods, such as those described in the scientific literature (Hirayama Y, et al. Eur J. Pharmacol. 2003, 467(1-3): 197-203; Magyar T, et al. Vaccine 2002, 20(13-14): 1797-802; Tiniakov R L, et al. J Appl Physiol 2003, 94(5): 1821-8). Testing can be conducted in mouse, guinea pig, dog or human in response to intranasal challenge with one or more irritants such as cold air, capsaicin, bradykinin, histamine, pollens, dextran sulfate, 2,4-tolylene diisocyanate, *Bordetella bronchiseptica, Pasteurella multodica* or acetic acid. In some cases, animals can be sensitized by pre-exposure to certain agents including, but not limited to, ragweed or ovalbumin. Prior to or following irritant administration, the test subject can receive, respectively, the prophylactic or therapeutic administration one or more times of a compound of Formula (I), or vehicle control, by the enteral or parenteral route. Significant differences indicative of nasal rhinitis or sensitization for the test compound-treated subjects compared with vehicle-treated subjects can be taken as evidence of anti-rhinitis activity. Independent variables include dose, frequency and route of administration, time interval between prophylactic or therapeutic test compound administration and irritant challenge as well as sex and non-sex genotype of the test subject.

Example 13

Conflict-induced Models of Anxiety, Panic Disorder and Other Non-adaptive Stressful or Phobic Responses Compounds of Formula (I) can be tested in animal models of anxiety, panic disorders and other non-adaptive responses, according to previously documented and validated methods, such as those described by Cryan and Holmes (Cryan J F, Holmes A. Nat Rev Drug Discov 2005, 4(9): 775-90) or Braw et. al. (Y. Braw et al. Behavioural Brain Research 2006, 167: 261-269). Specifically, for studies in rats, the following apparati may be utilized: an open-field arena (62 cm×62 cm) enclosed by opaque walls (30 cm high) and plus-maze consists of two open arms, 50 cm×10 cm, and two enclosed arms, 50 cm×10 cm×40 cm with an open roof, arranged such that the two arms of each type are opposite each other. The maze is elevated to a height of 70 cm. The walls of the enclosed arms are made from black Plexiglas, while the floors from white Plexiglas. Videotape recordings can be analyzed using the 'Observer' system (Noldus Information Technology). A subject rat can be removed from its home cage, weighed and placed gently in the center of the open-field arena. The rat can be allowed to explore the open-field freely while its behavior is videotaped for 5 min. Afterwards, it can be transferred to the plus-maze and placed at the center, facing a closed arm. The rat's behavior can again be videotaped for 5 min, after which it can be returned to its home cage. The apparatus can cleaned using a 70% ethanol solution between rats.

Open-field and plus-maze measures can be grouped into two behavioral classes, namely 'anxiety-like behaviors' and 'activity'. Open-field behavioral measures may include 1) Anxiety measures: % time in center square, % number of entries to center square (from total squares entered), % time freezing, latency to first freezing (freezing is scored when the subject is in an immobile state for at least 3 seconds; and 2) Activity measures: Total squares entered, number of rearings (standing on two hind legs), latency for first rearing. Plus-maze measures may include 1) Anxiety: % time in open arms, % number of entries to open arms (from total entries), number of unprotected head dips, latency to enter open arm; and 2) Activity: Total entries to all arms. Anxiety-like behaviors and activity can be analyzed by one-way ANOVA's on each of the measures, for each the between-subject comparisons. Plus-maze analyses can be conducted in a similar fashion.

Testing may also be conducted in mouse or rat in this fashion in order to measure avoidance of other aversive environmental stimuli such as Geller or Vogel anticonflict tests, the light/dark test and the hole-board test (see Cryan J F, Holmes A. Nat Rev Drug Discov 2005, 4(9): 775-90). Prior to environmental exposure, the test subject can receive the prophylactic administration one or more times of a compound of Formula (I), or vehicle control (e.g. 10% Solutol in sterile water), by the enteral or parenteral route. The cumulative time or number of times spent engaged in the aversive behavior can be measured. Significant differences in one or more of these measures for the test compound-treated subjects compared with vehicle-treated subjects can be taken as evidence of anxiolytic activity. These models are pharmacologically validated by the effectiveness of clinically useful anxiolytics (Cryan J F, Holmes A. Nat Rev Drug Discov 2005, 4(9): 775-90).

Example 14

Bladder Pressure- and Hypertrophy-induced Models of Urinary Incontinence

Compounds of Formula (I) can be tested in animal models of urinary incontinence according to previously documented and validated methods, such as those described by in the scientific literature (Kaiser S, Plath T, (Metagen Pharmaceuticals GmbH, Germany). 2003 De patent 10215321; McMurray G, et al. Br J Pharmacol 2006, 147 Suppl 2: S62-79). TRPM8 is expressed in human prostate, testicle, seminiferous tubules, scrotal skin and inflamed bladder (Stein R J, et al. J Urol. 2004, 172(3): 1175-8); (Stein R J, et al. J Urol. 2004, 172(3): 1175-8; Mukerji et al. BMC Urology 2006, 6:6). Excitation of TRPM8 receptors through cooling or application of menthol causes contraction in the bladder and a decrease in micturation threshold volume (Tsukimi Y, Mizuyachi K, et al. Urology. 2005, 65(2): 406-10). To assess compounds of Formula (I) for potential urinary incontinence activity, Sprague-Dawley rats are surgically implanted with bladder catheters allowing for the delivery of fluid (typically saline) and the monitoring of pressure (using a pressure transducer). Cystometry recordings can be monitored with a polygraph to evaluate voiding interval, threshold pressure, bladder capacity, bladder compliance, and the number of spontaneous bladder contractions. For example, the bladder catheter can be connected to a Harvard infusion pump, and bladders perfused overnight with saline at 2 mL/h. The next morning the bladder catheter can be attached (using a "T" connector) to a Statham pressure transducer (Model P23 Db) and to a Harvard infusion pump. A plastic beaker attached to a force displacement transducer (Grass FTO3) can be placed under the rat's cage to collect and record urine volume. The cystometric evaluation of bladder function can be started by infusing saline (20 mL/h) and after the first micturition the infusion is maintained for 20 min. Two hours after the first cystometry period, the rats can be dosed orally with a test compound of Formula (I) and a second cystometry is performed between 30 min and 4 h after administration of test compound. The appropriate vehicle (e.g. 10% Solutol in sterile water) can be similarly administered to groups of rats that served as controls and the cystometry can be performed at the same respective time points.

The compounds of the present invention can also be evaluated under conditions of bladder hypertrophy and instability. Under anesthesia, a silk ligature is tied around the proximal urethra of rodents producing a partial outlet obstruction and subsequent hypertrophied bladder development within 6-9 weeks (Woods M. et al., J. Urology. 2001, 166:1142-47). Cystometry recordings can then be evaluated as described above. Such preclinical procedures are sensitive to compounds having clinical utility for the treatment of urinary incontinence (Soulard C, et al. J Pharmacol Exp Ther 1992, 260(3): 1152-8).

Example 15

In Vivo Model for Cold-enhanced Central Pain States

Injury to the brain or spinal cord, such as that caused by trauma, interrupted blood flow or neurodegenerative diseases, often precipitates a central pain condition. Examples of such injuries characterized, in part by, a hypersensitivity to cold stimuli include multiple sclerosis (Morin C, et al. Clin J Pain. 2002, 18(3): 191-5; Svendsen K B, et al. Pain. 2005, 114(3): 473-81), stroke or cerebral ischemia (Greenspan J D, et al. Pain. 2004, 109(3): 357-66) and spinal cord injury (Defrin R, Ohry A, Blumen N, Urca G. Pain 2001, 89(2-3): 253-63; Defrin R, et al. Brain 2002, 125(Pt 3): 501-10; Finnerup N B, et al. Anesthesiology 2005, 102(5): 1023-30). Each of these conditions may be readily modeled in animals for assessment of the abililty of compounds of Formula (I) to mollify the hypersensitive state. For example, a spinal cord injury (SCI) can be performed in adult Sprague-Dawley rats having a body weight of 150-200 g at time of surgery (Erichsen et al. Pain 2005, 116: 347-358). The rats can be anaesthetized with chloral hydrate (300 mg/kg, i.p., Sigma, USA) and a catheter can be inserted into the jugular vein. A midline skin incision can then be made along the back to expose the T11-L2 vertebrae. The animals can be positioned beneath a tunable argon ion laser (Innova model 70, Coherent Laser Products Division, Calif., USA) operating at a wavelength of 514 nm with an average power of 0.17 W. The laser light can be focused into a thin beam covering the single T13 vertebra, which can be irradiated for 10 min. Immediately before the irradiation, erythrosin B (Aldrich, 32.5 mg/kg dissolved in 0.9% saline) can be injected intravenously via the jugular catheter. Due to rapid metabolism of erythrosin B, the injection can be repeated after 5 min in order to maintain adequate blood concentrations. During irradiation, the body core temperature can be maintained at 37-38° C. by a heating pad. After irradiation the wound can be closed in layers and the skin sutured together.

SCI rats can be routinely tested for the presence of pain-like behaviors from 3-4 weeks after surgery. The fur of the animals can be shaved at least a day prior to examination of the cutaneous pain threshold to avoid sensitization of the skin receptors. During testing, the rats can be gently held in a standing position by the experimenter and the flank area and hindlimbs can be examined for hypersensitivity to sensory stimulation. On the day of drug testing, SCI rats can be administered drug according to the experimental schedule and the time course of pain-like behaviors can be measured. To test for the presence of cold allodynia, ethyl chloride or acetone can be sprayed onto the skin of the animals, often that which has been previously determined to be sensitive to mechanical stimulation by von Fry filament testing. The subsequent response to cold stimulation can be observed and classified according to the following scale: 0, no visible response; 1, localized response (skin twitch) without vocalization; 2, transient vocalization; 3, sustained vocalization. Kruskal Wallis ANOVA on ranks can be used to analyze the overall effects of non-parametric data obtained in response to cold stimulation following pretreatment with either a compound of Formula (I) or vehicle.

Example 16

In Vivo Model for Post-anesthetic Shivering

Spontaneous post-anesthetic tremor that resembles shivering is common during recovery from anesthesia. Risks to postoperative patients include an increase in metabolic rate of up to 400%, hypoxemia, wound dehiscence, dental damage, and disruption of delicate surgical repairs. The etiology of spontaneous post-anesthetic tremor is most commonly attributed to normal thermoregulatory shivering in response to intraoperative hypothermia. In most operating and recovery rooms, shivering is controlled by the use of humidifiers, warming blankets, and inhalation of humidified heated oxygen. However, pharmacological control is an effective alternate treatment modality (Bhatnagar S, et al. Anaesth Intensive Care 2001, 29(2): 149-54; Tsai Y C, Chu K S. Anesth Analg 2001, 93(5): 1288-92). Compounds of Formula (I) may be assessed for their ability to mitigate post-ansethetic induced-shaking by using animal models such as that described by Nikki et al (Nikki P, Tammisto T. Acta Anaesthesiol Scand 1968, 12(3): 125-34 and Grahn (Grahn, D A, et al. J Applied Physiology. 1996, 81: 2547-2554). For example, Wistar rats (males, weighing 250-450 g;) may be surgically implanted with an EEG/EMG recording array to assess post anesthetic tremor activity. The EEG electrodes are located bilaterally 2 mm off midline and adjacent to bregma and lamda. Following a one-week recovery period, frontal-occipital EEG, raw EMG, and integrated EMG activities, as well as three temperatures (skin, rectal, and water blanket temperatures during anesthesia), and ambient temperature post-anesthesia can be monitored throughout the experiment using copper-constantin thermocouples. The EEG and EMG signals can be recorded on polygraph paper (5 mm/s, Grass model 7E polygraph) and, during recovery from anesthesia, the EEG is computer scored in 10 second epochs as either synchronized: high amplitude (0.100 pV), low frequency (1-4 Hz dominated) activity characteristic of slow-wave sleep (SWS-like) or desynchronized: low amplitude (75 µV), high frequency (5-15 Hz dominated), characteristic of waking and rapid-eye-movement sleep (W-like). The EMG activity can be quantified as the averaged summed voltage/time interval by processing the raw EMG signal through an integrator (Grass model 7P3, 0.5 s time constant). On the day of an experiment, the animal can be placed in a small acrylic box (15×15×15 cm) and exposed to a halothane vapor-air mixture (4% halothane). Immediately after the induction of anesthesia, the animal can be removed from the enclosure and subsequently anesthetized through a nose cone. Following cessation of anesthesia, two stages of recovery can be judged: emergence from anesthesia and restoration of behavioral activity (behavioral recovery). Emergence from anesthesia may be defined as an increase in tonic EMG activity and a change in the EEG from a SWS-like pattern to a W-like pattern. Behaviorally, recovery has occurred when the animal rises from a prone position and initiated coordinated movements. The time intervals from termination of anesthesia to emergence and behavioral recovery can be measured in all animals. Time interval data can be subjected to a repeated measure analysis of variance, and the Scheffe's method can be employed for testing differences between pairs of means.

Example 17

TRPM8 Patch Clamp Assays

For patch clamp experiments, HEK293 cells stably transfected with canine TRPM8 were cultured in DMEM supplemented with 10% fetal bovine serum, 100 units/ml penicillin, 100 µg/ml streptomycin and 1 mg/ml G418. Cells were maintained at 37° C. and in 5% $CO_2$.

The extracellular solution contained (in mM): NaCl, 132; EGTA, 1; KCl, 5.4; $MgCl_2$, 0.8; HEPES, 10; glucose, 10; pH=7.4. Recordings were performed using the conventional whole-cell patch clamp technique, 1-2 days after plating cells onto glass coverslips at densities appropriate for single cell recording. Currents were amplified by a patch clamp amplifier and filtered at 2 kHz (Axopatch 200B, Molecular Devices, Union City, Calif.). Menthol (100 µM) was applied to the cell at 0.5 ml/min via a gravity-fed perfusion system. Recordings involving menthol activation were performed at 22° C.

In experiments where temperatures were varied, temperature ramps were generated by cooling the perfusate in an in-line cooler (Model SC-20, Warner Instruments, Hamden, Conn.) controlled by a temperature controller (Model CL-100, Warner Instruments). The temperature in the vicinity of the recorded cell was measured with a custom-made miniature thermo-microprobe connected to a monitoring thermometer (Model TH-8, Physitemp, Clifton, N.J.), and sampled using Digidata 1322A and pClamp 9.0 (Molecular Devices), as were the currents concurrently measured in the whole-cell patch clamp mode. The current was continuously sampled (at 100 Hz) at a holding potential of −60 mV.

Compounds were diluted from 10 mM DMSO stocks (stored at −20° C.) into an extracellular solution either containing 100 µM menthol or subjecting to cooling. Increasing concentrations of a compound were applied to a cell in a cumulative manner and concentration-dependent responses were measured after steady-state activation was achieved by either 100 µM menthol or cooling to 10° C. A saturating concentration of a reference antagonist was applied at the end of an experiment (either in the presence of 100 µM menthol or 10° C. temperature) to establish the baseline from which all the other measurements were subtracted.

Percentage inhibition by a compound was calculated as follows: $100 \times (1 - I_{comp}/I_0)$; where $I_{comp}$ and $I_0$ are steady-state current amplitudes in either the presence or absence of a concentration of the compound. Concentration-response data were fitted to a logistic function as follows: $R = 100/(1 + c/IC_{50})^p$; where, R is the percentage inhibition, p is the Hill coefficient and c is the concentration of the test compound. The resultant data are displayed in Table 11.

TABLE 11

| | Mode of Activation | |
|---|---|---|
| | Menthol (100 µM) | Cold (10° C.) |
| Cpd | $IC_{50}$ (µM) | $IC_{50}$ (µM) |
| 155 | 0.0125 | |
| 234 | 0.0047 | 0.0016 |
| 235 | 0.0592 | |
| 236 | 0.0014 | 0.0029 |
| 238 | 0.00053 | |
| 239 | 0.0030 | 0.0058 |
| 241 | 0.0016 | |
| 242 | 0.0004 | |

Example 18

In Vitro Rat and Human TRPM8 Functional Assay

For functional expression of TRPM8, the full-length cDNAs encoding human and rat TRPM8 were subcloned into pCI-NEO mammalian expression vectors. The expression constructs were transiently transfected into HEK293 cells according to the FuGENE 6 transfection Reagent® (ROCHE) instructions. HEK293 cells were routinely grown as monolayers in Dulbecco's minimum essential medium supplemented with 10% FBS, 1 mM L-glutamine, 100 units/mL penicillin and 100 ug/mL streptomycin. Cells were maintained in 5% $CO_2$ at 37° C. Within twenty-four hours, transiently transfected human and rat TRPM8 were seeded into clear-base poly-D-lysine coated 384-well plates (BD Biosciences, NJ, USA) at a density of 10,000 cells per well in culture medium and grown overnight. The following day, all medium was removed and the cells were incubated with 52 µL of 0.5×calcium 3 dye (Molecular Devices) prepared in complete assay buffer containing 20 mM HEPES, 0.1% BSA, and 2.5 mM probenecid at 37° C. for thirty five minutes. The cells were then incubated for an additional fifteen minutes at room temperature before initiating experiments. Following incubation, plates were inserted into a FDSS instrument, where cells were challenged with a compound of Formula (I) (at varying concentrations) and intracellular $Ca^{2+}$ was measured for 5 min prior to the addition of 100 nM icilin. $IC_{50}$ values for compounds of the present invention were determined from eight-point dose-response studies Maximal fluorescence intensity (FI) achieved upon addition of icilin was exported from the FDSS and further analyzed using Graph Pad Prism 3.02 (Graph Pad Software Inc., CA, U.S.A.). Basal FI was subtracted prior to normalizing data to percent of maximal response. The dose response curves from the average of quadruplicate wells for each data point were analyzed by using nonlinear regression of either sigmoidal dose response or sigmoidal dose response (variable slope). Finally, the $IC_{50}$ values were calculated with the best-fit dose curve determined by Prism. The resultant data are displayed in Table 12.

TABLE 12

| Cpd | Receptor Subtype | |
|---|---|---|
| | rTRPM8 $IC_{50}$ (nM) | hTRPM8 $IC_{50}$ (nM) |
| 234 | 0.053 | 0.054 |
| 236 | 0.140 | 0.126 |
| 239 | 0.052 | 0.044 |
| 242 | 0.056 | 0.049 |

Example 19

Cold Pressor Test

Compounds of Formula (I) can be tested in animals and humans for their ability to mitigate cardiovascular pressor responses evoked by cold exposure. The clinical cold pressor test assesses changes in blood pressure (BP) and cold pain perception during a 2-3 minute immersion of one hand into ice water. This test may be utilized to characterize analgesic compounds (Koltzenberg M et al. Pain. 2006, 126(1-3): 165-74) and to assess cold hypersensitivity (Desmeules J A et al. Arthritis Rheum. 2003, 48(5): 1420-9). A compound of Formula (I) was studied in an anesthetized rat cold pressor paradigm to determine whether TRPM8 antagonism would interfere with the blood pressure pressor response to cold stimulation of the forepaws. Male Sprague-Dawley rats (300-450 g) anesthetized with sodium pentobarbital were instrumented with a jugular catheter and an indwelling carotid artery pressure transducer. Vehicle (10% Solutol in water) or test compound was infused (1 mL/kg) over one minute through the intravenous catheter. Ten minutes later both forelimbs were packed in crushed ice for 5 minutes. Percent changes in mean arterial pressure in response to this cold stimulus were calculated for vehicle and test compound pretreatments. Percent inhibition attributed to treatment with test compound was then determined using the following formula: % Inhibition=[1−(cold evoked % change in BP post-test compound/cold evoked % change in BP post-vehicle)]×100. The resultant data are displayed in Table 13.

TABLE 13

Inhibition of Cold-induced Pressor Response in Anesthetized Rat.

| Cpd | Dose (mg/kg) | Route | % I | Time |
|---|---|---|---|---|
| 242 | 6 | i.v. | 54 | 10' |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:
1. A compound of Formula (Ia)

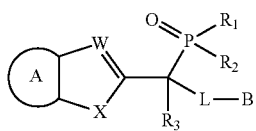

Formula (Ia)

selected from the group consisting of
a compound of Formula (Ia) wherein A is benzo, W is $C(R_4)$, $R_4$ is methyl, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is $C(R_4)$, $R_4$ is i-propyl, X is S, $R_1$ is ethoxy, $R_2$ is ethoxy, $R_3$ is H, L is $CH_2$, and B is 3,4-difluoro-phenyl;
a compound of Formula (Ia) wherein A is 4-fluoro-benzo, W is $C(R_4)$, $R_4$ is methyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 3-chloro-phenyl;
a compound of Formula (Ia) wherein A is benzo, W is $C(R_4)$, $R_4$ is cyclopentyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is isobutyl, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 3-fluoro-phenyl;
a compound of Formula (Ia) wherein A is 7-fluoro-benzo, W is $C(R_4)$, $R_4$ is methyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is $C(R_4)$, $R_4$ is methyl, X is O, $R_1$ is ethoxy, $R_2$ is ethoxy, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 2,3-difluoro-phenyl;
a compound of Formula (Ia) wherein A is benzo, W is $C(R_4)$, $R_4$ is methyl, X is O, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is $C(R_4)$, $R_4$ is chloro, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is $C(R_4)$, $R_4$ is bromo, X is S, $R_1$ is isopropyloxy, $R_2$ is isopropyloxy, $R_3$ is H, L is $CH_2$, and B is 3,4-difluoro-phenyl;
a compound of Formula (Ia) wherein A is 6-fluoro-benzo, W is $C(R_4)$, $R_4$ is methyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 3,5-difluoro-phenyl;
a compound of Formula (Ia) wherein A is benzo, W is $C(R_4)$, $R_4$ is methyl, X is S, $R_1$ is ethoxy, $R_2$ is ethoxy, $R_3$ is H, L is $CH_2$, and B is 3-methyl-phenyl;
a compound of Formula (Ia) wherein A is benzo, W is $C(R_4)$, $R_4$ is i-propyl, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is $C(R_4)$, $R_4$ is cyclopropyl, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3,4-dichloro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-3-chloro-phenyl;
a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3,4-dichloro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-methyl-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-4-fluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-3,5-difluoro-phenyl;
a compound of Formula (Ia) wherein A is benzo, W is C($R_4$), $R_4$ is cyclopropyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is ethoxy, $R_2$ is methyl, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-trifluoromethyl-4-fluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-methoxy-phenyl;
a compound of Formula (Ia) wherein A is benzo, W is C($R_4$), $R_4$ is methyl, X is S, $R_1$ is isobutyl, $R_2$ is isobutyl, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2,3-dichloro-phenyl;
a compound of Formula (Ia) wherein A is benzo, W is C($R_4$), $R_4$ is methyl, X is S, $R_1$ is ethoxy, $R_2$ is isobutyl, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-3-trifluoromethyl-phenyl;
a compound of Formula (Ia) wherein A is benzo, W is C($R_4$), $R_4$ is cyclopentyl, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 3-trifluoromethyl-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-bromo-phenyl;
a compound of Formula (Ia) wherein A is benzo, W is C($R_4$), $R_4$ is cyclobutyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is C($R_4$), $R_4$ is trifluoromethyl, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is n-propyl, $R_2$ is n-propyl, $R_3$ is H, L is $CH_2$, and B is 3,4-difluoro-phenyl;
a compound of Formula (Ia) wherein A is 5-fluoro-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2,5-dichloro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-trifluoromethyl-4-chloro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 4-fluoro-phenyl;
a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 4-fluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-trifluoromethyl-phenyl;
a compound of Formula (Ia) wherein A is benzo, W is C($R_4$), $R_4$ is methyl, X is S, $R_1$ is 2,2-dimethyl-propyl, $R_2$ is 2,2-dimethyl-propyl, $R_3$ is H, L is $CH_2$, and B is 3,4-difluoro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2,6-dichloro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 4-trifluoromethoxy-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-trifluoromethoxy-phenyl;
a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 3-fluoro-4-trifluoromethyl-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-trifluoromethyl-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-3-methyl-6-chloro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-trifluoromethoxy-phenyl;
a compound of Formula (Ia) wherein A is 5-methyl-benzo, W is C($R_4$), $R_4$ is methyl, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is C($R_4$), $R_4$ is H, X is S, $R_1$ is isopropyloxy, $R_2$ is isopropyloxy, $R_3$ is H, L is $CH_2$, and B is 3,4-difluoro-phenyl;
a compound of Formula (Ia) wherein A is benzo, W is C($R_4$), $R_4$ is phenyl, X is S, $R_1$ is ethoxy, $R_2$ is ethoxy, $R_3$ is H, L is $CH_2$, and B is 3,4-dichloro-phenyl;
a compound of Formula (Ia) wherein A is 4-chloro-benzo, W is C($R_4$), $R_4$ is methyl, X is S, $R_1$ is ethoxy, $R_2$ is ethoxy, $R_3$ is H, L is $CH_2$, and B is 3,4-dichloro-phenyl;
a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-bromo-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-5-trifluoromethyl-phenyl;

a compound of Formula (Ia) wherein A is benzo, W is C($R_4$), $R_4$ is H, X is S, $R_1$ ethoxy, $R_2$ is ethoxy, $R_3$ is H, L is $CH_2$, and B is 4-trifluoromethyl-phenyl;

a compound of Formula (Ia) wherein A is benzo, W is C($R_4$), $R_4$ is H, X is S, $R_1$ is isopropyloxy, $R_2$ is isopropyloxy, $R_3$ is H, L is $CH_2$, and B is 3-trifluoromethyl-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 4-bromo-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-(pyridin-4-yl)-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-3-chloro-5-trifluoromethyl-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2,4-dichloro-5-fluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-biphenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 3,4-dichloro-phenyl;

a compound of Formula (Ia) wherein A is benzo, W is C($R_4$), $R_4$ is methyl, X is S, $R_1$ is ethoxy, $R_2$ is ethoxy, $R_3$ is $CH_3$, L is $CH_2$, and B is 3,4-difluoro-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 2-fluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-3-trifluoromethyl-phenyl;

a compound of Formula (Ia) wherein A is 6-methoxy-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is 4-trifluoromethyl-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 2-chloro-phenyl;

a compound of Formula (Ia) wherein A is benzo, W is C($R_4$), $R_4$ is H, X is O, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is methyl, X is $SO_2$, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 2-methyl-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 4-trifluoromethyl-phenyl;

a compound of Formula (Ia) wherein A is 5-chloro-benzo, W is C($R_4$), $R_4$ is methyl, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is bromo, L is $CH_2$, and B is 3,4-difluoro-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 2,6-dichloro-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 3,5-trifluoromethyl-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 2-chloro-4-fluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-5-trifluoromethyl-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 2,3-dichloro-phenyl;

a compound of Formula (Ia) wherein A is benzo, W is C($R_4$), $R_4$ is methyl, X is S, $R_1$ is cyclohexyloxy, $R_2$ is cyclohexyloxy, $R_3$ is H, L is $CH_2$, and B is 3,4-difluoro-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 2-trifluoromethyl-phenyl;

a compound of Formula (Ia) wherein A is benzo, W is C($R_4$), $R_4$ is methyl, X is S, $R_1$ is ethoxy, $R_2$ is 2-(N,N-dimethylamino)-ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is methyl, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2,5-di-trifluoromethyl-phenyl;

a compound of Formula (Ia) wherein A is benzo, W is C($R_4$), X is S, $R_4$ is N,N-dimethylamino-methyl, $R_1$ is ethoxy, $R_2$ is ethoxy, $R_3$ is H, L is $CH_2$, and B is 2-fluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-biphenyl;

a compound of Formula (Ia) wherein A is 7-trifluoromethyl-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is 6-chloro-benzo, W is C($R_4$), $R_4$ is cyclopentyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S(O), $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is cyclohexyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is H, X is O, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is H, X is S, $R_1$ is isopropyloxy, $R_2$ is isopropyloxy, $R_3$ is H, L is $CH_2$, and B is 3,5-difluoro-phenyl;

a compound of Formula (Ia) wherein A is benzo, W is C($R_4$), $R_4$ is H, X is S, $R_1$ is isopropyloxy, $R_2$ is isopropyloxy, $R_3$ is H, L is $CH_2$, and B is 2,3-difluoro-phenyl;

a compound of Formula (Ia) wherein A is benzo, W is C($R_4$), $R_4$ is bromo, X is O, $R_1$ is isobutyl, $R_2$ is isobutyl, $R_3$ is H, L is $CH_2$, and B is 3,4-difluoro-phenyl;

a compound of Formula (Ia) wherein A is benzo, W is C($R_4$), $R_4$ is bromo, X is O, $R_1$ is isopropyloxy, $R_2$ isopropyloxy, $R_3$ is H, L is $CH_2$, and B is 3,4-difluoro-phenyl;

a compound of Formula (Ia) wherein A is benzo, W is C($R_4$), $R_4$ is H, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is H, X is S, $R_1$ is isopropyloxy, $R_2$ is isopropyloxy, $R_3$ is H, L is $CH_2$, and B is 2-fluoro-3-chloro-5-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is 2-fluoro-pyridin-3-yl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is 2,2-dimethyl-propyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is 2-fluoro-pyridin-5-yl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is H, X is S, $R_1$ is isopropyloxy, $R_2$ is isopropyloxy, $R_3$ is H, L is $CH_2$, and B is 3-fluoro-phenyl;

a compound of Formula (Ia) wherein A is benzo, W is C($R_4$), $R_4$ is H, X is S, $R_1$ is isopropyloxy, $R_2$ is isopropyloxy, $R_3$ is H, L is $CH_2$, and B is 3-chloro-phenyl;

diastereomer A, a compound of Formula (Ia) wherein A is benzo, W is C($R_4$), $R_4$ is methyl, X is S, $R_1$ is ethoxy, $R_2$ is 3-(4-methoxy-phenyl)-propyl, $R_3$ is H, L is $CH_2$, and B is 3,4-difluoro-phenyl;

diastereomer B, a compound of Formula (Ia) wherein A is benzo, W is C($R_4$), $R_4$ is methyl, X is S, $R_1$ is ethoxy, $R_2$ is 3-(4-methoxy-phenyl)-propyl, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-3-trimethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-chloro-3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-5-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-3-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-4-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trifluoromethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-5-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-chloro-5-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-4-trifluoromethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-4-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-chloro-3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trifluoromethyl-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethylthio-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-methoxy-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-methoxy-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-4-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2,3,5,6-tetrafluoro-4-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2,3,5,6-tetrafluoro-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-3-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-4-chloro-5-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-4-chloro-5-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-4-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-3-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-fluoro-5-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3,5-di-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-5-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-fluoro-4-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-4-methoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-chloro-3-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-chloro-5-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-bromo-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2,6-dichloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-4-trifluoromethoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-3-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-5-fluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-fluoro-4-chloro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-4-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-4-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3,5-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2,3-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-3-chloro-5-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-fluoro-phenyl;

a compound of Formula (Ia) wherein A is 4-bromo-benzo, W is C(R$_4$), R$_4$ is bromo, X is S, R$_1$ is isopropyloxy, R$_2$ is isopropyloxy, R$_3$ is H, L is CH$_2$, and B is 2-fluoro-phenyl;

a compound of Formula (Ia) wherein A is 6-bromo-benzyl, W is C(R$_4$), R$_4$ is bromo, X is S, R$_1$ is isopropyloxy, R$_2$ is isopropyloxy, R$_3$ is H, L is CH$_2$, and B is 2-fluoro-phenyl;

a compound of Formula (Ia) wherein A is 6-bromo-benzyl, W is C(R$_4$), R$_4$ is bromo, X is S, R$_1$ is isopropyloxy, R$_2$ is isopropyloxy, R$_3$ is H, L is CH$_2$, and B is 4-fluoro-phenyl;

a compound of Formula (Ia) wherein A is benzo, W is C(R$_4$), R$_4$ is bromo, X is S, R$_1$ is methoxy, R$_2$ is methoxy, R$_3$ is H, L is CH$_2$, and B is 3,4-difluoro-phenyl;

a compound of Formula (Ia) wherein A is 4-fluoro-benzo, W is C(R$_4$), R$_4$ is methyl, X is O, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is s-butyl, R$_2$ is s-butyl, R$_3$ is H, L is CH$_2$, and B is 3,4-difluoro-phenyl;

a compound of Formula (Ia) wherein A is benzo, W is C(R$_4$), R$_4$ is thien-3-yl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is n-butyloxy, R$_2$ is n-butyloxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is 2-(2-methoxy-ethoxy)-ethoxy, R$_2$ is 2-(2-methoxy-ethoxy)-ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is 3-methyl-butoxy, R$_2$ is 3-methyl-butoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is methoxycarbonyl-methoxy, R$_2$ is methoxycarbonyl-methoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is 2-acetoxy-ethoxy, R$_2$ is 2-acetoxy-ethoxy, R$_3$ is H, L is CH$_2$, and B is 3,4-difluoro-phenyl;

a compound of Formula (Ia) wherein A is benzo, W is C(R$_4$), R$_4$ is phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is 2-hydroxy-phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is 2-fluoro-phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is 3-fluoro-phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is 3-aminocarbonyl-phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is 3-methoxycarbonyl-phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is 4-fluoro-phenyl, X is S, R$_1$ is ethoxy, R$_2$ is ethoxy, R$_3$ is H, L is CH$_2$, and B is 3,4-difluoro-phenyl;

a compound of Formula (Ia) wherein A is 4-fluoro-benzo, W is C(R$_4$), R$_4$ is bromo, X is S, R$_1$ is isopropyloxy, R$_2$ is isopropyloxy, R$_3$ is H, L is CH$_2$, and B is 3,4-difluoro-phenyl;

a compound of Formula (Ia) wherein A is 4-fluoro-benzo, W is C(R$_4$), R$_4$ is bromo, X is S, R$_1$ is isopropyloxy, R$_2$ is isopropyloxy, R$_3$ is H, L is CH$_2$, and B is 3-trifluoromethyl-4-fluoro-phenyl;

a compound of Formula (Ia) wherein A is 4-fluoro-benzo, W is C(R$_4$), R$_4$ is bromo, X is S, R$_1$ is ethoxy, R$_2$ is ethoxy, R$_3$ is H, L is CH$_2$, and B is 3-trifluoromethyl-4-fluoro-phenyl;

a compound of Formula (Ia) wherein A is 4-fluoro-benzo, W is C(R$_4$), R$_4$ is bromo, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-hydroxy-4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-4-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-fluoro-4-hydroxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2,3,5,6-tetrafluoro-4-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2,3,5,6-tetrafluoro-4-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-3-hydroxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-4-chloro-5-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-chloro-5-hydroxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trifluoromethyl-4-hydroxy-phenyl;

enantiomer A, a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

enantiomer B, a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

enantiomer A, a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethoxy-phenyl;

enantiomer B, a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-phenyl;

enantiomer A, a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-phenyl;

enantiomer B, a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

enantiomer A, a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

enantiomer B, a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-trifluoromethyl-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trimethylthio-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-methylthio-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-chloro-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-trifluoromethyl-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethylthio-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-methylthio-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-methylsulfonyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-4-fluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-trifluoromethyl-4-fluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethylthio-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-methylthio-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-4-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-5-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3,5-di-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethylsulfonyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-trifluoromethylsulfonyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethylsulfonyl-phenyl;

a compound of Formula (Ia) wherein A is benzo, W is C($R_4$), $R_4$ is H, X is O, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is O, $R_1$ is ethoxy, $R^2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-chloro-2-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-chloro-3-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-chloro-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-trifluoromethoxy-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-chloro-4-trifluoromethoxy-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-chloro-2-fluoro-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-fluoro-4-trifluoromethyl-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-chloro-5-trifluoromethyl-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-bromo-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-chloro-5-fluoro-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-trifluoromethoxy-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-fluoro-5-trifluoromethyl-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-trifluoromethyl-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-chloro-3-trifluoromethyl-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-fluoro-3-trifluoromethyl-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3,5-di-trifluoromethyl-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-trifluoromethylthio-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-fluoro-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-trifluoromethyl-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-fluoro-5-trifluoromethyl-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-chloro-3-trifluoromethyl-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-chloro-phenyl;
a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-trifluoromethyl-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-chloro-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-fluoro-4-trifluoromethyl-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-methoxy-3-trifluoromethyl-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-chloro-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-fluoro-3-trifluoromethyl-phenyl;
a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-bromo-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-trifluoromethylthio-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-chloro-4-fluoro-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-fluoro-3-trifluoromethyl-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-methylthio-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-trifluoromethylsulfonyl-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethoxy-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-chloro-3-fluoro-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 5-chloro-2-fluoro-phenyl;
a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-trifluoromethylthio-phenyl;
a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 5-chloro-2-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 5-chloro-2-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 5-chloro-2-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-cyano-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-pyrrol-1-yl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-difluoromethoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-cyano-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-methoxycarbonyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-nitro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-amino-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3,5-dimethoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3,5-dihydroxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-hydroxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-methoxy-3-trifluoromethyl-phenyl;

a compound of Formula (Ia) wherein A is benzo, W is C(R$_4$), R$_4$ is H, X is S, R$_1$ is isopropyloxy, R$_2$ is isopropyloxy, R$_3$ is absent, L is =CH— taken to form an alkene with the phosphorus-bearing adjacent atom, and B is 3,4-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is absent, L is =CH— taken to form an alkene with the phosphorus-bearing adjacent atom, and B is 3,4-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-5-trifluoromethyl-phenyl;

and a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-trifluoromethyl-phenyl.

2. A compound of Formula (Ia)

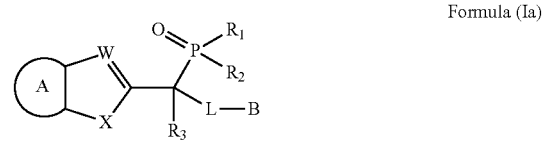

Formula (Ia)

selected from the group consisting of a compound of Formula (Ia) wherein A is benzo, W is C(R$_4$), R$_4$ is methyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is i-propyl, X is S, R$_1$ is ethoxy, R$_2$ is ethoxy, R$_3$ is H, L is CH$_2$, and B is 3,4-difluoro-phenyl;

a compound of Formula (Ia) wherein A is 4-fluoro-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-chloro-phenyl;

a compound of Formula (Ia) wherein A is benzo, W is C(R$_4$), R$_4$ is cyclopentyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is isobutyl, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-fluoro-phenyl;

a compound of Formula (Ia) wherein A is 7-fluoro-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is O, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,3-difluoro-phenyl;

a compound of Formula (Ia) wherein A is benzo, W is C($R_4$), $R_4$ is methyl, X is O, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

a compound of Formula (Ia) wherein A is 6-fluoro-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3,5-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-methyl-phenyl;

a compound of Formula (Ia) wherein A is benzo, W is C($R_4$), $R_4$ is i-propyl, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is cyclopropyl, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3,4-dichloro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-3-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3,4-dichloro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-methyl-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-4-fluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-3,5-difluoro-phenyl;

a compound of Formula (Ia) wherein A is benzo, W is C($R_4$), $R_4$ is cyclopropyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is methyl, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-trifluoromethyl-4-fluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-methoxy-phenyl;

a compound of Formula (Ia) wherein A is benzo, W is C($R_4$), $R_4$ is methyl, X is S, $R_1$ is isobutyl, $R_2$ is isobutyl, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2,3-dichloro-phenyl;

a compound of Formula (Ia) wherein A is benzo, W is C($R_4$), $R_4$ is methyl, X is S, $R_1$ is ethoxy, $R_2$ is isobutyl, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-3-trifluoromethyl-phenyl;

a compound of Formula (Ia) wherein A is benzo, W is C($R_4$), $R_4$ is cyclopentyl, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 3-trifluoromethyl-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-bromo-phenyl;

a compound of Formula (Ia) wherein A is benzo, W is C($R_4$), $R_4$ is cyclobutyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is trifluoromethyl, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is n-propyl, $R_2$ is n-propyl, $R_3$ is H, L is $CH_2$, and B is 3,4-difluoro-phenyl;

a compound of Formula (Ia) wherein A is 5-fluoro-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2,5-dichloro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-trifluoromethyl-4-chloro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-trifluoromethyl-phenyl;

a compound of Formula (Ia) wherein A is benzo, W is C($R_4$), $R_4$ is methyl, X is S, $R_1$ is 2,2-dimethyl-propyl, $R_2$ is 2,2-dimethyl-propyl, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2,6-dichloro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 4-trifluoromethoxy-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-fluoro-5-trifluoromethyl-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-trifluoromethoxy-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 3-fluoro-4-trifluoromethyl-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-trifluoromethyl-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-3-methyl-6-chloro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-trifluoromethoxy-phenyl;

a compound of Formula (Ia) wherein A is 5-methyl-benzo, W is C($R_4$), $R_4$ is methyl, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is H, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is phenyl, X is S, $R_1$ is ethoxy, $R_2$ is ethoxy, $R_3$ is H, L is $CH_2$, and B is 3,4-dichloro-phenyl;

a compound of Formula (Ia) wherein A is 4-chloro-benzo, W is C($R_4$), $R_4$ is methyl, X is S, $R_1$ is ethoxy, $R_2$ is ethoxy, $R_3$ is H, L is $CH_2$, and B is 3,4-dichloro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-bromo-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-5-trifluoromethyl-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 4-trifluoromethyl-phenyl;

a compound of Formula (Ia) wherein A is benzo, W is C($R_4$), $R_4$ is H, X is S, $R_1$ is isopropyloxy, $R_2$ is isopropyloxy, $R_3$ is H, L is $CH_2$, and B is 3-trifluoromethyl-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 4-bromo-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-(pyridin-4-yl)-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-fluoro-3-chloro-5-trifluoromethyl-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2,4-dichloro-5-fluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-biphenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 3,4-dichloro-phenyl;

a compound of Formula (Ia) wherein A is benzo, W is C($R_4$), $R_4$ is methyl, X is S, $R_1$ is ethoxy, $R_2$ is ethoxy, $R_3$ is $CH_3$, L is $CH_2$, and B is 3,4-difluoro-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 2-fluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-3-trifluoromethyl-phenyl;

a compound of Formula (Ia) wherein A is 6-methoxy-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is 4-trifluoromethyl-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 2-chloro-phenyl;

a compound of Formula (Ia) wherein A is benzo, W is C($R_4$), $R_4$ is H, X is O, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is methyl, X is $SO_2$, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 2-methyl-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 4-trifluoromethyl-phenyl;

a compound of Formula (Ia) wherein A is 5-chloro-benzo, W is C($R_4$), $R_4$ is methyl, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is bromo, L is $CH_2$, and B is 3,4-difluoro-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 2,6-dichloro-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 3,5-trifluoromethyl-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 2-chloro-4-fluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-5-trifluoromethyl-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 2,3-dichloro-phenyl;

a compound of Formula (Ia) wherein A is benzo, W is C($R_4$), $R_4$ is methyl, X is S, $R_1$ is cyclohexyloxy, $R_2$ is cyclohexyloxy, $R_3$ is H, L is $CH_2$, and B is 3,4-difluoro-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 2-trifluoromethyl-phenyl;

a compound of Formula (Ia) wherein A is benzo, W is C(R$_4$), R$_4$ is methyl, X is S, R$_1$ is ethoxy, R$_2$ is 2-(N,N-dimethylamino)-ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is methyl, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-methoxy-4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$ and B is 3-trifluoromethyl-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-3-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 5-chloro-2-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-methoxy-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-chloro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2,3,5,6-tetrafluoro-4-methoxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-methoxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-chloro-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-trifluoromethylsulfonyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-chloro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-chloro-5-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3,5-dimethoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 5-chloro-2-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-hydroxy-4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-chloro-4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-methoxy-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-trifluoromethylthio-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-trifluoromethylsulfonyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-bromo-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-fluoro-4-trifluoromethyl-phenyl;

a compound of Formula (Ia) wherein A is 4-fluoro-benzo, W is C(R$_4$), R$_4$ is bromo, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-hydroxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-3-methoxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-fluoro-4-chloro-phenyl;

a compound of Formula (Ia) wherein A is 4-fluoro-benzo, W is C(R$_4$), R$_4$ is bromo, X is S, R$_1$ is isopropyloxy, R$_2$ is isopropyloxy, R$_3$ is H, L is CH$_2$, and B is 3-trifluoromethyl-4-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-chloro-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-chloro-3-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-fluoro-4-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$ and B is 4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-trifluoromethyl-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-fluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-chloro-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2,3-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-nitro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-pyrrol-1-yl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-trifluoromethylthio-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-fluoro-3-trimethyl-phenyl;

a compound of Formula (Ia) wherein A is 4-fluoro-benzo, W is C(R$_4$), R$_4$ is bromo, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-methylthio-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-4-chloro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-trifluoromethoxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-chloro-2-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-trifluoromethylthio-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 5-chloro-2-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-trifluoromethyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-chloro-5-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-trifluoromethyl-phenyl;

a compound of Formula (Ia) wherein A is 4-fluoro-benzo, W is C(R$_4$), R$_4$ is bromo, X is S, R$_1$ is ethoxy, R$_2$ is ethoxy, R$_3$ is H, L is CH$_2$, and B is 3-trifluoromethyl-4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-difluoromethoxy-phenyl;

a compound of Formula (Ia) wherein A is 4-fluoro-benzo, W is C(R$_4$), R$_4$ is methyl, X is O, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-trifluoromethyl-4-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-3-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-trifluoromethyl-4-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-5-trifluoromethyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-methylthio-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-chloro-4-trifluoromethoxy-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethylthio-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-4-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3,5-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-4-trifluoromethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2,3,5,6-tetrafluoro-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-chloro-3-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-3-chloro-5-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-4-chloro-5-hydroxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-chloro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-fluoro-4-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethylsulfonyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-3-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 5-chloro-2-fluoro-phenyl;

a compound of Formula (Ia) wherein A is benzo, W is C($R_4$), $R_4$ is bromo, X is S, $R_1$ is n-butyloxy, $R_2$ is n-butyloxy, $R_3$ is H, L is $CH_2$, and B is 3,4-difluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-3-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3,5-di-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-bromo-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-chloro-3-fluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-trifluoromethyl-4-fluoro-phenyl;

a compound of Formula (Ia) wherein A is benzo, W is C($R_4$), $R_4$ is phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-4-chloro-5-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-methoxycarbonyl-phenyl;

a compound of Formula (Ia) wherein A is benzo, W is C($R_4$), $R_4$ is 2-hydroxy-phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-fluoro-3-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-methoxy-3-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-4-chloro-5-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-cyano-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-trifluoromethylsulfonyl-phenyl;

enantiomer B, a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-cyano-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-fluoro-4-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-4-trifluoromethyl-phenyl;

a compound of Formula (Ia) wherein A is benzo, W is C($R_4$), $R_4$ is bromo, X is S, $R_1$ is 3-methyl-butoxy, $R_2$ is 3-methyl-butoxy, $R_3$ is H, L is $CH_2$, and B is 3,4-difluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-4-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-fluoro-5-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-5-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-4-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trimethylthio-phenyl;

a compound of Formula (Ia) wherein A is benzo, W is C($R_4$), $R_4$ is thien-3-yl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-bromo-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-chloro-4-trifluoromethoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-5-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is absent, L is =CH— taken to form an alkene with the phosphorus-bearing adjacent atom, and B is 3,4-difluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-chloro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-chloro-2-fluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-chloro-5-fluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-chloro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-fluoro-4-trifluoromethyl-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-trifluoromethoxy-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-fluoro-3-trifluoromethyl-phenyl;

a compound of Formula (Ia) wherein A is benzo, W is C($R_4$), $R_4$ is bromo, X is S, $R_1$ is methoxycarbonyl-methoxy, $R_2$ is methoxycarbonyl-methoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trifluoromethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-chloro-3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-methylthio-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-fluoro-4-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-4-chloro-5-hydroxy-phenyl;

enantiomer A, a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethoxy-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-chloro-3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-trifluoromethyl-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-chloro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-trifluoromethylthio-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-4-trifluoromethyl-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-trifluoromethyl-phenyl;

a compound of Formula (Ia) wherein A is benzo, W is C(R$_4$), R$_4$ is 2-fluoro-phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-fluoro-5-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2,3,5,6-tetrafluoro-4-hydroxy-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethyl-4-methoxy-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2,6-dichloro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-fluoro-3-trifluoromethyl-phenyl;

a compound of Formula (Ia) wherein A is benzo, W is C(R$_4$), R$_4$ is bromo, X is S, R$_1$ is methoxy, R$_2$ is methoxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-trifluoromethylthio-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-chloro-3-trifluoromethyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-methylthio-phenyl;

a compound of Formula (Ia) wherein A is benzo, W is C(R$_4$), R$_4$ is 3-fluoro-phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2,3,5,6-tetrafluoro-4-hydroxy-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-fluoro-4-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-chloro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-5-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-fluoro-5-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-chloro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-chloro-5-trifluoromethyl-phenyl;

a compound of Formula (Ia) wherein A is benzo, W is C(R$_4$), R$_4$ is H, X is S, R$_1$ is isopropyloxy, R$_2$ is isopropyloxy, R$_3$ is absent, L is =CH— taken to form an alkene with the phosphorus-bearing adjacent atom, and B is 3,4-difluoro-phenyl;

a compound of Formula (Ia) wherein A is benzo, W is C(R$_4$), R$_4$ is bromo, X is S, R$_1$ is 2-acetoxy-ethoxy, R$_2$ is 2-acetoxy-ethoxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-trifluoromethoxy-phenyl;

a compound of Formula (Ia) wherein A is benzo, W is C(R$_4$), R$_4$ is 4-fluoro-phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-amino-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-methoxy-3-trifluoromethyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3,5-di-trifluoromethyl-phenyl;

enantiomer B, a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-fluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-chloro-3-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3,5-di-trifluoromethyl-phenyl;

enantiomer B, a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-trifluoromethyl-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 2-chloro-5-trifluoromethyl-phenyl;

enantiomer B, a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-trifluoromethoxy-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-chloro-5-trifluoromethyl-phenyl;

a compound of Formula (Ia) wherein A is 4-bromo-benzo, W is C(R$_4$), R$_4$ is bromo, X is S, R$_1$ is isopropyloxy, R$_2$ is isopropyloxy, R$_3$ is H, L is CH$_2$, and B is 2-fluoro-phenyl;

a compound of Formula (Ia) wherein A is benzo, W is C(R$_4$), R$_4$ is H, X is O, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is s-butyl, R$_2$ is s-butyl, R$_3$ is H, L is CH$_2$, and B is 3,4-difluoro-phenyl; and a compound of Formula (Ia) wherein A is benzo, W is C(R$_4$), R$_4$ is 3-aminocarbonyl-phenyl, X is S, R$_1$ is ethoxy, R$_2$ is ethoxy, R$_3$ is H, L is CH$_2$, and B is 3,4-difluoro-phenyl.

3. A compound of Formula (Ia)

$$\text{Formula (Ia)}$$

selected from the group consisting of a compound of Formula (Ia) wherein A is benzo, W is C(R$_4$), R$_4$ is methyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is i-propyl, X is S, R$_1$ is ethoxy, R$_2$ is ethoxy, R$_3$ is H, L is CH$_2$, and B is 3,4-difluoro-phenyl;

a compound of Formula (Ia) wherein A is 4-fluoro-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-chloro-phenyl;

a compound of Formula (Ia) wherein A is benzo, W is C(R$_4$), R$_4$ is cyclopentyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is isobutyl, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-fluoro-phenyl;

a compound of Formula (Ia) wherein A is 7-fluoro-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is O, R$_1$ is ethoxy, is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,3-difluoro-phenyl;

a compound of Formula (Ia) wherein A is benzo, W is C(R$_4$), R$_4$ is methyl, X is O, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3,4-difluoro-phenyl;

a compound of Formula (Ia) wherein A is 6-fluoro-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3,5-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-methyl-phenyl;

a compound of Formula (Ia) wherein A is benzo, W is C(R$_4$), R$_4$ is i-propyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is cyclopropyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3,4-dichloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-3-chloro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3,4-dichloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-methyl-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-chloro-4-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-chloro-3,5-difluoro-phenyl;

a compound of Formula (Ia) wherein A is benzo, W is C(R$_4$), R$_4$ is cyclopropyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is methyl, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-trifluoromethyl-4-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-methoxy-phenyl;

a compound of Formula (Ia) wherein A is benzo, W is C(R$_4$), R$_4$ is methyl, X is S, R$_1$ is isobutyl, R$_2$ is isobutyl, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,3-dichloro-phenyl;

a compound of Formula (Ia) wherein A is benzo, W is C(R$_4$), R$_4$ is methyl, X is S, R$_1$ is ethoxy, R$_2$ is isobutyl, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-3-trifluoromethyl-phenyl;

a compound of Formula (Ia) wherein A is benzo, W is C(R$_4$), R$_4$ is cyclopentyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 3-trifluoromethyl-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-bromo-phenyl;

a compound of Formula (Ia) wherein A is benzo, W is C(R$_4$), R$_4$ is cyclobutyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is trifluoromethyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is n-propyl, R$_2$ is n-propyl, R$_3$ is H, L is CH$_2$, and B is 3,4-difluoro-phenyl;

a compound of Formula (Ia) wherein A is 5-fluoro-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is naphthalen-2-yl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,5-dichloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-chloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-trifluoromethyl-4-chloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 4-fluoro-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 4-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-trifluoromethyl-phenyl;

a compound of Formula (Ia) wherein A is benzo, W is C(R$_4$), R$_4$ is methyl, X is S, R$_1$ is 2,2-dimethyl-propyl, R$_2$ is 2,2-dimethyl-propyl, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,6-dichloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 4-trifluoromethoxy-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-fluoro-5-trifluoromethyl-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-trifluoromethoxy-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 3-fluoro-4-trifluoromethyl-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-trifluoromethyl-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-3-methyl-6-chloro-phenyl;

a compound of Formula (Ia) wherein A is benzo, W is C(R$_4$), R$_4$ is methyl, X is S, R$_5$ is H, R$_1$ is ethoxy, R$_2$ is ethoxy, R$_3$ is H, L is CH$_2$, and B is 2-trifluoromethoxy-phenyl;

a compound of Formula (Ia) wherein A is 5-methyl-benzo, W is C(R$_4$), R$_4$ is methyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is H, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is phenyl, X is S, R$_1$ is ethoxy, R$_2$ is ethoxy, R$_3$ is H, L is CH$_2$, and B is 3,4-dichloro-phenyl;

a compound of Formula (Ia) wherein A is 4-chloro-benzo, W is C(R$_4$), R$_4$ is methyl, X is S, R$_1$ is ethoxy, R$_2$ is ethoxy, R$_3$ is H, L is CH$_2$, and B is 3,4-dichloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-bromo-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-5-trifluoromethyl-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 4-trifluoromethyl-phenyl;

a compound of Formula (Ia) wherein A is benzo, W is C(R$_4$), R$_4$ is H, X is S, R$_1$ is isopropyloxy, R$_2$ is isopropyloxy, R$_3$ is H, L is CH$_2$, and B is 3-trifluoromethyl-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 4-bromo-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-(pyridin-4-yl)-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-3-chloro-5-trifluoromethyl-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is phenyl;

a compound of Formula (Ia) wherein A is benzo, W is C(R$_4$), R$_4$ is H, X is S, R$_5$ is H, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,4-dichloro-5-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-biphenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 3,4-dichloro-phenyl;

a compound of Formula (Ia) wherein A is benzo, W is C(R$_4$), R$_4$ is methyl, X is S, R$_1$ is ethoxy, R$_2$ is ethoxy, R$_3$ is CH$_3$, L is CH$_2$, and B is 3,4-difluoro-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 2-fluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2-chloro-3-trifluoromethyl-phenyl;

a compound of Formula (Ia) wherein A is 6-methoxy-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is 4-trifluoromethyl-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is H, X is S, $R_1$ is ethoxy, $R_2$ is ethoxy, $R_3$ is H, L is $CH_2$, and B is 2-chloro-phenyl;

a compound of Formula (Ia) wherein A is benzo, W is C($R_4$), $R_4$ is H, X is O, $R_1$ is ethoxy, $R_2$ is ethoxy, $R_3$ is H, L is $CH_2$, and B is 4-fluoro-phenyl a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-methoxy-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-hydroxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L $CH_2$ is and B is 3-trifluoromethyl-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-hydroxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-3-hydroxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 5-chloro-2-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-methoxy-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-chloro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2,3,5,6-tetrafluoro-4-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-4-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-chloro-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-trifluoromethylsulfonyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-5-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3,5-dimethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 5-chloro-2-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-hydroxy-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-methoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethylthio-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethylsulfonyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-bromo-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-4-trifluoromethyl-phenyl;

a compound of Formula (Ia) wherein A is 4-fluoro-benzo, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-hydroxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-3-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-4-chloro-phenyl;

a compound of Formula (Ia) wherein A is 4-fluoro-benzo, W is C(R$_4$), R$_4$ is bromo, X is S, R$_1$ is isopropyloxy, R$_2$ is isopropyloxy, R$_3$ is H, L is CH$_2$, and B is 3-trifluoromethyl-4-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-chloro-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-chloro-3-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-fluoro-4-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-trifluoromethyl-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-fluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 3-chloro-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2,3-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-nitro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-pyrrol-1-yl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-trifluoromethylthio-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-fluoro-3-trimethyl-phenyl;

a compound of Formula (Ia) wherein A is 4-fluoro-benzo, W is C(R$_4$), R$_4$ is bromo, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-methylthio-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-4-chloro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-trifluoromethoxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-chloro-2-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-trifluoromethylthio-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 5-chloro-2-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-trifluoromethyl-phenyl;

a compound of Formula (Ia) wherein A is benzo, W is C(R$_4$), R$_4$ is bromo, X is O, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-chloro-5-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-trifluoromethyl-phenyl;

a compound of Formula (Ia) wherein A is 4-fluoro-benzo, W is C(R$_4$), R$_4$ is bromo, X is S, R$_1$ is ethoxy, R$_2$ is ethoxy, R$_3$ is H, L is CH$_2$, and B is 3-trifluoromethyl-4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-difluoromethoxy-phenyl;

a compound of Formula (Ia) wherein A is 4-fluoro-benzo, W is C(R$_4$), R$_4$ is methyl, X is O, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-trifluoromethyl-4-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-3-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-trifluoromethyl-4-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-fluoro-5-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-methylthio-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-4-trifluoromethoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethylthio-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-4-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3,5-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-4-trifluoromethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2,3,5,6-tetrafluoro-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-chloro-3-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-3-chloro-5-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-4-chloro-5-hydroxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-chloro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-fluoro-4-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethylsulfonyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-3-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 5-chloro-2-fluoro-phenyl;

a compound of Formula (Ia) wherein A is benzo, W is C($R_4$), $R_4$ is bromo, X is S, $R_1$ is n-butyloxy, $R_2$ is n-butyloxy, $R_3$ is H, L is $CH_2$, and B is 3,4-difluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-3-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3,5-di-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-bromo-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-chloro-3-fluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-trifluoromethyl-4-fluoro-phenyl;

a compound of Formula (Ia) wherein A is benzo, W is C($R_4$), $R_4$ is phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-4-chloro-5-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-methoxycarbonyl-phenyl;

a compound of Formula (Ia) wherein A is benzo, W is C($R_4$), $R_4$ is 2-hydroxy-phenyl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-fluoro-3-trifluoromethyl-phenyl;
a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-methoxy-3-trifluoromethyl-phenyl;
a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-4-chloro-5-methoxy-phenyl;
a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-cyano-phenyl;
a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-trifluoromethylsulfonyl-phenyl;
enantiomer B, a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;
a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-cyano-phenyl;
a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-fluoro-4-trifluoromethyl-phenyl;
a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-4-trifluoromethyl-phenyl;
a compound of Formula (Ia) wherein A is benzo, W is C($R_4$), $R_4$ is bromo, X is S, $R_1$ is 3-methyl-butoxy, $R_2$ is 3-methyl-butoxy, $R_3$ is H, L is $CH_2$, and B is 3,4-difluoro-phenyl;
a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-4-chloro-phenyl;
a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-fluoro-5-trifluoromethyl-phenyl;
a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-5-trifluoromethyl-phenyl;
a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-4-chloro-phenyl;
a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trimethylthio-phenyl;
a compound of Formula (Ia) wherein A is benzo, W is C($R_4$), $R_4$ is thien-3-yl, X is S, $R_1$ is ethoxy, $R_2$ is ethoxy, $R_3$ is H, L is $CH_2$, and B is 3,4-difluoro-phenyl;
a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-bromo-phenyl;
a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-chloro-4-trifluoromethoxy-phenyl;
a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-5-trifluoromethyl-phenyl;
a compound of Formula (Ia) wherein A is benzo, W is C($R_4$), $R_4$ is bromo, X is S, $R_1$ is isopropyloxy, $R_2$ is isopropyloxy, $R_3$ is absent, L is =CH— taken to form an alkene with the phosphorus-bearing adjacent atom, and B is 3,4-difluoro-phenyl;
a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-chloro-phenyl;
a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-chloro-2-fluoro-phenyl;
a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-chloro-5-fluoro-phenyl;
a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-chloro-phenyl;
a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-fluoro-4-trifluoromethyl-phenyl;
a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-trifluoromethoxy-phenyl;
a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-fluoro-3-trifluoromethyl-phenyl;
a compound of Formula (Ia) wherein A is benzo, W is C($R_4$), $R_4$ is bromo, X is S, $R_1$ is methoxycarbonyl-methoxy, $R_2$ is methoxycarbonyl-methoxy, $R_3$ is H, L is $CH_2$, and B is 3,4-difluoro-phenyl;
a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trifluoromethoxy-phenyl;
a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-chloro-3-trifluoromethyl-phenyl;
a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-methylthio-phenyl;
a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-fluoro-4-chloro-phenyl;
a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-4-chloro-5-hydroxy-phenyl;
enantiomer A, a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethoxy-phenyl;
a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-chloro-3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-trifluoromethyl-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-chloro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-trifluoromethylthio-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-4-trifluoromethyl-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-trifluoromethyl-phenyl;

a compound of Formula (Ia) wherein A is benzo, W is C($R_4$), $R_4$ is 2-fluoro-phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 2-fluoro-5-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2,3,5,6-tetrafluoro-4-hydroxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-4-methoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2,6-dichloro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 2-fluoro-3-trifluoromethyl-phenyl;

a compound of Formula (Ia) wherein A is benzo, W is C($R_4$), $R_4$ is bromo, X is S, $R_1$ is methoxy, $R_2$ is methoxy, $R_3$ is H, L is $CH_2$, and B is 3,4-difluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-trifluoromethylthio-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-chloro-3-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-trifluoromethyl-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-methylthio-phenyl;

a compound of Formula (Ia) wherein A is benzo, W is C($R_4$), $R_4$ is 3-fluoro-phenyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2,3,5,6-tetrafluoro-4-hydroxy-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 2-fluoro-4-trifluoromethyl-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 4-chloro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-5-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-trifluoromethyl-phenyl;

and a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-fluoro-5-trifluoromethyl-phenyl.

4. A compound of Formula (Ia)

Formula (Ia)

selected from the group consisting of a compound of Formula (Ia) wherein A is benzo, W is C($R_4$), $R_4$ is methyl, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is i-propyl, X is S, $R_1$ is ethoxy, $R_2$ is ethoxy, $R_3$ is H, L is $CH_2$, and B is 3,4-difluoro-phenyl;

a compound of Formula (Ia) wherein A is 4-fluoro-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-chloro-phenyl;

a compound of Formula (Ia) wherein A is benzo, W is C($R_4$), $R_4$ is cyclopentyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is isobutyl, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 3-fluoro-phenyl;

a compound of Formula (Ia) wherein A is 7-fluoro-benzo, W is C($R_4$), $R_4$ is methyl, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is O, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is methyl, X is S, $R_1$ is ethoxy, $R_2$ is ethoxy, $R_3$ is H, L is $CH_2$, and B is 2,3-difluoro-phenyl;

a compound of Formula (Ia) wherein A is benzo, W is C($R_4$), $R_4$ is methyl, X is O, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3,4-difluoro-phenyl;

a compound of Formula (Ia) wherein A is 6-fluoro-benzo, W is C(R$_4$), R$_4$ is methyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3,5-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-methyl-phenyl;

a compound of Formula (Ia) wherein A is benzo, W is C(R$_4$), R$_4$ is i-propyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is cyclopropyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3,4-dichloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-3-chloro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3,4-dichloro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-methyl-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-chloro-4-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-chloro-3,5-difluoro-phenyl;

a compound of Formula (Ia) wherein A is benzo, W is C(R$_4$), R$_4$ is cyclopropyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is methyl, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-trifluoromethyl-4-fluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-methoxy-phenyl;

a compound of Formula (Ia) wherein A is benzo, W is C(R$_4$), R$_4$ is methyl, X is S, R$_1$ is isobutyl, R$_2$ is isobutyl, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2,3-dichloro-phenyl;

a compound of Formula (Ia) wherein A is benzo, W is C(R$_4$), R$_4$ is methyl, X is S, R$_1$ is ethoxy, R$_2$ is isobutyl, R$_3$ is H, L is CH$_2$, and B is 3,4-difluoro-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 2-fluoro-3-trifluoromethyl-phenyl;

a compound of Formula (Ia) wherein A is benzo, W is C(R$_4$), R$_4$ is cyclopentyl, X is S, R$_1$ is isopropyloxy, R$_2$ is isopropyloxy, R$_3$ is H, L is CH$_2$, and B is 3,4-difluoro-phenyl;

a compound of Formula (Ia) wherein A is benzo, W is C(R$_4$), R$_4$ is H, X is S, R$_1$ is ethoxy, R$_2$ is ethoxy, R$_3$ is H, L is CH$_2$, and B is 3-trifluoromethyl-phenyl;

a compound of Formula (Ia) wherein A is benzo, W is C(R$_4$), R$_4$ is methyl, X is S, R$_1$ is ethoxy, R$_2$ is ethoxy, R$_3$ is H, L is CH$_2$, and B is 3-bromo-phenyl;

a compound of Formula (Ia) wherein A is benzo, W is C(R$_4$), R$_4$ is cyclobutyl, X is S, R$_1$ is ethoxy, R$_2$ is ethoxy, R$_3$ is H, L is CH$_2$, and B is 3,4-difluoro-phenyl a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-methoxy-4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is and B is 3-trifluoromethyl-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L CH$_2$ is CH$_2$, and B is 3-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-3-hydroxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 5-chloro-2-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-methoxy-4-fluoro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-chloro-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2,3,5,6-tetrafluoro-4-methoxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-methoxy-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-chloro-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-trifluoromethylsulfonyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-5-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3,5-dimethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 5-chloro-2-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-hydroxy-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-methoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethylthio-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethylsulfonyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-bromo-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 2-fluoro-4-trifluoromethyl-phenyl;

a compound of Formula (Ia) wherein A is 4-fluoro-benzo, W is C($R_4$), $R_4$ is bromo, X is S, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-hydroxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-3-methoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-4-chloro-phenyl;

a compound of Formula (Ia) wherein A is 4-fluoro-benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-chloro-3-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-fluoro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-chloro-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2,3-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-nitro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-pyrrol-1-yl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethylthio-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-3-trimethyl-phenyl;

a compound of Formula (Ia) wherein A is 4-fluoro-benzo, W is C($R_4$), $R_4$ is bromo, X is S, $R_1$ is ethoxy, $R_2$ is ethoxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-methylthio-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-4-chloro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-chloro-2-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3-trifluoromethylthio-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 5-chloro-2-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-5-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-4-trifluoromethyl-phenyl;

a compound of Formula (Ia) wherein A is 4-fluoro-benzo, W is C($R_4$), $R_4$ is bromo, X is S, $R_1$ is ethoxy, $R_2$ is ethoxy, $R_3$ is H, L is $CH_2$, and B is 3-trifluoromethyl-4-fluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-difluoromethoxy-phenyl;

a compound of Formula (Ia) wherein A is 4-fluoro-benzo, W is C($R_4$), $R_4$ is methyl, X is O, $R_1$ is isopropyloxy, $R_2$ is isopropyloxy, $R_3$ is H, L is $CH_2$, and B is 3,4-difluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-trifluoromethyl-4-fluoro-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2-fluoro-3-trifluoromethyl-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-trifluoromethyl-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-5-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-methylthio-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-chloro-4-trifluoromethoxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethylthio-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-4-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 3,5-difluoro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-fluoro-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 3-chloro-4-trifluoromethoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 2,3,5,6-tetrafluoro-4-methoxy-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-chloro-3-trifluoromethyl-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-3-chloro-5-trifluoromethyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-trifluoromethoxy-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 2-fluoro-4-chloro-5-hydroxy-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 3-trifluoromethyl-4-fluoro-phenyl;

a compound of Formula (Ia) wherein A is benzo, W is C($R_4$), $R_4$ is bromo, X is S, $R_1$ is isopropyloxy, $R_2$ is isopropyloxy, $R_3$ is H, L is $CH_2$, and B is 4-chloro-phenyl;

a compound of Formula (Ia) wherein A is benzo, W is C($R_4$), $R_4$ is chloro, X is S, $R_1$ is ethoxy, $R_2$ is ethoxy, $R_3$ is H, L is $CH_2$, and B is 3-fluoro-4-chloro-phenyl;

a compound of Formula (Ia) wherein A is benzo, W is C($R_4$), $R_4$ is bromo, X is S, $R_1$ is ethoxy, $R_2$ is ethoxy, $R_3$ is H, L is $CH_2$, and B is 4-trifluoromethylsulfonyl-phenyl;

a compound of Formula (Ia) wherein A is benzo, W is C($R_4$), $R_4$ is chloro, X is S, $R_1$ is isopropyloxy, $R_2$ is isopropyloxy, $R_3$ is H, L is $CH_2$, and B is 4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-3-chloro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 5-chloro-2-fluoro-phenyl;

a compound of Formula (Ia) wherein A is benzo, W is C(R$_4$), R$_4$ is bromo, X is S, R$_1$ is n-butyloxy, R$_2$ is n-butyloxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-fluoro-3-chloro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-trifluoromethyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3,5-di-trifluoromethyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-bromo-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-chloro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-fluoro-3-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-trifluoromethyl-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 4-chloro-3-fluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-fluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 2-trifluoromethyl-4-fluoro-phenyl;

a compound of Formula (Ia) wherein A is benzo, W is C(R$_4$), R$_4$ is phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-4-chloro-5-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-methoxycarbonyl-phenyl;

a compound of Formula (Ia) wherein A is benzo, W is C(R$_4$), R$_4$ is 2-hydroxy-phenyl, X is S, R$_1$ is ethoxy, R$_2$ is ethoxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-fluoro-3-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-methoxy-3-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-4-chloro-5-methoxy-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 3-cyano-phenyl;

a compound of Formula (Ia) wherein A is benzo, W is C(R$_4$), R$_4$ is chloro, X is S, R$_1$ is ethoxy, R$_2$ is ethoxy, R$_3$ is H, L is CH$_2$, and B is 4-trifluoromethylsulfonyl-phenyl;

enantiomer B, a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 3-trifluoromethyl-4-fluoro-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 4-cyano-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-fluoro-4-trifluoromethyl-phenyl;

a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-4-trifluoromethyl-phenyl;

a compound of Formula (Ia) wherein A is benzo, W is C(R$_4$), R$_4$ is bromo, X is S, R$_1$ is 3-methyl-butoxy, R$_2$ is 3-methyl-butoxy, R$_3$ is H, L is CH$_2$, and B is 3,4-difluoro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-trifluoromethyl-4-chloro-phenyl;

a compound of Formula (Ia) wherein A is benzo, W is C(R$_4$), R$_4$ is chloro, X is S, R$_1$ is isopropyloxy, R$_2$ is isopropyloxy, R$_3$ is H, L is CH$_2$, and B is 3-fluoro-5-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 2-fluoro-5-trifluoromethyl-phenyl;

a compound of Formula (Ia) wherein A is benzo, W is C(R$_4$), R$_4$ is bromo, X is S, R$_1$ is isopropyloxy, R$_2$ is isopropyloxy, R$_3$ is H, L is CH$_2$, and B is 4-trifluoromethyl-phenyl;

and a compound of Formula (Ia) wherein A is benzo, W is C(R$_4$), R$_4$ is bromo, X is S, R$_1$ is ethoxy, R$_2$ is ethoxy, R$_3$ is H, L is CH$_2$, and B is 2-fluoro-5-trifluoromethyl-phenyl.

* * * * *